US012807619B2

United States Patent

(12) United States Patent
Zhang et al.

(10) Patent No.: US 12,807,619 B2
(45) Date of Patent: Nov. 24, 2026

(54) COMPOUNDS FOR THE TREATMENT OF ALZHEIMER'S DISEASE

(71) Applicant: Icahn School of Medicine at Mount Sinai, New York, NY (US)

(72) Inventors: Bin Zhang, New York, NY (US); Jian Jin, New York, NY (US); Husnu Umit Kaniskan, New York, NY (US); Lihuai Qin, New York, NY (US); Minghui Wang, New York, NY (US); Aiqun Li, New York, NY (US); Kristen J. Brennand, New York, NY (US); Eric E. Schadt, New York, NY (US); Vahram Haroutunian, New York, NY (US); Lap Ho, New York, NY (US); Xianxiao Zhou, New York, NY (US); Zhenyu Yue, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 692 days.

(21) Appl. No.: 18/249,829

(22) PCT Filed: Oct. 22, 2021

(86) PCT No.: PCT/US2021/056310
§ 371 (c)(1),
(2) Date: Apr. 20, 2023

(87) PCT Pub. No.: WO2022/087456
PCT Pub. Date: Apr. 28, 2022

(65) Prior Publication Data

US 2024/0327427 A1 Oct. 3, 2024

Related U.S. Application Data

(60) Provisional application No. 63/105,038, filed on Oct. 23, 2020.

(51) Int. Cl.

| | |
|---|---|
| ***C07D 513/04*** | (2006.01) |
| ***A61K 31/426*** | (2006.01) |
| ***A61K 31/427*** | (2006.01) |
| ***A61K 31/428*** | (2006.01) |
| ***A61K 31/437*** | (2006.01) |
| ***A61K 31/4439*** | (2006.01) |
| ***A61K 31/4725*** | (2006.01) |
| ***A61P 25/28*** | (2006.01) |
| ***C07D 277/46*** | (2006.01) |
| ***C07D 277/82*** | (2006.01) |
| ***C07D 417/04*** | (2006.01) |

(52) U.S. Cl.
CPC .......... *C07D 513/04* (2013.01); *A61K 31/426* (2013.01); *A61K 31/427* (2013.01); *A61K 31/428* (2013.01); *A61K 31/437* (2013.01); *A61K 31/4439* (2013.01); *A61K 31/4725* (2013.01); *A61P 25/28* (2018.01); *C07D 277/46* (2013.01); *C07D 277/82* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 5,034,395 | A | 7/1991 | Tamada et al. |
| 2006/0047123 | A1 | 3/2006 | Ahmed |

FOREIGN PATENT DOCUMENTS

| | | | | |
|---|---|---|---|---|
| WO | WO 200246129 | | 6/2002 | |
| WO | WO 2008/101029 | * | 8/2008 | ......... A61K 31/4161 |
| WO | WO 2009/117831 | * | 1/2009 | ........... C07C 401/00 |

OTHER PUBLICATIONS

CAS RN 848354-66-5 (entered into STN on Apr. 12, 2005) (Year: 2005).*
"International Search Report and Written Opinion in International Application No. PCT/US2021/056310", Mar. 22, 2022, 15 Pages.
Pubchem, "S-[7-oxo-7[(4-phenyl-1, 3-thiazol-2-yl)amino]heptyl]2-benzyl-3-phenylpropanethioate).", SID 90057628, Pubchem Entry (online). National Center for Biotechnology Information, Feb. 22, 2010.
Romeiro, et al., "Novel Sustainable-by-Design HDAC Inhibitors for the Treatment of Alzheimer's Disease", ACS Medicinal Cheistry Letters, vol. 10, No. 4,, Mar. 29, 2019, pp. 671-676.
Victoriano, et al., "Novel histone deacetylase inhibitor NCH-51 activates latent HIV-1 gene expression", gene expression, FEBS Letters, vol. 585, Apr. 6, 2011, pp. 1103-1111; p. 1104, Figure 1.
"Notification Concerning Transmittal of International Preliminary Report on Patentability in U.S. International Application No. PCT/US2021/056310", May 4, 2023.

* cited by examiner

*Primary Examiner* — Craig D Ricci
(74) *Attorney, Agent, or Firm* — IP Spring

(57) ABSTRACT

Disclosed herein are novel drugs useful in treating Alzheimer's Disease and methods of use.

3 Claims, 39 Drawing Sheets

Specification includes a Sequence Listing.

FIG. 2A
SNHG14
GABRA1
SLC4A10
SCN2A
SYT1
RDX
STAG2
TROVE2
HECW1
PARD3B
WDR47
ATP6V1A
ST18
STAT3
LPR10
TLN1
MAVS
AP2M1
SLC25A46
TTBK1
PRRC2A
TNRC18
KMT2B
AKT2
ZFHX2
LENG8
CLTC
SKP1
DNAJA2
COPS4
NUD121
RSL24D1

NCH-51

LQ081-166

LQ108-32

SEQUENCE LISTING

```
<160> NUMBER OF SEQ ID NOS: 56

<210> SEQ ID NO 1
<211> LENGTH: 25
<212> TYPE: RNA
<213> ORGANISM: Artificial Sequence
<220> FEATURE:
<223> OTHER INFORMATION: Polynucleotide

<400> SEQUENCE: 1

caccggcggg aacgaccaca cuugg                                              25


<210> SEQ ID NO 2
<211> LENGTH: 25
<212> TYPE: RNA
<213> ORGANISM: Artificial Sequence
<220> FEATURE:
<223> OTHER INFORMATION: Polynucleotide
```

<400> SEQUENCE: 2
aaacccaagu gugggucguuc ccgcc 25

<210> SEQ ID NO 3
<211> LENGTH: 25
<212> TYPE: RNA
<213> ORGANISM: Artificial Sequence
<220> FEATURE:
<223> OTHER INFORMATION: Polynucleotide

<400> SEQUENCE: 3
caccgggcga ccgguaacug gcgag 25

<210> SEQ ID NO 4
<211> LENGTH: 25
<212> TYPE: RNA
<213> ORGANISM: Artificial Sequence
<220> FEATURE:
<223> OTHER INFORMATION: Polynucleotide

<400> SEQUENCE: 4
aaaccucgcc aguuaccggu cgccc 25

<210> SEQ ID NO 5
<211> LENGTH: 25
<212> TYPE: RNA
<213> ORGANISM: Artificial Sequence
<220> FEATURE:
<223> OTHER INFORMATION: Polynucleotide

<400> SEQUENCE: 5
caccggguga gcggcgaccg guaac 25

<210> SEQ ID NO 6
<211> LENGTH: 25
<212> TYPE: RNA
<213> ORGANISM: Artificial Sequence
<220> FEATURE:
<223> OTHER INFORMATION: Polynucleotide

<400> SEQUENCE: 6
aaacguuacc ggucgccgcu caccc 25

<210> SEQ ID NO 7
<211> LENGTH: 25
<212> TYPE: RNA
<213> ORGANISM: Artificial Sequence
<220> FEATURE:
<223> OTHER INFORMATION: Polynucleotide

<400> SEQUENCE: 7
caccggggga aguccucagc ugcac 25

<210> SEQ ID NO 8
<211> LENGTH: 25
<212> TYPE: RNA
<213> ORGANISM: Artificial Sequence
<220> FEATURE:
<223> OTHER INFORMATION: Polynucleotide

<400> SEQUENCE: 8
aaacgugcag cugaggacuu ccccc 25

<210> SEQ ID NO 9
<211> LENGTH: 24

-continued

<212> TYPE: RNA
<213> ORGANISM: Artificial Sequence
<220> FEATURE:
<223> OTHER INFORMATION: Polynucleotide

<400> SEQUENCE: 9 caccggugu cguucccgcu acuu 24

<210> SEQ ID NO 10
<211> LENGTH: 24
<212> TYPE: RNA
<213> ORGANISM: Artificial Sequence
<220> FEATURE:
<223> OTHER INFORMATION: Polynucleotide

<400> SEQUENCE: 10
aaacaaguag cgggaacgac cacc 24

<210> SEQ ID NO 11
<211> LENGTH: 25
<212> TYPE: RNA
<213> ORGANISM: Artificial Sequence
<220> FEATURE:
<223> OTHER INFORMATION: Polynucleotide

<400> SEQUENCE: 11
caccggaugu ucacgugcuu cggau 25

<210> SEQ ID NO 12
<211> LENGTH: 25
<212> TYPE: RNA
<213> ORGANISM: Artificial Sequence
<220> FEATURE:
<223> OTHER INFORMATION: Polynucleotide

<400> SEQUENCE: 12
aaacauccga agcacgugaa caucc 25

<210> SEQ ID NO 13
<211> LENGTH: 21
<212> TYPE: DNA
<213> ORGANISM: Artificial Sequence
<220> FEATURE:
<223> OTHER INFORMATION: Polynucleotide

<400> SEQUENCE: 13
gagatcctgt acttcgcact g 21

<210> SEQ ID NO 14
<211> LENGTH: 20
<212> TYPE: DNA
<213> ORGANISM: Artificial Sequence
<220> FEATURE:
<223> OTHER INFORMATION: Polynucleotide

<400> SEQUENCE: 14
tgtcccccaa cttgagatgt 20

<210> SEQ ID NO 15
<211> LENGTH: 21
<212> TYPE: DNA
<213> ORGANISM: Artificial Sequence
<220> FEATURE:
<223> OTHER INFORMATION: Polynucleotide

<400> SEQUENCE: 15

-continued gggatgtaga tgctttgggt c 21

<210> SEQ ID NO 16
<211> LENGTH: 23
<212> TYPE: DNA
<213> ORGANISM: Artificial Sequence
<220> FEATURE:
<223> OTHER INFORMATION: Polynucleotide

<400> SEQUENCE: 16
tgtgcacttt tattcaactg gtc 23

<210> SEQ ID NO 17
<211> LENGTH: 22
<212> TYPE: DNA
<213> ORGANISM: Artificial Sequence
<220> FEATURE:
<223> OTHER INFORMATION: Polynucleotide

<400> SEQUENCE: 17
gacgaaatca aggctaaggt cg 22

<210> SEQ ID NO 18
<211> LENGTH: 20
<212> TYPE: DNA
<213> ORGANISM: Artificial Sequence
<220> FEATURE:
<223> OTHER INFORMATION: Polynucleotide

<400> SEQUENCE: 18
actacgcacc aaggtcaagg 20

<210> SEQ ID NO 19
<211> LENGTH: 21
<212> TYPE: DNA
<213> ORGANISM: Artificial Sequence
<220> FEATURE:
<223> OTHER INFORMATION: Polynucleotide

<400> SEQUENCE: 19
acctctttcc gtggaacttg g 21

<210> SEQ ID NO 20
<211> LENGTH: 21
<212> TYPE: DNA
<213> ORGANISM: Artificial Sequence
<220> FEATURE:
<223> OTHER INFORMATION: Polynucleotide

<400> SEQUENCE: 20
caaatatgga cgtgtcttcg c 21

<210> SEQ ID NO 21
<211> LENGTH: 20
<212> TYPE: DNA
<213> ORGANISM: Artificial Sequence
<220> FEATURE:
<223> OTHER INFORMATION: Polynucleotide

<400> SEQUENCE: 21
tgctctgttc atcgcccaat 20

<210> SEQ ID NO 22
<211> LENGTH: 20
<212> TYPE: DNA
<213> ORGANISM: Artificial Sequence
<220> FEATURE:
<223> OTHER INFORMATION: Polynucleotide

<400> SEQUENCE: 22
ttcatcgcct ccaagttccc 20

<210> SEQ ID NO 23
<211> LENGTH: 20
<212> TYPE: DNA
<213> ORGANISM: Artificial Sequence
<220> FEATURE:
<223> OTHER INFORMATION: Polynucleotide

<400> SEQUENCE: 23
acatggtgcc agccatttca 20

<210> SEQ ID NO 24
<211> LENGTH: 20
<212> TYPE: DNA
<213> ORGANISM: Artificial Sequence
<220> FEATURE:
<223> OTHER INFORMATION: Polynucleotide

<400> SEQUENCE: 24
ccgagacgtg ttcaacgaca 20

<210> SEQ ID NO 25
<211> LENGTH: 20
<212> TYPE: DNA
<213> ORGANISM: Artificial Sequence
<220> FEATURE:
<223> OTHER INFORMATION: Polynucleotide

<400> SEQUENCE: 25
tttggctaca caacgtcgga 20

<210> SEQ ID NO 26
<211> LENGTH: 20
<212> TYPE: DNA
<213> ORGANISM: Artificial Sequence
<220> FEATURE:
<223> OTHER INFORMATION: Polynucleotide

<400> SEQUENCE: 26
ttgagtccaa gagcggtgtc 20

<210> SEQ ID NO 27
<211> LENGTH: 20
<212> TYPE: DNA
<213> ORGANISM: Artificial Sequence
<220> FEATURE:
<223> OTHER INFORMATION: Polynucleotide

<400> SEQUENCE: 27
tggctcaatc gcaatgcaac 20

<210> SEQ ID NO 28
<211> LENGTH: 20
<212> TYPE: DNA
<213> ORGANISM: Artificial Sequence
<220> FEATURE:
<223> OTHER INFORMATION: Polynucleotide

<400> SEQUENCE: 28
cgagagcttc tcgtcgaaca 20

<210> SEQ ID NO 29
<211> LENGTH: 20
<212> TYPE: DNA
<213> ORGANISM: Artificial Sequence
<220> FEATURE:
<223> OTHER INFORMATION: Polynucleotide

<400> SEQUENCE: 29
ctcagggcga tcgtattgct 20

<210> SEQ ID NO 30
<211> LENGTH: 20
<212> TYPE: DNA
<213> ORGANISM: Artificial Sequence
<220> FEATURE:
<223> OTHER INFORMATION: Polynucleotide

<400> SEQUENCE: 30
tggcgggtgc attcgatatt 20

<210> SEQ ID NO 31
<211> LENGTH: 20
<212> TYPE: DNA
<213> ORGANISM: Artificial Sequence
<220> FEATURE:
<223> OTHER INFORMATION: Polynucleotide

<400> SEQUENCE: 31
aattcgcaca gcaatctgcc 20

<210> SEQ ID NO 32
<211> LENGTH: 20
<212> TYPE: DNA
<213> ORGANISM: Artificial Sequence
<220> FEATURE:
<223> OTHER INFORMATION: Polynucleotide

<400> SEQUENCE: 32
tgtcaggttc ctcgcatgtc 20

<210> SEQ ID NO 33
<211> LENGTH: 20
<212> TYPE: DNA
<213> ORGANISM: Artificial Sequence
<220> FEATURE:
<223> OTHER INFORMATION: Polynucleotide

<400> SEQUENCE: 33
cgtgctcgcg tttagtgatg 20

<210> SEQ ID NO 34
<211> LENGTH: 23
<212> TYPE: DNA
<213> ORGANISM: Artificial Sequence
<220> FEATURE:
<223> OTHER INFORMATION: Polynucleotide

<400> SEQUENCE: 34
ggttatcgaa aacgaactga gca 23

<210> SEQ ID NO 35
<211> LENGTH: 21
<212> TYPE: DNA
<213> ORGANISM: Artificial Sequence
<220> FEATURE:
<223> OTHER INFORMATION: Polynucleotide

<400> SEQUENCE: 35
acgaggatga aggtccacaa c 21

<210> SEQ ID NO 36
<211> LENGTH: 20
<212> TYPE: DNA
<213> ORGANISM: Artificial Sequence
<220> FEATURE:
<223> OTHER INFORMATION: Polynucleotide

<400> SEQUENCE: 36
ggcatcccgg ttatctcgtg 20

<210> SEQ ID NO 37
<211> LENGTH: 22
<212> TYPE: DNA
<213> ORGANISM: Artificial Sequence
<220> FEATURE:
<223> OTHER INFORMATION: Polynucleotide

<400> SEQUENCE: 37
aatgggtgtc gctgaagaag tc 22

<210> SEQ ID NO 38
<211> LENGTH: 20
<212> TYPE: DNA
<213> ORGANISM: Artificial Sequence
<220> FEATURE:
<223> OTHER INFORMATION: Polynucleotide

<400> SEQUENCE: 38
ctttgccact tccagggtca 20

<210> SEQ ID NO 39
<211> LENGTH: 22
<212> TYPE: DNA
<213> ORGANISM: Artificial Sequence
<220> FEATURE:
<223> OTHER INFORMATION: Polynucleotide

<400> SEQUENCE: 39
gcagttgtgt tgacaccttt gg 22

<210> SEQ ID NO 40
<211> LENGTH: 20
<212> TYPE: DNA
<213> ORGANISM: Artificial Sequence
<220> FEATURE:
<223> OTHER INFORMATION: Polynucleotide

<400> SEQUENCE: 40
ccggatctcc gacagttacg 20

<210> SEQ ID NO 41
<211> LENGTH: 20
<212> TYPE: DNA
<213> ORGANISM: Artificial Sequence
<220> FEATURE:
<223> OTHER INFORMATION: Polynucleotide

<400> SEQUENCE: 41
cgacggctat gatgagggac 20

<210> SEQ ID NO 42

<211> LENGTH: 20
<212> TYPE: DNA
<213> ORGANISM: Artificial Sequence
<220> FEATURE:
<223> OTHER INFORMATION: Polynucleotide

<400> SEQUENCE: 42
gctggatagg taacgccctc 20

<210> SEQ ID NO 43
<211> LENGTH: 20
<212> TYPE: DNA
<213> ORGANISM: Artificial Sequence
<220> FEATURE:
<223> OTHER INFORMATION: Polynucleotide

<400> SEQUENCE: 43
aagccgttct cagccatgat 20

<210> SEQ ID NO 44
<211> LENGTH: 20
<212> TYPE: DNA
<213> ORGANISM: Artificial Sequence
<220> FEATURE:
<223> OTHER INFORMATION: Polynucleotide

<400> SEQUENCE: 44
ggctatgtcc ggtgccataa 20

<210> SEQ ID NO 45
<211> LENGTH: 20
<212> TYPE: DNA
<213> ORGANISM: Artificial Sequence
<220> FEATURE:
<223> OTHER INFORMATION: Polynucleotide

<400> SEQUENCE: 45
ggtcgtggtg gatccttgtt 20

<210> SEQ ID NO 46
<211> LENGTH: 20
<212> TYPE: DNA
<213> ORGANISM: Artificial Sequence
<220> FEATURE:
<223> OTHER INFORMATION: Polynucleotide

<400> SEQUENCE: 46
cgtttgggtg gttctctcca 20

<210> SEQ ID NO 47
<211> LENGTH: 20
<212> TYPE: DNA
<213> ORGANISM: Artificial Sequence
<220> FEATURE:
<223> OTHER INFORMATION: Polynucleotide

<400> SEQUENCE: 47
gaccgtggcg tattccagta 20

<210> SEQ ID NO 48
<211> LENGTH: 20
<212> TYPE: DNA
<213> ORGANISM: Artificial Sequence
<220> FEATURE:
<223> OTHER INFORMATION: Polynucleotide

<400> SEQUENCE: 48
gaagtatacg gtgaggcggg 20

<210> SEQ ID NO 49
<211> LENGTH: 20
<212> TYPE: DNA
<213> ORGANISM: Artificial Sequence
<220> FEATURE:
<223> OTHER INFORMATION: Polynucleotide

<400> SEQUENCE: 49
ggtgcgtaga acatgggtga 20

<210> SEQ ID NO 50
<211> LENGTH: 20
<212> TYPE: DNA
<213> ORGANISM: Artificial Sequence
<220> FEATURE:
<223> OTHER INFORMATION: Polynucleotide

<400> SEQUENCE: 50
tctcgtgatg caagggttcc 20

<210> SEQ ID NO 51
<211> LENGTH: 20
<212> TYPE: DNA
<213> ORGANISM: Artificial Sequence
<220> FEATURE:
<223> OTHER INFORMATION: Polynucleotide

<400> SEQUENCE: 51
acagctcaaa gagtccgagc 20

<210> SEQ ID NO 52
<211> LENGTH: 20
<212> TYPE: DNA
<213> ORGANISM: Artificial Sequence
<220> FEATURE:
<223> OTHER INFORMATION: Polynucleotide

<400> SEQUENCE: 52
ctgactggcg cttttggaag 20

<210> SEQ ID NO 53
<211> LENGTH: 20
<212> TYPE: DNA
<213> ORGANISM: Artificial Sequence
<220> FEATURE:
<223> OTHER INFORMATION: Polynucleotide

<400> SEQUENCE: 53
ttctggtact cggcgcattt 20

<210> SEQ ID NO 54
<211> LENGTH: 22
<212> TYPE: DNA
<213> ORGANISM: Artificial Sequence
<220> FEATURE:
<223> OTHER INFORMATION: Polynucleotide

<400> SEQUENCE: 54
cttccaaagc atggtaagct ac 22

<210> SEQ ID NO 55
<211> LENGTH: 21
<212> TYPE: DNA

-continued

<213> ORGANISM: Artificial Sequence
<220> FEATURE:
<223> OTHER INFORMATION: Polynucleotide

<400> SEQUENCE: 55
acgacgtatc ggattgaatg g 21

<210> SEQ ID NO 56
<211> LENGTH: 21
<212> TYPE: DNA
<213> ORGANISM: Artificial Sequence
<220> FEATURE:
<223> OTHER INFORMATION: Polynucleotide

<400> SEQUENCE: 56
agaactggtg ccacttgtag c 21

COMPOUNDS FOR THE TREATMENT OF ALZHEIMER'S DISEASE

RELATED APPLICATION

This application is a § 371 national stage of PCT International Application No. PCT/US21/56310, entitled "New Compounds for the Treatment of Alzheimer's Disease" filed on Oct. 22, 2021, which claims priority to U.S. Provisional Application No. 63/105,038, filed Oct. 23, 2020, which is incorporated herein by reference in their entirety.

STATEMENT REGARDING FEDERALLY SPONSORED RESEARCH

This invention was made with government support under U01AG046170 and R01AG068030 awarded by NIH on May 15, 2014 and Sep. 15, 2020, respectively. The government has certain rights in the invention.

SEQUENCE LISTING

The instant application contains a Sequence Listing which has been submitted via Patent Center and is hereby incorporated by reference in its entirety. Said .txt copy, created on Sep. 8, 2023 is named MS-0030-01-US-NP_ST25, and is 11,042 bytes in size.

BACKGROUND

Alzheimer's disease ("AD") is the most common cause of dementia, an affliction that ultimately occurs in over 43 million people worldwide. The majority of dementia cases occur after age 65, which impose an increasing burden on societies with aging populations. AD is defined biologically by the presence of a specific neuropathology of the brain: extracellular deposition of amyloid-β (Aβ) in the form of diffuse and neuritic plaques and the presence of neuropil threads within dystrophic neurites that contain aggregated, hyperphosphorylated tau protein and intraneuronal neurofibrillary tangles.

Despite the heavy burden on society and on aging populations, there are only four medications currently approved by the FDA for treating AD, and they are approved only for managing the cognitive impairment that are present in symptomatic AD. The drugs are: donepezil, rivastigmine, galantamine (all cholinesterase inhibitors), and memantine (an NMDA modulator). But none shows any efficacy in slowing cognitive decline or improving global functioning. Thus, there is a need for identifying AD treatments that are effective in treating the disease at all stages.

Sporadic Late-Onset Alzheimer's Disease ("LOAD"), the most prevalent form of dementia among people over age 65, is a progressive and irreversible brain disorder. Over 5.5 million in the US are affected by LOAD, which is currently the sixth leading cause of death in the US and costs more than $200 billion annually. There is an urgent need to develop effective methods to prevent, treat, or delay the onset or progression of LOAD. Conventional genome-wide association studies (GWAS) have revealed ~30 loci associated with LOAD (Jansen et al., 2019; Kunkle et al., 2019; Lambert et al., 2013; Marioni et al., 2018), with ~40% of the total phenotypic variance explained by these common variants (Ridge et al., 2013). Yet the genuine causal variants responsible for the functional effect on the disease remain uncharacterized. Translating these genetic associations into biologically mechanisms of disease pathogenesis and therapeutic interventions remains a huge challenge in the field.

Previous studies have illuminated some of the potential systems and pathways for identifying potential treatment targets. One such study provided a systems biology approach to integrate genotyping and microarray transcriptomic data from over 500 brains of LOAD and control subjects from the Harvard Brain Tissue Resource Center (HBTRC) (Zhang et al., 2013a). The study analyzed transcriptomic networks in 3 brain regions including the dorsolateral prefrontal cortex (DLPFC), the visual cortex (VC), and the cerebellum (CB), and it highlighted an immune-microglia network module and its network key driver TYROBP for relevance to LOAD pathology. Additional, similar studies utilizing systems approaches have been performed on several large-scale Omics studies of LOAD (Allen et al., 2016; De Jager et al., 2018; Johnson et al., 2020; Mostafavi et al., 2018; Ping et al., 2018). Although these studies have identified various dysfunctional subnetworks and genes associated with LOAD, none has identified specific targets for treating LOAD or therapeutics for targeting the identified dysfunctional targets.

SUMMARY

The present disclosure overcomes the deficiencies noted above and provides an integrative network analysis-based, target nomination method that complements conventional linkage and linkage disequilibrium-based gene mapping methods currently used to identify the most relevant genes for functional studies.

Applying these methods, the present disclosure identifies for the first time certain neuronal and neurodegenerative phenotypes present in LOAD that are responsive to treatment, specifically those exhibiting ATP6V1A deficits.

The present disclosure relates to novel compounds useful for disease treatment, methods for designing and making them, and methods for their use in treating a subject in need thereof. Such disclosed compounds are useful for treating AD.

The present disclosure provides a method of treating Alzheimer's Disease (AD) or Late Onset Alzheimer's Disease (LOAD) by administering to a subject in need thereof a therapeutically effective amount of a compound that targets ATP6V1A production.

The present disclosure also identifies a compound of Formula (I):

FORMULA I

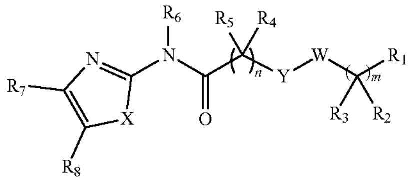

or a pharmaceutically acceptable salt thereof, wherein:

X is selected from S, O, NH or $CH_2$;

Y and W are independently selected from S, O, NH, CO, SO2, SO or $CH_2$;

$R_1$, $R_7$, and $R_8$ are independently selected from hydrogen, halogen, oxo, CN, $NO_2$, $OR_9$, $SR_9$, $NR_9R_{10}$, $C(O)R_9$, $C(O)OR_9$, $C(O)NR_9R_{10}$, $S(O)R_9$, $S(O)_2R_{10}$, $S(O)_2NR_9R_{10}$, $NR_{11}C(O)OR_9$, $NR_{11}C(O)R_9$, $NR_{11}C(O)$ $NR_9R_{10}$, $NR_{11}S(O)R_9$, $NR_{11}S(O)_2R_9$, $NR_{11}S(O)_2NR_9R_{10}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl, wherein $R_9$, $R_{10}$, and $R_{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R_9$ and $R_{10}$, $R_9$ and $R_{11}$, $R_{10}$ and $R_{11}$ together with the atom to which they are connected form an optionally substituted 3-20 membered cycloalkyl or heterocyclyl ring;

$R_2$, $R_3$, $R_4$ and $R_5$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

$R_6$ is selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; and m, n, are independently selected from 1-15.

The present disclosure provides a method of treating Alzheimer's Disease (AD) or Late Onset Alzheimer's Disease (LOAD) by administering to a subject in need thereof a therapeutically effective amount of a compound of Formula I.

The present disclosure also identifies a compound of Formula I (A):

FORMULA I (A)

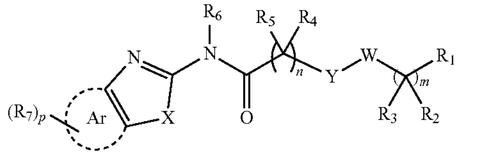

or a pharmaceutically acceptable salt thereof, wherein:

the definitions of X, Y, W, $R_1$, $R_2$, $R_3$, $R_4$, $R_5$, $R_6$, and $R_7$ are the same as for FORMULA 1;

Ar is a fused, optionally substituted with $R_7$, 4-8 membered heterocyclyl, optionally substituted with $R_7$ aryl, and optionally substituted with $R_7$ heteroaryl;

m, n, are independently selected from 1-15; and p is selected from 0-5.

The present disclosure provides a method of treating Alzheimer's Disease (AD) or Late Onset Alzheimer's Disease (LOAD) by administering to a subject in need thereof a therapeutically effective amount of a compound of Formula I (A).

The present disclosure also identifies a compound of Formula I (B):

FORMULA I (B)

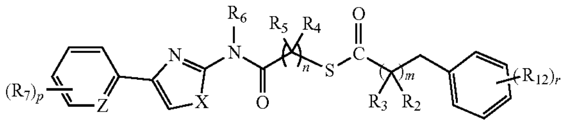

or a pharmaceutically acceptable salt thereof, wherein:

the definitions of X, $R_1$, $R_2$, $R_3$, $R_4$, $R_5$, $R_6$, and $R_7$ are the same as for FORMULA 1;

$R_{12}$ is selected from hydrogen, halogen, oxo, CN, $NO_2$, $OR_{13}$, $SR_{13}$, $NR_{13}R_{14}$, $C(O)R_{13}$, $C(O)OR_{13}$, $C(O)NR_{13}R_{14}$, $S(O)R_{13}$, $S(O)_2R_{14}$, $S(O)_2NR_{13}R_{14}$, $NR_{15}C(O)OR_{13}$, $NR_{15}C(O)R_{13}$, $NR_{15}C(O)NR_{13}R_{14}$, $NR_{15}S(O)R_{13}$, $NR_{15}S(O)_2R_{13}$, $NR_{15}S(O)_2NR_{13}R_{14}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R_{13}$, $R_{14}$, and $R_{15}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R_{13}$ and $R_{14}$, $R_{13}$ and $R_{15}$, $R_{14}$ and $R_{15}$ together with the atom to which they are connected form an optionally substituted 3-20 membered cycloalkyl or heterocyclyl ring;

m, n are independently selected from 1-15; and p, r are independently selected from 0-5

The present disclosure provides a method of treating Alzheimer's Disease (AD) or Late Onset Alzheimer's Disease (LOAD) by administering to a subject in need thereof a therapeutically effective amount of a compound of Formula I (B).

The present disclosure also identifies a compound of Formula II:

FORMULA II

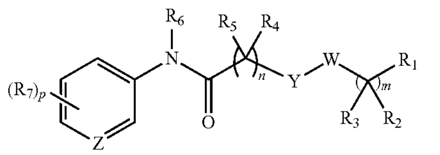

or a pharmaceutically acceptable salt thereof, wherein:

the definitions of X, Y, W, $R_1$, $R_2$, $R_3$, $R_4$, $R_5$, $R_6$, and $R_7$ are the same as for FORMULA 1;

Z is selected from N or CH;

m, n, are independently selected from 1-15; and p is selected from 0-5.

The present disclosure provides a method of treating Alzheimer's Disease (AD) or Late Onset Alzheimer's Disease (LOAD) by administering to a subject in need thereof a therapeutically effective amount of a compound of Formula II.

The present disclosure also identifies multiple novel compounds, including, for example, LQ081-166; LQ081-168; LQ081-175; LQ081-176; LQ108-13; LQ108-15; LQ108-16; LQ108-17; LQ108-18; LQ108-19; LQ108-20; LQ108-22; LQ108-41; LQ108-46; LQ108-47; LQ108-48; LQ108-49; LQ108-50; LQ108-51; LQ108-52; LQ108-53; and LQ108-184.

The present disclosure identifies the novel compound LQ081-166.

The present disclosure provides a method of treating Alzheimer's Disease (AD) or Late Onset Alzheimer's Disease (LOAD) by administering to a subject in need thereof a therapeutically effective amount of a compound selected from the group consisting of: LQ081-166; LQ081-168; LQ081-175; LQ081-176; LQ108-13; LQ108-15; LQ108-16; LQ108-17; LQ108-18; LQ108-19; LQ108-20; LQ108-22; LQ108-41; LQ108-46; LQ108-47; LQ108-48; LQ108-49; LQ108-50; LQ108-51; LQ108-52; LQ108-53; and LQ108-184.

The present disclosure provides a method of treating Alzheimer's Disease (AD) or Late Onset Alzheimer's Disease (LOAD) by administering to a subject in need thereof a therapeutically effective amount of LQ081-166.

DETAILED DESCRIPTION

Mechanisms and Therapeutic Targets for LOAD

Figure 1:
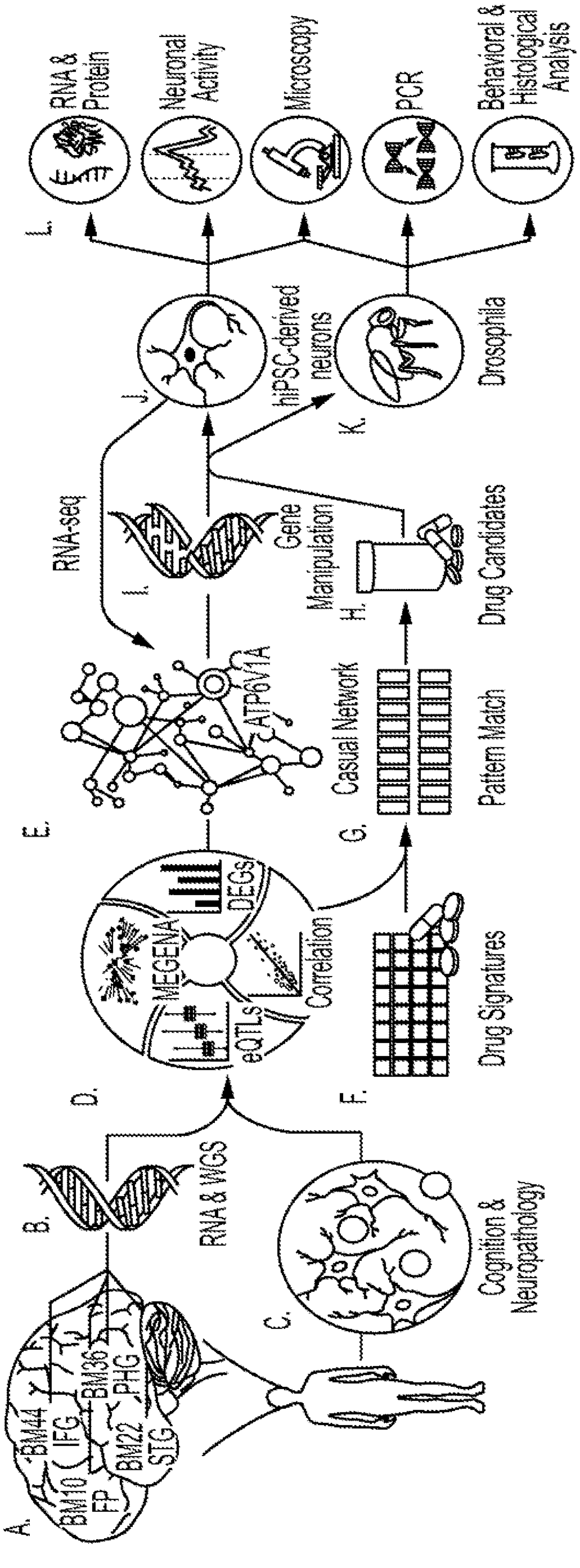
FIG. 1 provides a diagram of transformative network modeling platform for mechanism discovery, target identification, and therapeutics development for Alzheimer's disease, in accordance with some embodiments.

The present disclosure identifies thousands of molecular changes and neuronal gene subnetworks that result in the greatest degree of dysregulation in LOAD. It provides for the first time a global landscape and detailed map of signaling circuits of complex molecular interactions in 4 key brain regions affected by LOAD, information that is critical for identifying specific treatment targets and identifying LOAD therapeutics. The present disclosure further provides multiple neuronal modules particularly relevant to LOAD pathology and predicts key regulators of these modules.

The models of the present disclosure reveal that ATP6V1A is a key regulator of a top-ranked neuronal subnetwork. It also establishes the role of ATP6V1A in disease-related processes through CRISPR-based manipulation in human induced pluripotent stem cell derived-neurons and in RNAi-based knockdown in *Drosophila* models. Using CRISPRi, the present disclosure reveals that ATP6V1A down-regulates neuronal activity-associated functional pathways, particularly in the presence of Aβ42 peptides. The disclosure further shows in Aβ42 flies that the mRNA levels of fly orthologs of ATP6V1A and of Vha68-1/Vha68-2 are reduced and that the neuronal KD of Vha68-1 exacerbates age-dependent behavioral deficits and neurodegeneration accompanied by downregulation of synaptic genes. These results reveal, in combination, that there are evolutionarily conserved roles of ATP6V1A in maintaining neuronal activity and synaptic integrity.

The present disclosure provides a method of treating Alzheimer's Disease by administering to a subject in need thereof a therapeutically effective amount of a drug that targets ATP6V1A production.

The present disclosure provides a method of treating LOAD by administering to a subject in need thereof a therapeutically effective amount of a drug that targets ATP6V1A production.

The present disclosure provides a computer-implemented method to predict for identifying candidate compounds for use in targeting ATP6V1A production for the treatment of Alzheimer's Disease, the method comprising: obtaining data of drug induced signatures for candidate compounds and ATP6V1A signatures associated with Alzheimer's Disease, wherein the ATP6V1A signatures are selected from the group consisting of ATP6V1A downregulation across brain regions and disease stages; significant down-regulation of ATP6V1A in the BM36-PHG region; marginal down-regulation of ATP6V1A in the BM10-FP region; negative correlation of ATP6V1A expression with clinical and pathological traits in BM22-STG and BM36-PHG; down-regulation in the excitatory and inhibitory neurons in animal models of early-pathology of LOAD; enrichment for down-regulation signals of ATP6V1A in knock out or inhibition models; AD disease signatures from the BM36-PHG region; and methods of increasing mRNA expression of ATP6V1A in neuronal network or animal models of AD; providing the data as input to a trained machine learning model, wherein the model is EDMURA; and obtaining from the model, the drug associated with an AD subtype.

The present disclosure provides a method of treating LOAD by administering to a subject in need thereof a therapeutically effective amount of a novel drug that targets ATP6V1A production, wherein the novel drug is selected from the group consisting of: LQ081-166; LQ081-168; LQ081-175; LQ081-176; LQ108-13; LQ108-15; LQ108-16; LQ108-17; LQ108-18; LQ108-19; LQ108-20; LQ108-22; LQ108-41; LQ108-46; LQ108-47; LQ108-48; LQ108-49; LQ108-50; LQ108-51; LQ108-52; LQ108-53; and LQ108-184.

The present disclosure provides a method of treating Alzheimer's Disease by administering to a subject in need thereof a therapeutically effective amount of a novel drug that targets ATP6V1A production, wherein the novel drug is selected from the group consisting of: LQ081-166; LQ081-168; LQ081-175; LQ081-176; LQ108-13; LQ108-15; LQ108-16; LQ108-17; LQ108-18; LQ108-19; LQ108-20; LQ108-22; LQ108-41; LQ108-46; LQ108-47; LQ108-48; LQ108-49; LQ108-50; LQ108-51; LQ108-52; LQ108-53; and LQ108-184.

The present disclosure provides a method of treating LOAD or Alzheimer's Disease by administering to a subject in need thereof a therapeutically effective amount of the known compound NCH-51.

The present disclosure provides a method of treating Alzheimer's Disease by administering to a subject in need thereof a therapeutically effective amount of LQ081-166.

The present disclosure provides each of the following novel compounds:

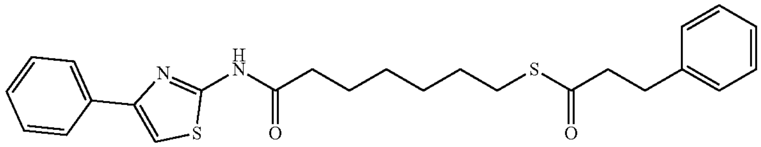
;

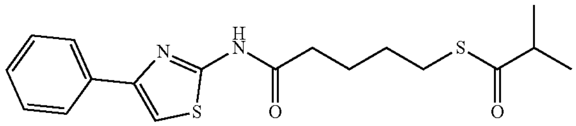
;

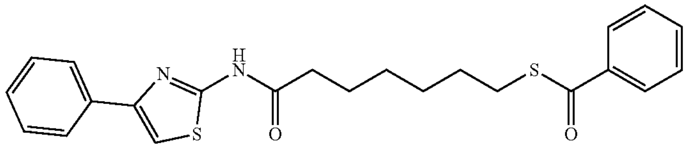
;

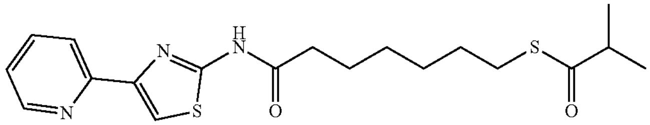
;

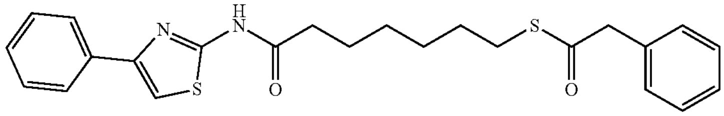
;

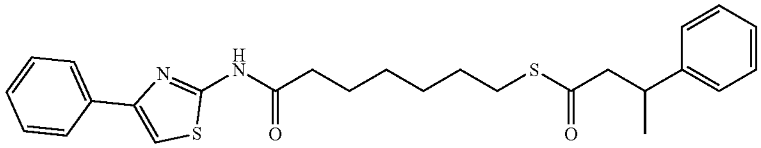
;

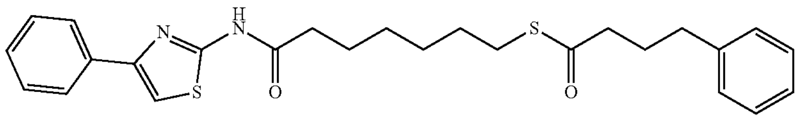
;

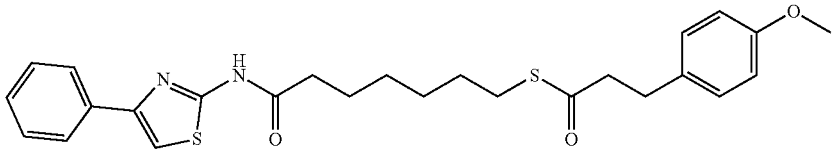
;

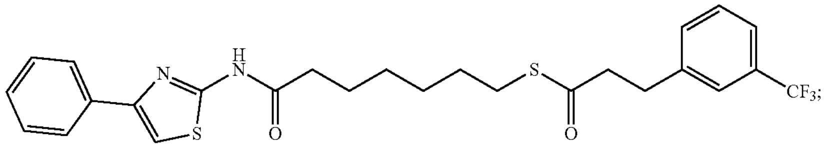
;

-continued
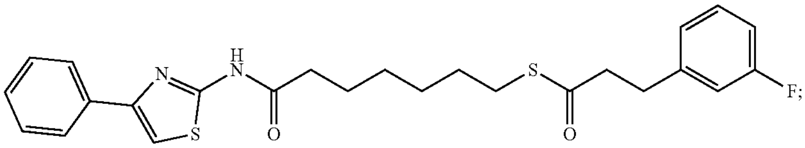
;
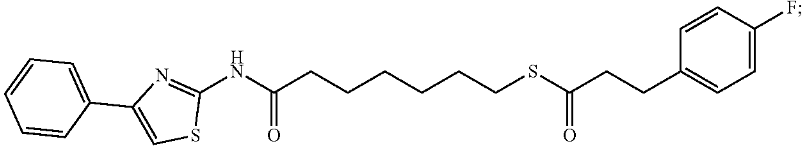
;
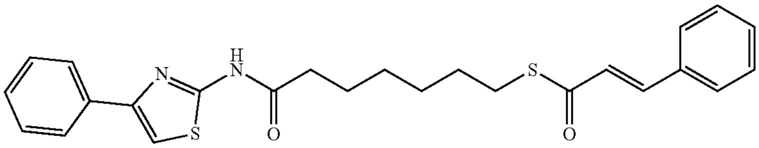
;
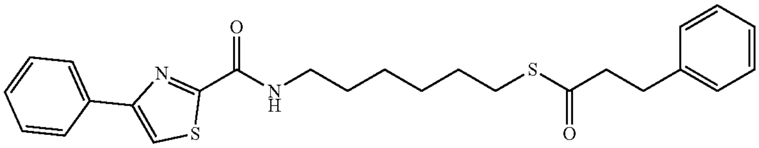
;
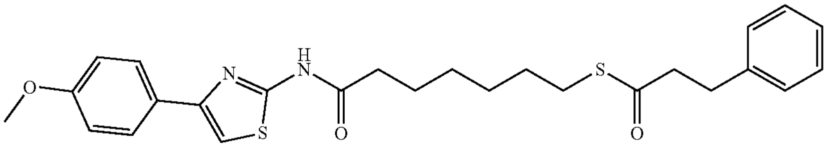
;
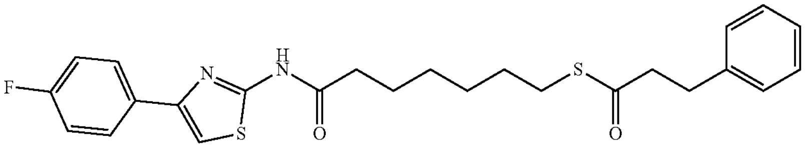
;
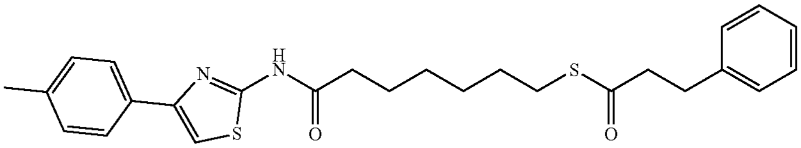
;
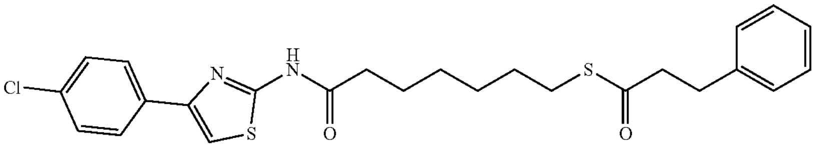
;
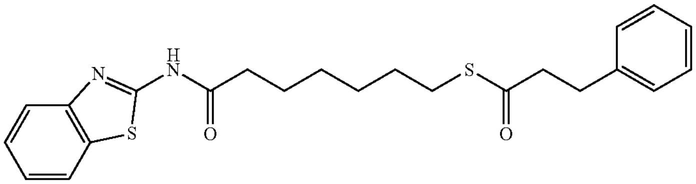
;
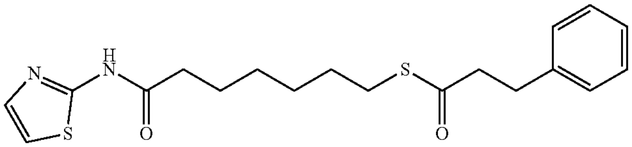
;
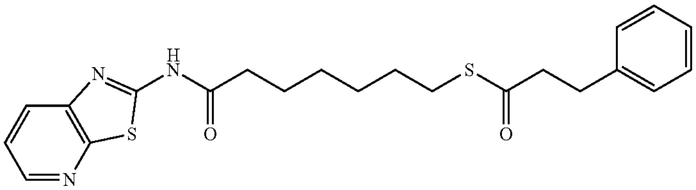
;

-continued
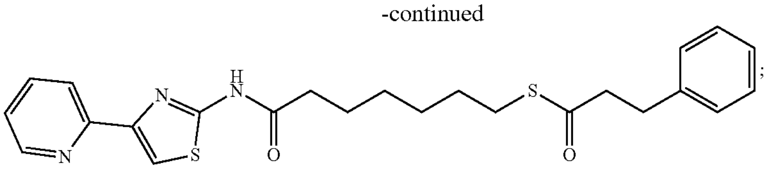
; and
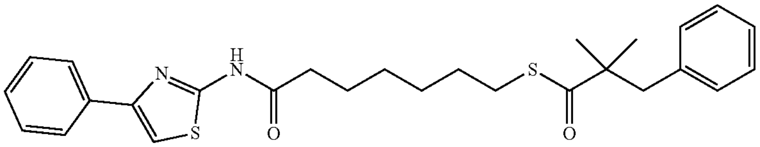
and methods for making them.
The present disclosure provides each of the following novel compounds:
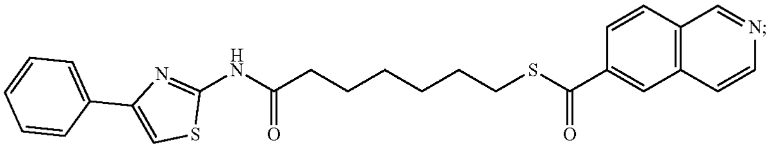
;
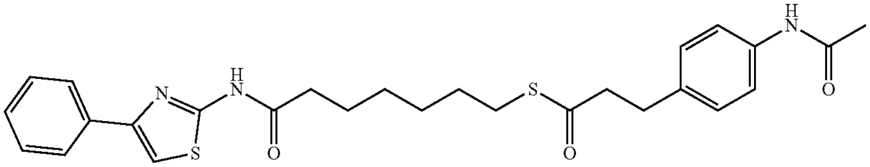
;
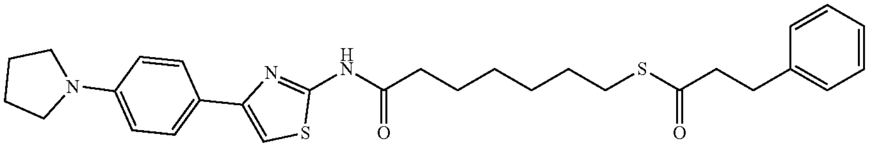
;
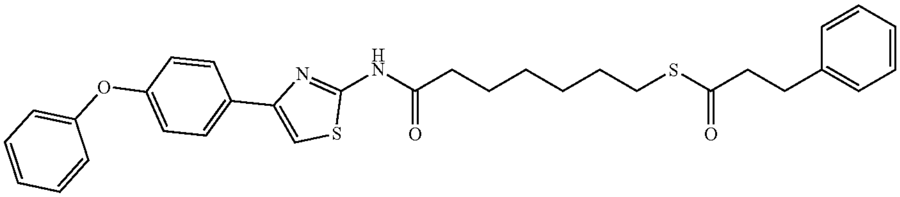
;
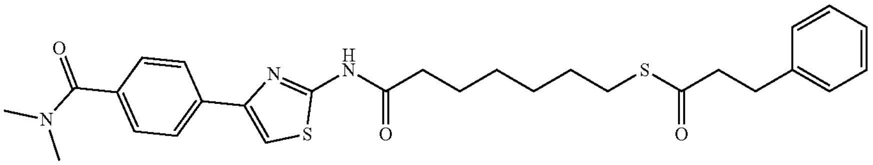
;
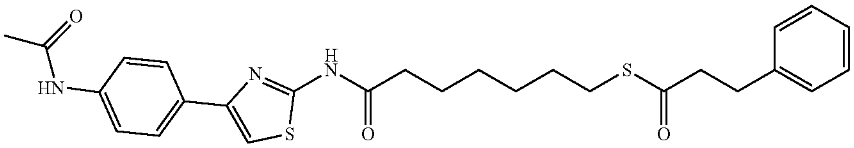
;
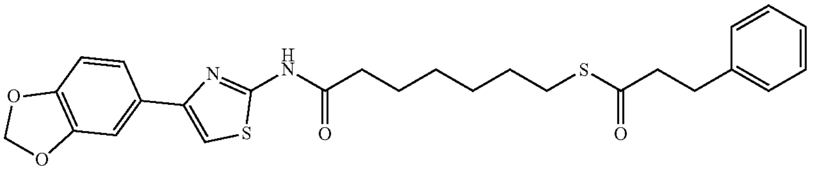
;

-continued
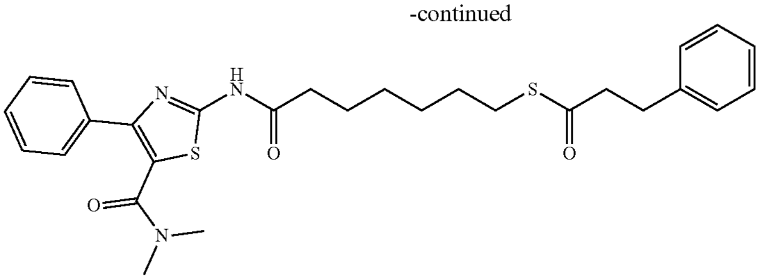
;
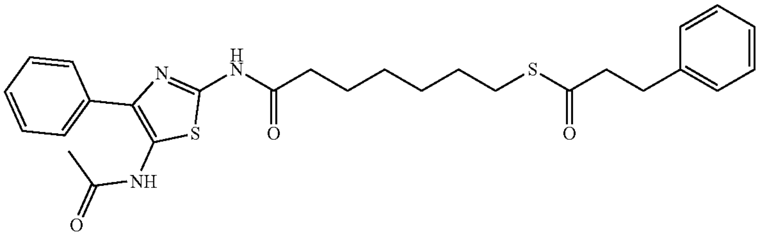
;
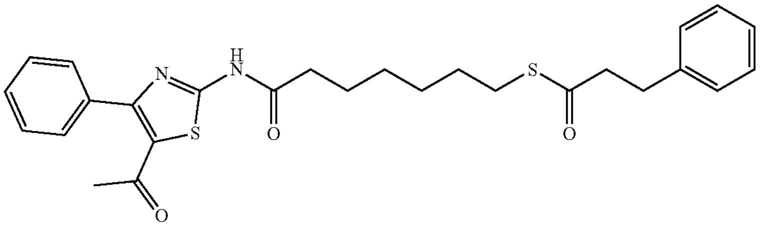
; and
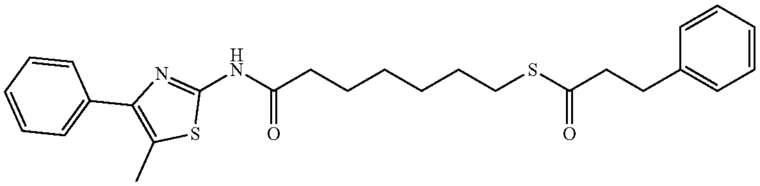
.
The present disclosure provides a method of treating Alzheimer's Disease or LOAD by administering to a subject in need thereof a therapeutically amount of a compound selected from the group consisting of:
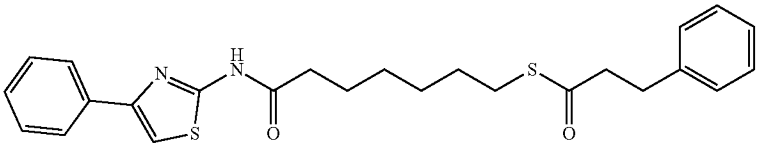
;
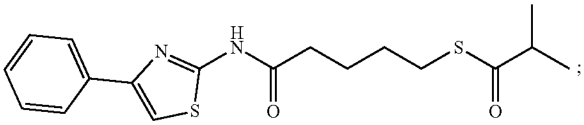
;
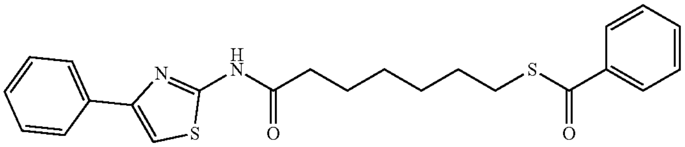
;
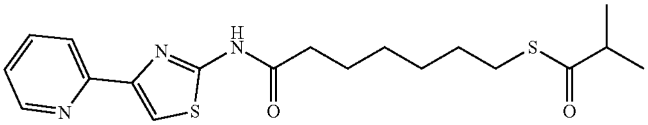
;
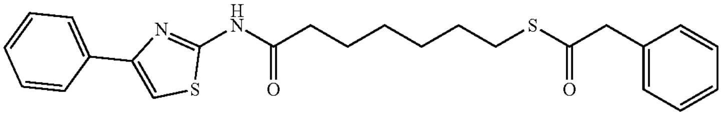
;

-continued
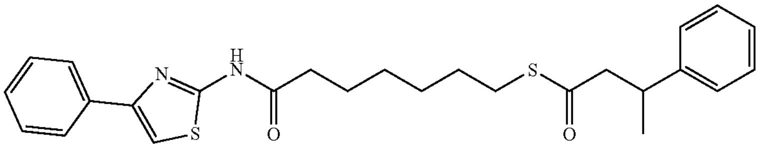
;
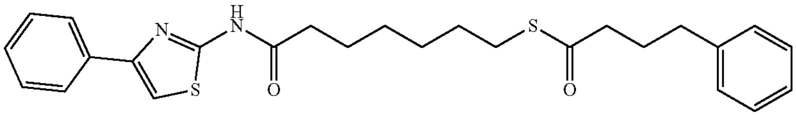
;
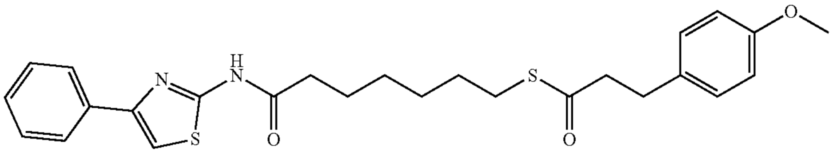
;
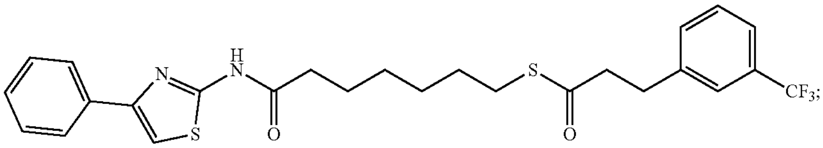
;
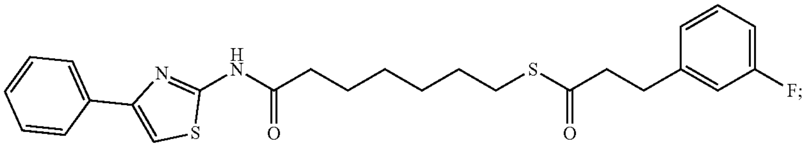
;
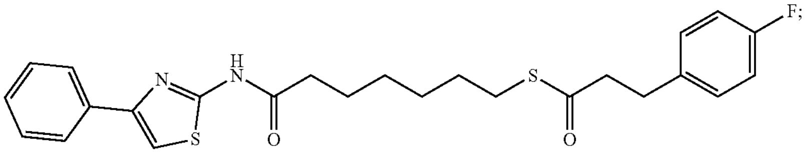
;
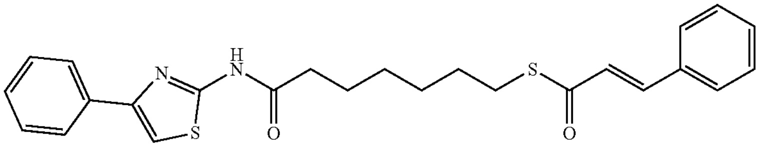
;
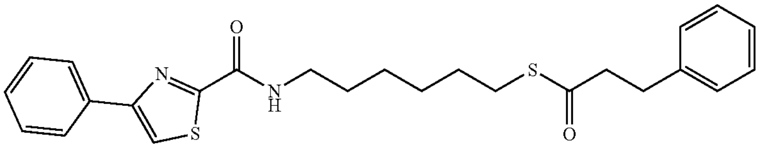
;
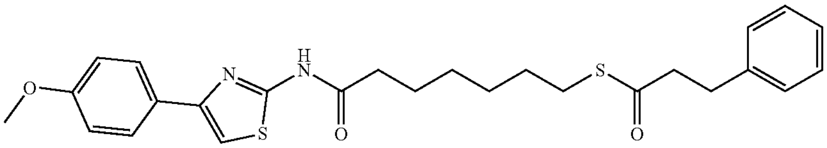
;
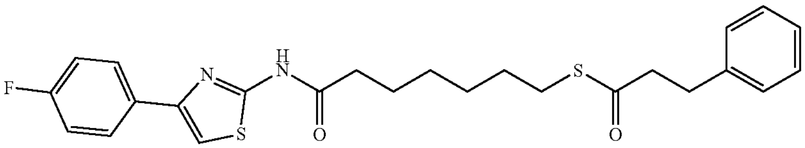
;
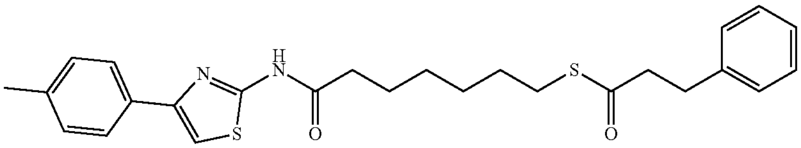
;

-continued

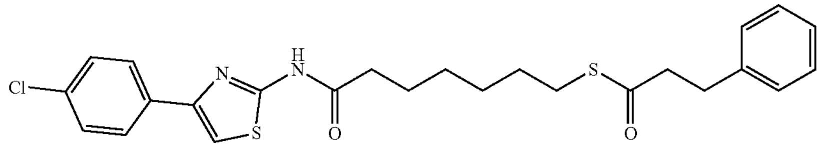
;

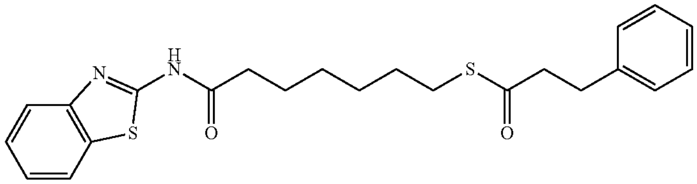
;

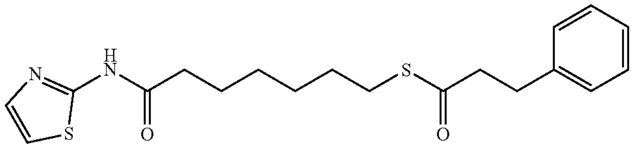
;

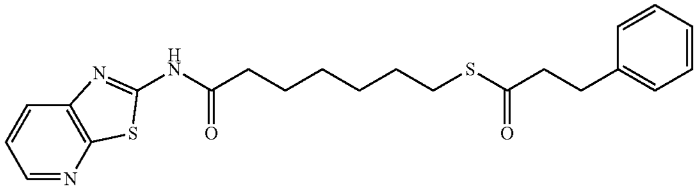
;

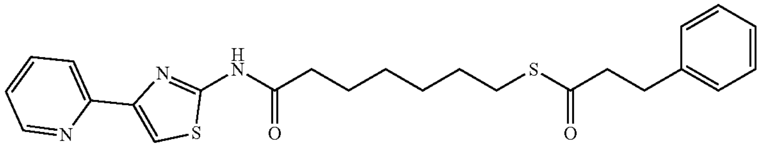
; and

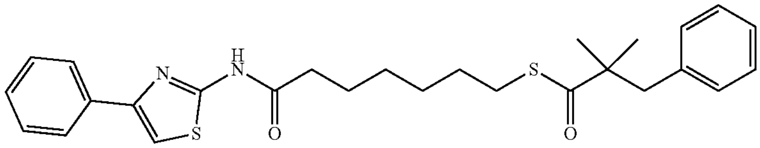
.

The present disclosure provides a method of treating Alzheimer's Disease or LOAD by administering to a subject in need thereof a therapeutically amount of the compound:

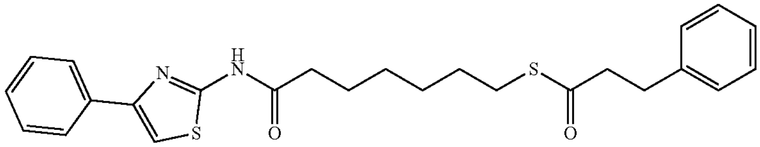
.

The present disclosure provides a method of treating Alzheimer's Disease or LOAD by administering to a subject in need thereof a therapeutically amount of a compound selected from the group consisting of:

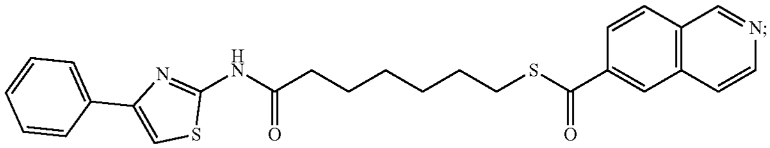
;

-continued
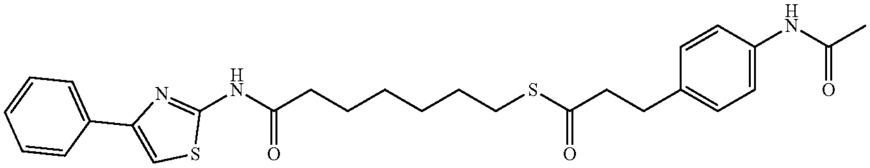
;
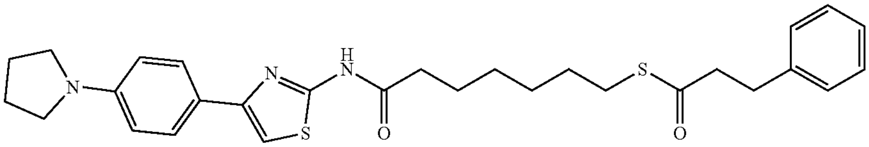
;
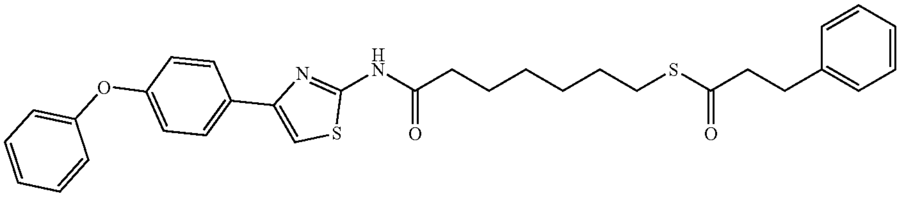
;
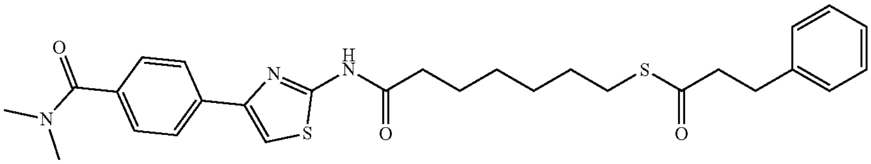
;
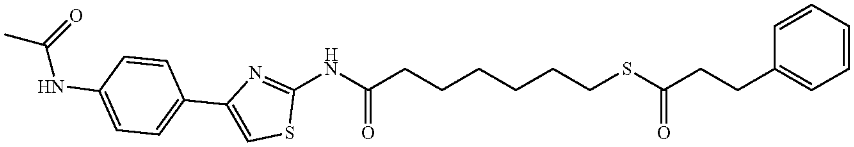
;
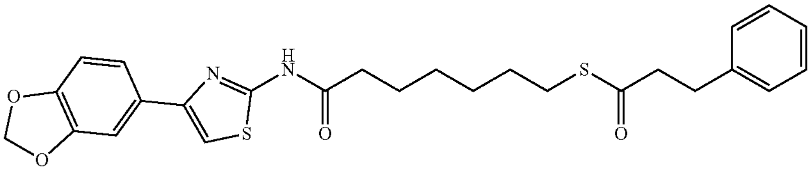
;
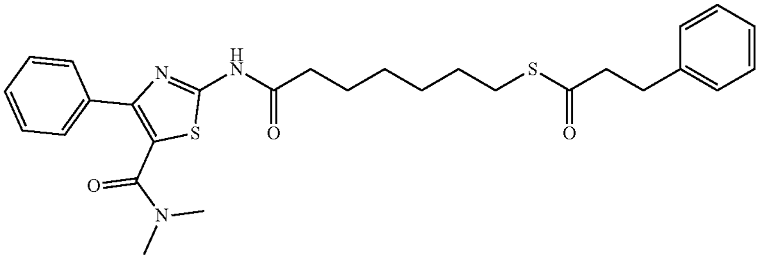
;
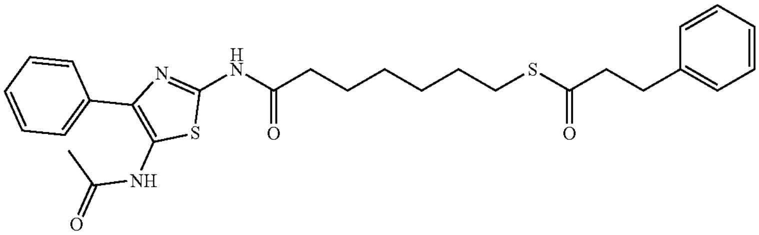
;
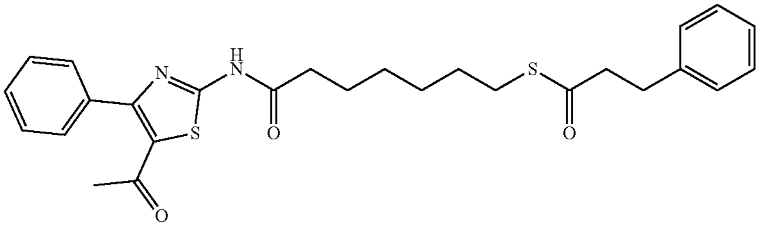
; and -continued

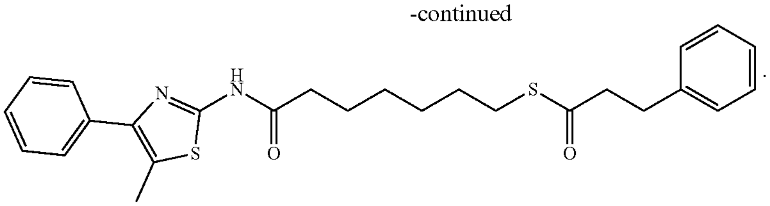

The present disclosure provides methods for treating disease by administering to a subject in need thereof a therapeutically effective amount of a compound selected from the group consisting of S-(7-oxo-7-(thiazol-2-ylamino) heptyl) 2-methylpropanethioate; S-(7-([1,1'-biphenyl]-4-ylamino)-7-oxoheptyl) 2-methylpropanethioate; S-(7-(methyl(4-phenylthiazol-2-yl)amino)-7-oxoheptyl) 2-methylpropanethioate; 7-acetamido-N-(4-phenylthiazol-2-yl)heptanamide; N-(4-phenylthiazol-2-yl)-7-propionamidoheptanamide; 7-isobutyramido-N-(4-phenylthiazol-2-yl) heptanamide; N-(7-oxo-7-((4-phenylthiazol-2-yl)amino) heptyl)cyclopropanecarboxamide; N-(7-oxo-7-((4-phenylthiazol-2-yl)amino)heptyl)cyclohexanecarboxamide; N-(7-oxo-7-((4-phenylthiazol-2-yl)amino)heptyl)benzamide; 7-oxo-7-((4-phenylthiazol-2-yl)amino)heptyl isobutyrate; 7-isobutyramido-N-(naphthalen-2-yl)heptanamide; 7-isobutyramido-N-(3-(trifluoromethyl)phenyl)heptanamide; N-(benzo[d]thiazol-2-yl)-7-isobutyramidoheptanamide; 7-isobutyramido-N-(quinolin-3-yl)heptanamide; 7-isobutyramido-N-(3-phenoxyphenyl)heptanamide; N-(3-(dimethylamino)phenyl)-7-isobutyramidoheptanamide; 9-isobutyramido-N-(4-phenylthiazol-2-yl)nonanamide; 3-isobutyramido-N-(4-phenylthiazol-2-yl)propenamide; $N^1$-isopropyl-$N^8$-(4-phenylthiazol-2-yl)octanediamide; $N^1$-isopropyl-$N^1$-methyl-$N^8$-(4-phenylthiazol-2-yl)octanediamide; 8-oxo-N-(4-phenylthiazol-2-yl)-8-(piperidin-1-yl) octanamide; 7-(isopropylamino)-N-(4-phenylthiazol-2-yl) heptanamide; 7-(isopropyl(methyl)amino)-N-(4-phenylthiazol-2-yl)heptanamide; S-(7-oxo-7-((4-phenylthiazol-2-yl)amino)heptyl) 3-phenylpropanethioate; S-(4-oxo-4-((4-phenylthiazol-2-yl)amino)butyl) 2-methylpropanethioate; S-(5-oxo-5-((4-phenylthiazol-2-yl)amino) pentyl) 2-methylpropanethioate; S-(6-oxo-6-((4-phenylthiazol-2-yl)amino)hexyl) 2-methylpropanethioate; S-(8-oxo-8-((4-phenylthiazol-2-yl)amino)octyl) 2-methylpropanethioate; S-(7-oxo-7-((4-phenylthiazol-2-yl) amino)heptyl) benzothioate; S-(7-oxo-7-((4-(pyridin-2-yl) thiazol-2-yl)amino)heptyl) 2-methylpropanethioate; 7-(methylthio)-N-(4-phenylthiazol-2-yl)heptanamide; S-(7-((1H-indol-6-yl)amino)-7-oxoheptyl) 2-methylpropanethioate; S-(7-((3-chlorophenyl)amino)-7-oxoheptyl) 2-methylpropanethioate; S-(7-(benzo[d]oxazol-2-ylamino)-7-oxoheptyl) 2-methylpropanethioate; S-(7-oxo-7-((4-phenylthiazol-2-yl)amino)heptyl) 2-phenylethanethioate; S-(7-oxo-7-((4-phenylthiazol-2-yl)amino)heptyl) 3-phenylbutanethioate; S-(7-oxo-7-((4-phenylthiazol-2-yl)amino) heptyl) 4-phenylbutanethioate; S-(7-oxo-7-((4-phenylthiazol-2-yl)amino)heptyl) 3-(4-methoxyphenyl) propanethioate; S-(7-oxo-7-((4-phenylthiazol-2-yl)amino) heptyl) 3-(3-(trifluoromethyl)phenyl)propanethioate; S-(7-oxo-7-((4-phenylthiazol-2-yl)amino)heptyl) 3-(3-fluorophenyl)propanethioate; S-(7-oxo-7-((4-phenylthiazol-2-yl)amino)heptyl) 3-(4-fluorophenyl)propanethioate; S-(7-oxo-7-((4-phenylthiazol-2-yl)amino)heptyl) (E)-3-phenylprop-2-enethioate; S-phenethyl 8-oxo-8-((4-phenylthiazol-2-yl)amino)octanethioate; S-(6-(4-phenylthiazole-2-carboxamido)hexyl) 3-phenylpropanethioate; N-(benzo[d]thiazol-2-yl)-7-(isopropyl(methyl)amino)heptanamide; 7-(isopropyl(methyl) amino)-N-(thiazol-2-yl)heptanamide; 7-(isopropyl(methyl) amino)-N-(thiazolo[5,4-b]pyridin-2-yl)heptanamide; 7-(isopropyl(methyl)amino)-N-(4-(pyridin-2-yl)thiazol-2-yl)heptanamide; S-(7-((4-(4-methoxyphenyl)thiazol-2-yl) amino)-7-oxoheptyl) 3-phenylpropanethioate; S-(7-((4-(4-fluorophenyl)thiazol-2-yl)amino)-7-oxoheptyl) 3-phenylpropanethioate; S-(7-oxo-7-((4-(p-tolyl)thiazol-2-yl)amino)heptyl) 3-phenylpropanethioate; S-(7-((4-(4-chlorophenyl)thiazol-2-yl)amino)-7-oxoheptyl) 3-phenylpropanethioate; S-(7-(benzo[d]thiazol-2-ylamino)-7-oxoheptyl) 3-phenylpropanethioate; S-(7-oxo-7-(thiazol-2-ylamino) heptyl) 3-phenylpropanethioate; S-(7-oxo-7-(thiazolo[5,4-b]pyridin-2-ylamino)heptyl) 3-phenylpropanethioate; S-(7-oxo-7-((4-(pyridin-2-yl)thiazol-2-yl)amino)heptyl) 3-phenylpropanethioate; S-(7-oxo-7-((4-phenylthiazol-2-yl) amino)heptyl) 2,2-dimethyl-3-phenylpropanethioate; S-(7-oxo-7-((4-phenylthiazol-2-yl)amino)heptyl) isoquinoline-6-carbothioate; S-(7-oxo-7-((4-phenylthiazol-2-yl)amino) heptyl) 3-(4-acetamidophenyl)propanethioate; S-(7-oxo-7-((4-(4-(pyrrolidin-1-yl)phenyl)thiazol-2-yl)amino)heptyl) 3-phenylpropanethioate; S-(7-oxo-7-((4-(4-phenoxyphenyl) thiazol-2-yl)amino)heptyl) 3-phenylpropanethioate; S-(7-((4-(4-(dimethylcarbamoyl)phenyl)thiazol-2-yl)amino)-7-oxoheptyl) 3-phenylpropanethioate; S-(7-((4-(4-acetamidophenyl)thiazol-2-yl)amino)-7-oxoheptyl) 3-phenylpropanethioate; S-(7-((4-(benzo[d][1,3]dioxol-5-yl)thiazol-2-yl)amino)-7-oxoheptyl) 3-phenylpropanethioate; S-(7-((5-(dimethylcarbamoyl)-4-phenylthiazol-2-yl) amino)-7-oxoheptyl) 3-phenylpropanethioate; S-(7-((5-acetamido-4-phenylthiazol-2-yl)amino)-7-oxoheptyl) 3-phenylpropanethioate; S-(7-((5-acetyl-4-phenylthiazol-2-yl)amino)-7-oxoheptyl) 3-phenylpropanethioate; and S-(7-((5-methyl-4-phenylthiazol-2-yl)amino)-7-oxoheptyl) 3-phenylpropanethioate.

The present disclosure provides a method of treating LOAD by administering to a subject in need thereof a therapeutically effective amount of a compound selected from the group consisting of S-(7-oxo-7-(thiazol-2-ylamino) heptyl) 2-methylpropanethioate; S-(7-([1,1'-biphenyl]-4-ylamino)-7-oxoheptyl) 2-methylpropanethioate; S-(7-(methyl(4-phenylthiazol-2-yl)amino)-7-oxoheptyl) 2-methylpropanethioate; 7-acetamido-N-(4-phenylthiazol-2-yl)heptanamide; N-(4-phenylthiazol-2-yl)-7-propionamidoheptanamide; 7-isobutyramido-N-(4-phenylthiazol-2-yl) heptanamide; N-(7-oxo-7-((4-phenylthiazol-2-yl)amino) heptyl)cyclopropanecarboxamide; N-(7-oxo-7-((4-phenylthiazol-2-yl)amino)heptyl)cyclohexanecarboxamide; N-(7-oxo-7-((4-phenylthiazol-2-yl)amino)heptyl)benzamide; 7-oxo-7-((4-phenylthiazol-2-yl)amino)heptyl isobutyrate; 7-isobutyramido-N-(naphthalen-2-yl)heptanamide; 7-isobutyramido-N-(3-(trifluoromethyl)phenyl)heptanamide; N-(benzo[d]thiazol-2-yl)-7-isobutyramidoheptanamide; 7-isobutyramido-N-(quinolin-3-yl)heptanamide;

7-isobutyramido-N-(3-phenoxyphenyl)heptanamide; N-(3-(dimethylamino)phenyl)-7-isobutyramidoheptanamide; 9-isobutyramido-N-(4-phenylthiazol-2-yl)nonanamide; 3-isobutyramido-N-(4-phenylthiazol-2-yl)propenamide; $N^1$-isopropyl-$N^8$-(4-phenylthiazol-2-yl)octanediamide; $N^1$-isopropyl-$N^1$-methyl-$N^8$-(4-phenylthiazol-2-yl)octanediamide; 8-oxo-N-(4-phenylthiazol-2-yl)-8-(piperidin-1-yl) octanamide; 7-(isopropylamino)-N-(4-phenylthiazol-2-yl) heptanamide; 7-(isopropyl(methyl)amino)-N-(4-phenylthiazol-2-yl)heptanamide; S-(7-oxo-7-((4-phenylthiazol-2-yl)amino)heptyl) 3-phenylpropanethioate; S-(4-oxo-4-((4-phenylthiazol-2-yl)amino)butyl) 2-methylpropanethioate; S-(5-oxo-5-((4-phenylthiazol-2-yl)amino) pentyl) 2-methylpropanethioate; S-(6-oxo-6-((4-phenylthiazol-2-yl)amino)hexyl) 2-methylpropanethioate; S-(8-oxo-8-((4-phenylthiazol-2-yl)amino)octyl) 2-methylpropanethioate; S-(7-oxo-7-((4-phenylthiazol-2-yl) amino)heptyl) benzothioate; S-(7-oxo-7-((4-(pyridin-2-yl) thiazol-2-yl)amino)heptyl) 2-methylpropanethioate; 7-(methylthio)-N-(4-phenylthiazol-2-yl)heptanamide; S-(7-((1H-indol-6-yl)amino)-7-oxoheptyl) 2-methylpropanethioate; S-(7-((3-chlorophenyl)amino)-7-oxoheptyl) 2-methylpropanethioate; S-(7-(benzo[d]oxazol-2-ylamino)-7-oxoheptyl) 2-methylpropanethioate; S-(7-oxo-7-((4-phenylthiazol-2-yl)amino)heptyl) 2-phenylethanethioate; S-(7-oxo-7-((4-phenylthiazol-2-yl)amino)heptyl) 3-phenylbutanethioate; S-(7-oxo-7-((4-phenylthiazol-2-yl)amino) heptyl) 4-phenylbutanethioate; S-(7-oxo-7-((4-phenylthiazol-2-yl)amino)heptyl) 3-(4-methoxyphenyl) propanethioate; S-(7-oxo-7-((4-phenylthiazol-2-yl)amino) heptyl) 3-(3-(trifluoromethyl)phenyl)propanethioate; S-(7-oxo-7-((4-phenylthiazol-2-yl)amino)heptyl) 3-(3-fluorophenyl)propanethioate; S-(7-oxo-7-((4-phenylthiazol-2-yl)amino)heptyl) 3-(4-fluorophenyl)propanethioate; S-(7-oxo-7-((4-phenylthiazol-2-yl)amino)heptyl) (E)-3-phenylprop-2-enethioate; S-phenethyl 8-oxo-8-((4-phenylthiazol-2-yl)amino)octanethioate; S-(6-(4-phenylthiazole-2-carboxamido)hexyl) 3-phenylpropanethioate; N-(benzo[d]thiazol-2-yl)-7-(isopropyl(methyl)amino)heptanamide; 7-(isopropyl(methyl) amino)-N-(thiazol-2-yl)heptanamide; 7-(isopropyl(methyl) amino)-N-(thiazolo[5,4-b]pyridin-2-yl)heptanamide; 7-(isopropyl(methyl)amino)-N-(4-(pyridin-2-yl)thiazol-2-yl)heptanamide; S-(7-((4-(4-methoxyphenyl)thiazol-2-yl) amino)-7-oxoheptyl) 3-phenylpropanethioate; S-(7-((4-(4-fluorophenyl)thiazol-2-yl)amino)-7-oxoheptyl) 3-phenylpropanethioate; S-(7-oxo-7-((4-(p-tolyl)thiazol-2-yl)amino)heptyl) 3-phenylpropanethioate; S-(7-((4-(4-chlorophenyl)thiazol-2-yl)amino)-7-oxoheptyl) 3-phenylpropanethioate; S-(7-(benzo[d]thiazol-2-ylamino)-7-oxoheptyl) 3-phenylpropanethioate; S-(7-oxo-7-(thiazol-2-ylamino) heptyl) 3-phenylpropanethioate; S-(7-oxo-7-(thiazolo[5,4-b]pyridin-2-ylamino)heptyl) 3-phenylpropanethioate; S-(7-oxo-7-((4-(pyridin-2-yl)thiazol-2-yl)amino)heptyl) 3-phenylpropanethioate; S-(7-oxo-7-((4-phenylthiazol-2-yl) amino)heptyl) 2,2-dimethyl-3-phenylpropanethioate; S-(7-oxo-7-((4-phenylthiazol-2-yl)amino)heptyl) isoquinoline-6-carbothioate; S-(7-oxo-7-((4-phenylthiazol-2-yl)amino) heptyl) 3-(4-acetamidophenyl)propanethioate; S-(7-oxo-7-((4-(4-(pyrrolidin-1-yl)phenyl)thiazol-2-yl)amino)heptyl) 3-phenylpropanethioate; S-(7-oxo-7-((4-(4-phenoxyphenyl) thiazol-2-yl)amino)heptyl) 3-phenylpropanethioate; S-(7-((4-(4-(dimethylcarbamoyl)phenyl)thiazol-2-yl)amino)-7-oxoheptyl) 3-phenylpropanethioate; S-(7-((4-(4-acetamidophenyl)thiazol-2-yl)amino)-7-oxoheptyl) 3-phenylpropanethioate; S-(7-((4-(benzo[d][1,3]dioxol-5-yl)thiazol-2-yl)amino)-7-oxoheptyl) 3-phenylpropanethioate; S-(7-((5-(dimethylcarbamoyl)-4-phenylthiazol-2-yl) amino)-7-oxoheptyl) 3-phenylpropanethioate; S-(7-((5-acetamido-4-phenylthiazol-2-yl)amino)-7-oxoheptyl) 3-phenylpropanethioate; S-(7-((5-acetyl-4-phenylthiazol-2-yl)amino)-7-oxoheptyl) 3-phenylpropanethioate; and S-(7-((5-methyl-4-phenylthiazol-2-yl)amino)-7-oxoheptyl) 3-phenylpropanethioate.

The present disclosure provides a method of treating Alzheimer's Disease by administering to a subject in need thereof a therapeutically effective amount of a compound selected from the group consisting of: S-(7-oxo-7-(thiazol-2-ylamino)heptyl) 2-methylpropanethioate; S-(7-([1,1'-biphenyl]-4-ylamino)-7-oxoheptyl) 2-methylpropanethioate; S-(7-(methyl(4-phenylthiazol-2-yl)amino)-7-oxoheptyl) 2-methylpropanethioate; 7-acetamido-N-(4-phenylthiazol-2-yl)heptanamide; N-(4-phenylthiazol-2-yl)-7-propionamidoheptanamide; 7-isobutyramido-N-(4-phenylthiazol-2-yl) heptanamide; N-(7-oxo-7-((4-phenylthiazol-2-yl)amino) heptyl)cyclopropanecarboxamide; N-(7-oxo-7-((4-phenylthiazol-2-yl)amino)heptyl)cyclohexanecarboxamide; N-(7-oxo-7-((4-phenylthiazol-2-yl)amino)heptyl)benzamide; 7-oxo-7-((4-phenylthiazol-2-yl)amino)heptyl isobutyrate; 7-isobutyramido-N-(naphthalen-2-yl)heptanamide; 7-isobutyramido-N-(3-(trifluoromethyl)phenyl)heptanamide; N-(benzo[d]thiazol-2-yl)-7-isobutyramidoheptanamide; 7-isobutyramido-N-(quinolin-3-yl)heptanamide; 7-isobutyramido-N-(3-phenoxyphenyl)heptanamide; N-(3-(dimethylamino)phenyl)-7-isobutyramidoheptanamide; 9-isobutyramido-N-(4-phenylthiazol-2-yl)nonanamide; 3-isobutyramido-N-(4-phenylthiazol-2-yl)propenamide; $N^1$-isopropyl-$N^8$-(4-phenylthiazol-2-yl)octanediamide; N-isopropyl-$N^1$-methyl-$N^8$-(4-phenylthiazol-2-yl)octanediamide; 8-oxo-N-(4-phenylthiazol-2-yl)-8-(piperidin-1-yl) octanamide; 7-(isopropylamino)-N-(4-phenylthiazol-2-yl) heptanamide; 7-(isopropyl(methyl)amino)-N-(4-phenylthiazol-2-yl)heptanamide; S-(7-oxo-7-((4-phenylthiazol-2-yl)amino)heptyl) 3-phenylpropanethioate; S-(4-oxo-4-((4-phenylthiazol-2-yl)amino)butyl) 2-methylpropanethioate; S-(5-oxo-5-((4-phenylthiazol-2-yl)amino) pentyl) 2-methylpropanethioate; S-(6-oxo-6-((4-phenylthiazol-2-yl)amino)hexyl) 2-methylpropanethioate; S-(8-oxo-8-((4-phenylthiazol-2-yl)amino)octyl) 2-methylpropanethioate; S-(7-oxo-7-((4-phenylthiazol-2-yl) amino)heptyl) benzothioate; S-(7-oxo-7-((4-(pyridin-2-yl) thiazol-2-yl)amino)heptyl) 2-methylpropanethioate; 7-(methylthio)-N-(4-phenylthiazol-2-yl)heptanamide; S-(7-((1H-indol-6-yl)amino)-7-oxoheptyl) 2-methylpropanethioate; S-(7-((3-chlorophenyl)amino)-7-oxoheptyl) 2-methylpropanethioate; S-(7-(benzo[d]oxazol-2-ylamino)-7-oxoheptyl) 2-methylpropanethioate; S-(7-oxo-7-((4-phenylthiazol-2-yl)amino)heptyl) 2-phenylethanethioate; S-(7-oxo-7-((4-phenylthiazol-2-yl)amino)heptyl) 3-phenylbutanethioate; S-(7-oxo-7-((4-phenylthiazol-2-yl)amino) heptyl) 4-phenylbutanethioate; S-(7-oxo-7-((4-phenylthiazol-2-yl)amino)heptyl) 3-(4-methoxyphenyl) propanethioate; S-(7-oxo-7-((4-phenylthiazol-2-yl)amino) heptyl) 3-(3-(trifluoromethyl)phenyl)propanethioate; S-(7-oxo-7-((4-phenylthiazol-2-yl)amino)heptyl) 3-(3-fluorophenyl)propanethioate; S-(7-oxo-7-((4-phenylthiazol-2-yl)amino)heptyl) 3-(4-fluorophenyl)propanethioate; S-(7-oxo-7-((4-phenylthiazol-2-yl)amino)heptyl) (E)-3-phenylprop-2-enethioate; S-phenethyl 8-oxo-8-((4-phenylthiazol-2-yl)amino)octanethioate; S-(6-(4-phenylthiazole-2-carboxamido)hexyl) 3-phenylpropanethioate; N-(benzo[d]thiazol-2-yl)-7-(isopropyl(methyl)amino)heptanamide; 7-(isopropyl(methyl) amino)-N-(thiazol-2-yl)heptanamide; 7-(isopropyl(methyl)

amino)-N-(thiazolo[5,4-b]pyridin-2-yl)heptanamide; 7-(isopropyl(methyl)amino)-N-(4-(pyridin-2-yl)thiazol-2-yl)heptanamide; S-(7-((4-(4-methoxyphenyl)thiazol-2-yl)amino)-7-oxoheptyl) 3-phenylpropanethioate; S-(7-((4-(4-fluorophenyl)thiazol-2-yl)amino)-7-oxoheptyl) 3-phenylpropanethioate; S-(7-oxo-7-((4-(p-tolyl)thiazol-2-yl)amino)heptyl) 3-phenylpropanethioate; S-(7-((4-(4-chlorophenyl)thiazol-2-yl)amino)-7-oxoheptyl) 3-phenylpropanethioate; S-(7-(benzo[d]thiazol-2-ylamino)-7-oxoheptyl) 3-phenylpropanethioate; S-(7-oxo-7-(thiazol-2-ylamino)heptyl) 3-phenylpropanethioate; S-(7-oxo-7-(thiazolo[5,4-b]pyridin-2-ylamino)heptyl) 3-phenylpropanethioate; S-(7-oxo-7-((4-(pyridin-2-yl)thiazol-2-yl)amino)heptyl) 3-phenylpropanethioate; S-(7-oxo-7-((4-phenylthiazol-2-yl)amino)heptyl) 2,2-dimethyl-3-phenylpropanethioate; S-(7-oxo-7-((4-phenylthiazol-2-yl)amino)heptyl) isoquinoline-6-carbothioate; S-(7-oxo-7-((4-phenylthiazol-2-yl)amino)heptyl) 3-(4-acetamidophenyl)propanethioate; S-(7-oxo-7-((4-(4-(pyrrolidin-1-yl)phenyl)thiazol-2-yl)amino)heptyl) 3-phenylpropanethioate; S-(7-oxo-7-((4-(4-phenoxyphenyl)thiazol-2-yl)amino)heptyl) 3-phenylpropanethioate; S-(7-((4-(4-(dimethylcarbamoyl)phenyl)thiazol-2-yl)amino)-7-oxoheptyl) 3-phenylpropanethioate; S-(7-((4-(4-acetamidophenyl)thiazol-2-yl)amino)-7-oxoheptyl) 3-phenylpropanethioate; S-(7-((4-(benzo[d][1,3]dioxol-5-yl)thiazol-2-yl)amino)-7-oxoheptyl) 3-phenylpropanethioate; S-(7-((5-(dimethylcarbamoyl)-4-phenylthiazol-2-yl)amino)-7-oxoheptyl) 3-phenylpropanethioate; S-(7-((5-acetamido-4-phenylthiazol-2-yl)amino)-7-oxoheptyl) 3-phenylpropanethioate; S-(7-((5-acetyl-4-phenylthiazol-2-yl)amino)-7-oxoheptyl) 3-phenylpropanethioate; and S-(7-((5-methyl-4-phenylthiazol-2-yl)amino)-7-oxoheptyl) 3-phenylpropanethioate.

The present disclosure provides a method of treating Alzheimer's Disease by administering to a subject in need thereof a therapeutically effective amount of: S-(7-oxo-7-((4-phenylthiazol-2-yl)amino)heptyl) 3-phenylpropanethioate.

In one refinement, compounds of the present disclosure comprise a moiety of FORMULA I:

FORMULA I

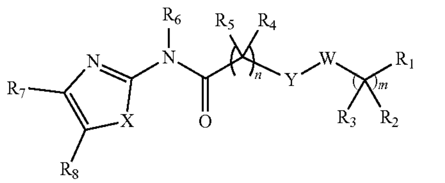

or a pharmaceutically acceptable salt thereof, wherein:

X is selected from S, O, NH or $CH_2$;

Y and W are independently selected from S, O, NH, CO, SO2, SO or $CH_2$;

$R_1$, $R_7$, and $R_8$ are independently selected from hydrogen, halogen, oxo, CN, $NO_2$, $OR_9$, $SR_9$, $NR_9R_{10}$, $C(O)R_9$, $C(O)OR_9$, $C(O)NR_9R_{10}$, $S(O)R_9$, $S(O)_2R_{10}$, $S(O)_2NR_9R_{10}$, $NR_{11}C(O)OR_9$, $NR_{11}C(O)R_9$, $NR_{11}C(O)NR_9R_{10}$, $NR_{11}S(O)R_9$, $NR_{11}S(O)_2R_9$, $NR_{11}S(O)_2NR_9R_{10}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R_9$, $R_{10}$, and $R_{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R_9$ and $R_{10}$, $R_9$ and $R_{11}$, $R_{10}$ and $R_{11}$ together with the atom to which they are connected form an optionally substituted 3-20 membered cycloalkyl or heterocyclyl ring;

$R_2$, $R_3$, $R_4$ and $R_5$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

$R_6$ is selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; and m, n, are independently selected from 1-15.

In one refinement, compounds of the present disclosure comprise a moiety of FORMULA I is FORMULA I (A):

FORMULA I (A)

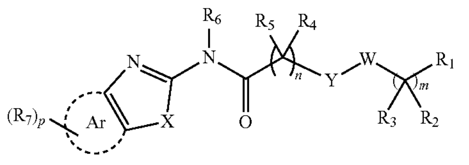

or a pharmaceutically acceptable salt thereof, wherein:

the definitions of X, Y, W, $R_1$, $R_2$, $R_3$, $R_4$, $R_5$, $R_6$, and $R_7$ are the same as for FORMULA I;

Ar is a fused, optionally substituted with $R_7$, 4-8 membered heterocyclyl, optionally substituted with $R_7$ aryl, and optionally substituted with $R_7$ heteroaryl;

m, n, are independently selected from 1-15;

p is selected from 0-5.

In one refinement, compounds of the present disclosure comprise a moiety of FORMULA I is FORMULA I (B):

FORMULA I (B)

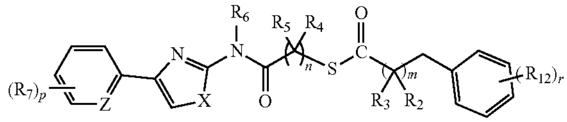

or a pharmaceutically acceptable salt thereof, wherein:

the definitions of X, $R_1$, $R_2$, $R_3$, $R_4$, $R_5$, $R_6$, and $R_7$ are the same as for FORMULA I;

$R_{12}$ is selected from hydrogen, halogen, oxo, CN, $NO_2$, $OR_{13}$, $SR_{13}$, $NR_{13}R_{14}$, $C(O)R_{13}$, $C(O)OR_{13}$, $C(O)NR_{13}R_{14}$, $S(O)R_{13}$, $S(O)_2R_{14}$, $S(O)_2NR_{13}R_{14}$, $NR_{15}C(O)OR_{13}$, $NR_{15}C(O)R_{13}$, $NR_{15}C(O)NR_{13}R_{14}$, $NR_{15}S(O)R_{13}$, $NR_{15}S(O)_2R_{13}$, $NR_{15}S(O)_2NR_{13}R_{14}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R_{13}$, $R_{14}$, and $R_{15}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R_{13}$ and $R_{14}$, $R_{13}$ and $R_{15}$, $R_{14}$ and $R_{15}$ together with the atom to which they are connected form an optionally substituted 3-20 membered cycloalkyl or heterocyclyl ring;

m, n are independently selected from 1-15; and p, r are independently selected from 0-5.

In one refinement, compounds of the present disclosure comprise a moiety of FORMULA II

FORMULA II

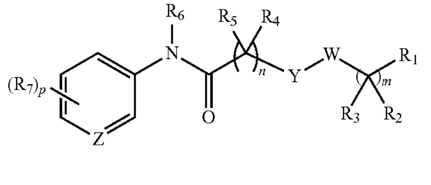

the definitions of X, Y, W, $R_1$, $R_2$, $R_3$, $R_4$, $R_5$, $R_6$, and $R_7$ are the same as for FORMULA 1;

Z is selected from N or CH;

m, n, are independently selected from 1-15;

p is selected from 0-5;

and pharmaceutically acceptable salts thereof.

In some aspects, the compound is a compound selected from those synthesized in the examples below, including, but not limited to: LQ081-166, LQ108-17, LQ108-18, LQ108-46, LQ108-48, LQ108-53, or analogs thereof.

In some aspects of the disclosed methods, the compounds can be administered by any of several routes of administration including, e.g., orally, parenterally, intradermally, subcutaneously, topically, and/or rectally. Any of the above-described methods can further include treating the subject with one or more additional therapeutic regimens for treatment.

Definitions

Unless defined otherwise, all technical and scientific terms used herein have the meaning commonly understood by a person skilled in the art to which this disclosure belongs. The meaning and scope of the terms should be clear, however, in the event of any latent ambiguity, definitions provided herein take precedent over any dictionary or extrinsic definition.

As used herein, the following terms have the meanings ascribed to them below, unless specified otherwise. The terminology used herein is for the purpose of describing particular embodiments only and is not intended to be limiting of the disclosure. As used herein, the singular forms "a", "an" and "the" are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the terms "comprising" and "including" are used in their open, non-limiting sense.

As used herein, the term "alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

As used herein, the term "Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a $—CH_2CH{=}CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+2) π-electron system in accordance with the Hückel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a $—C_6H_5$ group.

As used herein, the term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

As used herein, the term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a hetercyclyl group comprises 3 to 10 ring atoms (3-10 membered heterocyclyl). In certain embodiments, a hetercyclyl group comprises 3 to 8 ring atoms (3-8 membered heterocyclyl). In certain embodiments, a hetercyclyl group comprises 4 to 8 ring atoms (4-8 membered heterocyclyl). In certain embodiments, a hetercyclyl group comprises 3 to 6 ring atoms (3-6 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

As used herein, the term "cycloalkyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms ($C_3$-$C_8$ cycloalkyl). In certain embodiments, a cycloalkyl comprises 3 to 6 carbon ring atoms ($C_3$-$C_6$ cycloalkyl). Examples of such groups include, but are not limited to, cyclopropyl, cyclobutyl, cyclopentyl, cyclopentenyl, cyclohexyl, cycloheptyl, adamantyl, and the like.

As used herein, the term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term "cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —$SO_2$alkyl, as defined herein.

An "amino" group refers to an optionally substituted —$NH_2$.

An "aminoalkyl" group refers to an -alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —$SO_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —$NO_2$ group.

An "oxo" group refers to the ═O substituent.

A "trihalomethyl" group refers to a methyl substituted with three halogen atoms.

As used herein, the term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2$H, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein, the term "pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

As used herein, the term "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

As used herein, the term "pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, the term LQ081-166 refers to a compound having the name S-(7-oxo-7-((4-phenylthiazol-2-yl)amino) heptyl) 3-phenylpropanethioate and the structure:

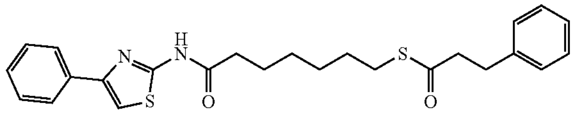

As used herein, the term "effective amount" or "therapeutically effective amount" refers to a quantity of a drug identified in this disclosure that is sufficient to achieve a desired effect or a desired therapeutic effect. In the context of therapeutic applications, the amount of any such disclosed drug that is administered to the subject can depend on the type and severity of the disease or symptom and on the characteristics of the individual, such as general health, age, sex, body weight and tolerance to drugs. The skilled artisan will be able to determine appropriate dosages depending on these and other factors.

As used herein, the term "treatment" includes any treatment of a condition or disease in a subject, or particularly a human, and may include: (i) preventing the disease or condition from occurring in the subject that may be predisposed to the disease but has not yet been diagnosed as having it; (ii) inhibiting the disease or condition, i.e., arresting or slowing down its progression; relieving the disease or condition, i.e., causing regression of the condition; or (iii) ameliorating or relieving the conditions caused by the disease, i.e., symptoms of the disease. "Treatment," as used herein, can be used in combination with other standard therapies or alone.

As used herein, the terms Alzheimer's Disease ("AD") and Late Onset Alzheimer's Disease ("LOAD") each have the meaning that is commonly understood by a person skilled in the art.

Pharmaceutical Compositions

In some aspects, the compositions and methods described herein include the manufacture and use of pharmaceutical compositions and medicaments that include one or more compounds as disclosed herein. Also included are the pharmaceutical compositions themselves.

In some aspects, the compositions disclosed herein can include other compounds, drugs, or agents used for the treatment. For example, in some instances, pharmaceutical compositions disclosed herein can be combined with one or more (e.g., one, two, three, four, five, or less than ten) compounds.

In some aspects, the pH of the compositions disclosed herein can be adjusted with pharmaceutically acceptable acids, bases, or buffers to enhance the stability of the compounds or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the compounds disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, $5^{th}$ Edition, Vol. 1: Principles and Practice, which is incorporated herein by reference to the extent of teaching such derivatives.

The compounds disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivative thereof.

In particular, pharmaceutically acceptable salts of the compounds disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium salts. The invention also envisions the quaternization of any basic nitrogen-containing groups of the compounds disclosed herein. Water or oil-soluble or dispersible products can be obtained by such quaternization.

In some aspects, the pharmaceutical compositions disclosed herein can include an effective amount of one or more compounds. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome. In some aspects, pharmaceutical compositions can further include one or more additional compounds, drugs, or agents used for the treatment in amounts effective for causing an intended effect or physiological outcome.

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein and one or more additional compounds (e.g., one or more additional compounds, drugs, or agents used for the treatment of Alzheimer's Disease (AD) or any other age related condition or disease, including conditions or diseases known to be associated with or caused by AD), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising a compound, including pharmaceutical compositions (indicated below as 'X') disclosed herein in the following methods Substance X for use as a medicament in the treatment of one or more diseases or conditions disclosed herein. Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of AD or age related diseases.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering. In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any way that one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention. In some aspects, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention.

As used herein, the term "preventing a disease" in a subject means for example, to stop the development of one or more symptoms of a disease in a subject before they occur or are detectable, e.g., by the patient or the patient's doctor. Preferably, the disease does not develop at all, i.e., no symptoms of the disease are detectable. However, it can also mean delaying or slowing of the development of one or more symptoms of the disease. Alternatively, or in addition, it can mean decreasing the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms

EXAMPLES

The following examples are put forth to provide those of ordinary skill in the art with a complete disclosure and description of how to make and use the compositions, and assay, screening, and therapeutic methods of the invention, and are not intended to limit the scope of what the inventors regard as their invention.

Example 1

Network Modeling Platform

The inventors generated matched whole-genome sequencing (WGS) and RNA sequencing (RNA-seq) data from a cohort of 364 brains spanning the full spectrum of LOAD-related cognitive and neuropathological disease severities represented in the Mount Sinai Brain Bank (MSBB). Specifically, RNA-seq was performed in 4 brain regions: Brodmann area 10 frontal pole (BM10-FP), Brodmann area 22 superior temporal gyrus (BM22-STG), Brodmann area 36 parahippocampal gyrus (BM36-PHG), and Brodmann area 44 inferior frontal gyrus (BM44-IFG) (FIG. 1). To integrate omics and disease trait data, a transformative network modeling platform (FIG. 1) was employed that includes signature calling, co-expression network (Zhang and Horvath, 2005), causal network (Schadt et al., 2005a; Zhu et al., 2007a), drug repositioning (Zhou et al., 2018a), and in vitro and in vivo functional validations. A unique feature of the platform is the use of gene regulatory networks as a target-rich environment for integrating multiple levels of data to identify key pathways and driver genes whose perturbation responses can recapitulate predicted network structures through systems like human induced pluripotent stem cell (hiPSC)-derived neurons and fly models of Aβ toxicity (FIG. 1).

BM36-PHG Shows the Most Expression Change in LOAD

After data preprocessing, differentially expressed genes (DEGs) were called with respect to 4 LOAD related semi-quantitative traits. The inventors discovered that BM36-PHG had the largest number of DEGs, followed by BM22-STG, BM10-FP, and BM44-IFG. The inventors also found that down-regulated genes were enriched in the neuronal system, transmission across chemical synapses, and neuro-active ligand receptor interactions. The DEG signatures identified by the inventors are preserved (adjusted Fisher's exact test (FET) P-value up to 1.0E-100) in 10 publicly available AD transcriptomic studies. Moreover, the down-regulated identified by the inventors were primarily preserved in down-regulated genes in astrocytes, neurons, oligodendrocytes, and oligodendrocyte progenitor cells from a recent single-nucleus RNA-seq (snRNA-seq) of LOAD brains. Meanwhile, the up-regulated genes identified by the inventors were primarily preserved in up-regulated genes in astrocytes and oligodendrocytes (adjusted FET P-value up to 6.5E-45).

Networks of LOAD Brains Highlight Multiple Neuronal Modules

Figure 2A:
FIG. 2 provides a gene coexpression network analysis that prioritizes neuronal modules associated with LOAD, in accordance with some embodiments.
Figure 2B:
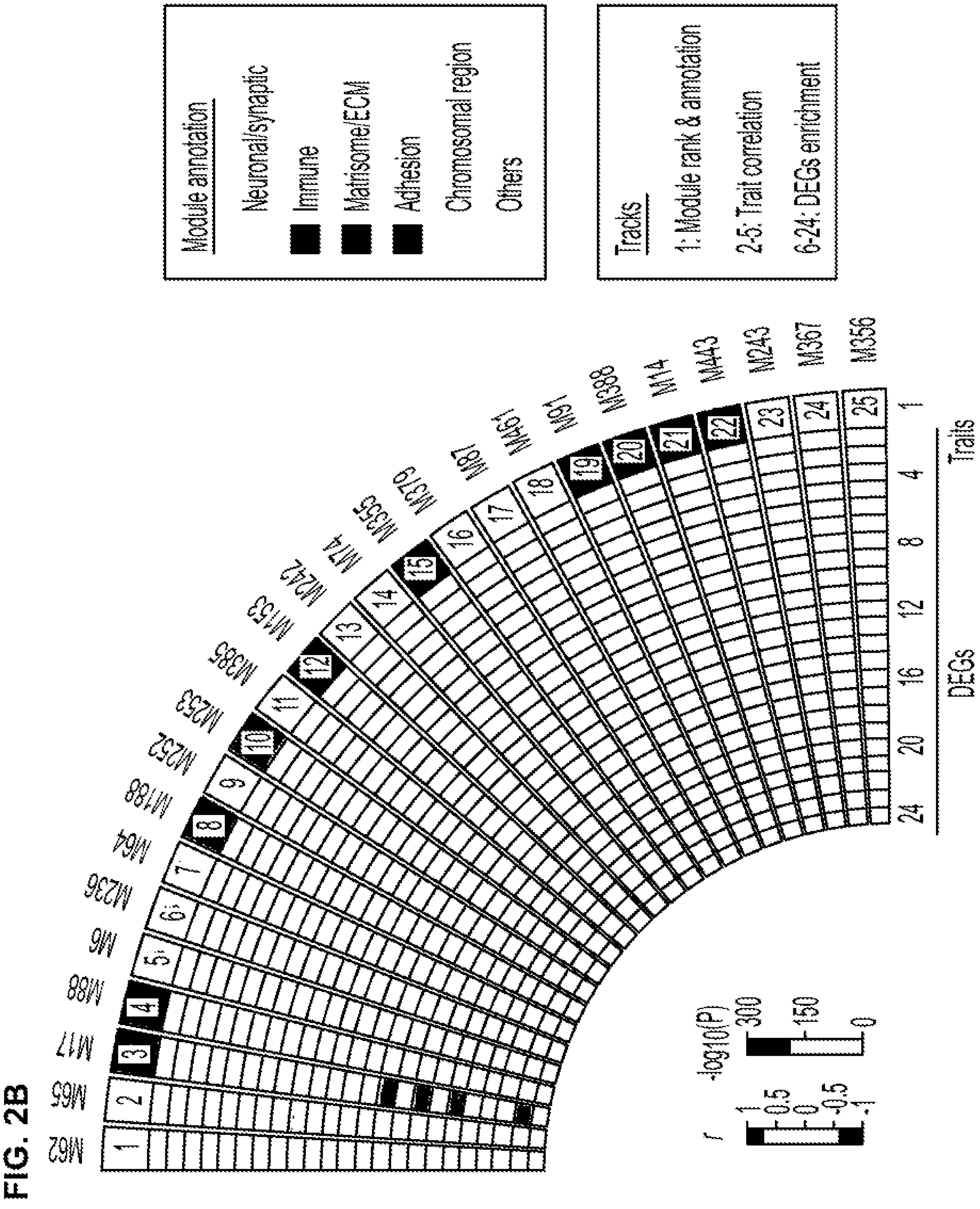
Figure 2C:
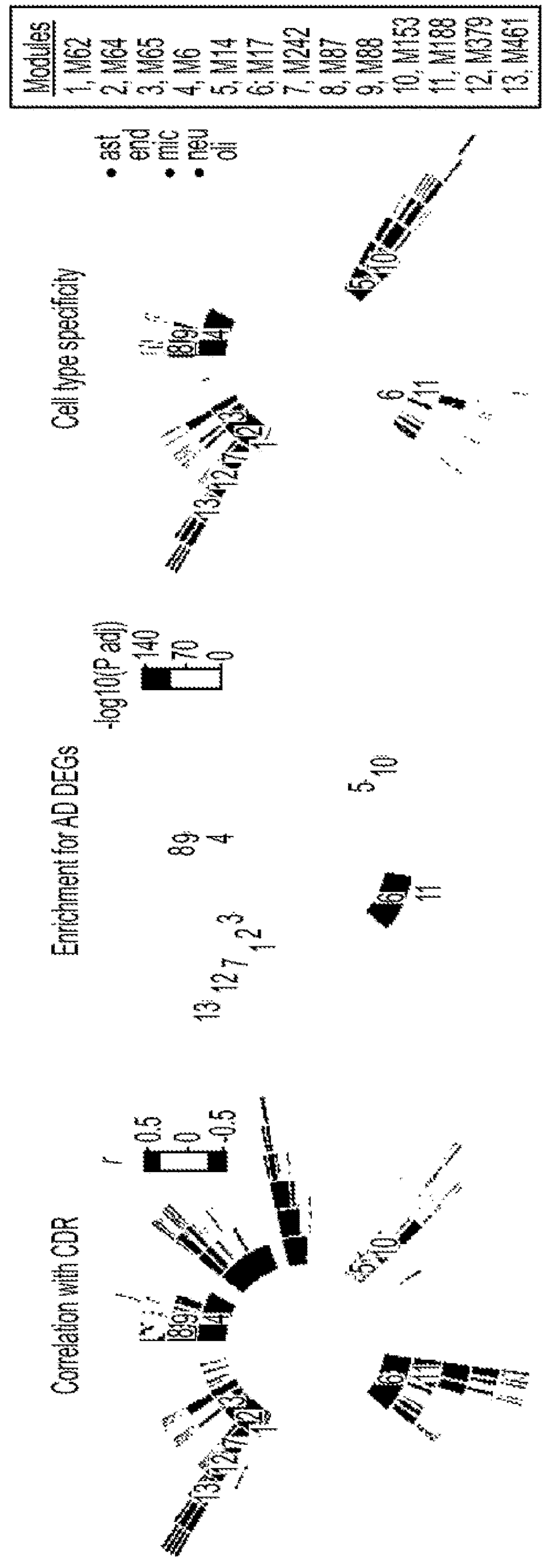
Figure 2D:
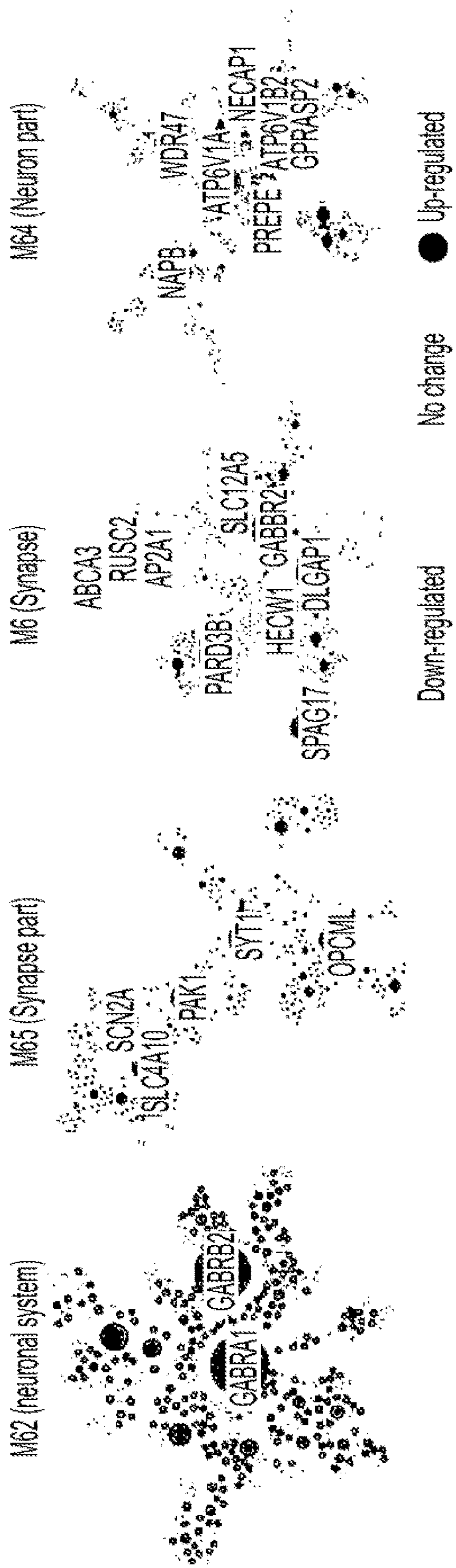
Figure 2E:
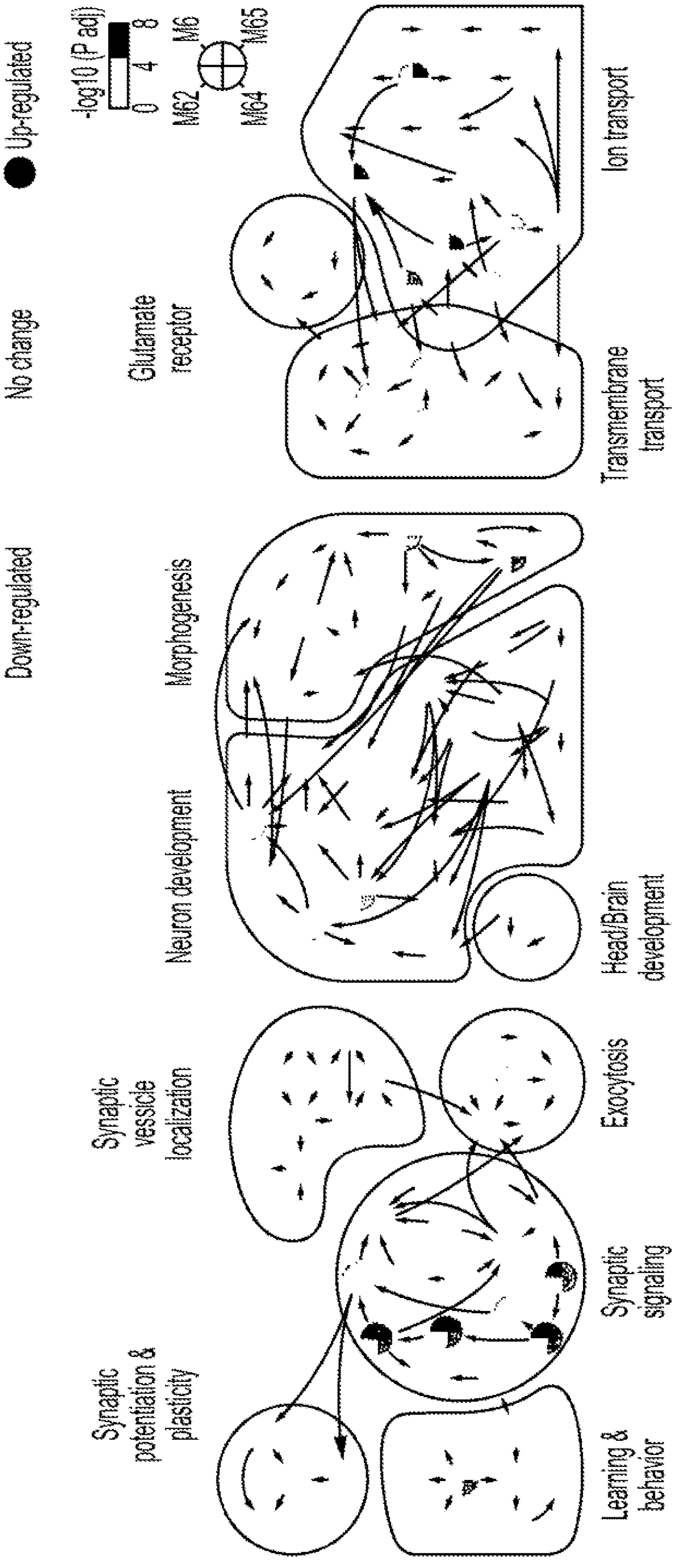

The inventors constructed gene coexpression networks using the multiscale embedded gene coexpression network analysis (MEGENA) to elucidate the interactions among genome-wide gene expression traits of LOAD and to identify gene modules (FIG. 2A). In a marked distinction from prior transcriptomic analyses of the DLPFC in the HBTRC cohort (which prioritized an immune-microglial module), the current disclosure highlights the significance of multiple neuronal modules (FIG. 2B). The inventors discovered that 9 of the top 25 modules were enriched for neuron cell markers, negatively correlated with disease traits, and enriched for DEGs that they identified as being down regulated in LOAD. These included M62, M65, M6, M236, M64, M252, M385, M87, and M243 (FIG. 2C). The inventors further found that M64 was overrepresented with inhibitory neuron-enriched genes, while 6 others (M6, M87, M65, M236, M62, and M252) were overrepresented with excitatory neuron-enriched genes. Topological structures of 4 of the top-ranked neuronal modules (i.e., M6, M62, M64, and M65) are shown in FIG. 2D. The inventors discovered that all 4 modules were enriched in synaptic signaling to different degrees, but M6 and M64 were also enriched in regulation of long-term synaptic potentiation, synaptic vesicle trafficking, and localization (FIG. 2E).

The inventors validated the biological coherence of the present network modules using information from previous transcriptomic network studies of LOAD. In the ROSMAP data, for example, the inventors found that more than 46.2% of the modules were strongly preserved (preservation statistics >10). Specifically, the top 25 modules showed strong preservation except M74, which was moderately preserved. Moreover, in the ROSMAP data (Mostafavi et al., 2018), there were 4 neuronal modules, m16, m21, m22, and m23, in which all, but m16, were associated with cognitive decline or amyloid-O burden (P<0.05). The inventors found that m21 and m23 significantly overlapped all the current 9 top-ranked neuronal modules, while m16 and m22 were enriched in 3 and 7 of the current top-ranked neuronal modules, respectively (Fold enrichment (FE)=1.4~14.1, false discovery rate (FDR) up to 2.2E-39)

Example 2

Identifying Novel Key Drivers of Top-Ranked Neuronal Modules

Figure 3A:
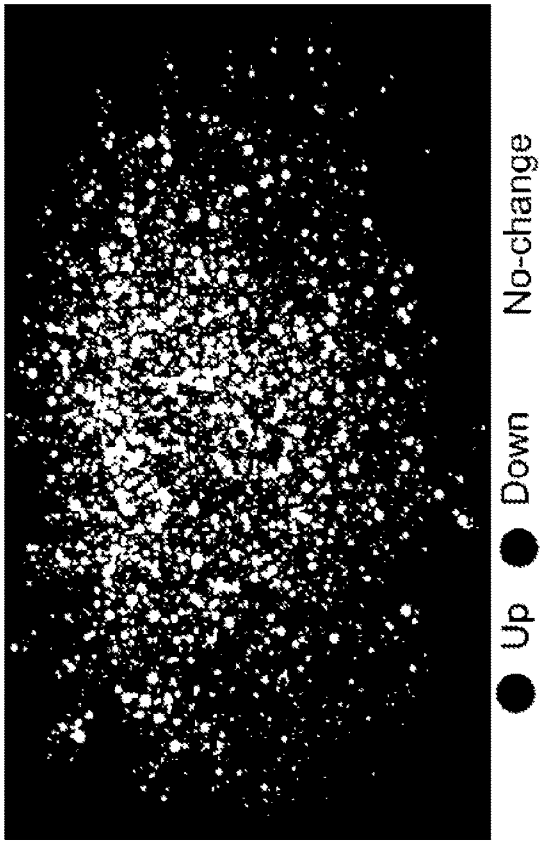
FIG. 3 shows that Bayesian probabilistic causal network (BN) analysis predicts novel key drivers of LOAD, in accordance with some embodiments.
Figure 3B:
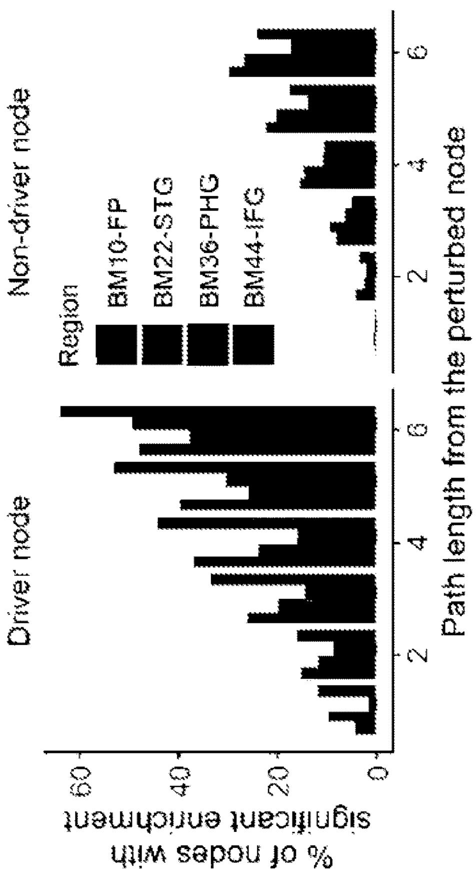

The inventors constructed Bayesian probabilistic causal networks (BNs) (FIG. 3A) using structural priors from expression quantitative traits (eQTLs) and transcription factor-target relationships to determine potential network regulators (called key drivers) in the top-ranked modules. The inventors performed fine mapping of AD GWAS causal genes by integrating eQTLs and GWAS statistics that led to marginally significant gene prioritization at two GWAS loci. The inventors examined whether the BNs they generated could predict publicly available gene perturbation signatures of the inferred key drivers. They discovered that 50~60% of the key driver perturbation signatures were enriched (i.e. significantly predicted) in the network neighborhoods of the corresponding key drivers (as illustrated in FIG. 3B). In contrast, the inventors discovered that the proportion of enriched perturbation signatures decreased to 20~30% in the network neighborhood of non-driver genes, showing the predictive power of the gene regulatory networks.

Figure 3C:
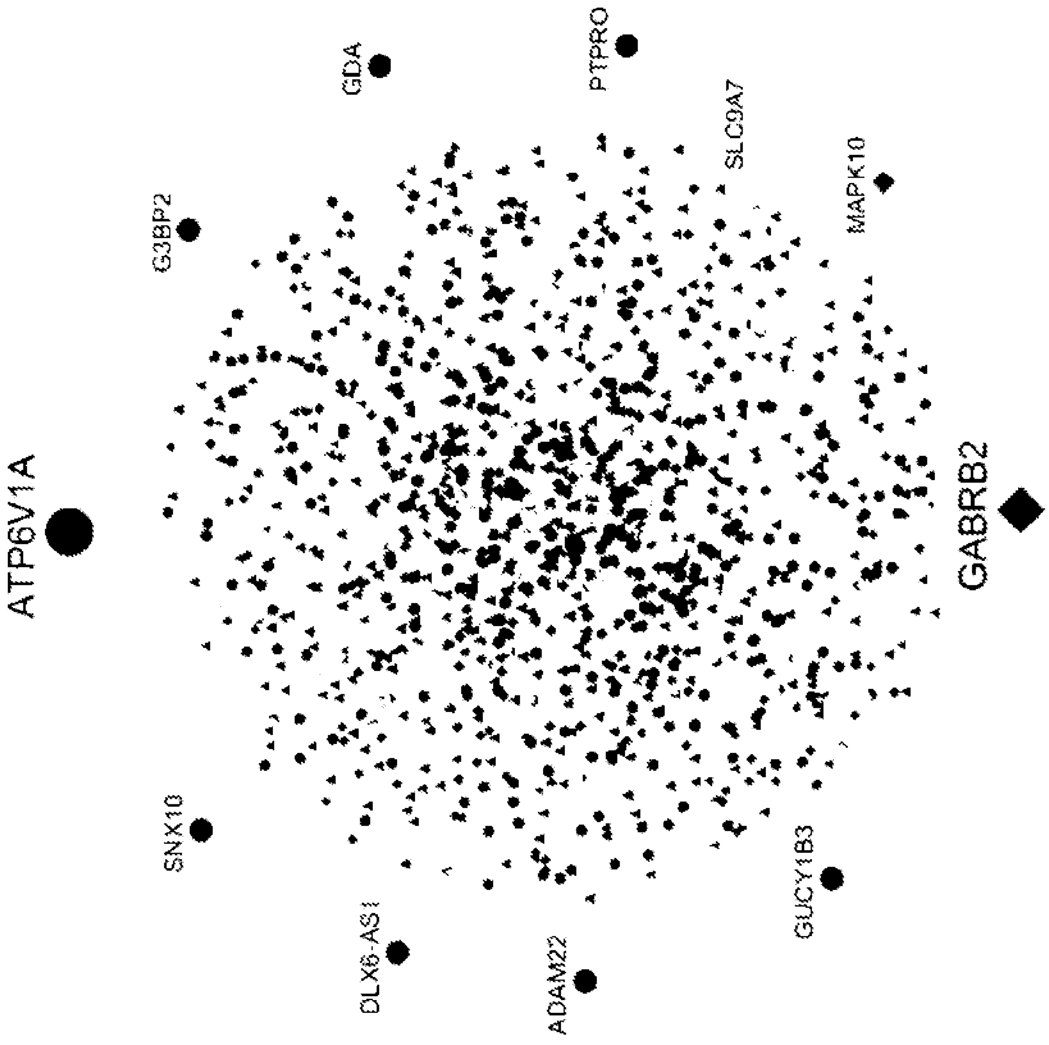

To further refine the population of key drivers, the inventors projected each of the 9 top-ranked neuronal modules (FIG. 2B) onto the BM36-PHG BN and identified 48 key drivers (42 unique genes), including 10 that were root nodes (without parental nodes). They found that the key drivers ATP6V1A in M64 and GABRB2 in M62 remained as root nodes in a union BN that combined directed edges from 4 region wide BNs (FIG. 3C). The inventors discovered that only one prioritized key driver, ATP6V1A, was consistently downregulated across brain regions and disease stages in LOAD. This gene encodes a component (V1 subunit A) of vacuolar- or vesicular-type ATPase (v-ATPase), a multi-subunit enzyme that mediates lysosomal acidification and energizes synaptic membranes in neurons.

Figure 3D:
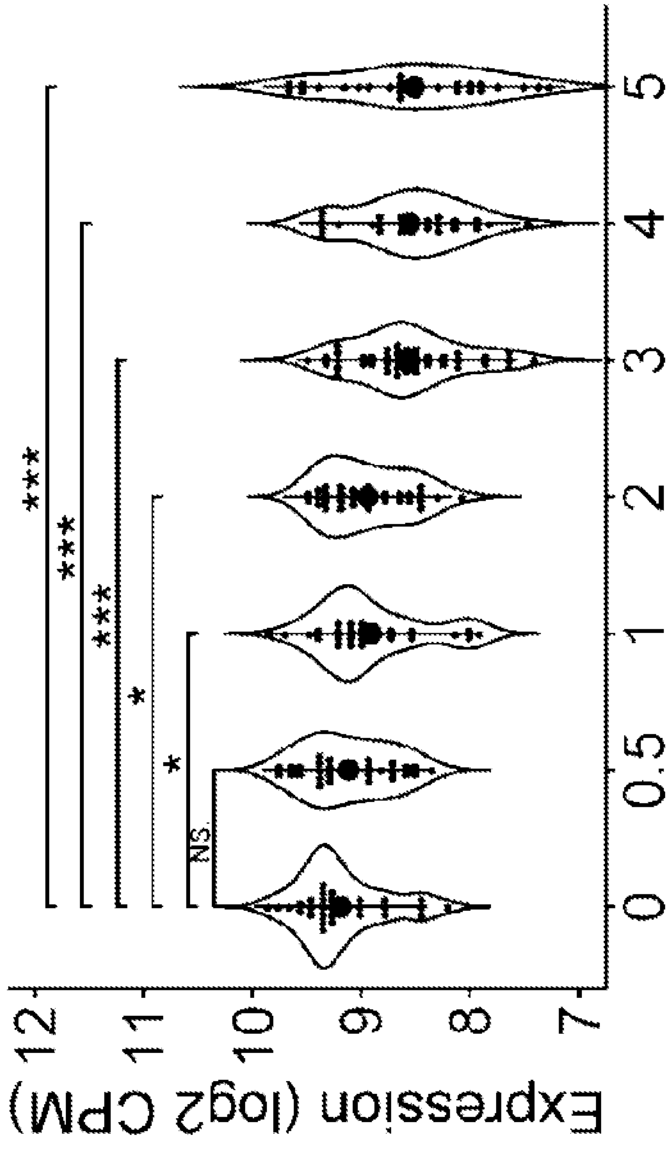
Figure 3E:
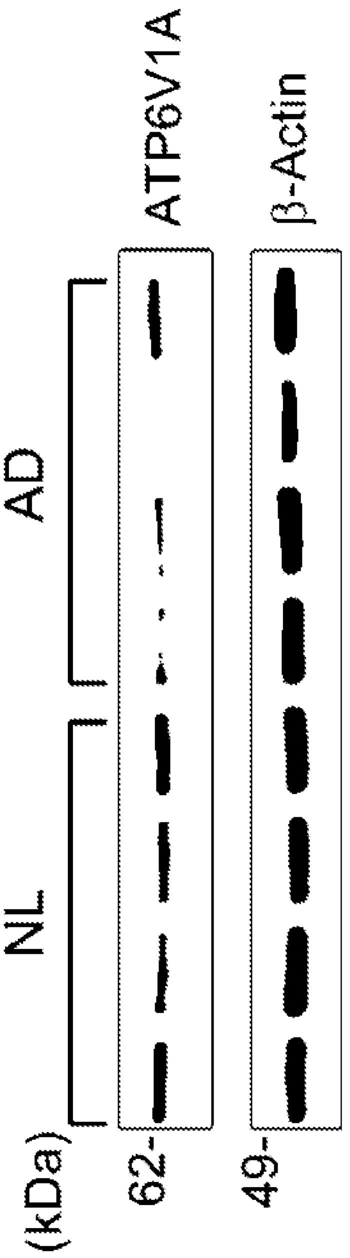
Figure 3G:
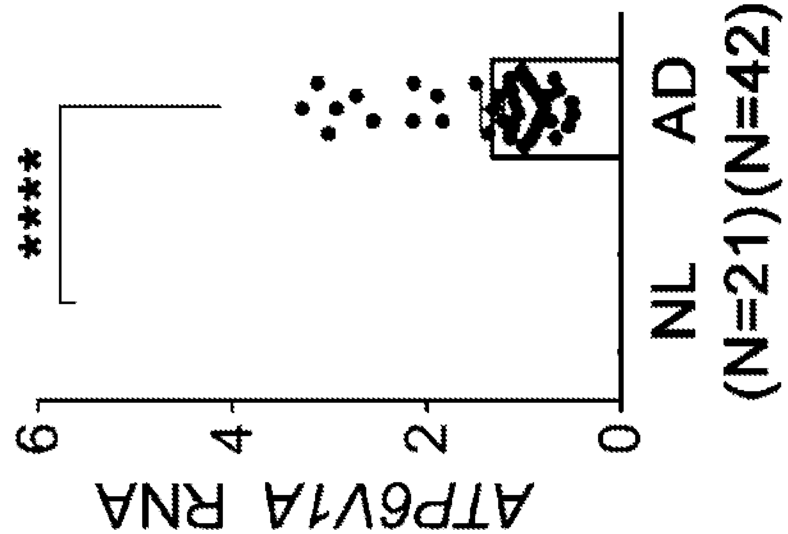
Figure 3F:
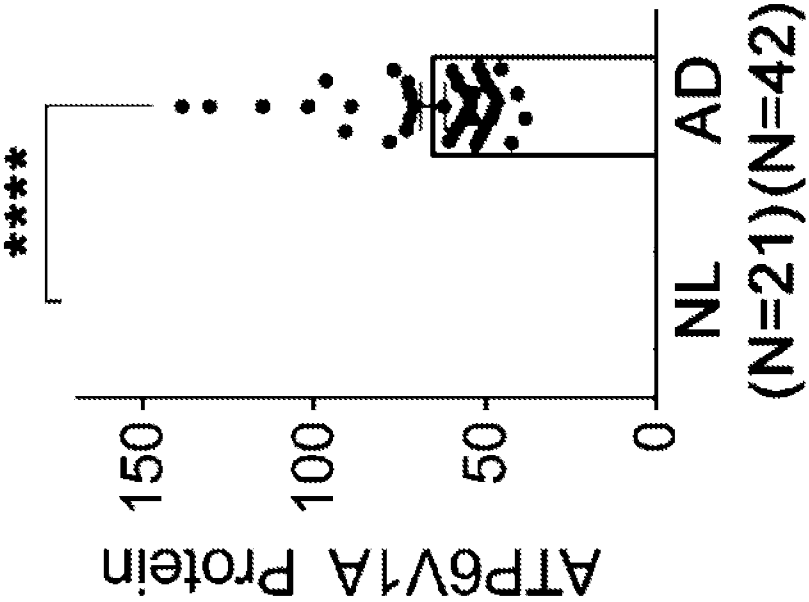

The inventors further discovered that ATP6V1A was significantly down-regulated in the BM36-PHG (−1.43 fold, P-value=1.5E-6) and BM22-STG (−1.25 fold, P-value=2.1E-3) regions of persons with dementia (clinical dementia rating CDR≥1), and marginally down-regulated in the BM10-FP region of persons with MCI and frank dementia (CDR=0.5) (−1.11 fold, P-value <0.098) (FIG. 3D). The inventors also found that ATP6V1A expression was negatively correlated with clinical and pathological traits in BM22-STG and BM36-PHG (Spearman correlation coefficients between −0.21 and −0.44, P values between 5.9E-11 and 3.3E-4), providing evidence of a consistent down-regulation of ATP6V1A at both early and late stages of the disease. The inventors independently validated the reduced expression of ATP6V1A in LOAD brains (FIG. 3E-G; 42% decrease at mRNA level and 35% decrease at the protein level, P<1.0E-4). In addition, the inventors found that ATP6V1A was down-regulated in the excitatory (0.8 fold, adjusted P-value 2.6E-117) and inhibitory (0.83 fold, adjusted P-value 6.7E-22) neurons in brains with early-pathology of LOAD compared to no-pathology brains in the ROSMAP cohort. The inventors performed gene perturbation experiments in in vitro (neurons) and in vivo (transgenic flies) models to validate the functional role of ATP6V1A in LOAD.

Example 3

Effects of Neuronal Knockdown of a Fly Ortholog of ATP6V1A in A/42 Flies

The effects of knocking down fly ortholog of ATP6V1A on neuronal integrity were examined in *Drosophila*. The results showed that that ATP6V1A Vha68-1 deficiency and Aβ42 synergistically downregulate key regulator genes of neuronal activity and exaggerate Aβ42-induced toxicities in flies. According to the DRSC Integrative Ortholog Prediction Tool, *Drosophila* Vacuolar $H^+$ ATPase 68 kD subunit 1 (Vha68-1, CG12403) and Vha68-2 (CG3762) are the best orthologs of human ATP6V1A protein. Several shRNAi constructs were generated to target different regions of Vha68-1 or Vha68-2 and expressed them in neurons using the pan-neuronal elav-GAL4 driver in a GAL4-UAS system. Both Vha68-1 and Vha68-2 are essential genes and strong knock-down causes lethality; therefore, selected an RNAi line that modestly reduced Vha68-1 levels was selected. Using the forced climbing assay, a quantitative way to assess neuronal dysfunction (Iijima et al., 2004), neuronal KD of Vha68-1 by itself was found to cause a modest decline in climbing ability in aged flies.

Figure 4A:
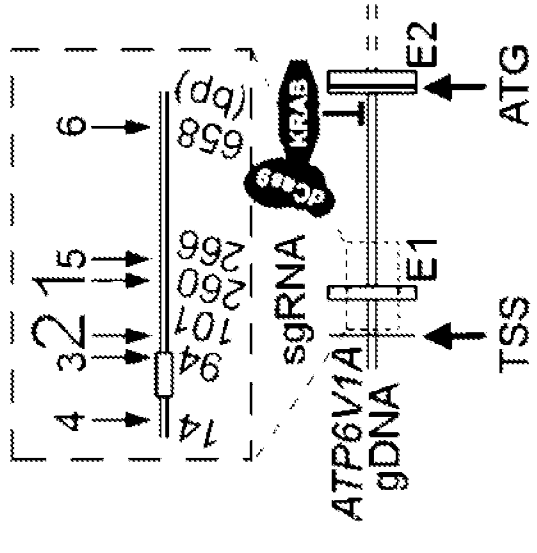
FIG. 4 illustrates how repression of ATP6V1A leads to neuronal malfunction in human NGN2-neurons and Aβ42 transgenic flies.
Figure 4B:
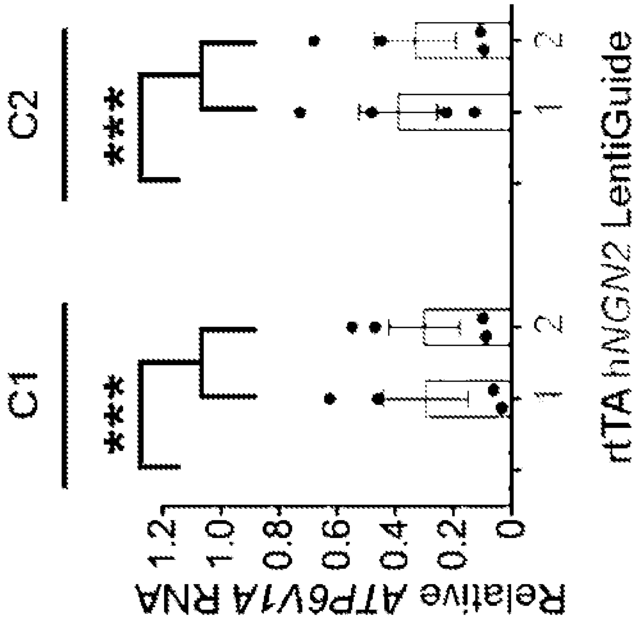
Figure 4D:
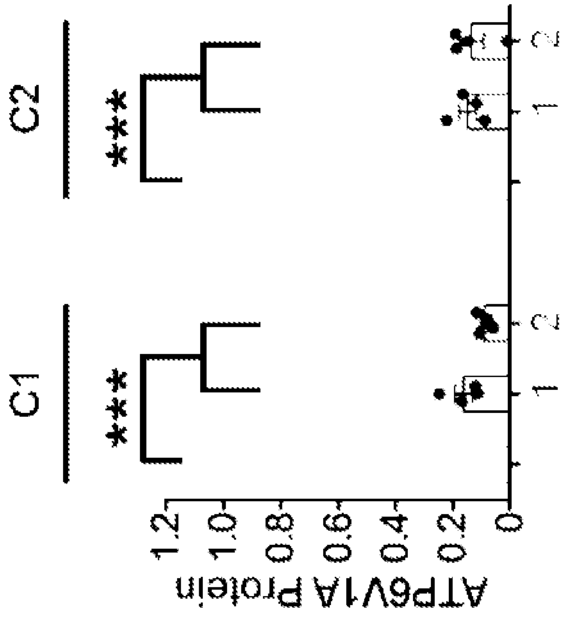
Figure 4C:
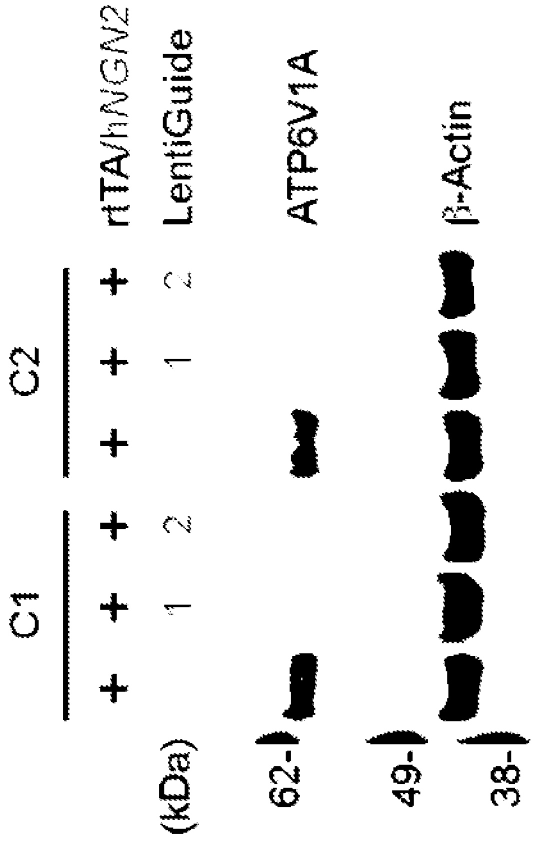
Figures 4E, 4F, 4G:
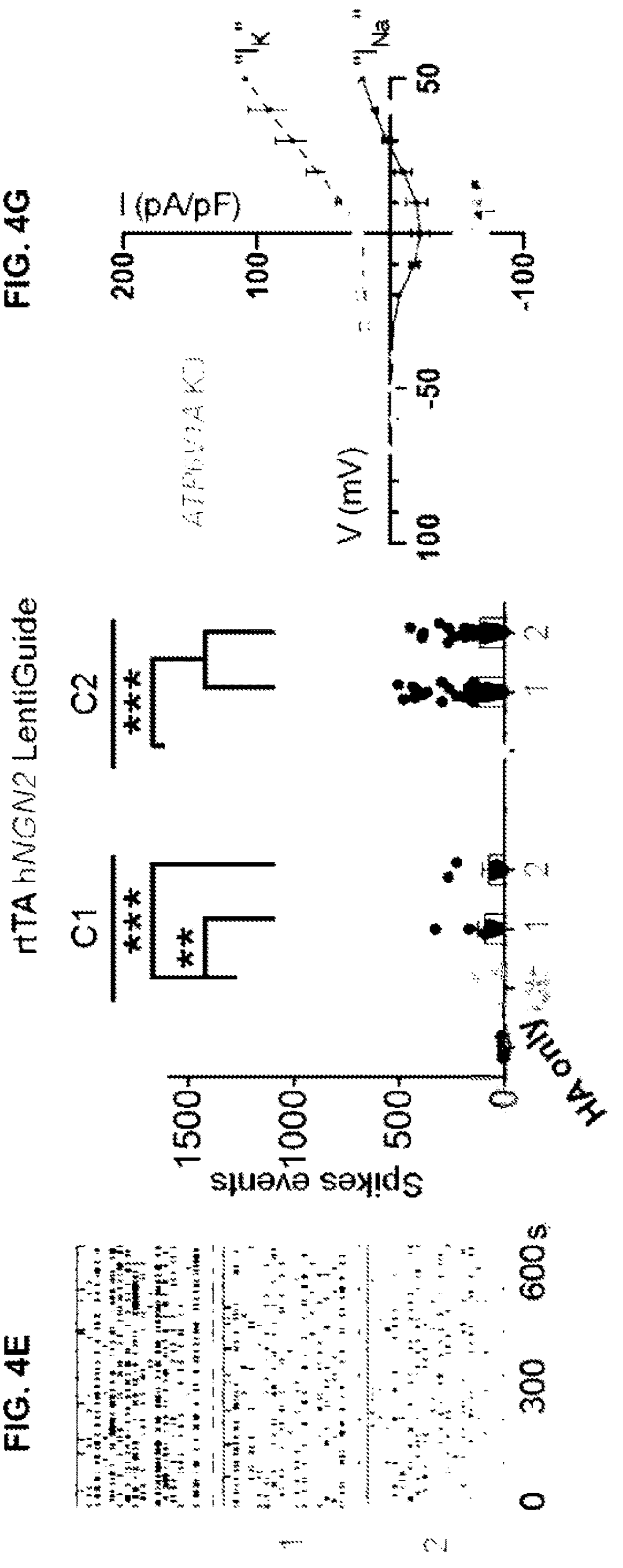
Figures 4H, 4I, 4J:
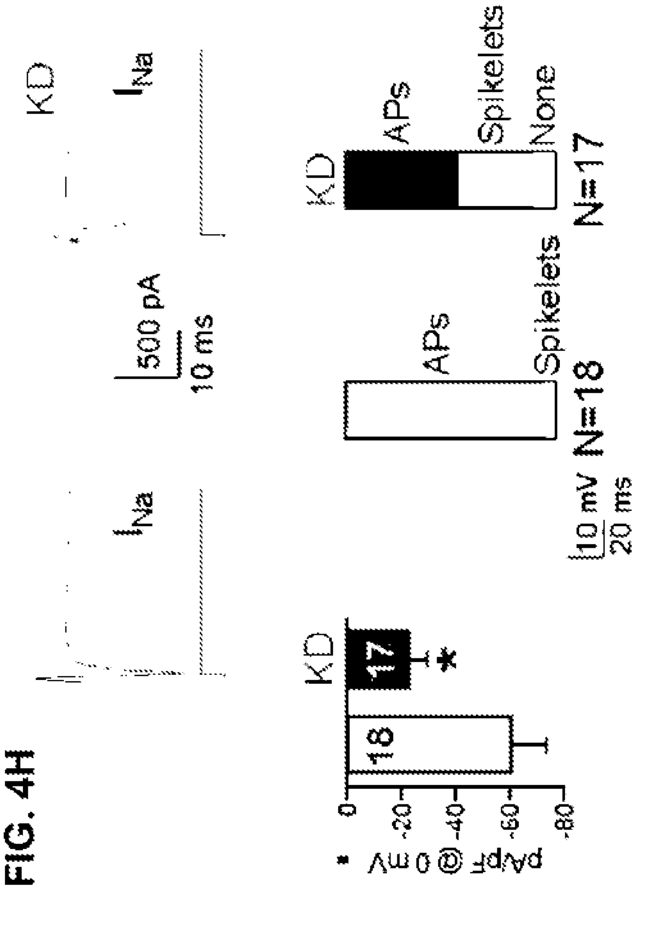
Figure 4K:
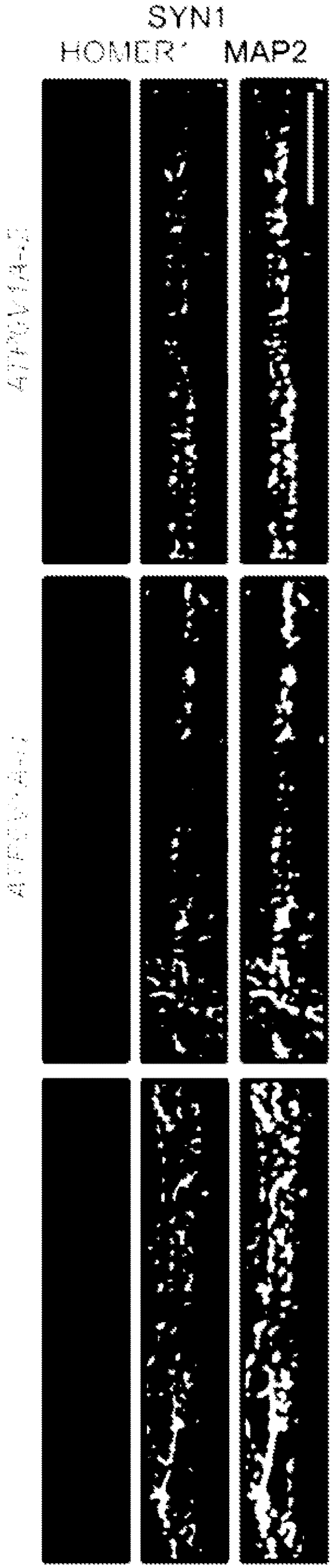
Figure 4L:
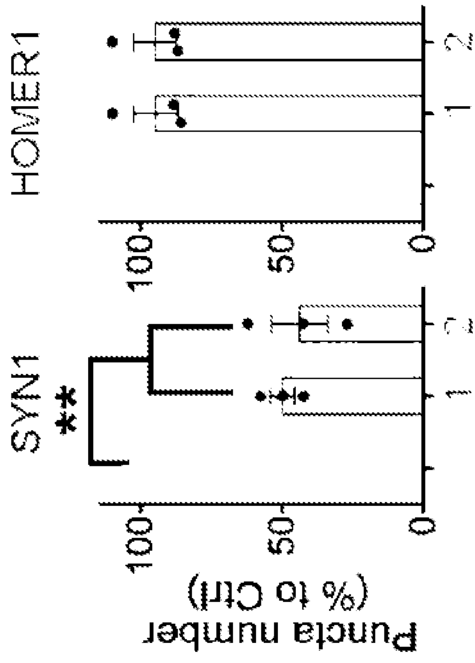
Figure 4P:
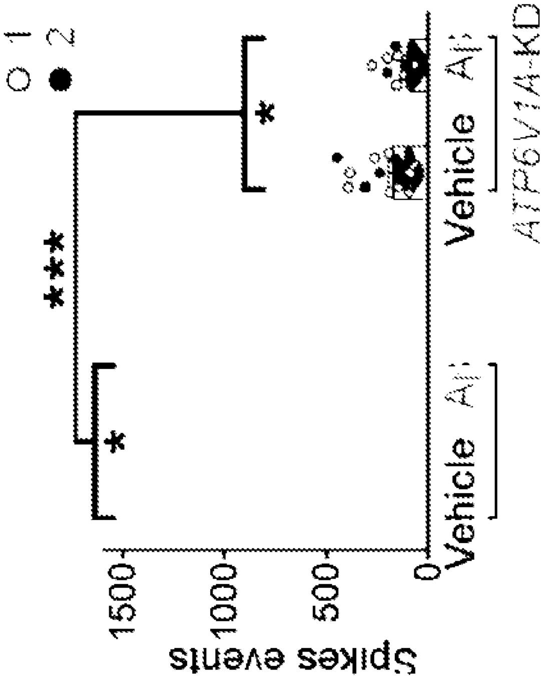
Figure 4O:
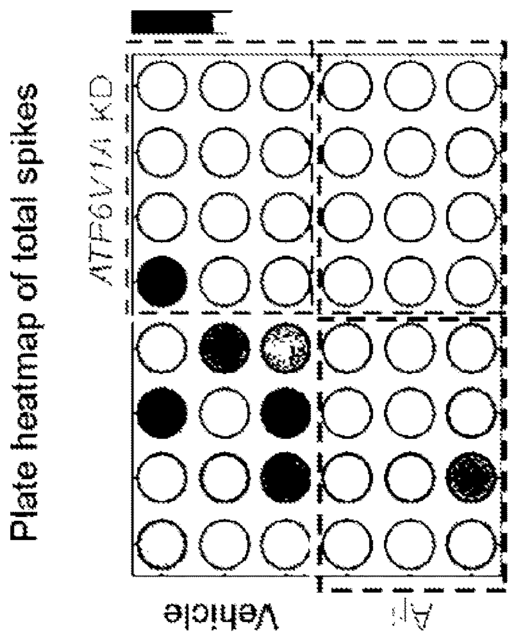
Figure 4N:
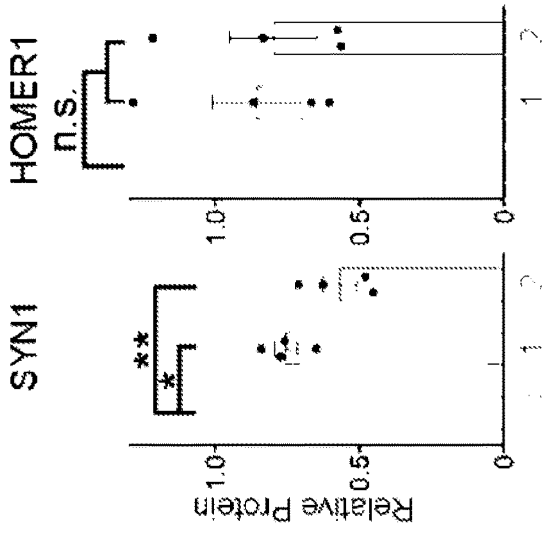
Figure 4M:
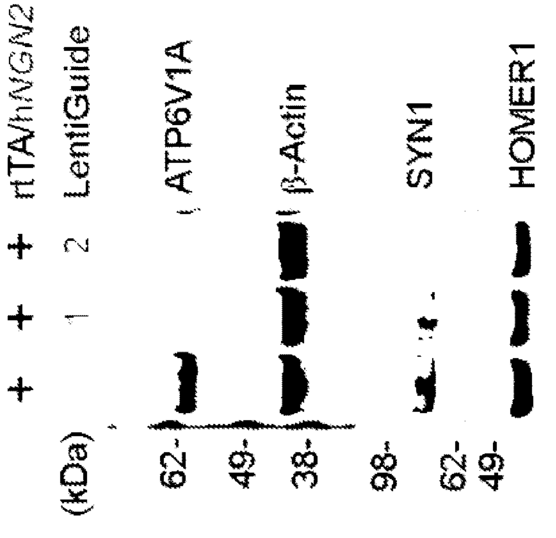
Figure 4R:
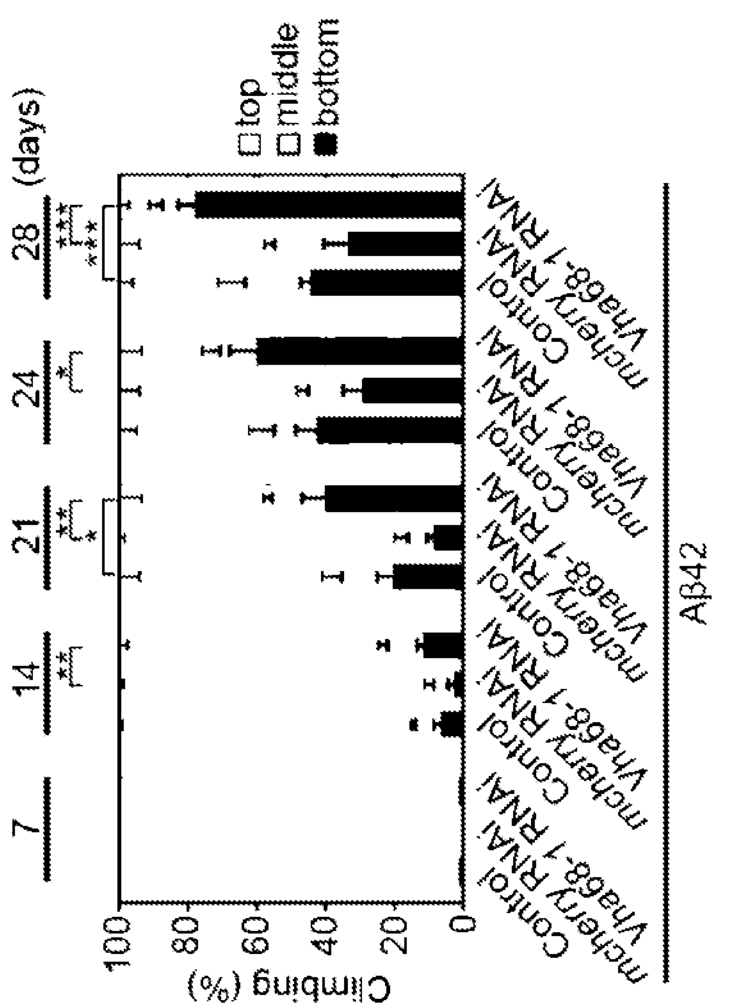
Figure 4Q:
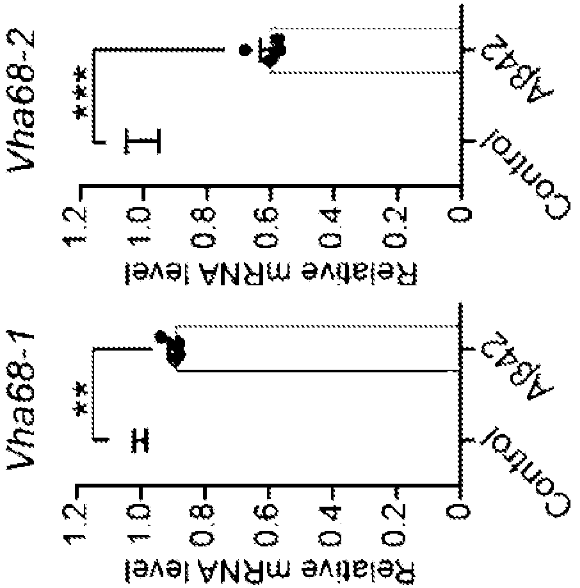

A transgenic *Drosophila* expressing human Aβ42 shows age-dependent locomotor deficits and neurodegeneration in the brain (Iijima et al., 2004). An examination of mRNA levels of both Vha68-1 and Vha68-2 significantly reduced expression in Aβ42 flies (FIG. 4Q), suggesting a role in Aβ42-mediated toxicity. Locomotor deficits were also found to be significantly exacerbated by neuronal KD of Vha68-1 (FIG. 4R). Similar results were obtained using shRNA that targets a different region of Vha68-1, thus minimizing potential off-target effects. A mutant allele of Vha68-1

(Vha68-1') with a loss-of-function single-nucleotide mutation (Q519L) caused by mutagenesis was also used to confirm these results. The results showed that locomotor deficits were significantly worsened in Aβ42 flies with a heterozygous mutation of Vha68-1', while a heterozygous Vha68-1' by itself did not cause climbing defects.

Figure 4S:
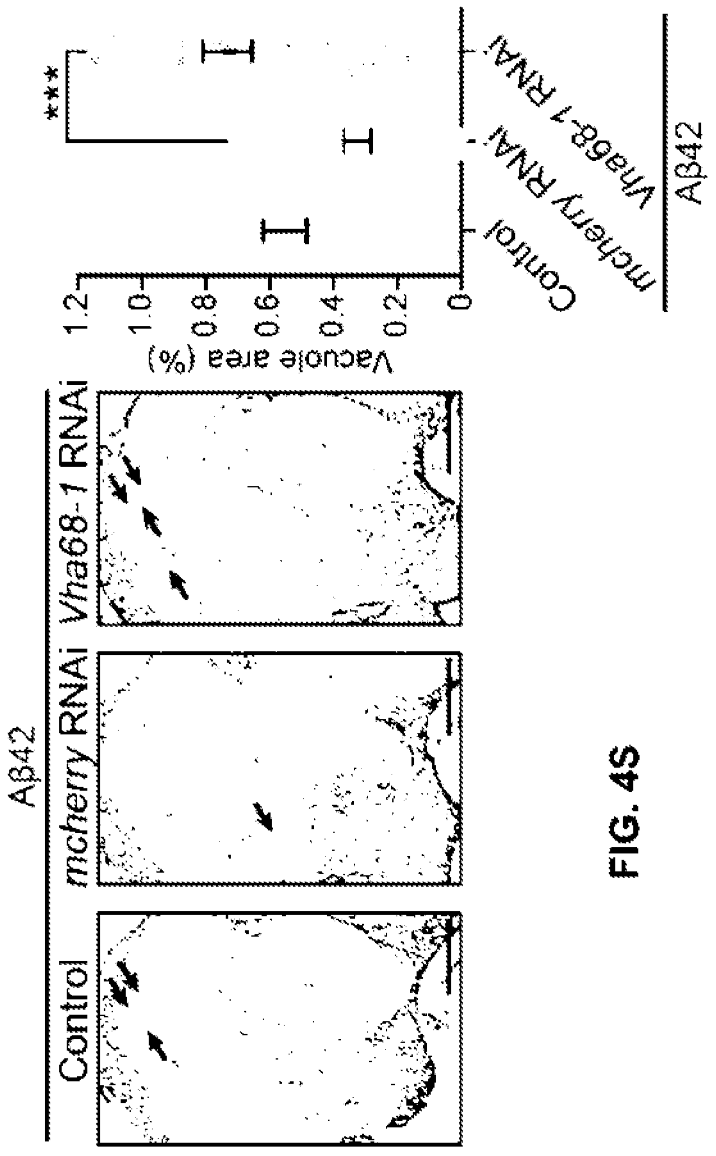

In *Drosophila*, brain vacuolation is a morphological hallmark of neurodegeneration that can be quantitatively assessed. Neuronal expression of Aβ42 causes an age-dependent appearance of vacuoles in the fly brains (Iijima et al., 2004). Experiments directed to RNAi-mediated KD of Vha68-1 significantly worsened this neurodegeneration (FIG. 4S). Neurodegeneration was also slightly worsened in the flies with heterozygous Vha68-1', with no statistically significant difference.

Figure 4T:
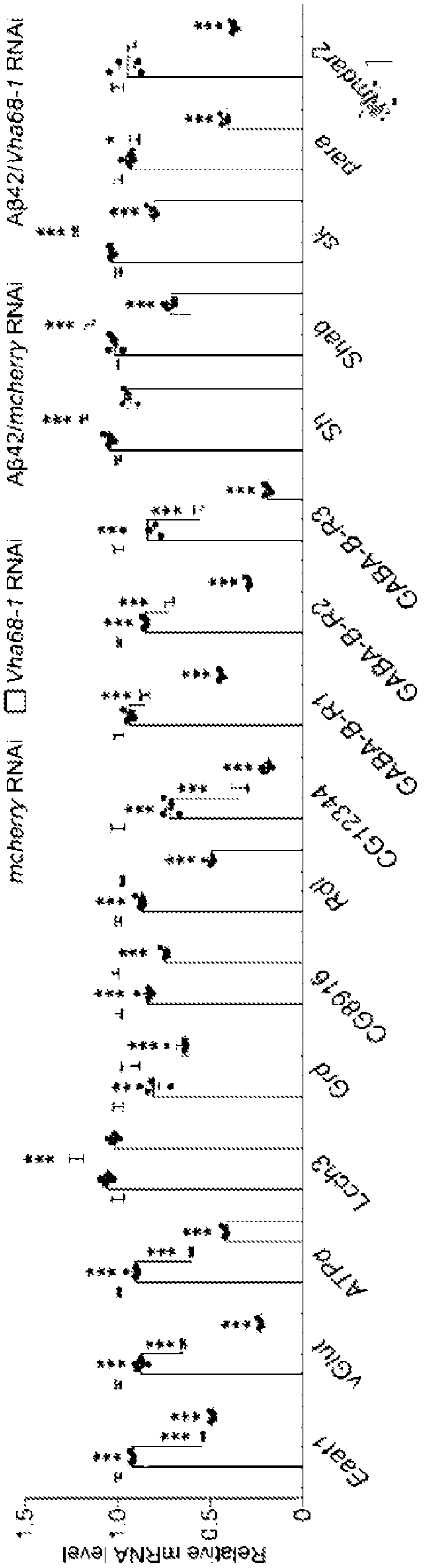

To assess whether altered neuronal activity underlies toxic interactions between Vha68-1 deficiency and Aβ42 in flies, the mRNA levels of 16 genes related to synaptic biology were examined, with a focus on GABAergic/glutamatergic systems and ion channels (FIG. 4T). The results showed that compared to control flies, mRNA levels of 9 genes were significantly reduced by neuronal KD of Vha68-1, while 8 genes were significantly reduced by Aβ42 (FIG. 4T). Six genes (SLC1A2/Eaat1, SLC17A6-8/vGlut, ATP1A1-3/ATPα, GLRA2/CG12344, GABBR2/GABA-B-R2, and GABBR2/GABA-B-R3) were commonly reduced in both conditions (FIG. 4T). By contrast, neuronal KD of Vha68-1 in Aβ42 flies dramatically reduced mRNA levels of 14 out of 16 genes compared to control flies (FIG. 4T). Key driver genes, including GABRA1/Grd in M62, SCN2A/para in M65, and GABBR2/GABA-B-R2,3 in M6 (FIG. 2D) were downregulated in these fly brains, suggesting functional links between these networks and ATP6V1A/Vha68-1 in M64 module.

Example 4

Figure 5A:
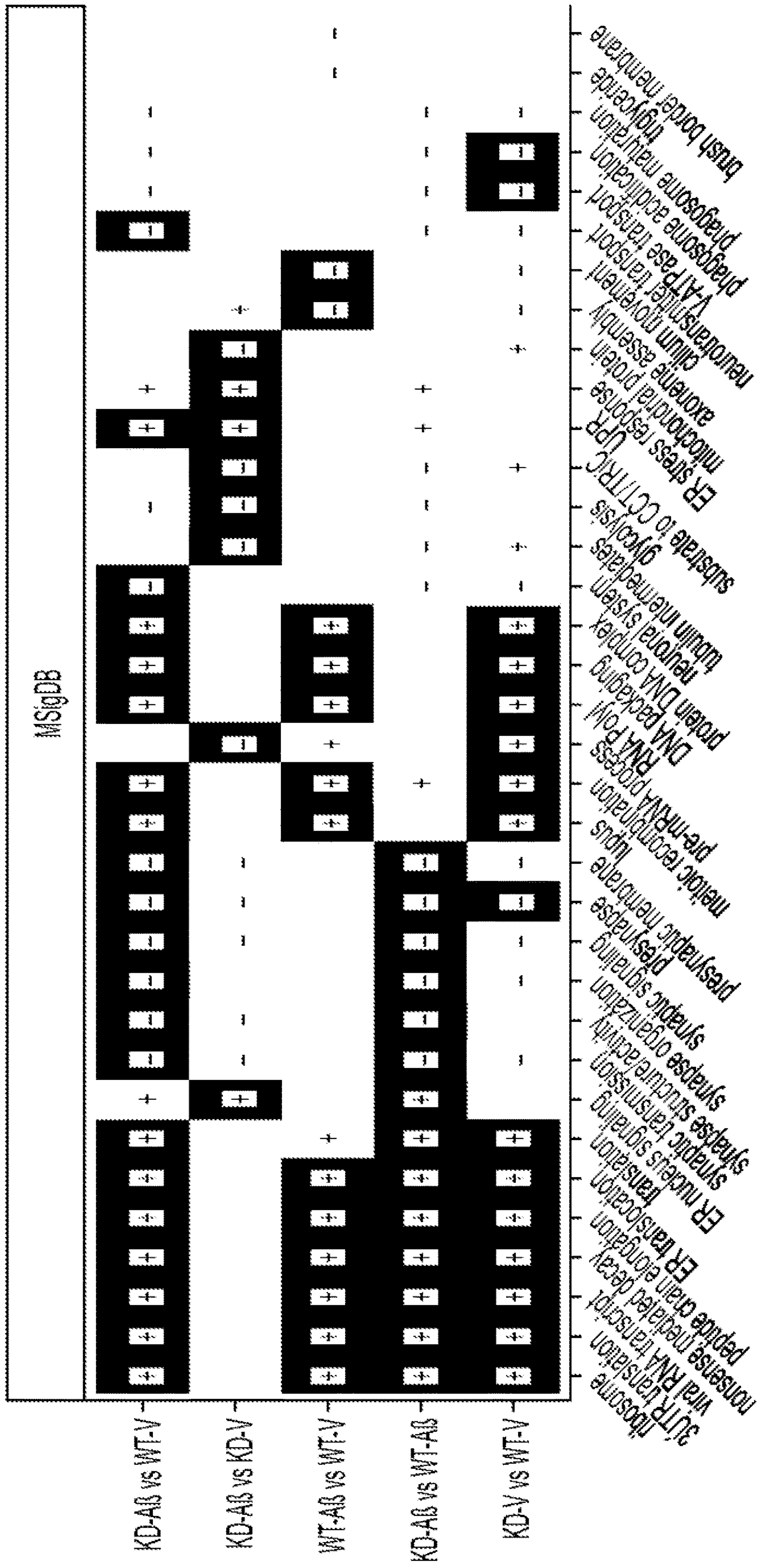
FIG. 5 provides RNA-seq analysis of ATP6V1A KD neurons and validates ATP6V1A regulated neuronal networks in LOAD brains.
Figure 5A:
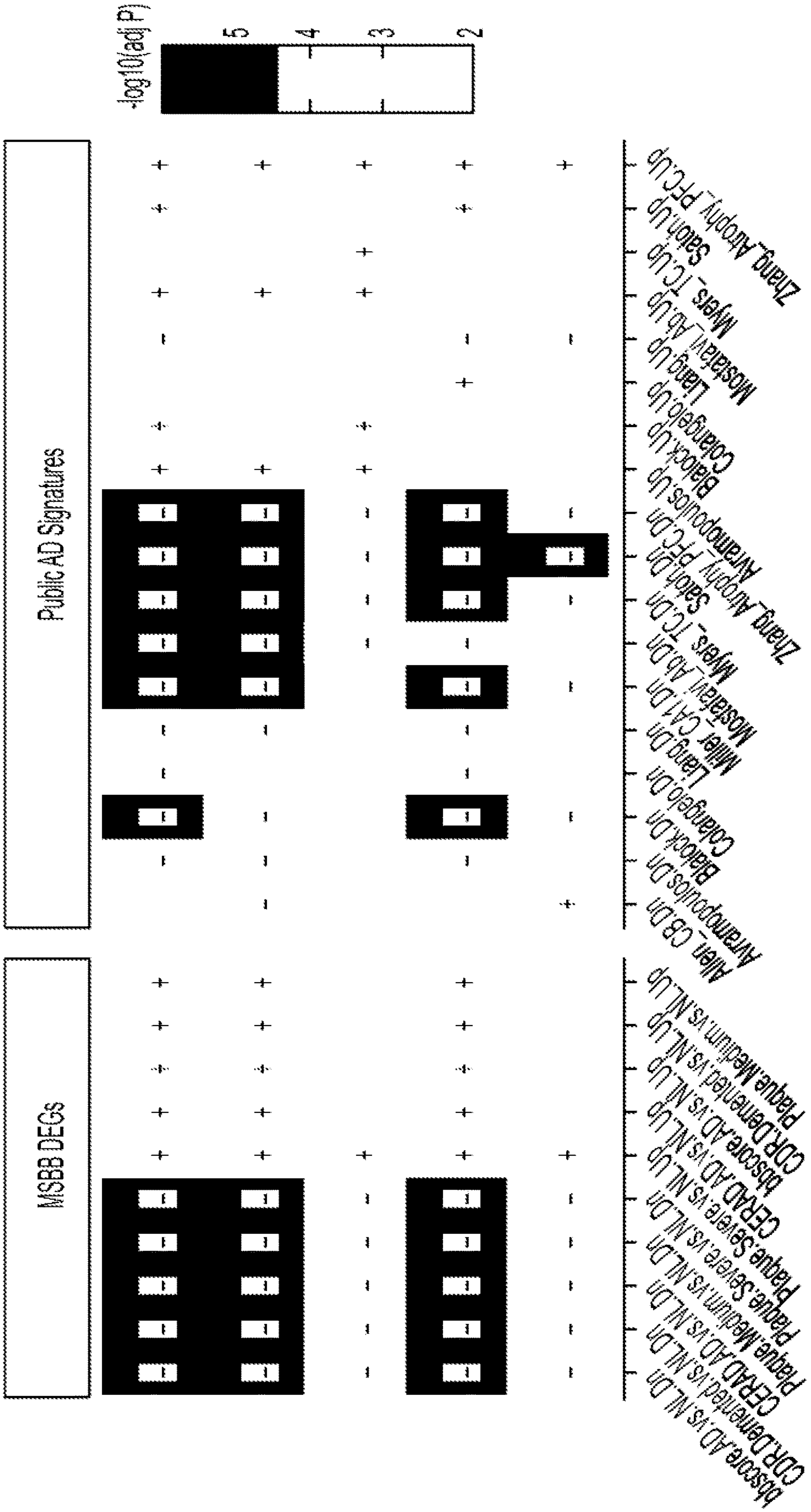

Enrichment of ATP6V1A Knockdown Signatures in ATP6V1A Regulated Networks of LOAD Brains To characterize the molecular changes and validate the sub-network regulated by ATP6V1A, the inventors performed RNA-seq on 4 groups of iNs (designated WT-V and WT-Aβ for vehicle-treated and Aβ-treated ATP6V1A wild-type (WT) neurons, respectively, and KD-V and KD-Aβ for vehicle-treated and Aβ-treated ATP6V1A KD neurons, respectively). The inventors found that no gene shows significant changes between Aβ-treated and vehicle-treated cells in either ATP6V1A KD or WT genotype. In contrast, the inventors discovered that there were 3 DEGs from KD-V vs. WT-V, 55 DEGs from KD-Aβ vs. WT-Aβ, and 326 DEGs from KD-Aβ vs. WT-V. By employing the Gene Set Enrichment Analysis (GSEA), the inventors discovered V-ATPase transport and phagosome maturation/acidification down-regulated in KD-V vs. WT-V (FIG. 5A). Consistent with the functional assay above, KD-V vs. WT-V led to down-regulation of multiple synapse biology pathways, with greater down-regulation after the exposure to Aβ treatment in KD-Aβ vs. WT-Aβ.

Figure 5B:
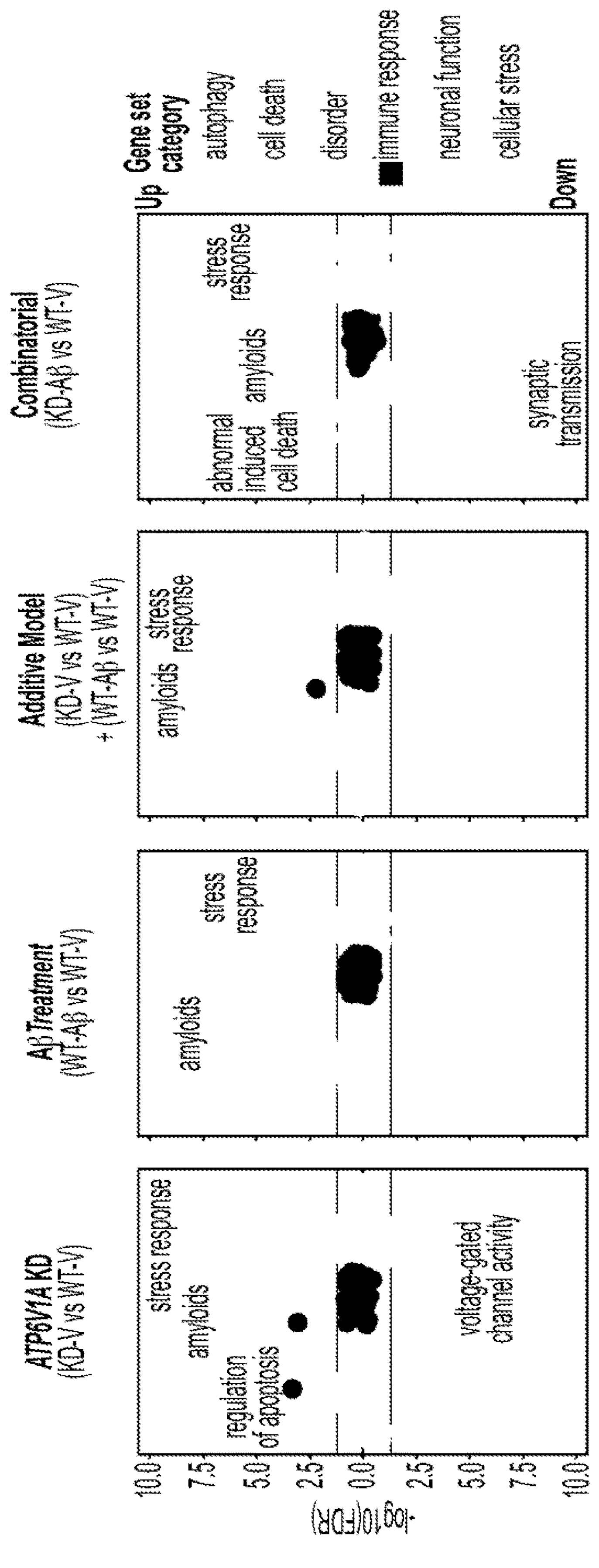
Figure 5C:
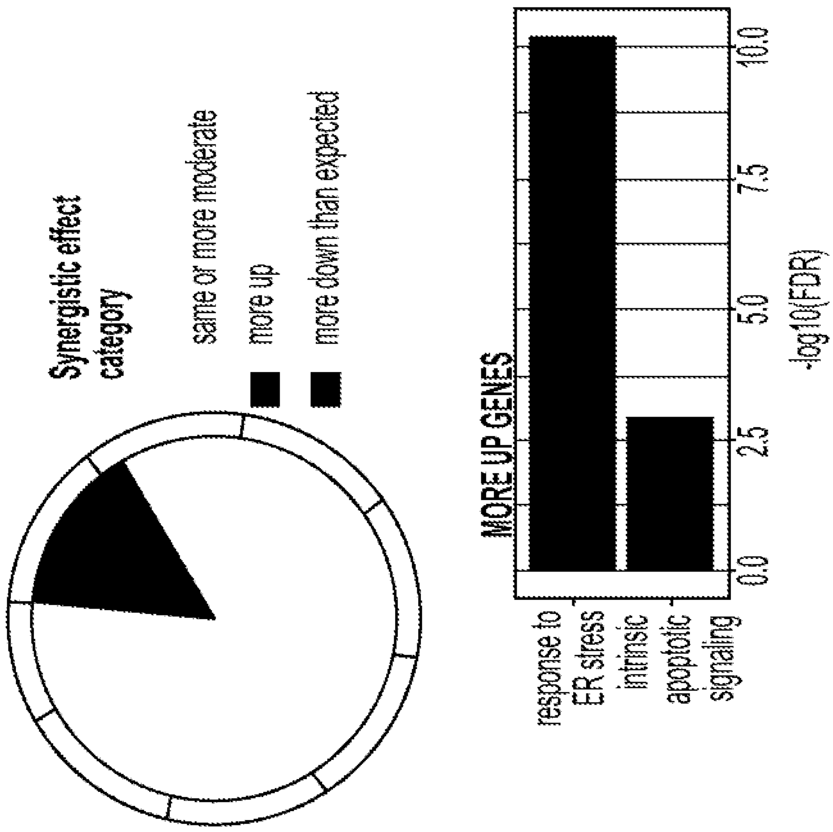

As a combination of ATP6V1A KD and Aβ treatment led to an increase in molecular changes than individual factor perturbation, the inventors examined the synergistic effects between the two factors. Surprisingly, the hierarchical clustering of the log FCs of all genes for each contrast showed differences between the predicted and observed cumulative effects. The inventors found a strong enrichment of disorder and cellular stress gene sets after individual KD or Aβ treatment, while the KD showed further associations with cell death and negative correlation with neuronal function signatures. The latter was markedly amplified in the combinatorial modulation (FIG. 5B). The inventors grouped genes into synergism categories based on differential expression between the additive model and the combinatorial modulation. Alterations of most genes that matched the inventors' predictions, but they discovered that 6% more (1152 genes) were downregulated and 9% more (1773 genes) were upregulated than originally expected (FIG. 5C). Those genes that they identified as more upregulated than expected (based on an additive model) were significantly enriched for cell death and cellular stress gene sets (FIG. 5C).

Figure 5D:
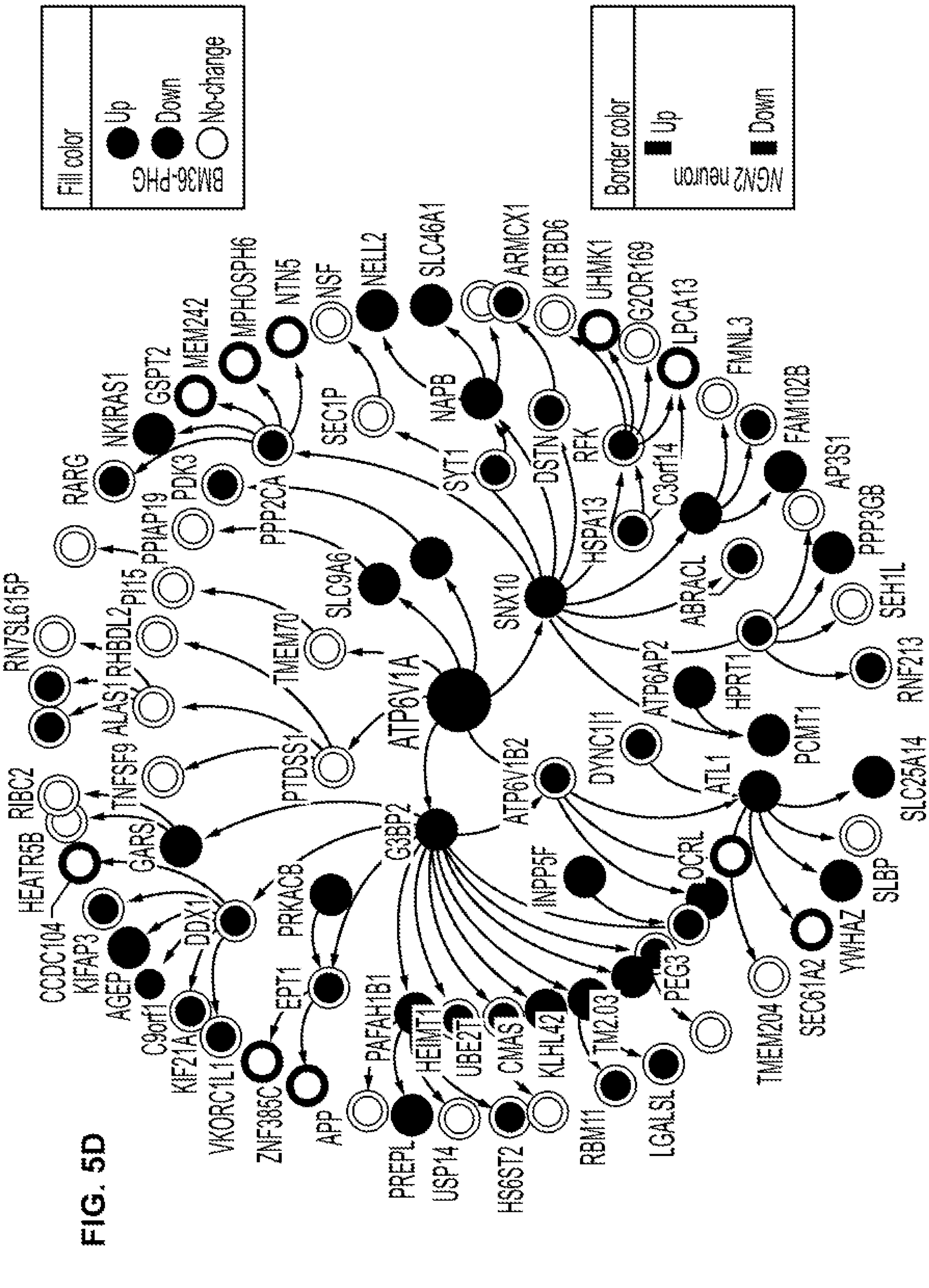

The inventors found that ATP6V1A KD and Aβ perturbation led to the significant enrichment in the LOAD signatures of genes identified from the current study as well as 10 published datasets (FIG. 5A). By GSEA, the inventors noted that the top-ranked neuronal modules (M64, which contains ATP6V1A, M62, M65, M6, M236, M252, M385, M87, and M243) were down-regulated in KD-Aβ cells compared to WT-V cells. Meanwhile, several immune response modules (M14, M153, M366, and M428) were up-regulated in KD-Aβ cells compared to WT-V cells. As exemplified in FIG. 5D, the genes surrounding ATP6V1A on the BM36-PHG BN were enriched for down-regulation signals of ATP6V1A KD, with the most significant enrichment from KD-Aβ vs. WT-V (FDR=4.1E-6). In summary, the inventors discovered that the ATP6V1A deficit signature in iNs mirrors the prediction made by the inventors using the human LOAD gene networks.

Example 5

Figure 6A:
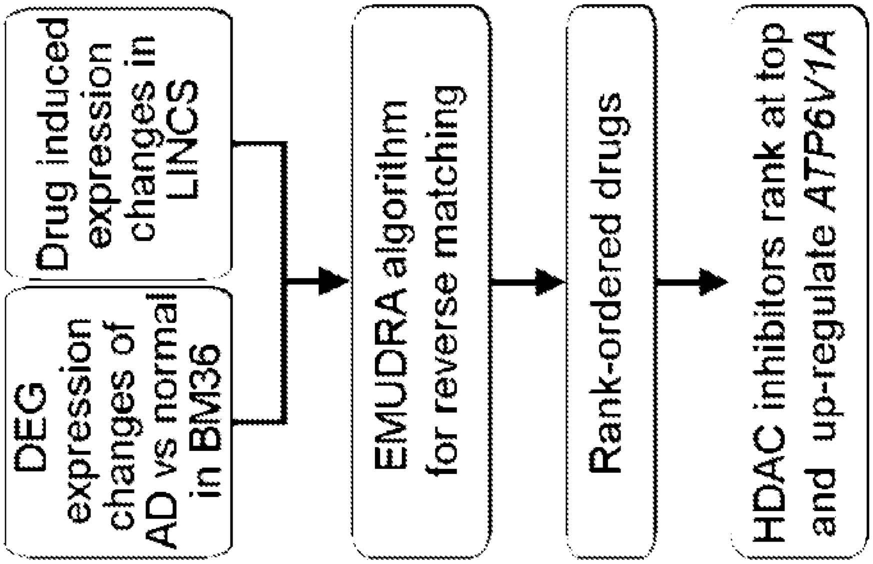
FIG. 6 shows that a novel compound NCH-51 increases ATP6V1A expression and partially restores neuronal function.

Identifying Novel Drug NCH-51 for Use to Improve ATP6V1A Levels and Neuronal Activity Compounds were screened for drugs that can rescue the in vitro and in vivo phenotypes arising from ATP6V1A deficits. Using their drug repositioning tool, Ensemble of Multiple Drug Repositioning Approaches (EMUDRA) (Zhou et al., 2018b), the inventors matched the disease signature from the BM36-PHG region and the signatures of 3,629 drugs tested in the NPCs in the Library of Integrated Network-based Cellular Signatures (LINCS) project (FIG. 6A). The inventors further prioritized candidate drugs by their potential to increase the mRNA expression of ATP6V1A in the NPCs. Interestingly, the top prioritized drugs contain several histone deacetylase (HDAC) inhibitors such as SAHA, NCH-51, and MS-275 (Table 1).

TABLE 1

Top 25 drug compounds predicted by EMUDRA

| Compound | Z score | ATP6V1A (log2FC) | P value | Adjusted P value |
|---|---|---|---|---|
| BRD-A25687296 | −6.69 | 2.37 | 5.57E−11 | 4.04E−09 |
| BRD-K36055864 | −5.64 | 2.00 | 3.87E−08 | 1.33E−05 |
| bg-1025 | −5.49 | 0.83 | 2.14E−04 | 1.01E−03 |
| nch-51 | −4.51 | 0.71 | 1.40E−03 | 4.99E−03 |
| bg-1008 | −3.76 | 0.69 | 3.33E−03 | 9.98E−03 |
| BRD-A34806832 | −3.76 | 1.49 | 2.44E−06 | 2.50E−05 |
| saha | −3.09 | 0.77 | 2.02E−03 | 7.27E−03 |
| fluoro-saha | −2.73 | 1.09 | 3.41E−05 | 2.66E−04 |
| BRD-K84595254 | −2.73 | 2.98 | 6.57E−14 | 4.93E−11 |
| apicidin | −2.14 | 0.99 | 1.57E−05 | 7.01E−05 |
| scriptaid | −1.89 | 0.78 | 3.34E−04 | 1.08E−03 |
| s1085 | −1.78 | 1.69 | 4.05E−04 | 4.33E−03 |
| m-344 | −1.77 | 0.84 | 1.08E−04 | 3.87E−04 |
| BRD-K77908580 | −1.61 | 1.54 | 6.78E−04 | 7.85E−03 |

TABLE 1-continued

| Top 25 drug compounds predicted by EMUDRA | | | | |
|---|---|---|---|---|
| Compound | Z score | ATP6V1A (log2FC) | P value | Adjusted P value |
| BRD-K56196992 | −0.74 | 1.47 | 8.48E−05 | 8.53E−04 |
| s1030 | −0.71 | 1.39 | 1.89E−04 | 1.46E−03 |
| bg-1004 | −0.54 | 0.85 | 1.02E−03 | 7.16E−03 |
| bg-1030 | −0.50 | 0.65 | 4.38E−03 | 9.92E−03 |
| BRD-A62184259 | −0.35 | 1.46 | 3.49E−06 | 1.10E−04 |
| BRD-K80348542 | −0.32 | 1.09 | 6.74E−04 | 2.84E−03 |
| bg-1028 | −0.31 | 0.76 | 5.67E−04 | 1.76E−03 |
| brd-k24656059 | −0.18 | 1.11 | 1.98E−04 | 5.06E−03 |
| BRD-K64606589 | −0.14 | 0.66 | 1.05E−03 | 2.66E−03 |
| trichostatin a | −0.09 | 0.61 | 2.85E−05 | 6.51E−05 |

Figure 6B:
Figure 6C:
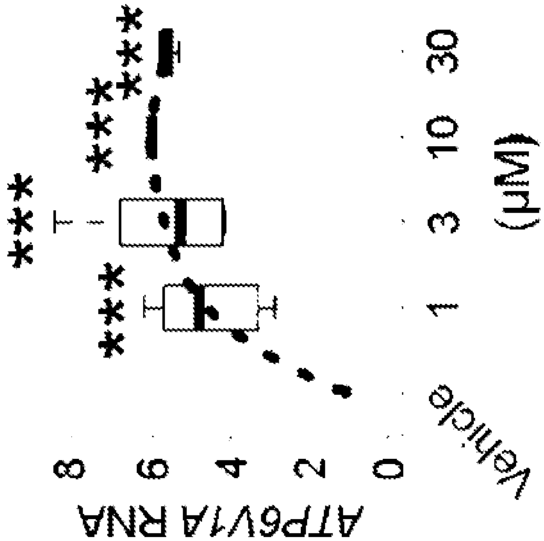
Figure 6D:
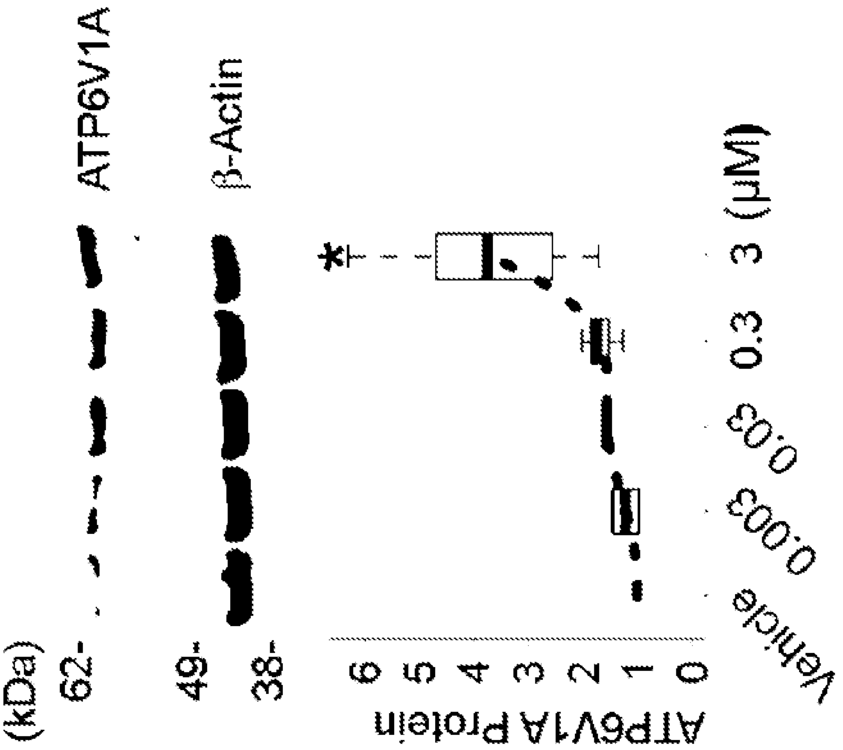

To verify this discovery, the inventors measured the transcriptional and translational levels of ATP6V1A in D21 iNs treated with the 3 HDAC inhibitors at a series of concentrations between 1 and 30 μM. The inventors found that only the novel compound NCH-51 effectively increased ATP6V1A levels (FIG. 6B-D), whereas SAHA and MS-275 were ineffective. This result suggests that the HDAC inhibitory activity of NCH-51 may not be required for modulating ATP6V1A. The inventors performed a time-course experiment and found that 24-hour treatment with NCH-51 resulted in the production of ATP6V1A mRNA. Specifically, administration of 3 μM NCH-51 was sufficient to significantly increase the protein yield (FIG. 6D).

Figure 6E:
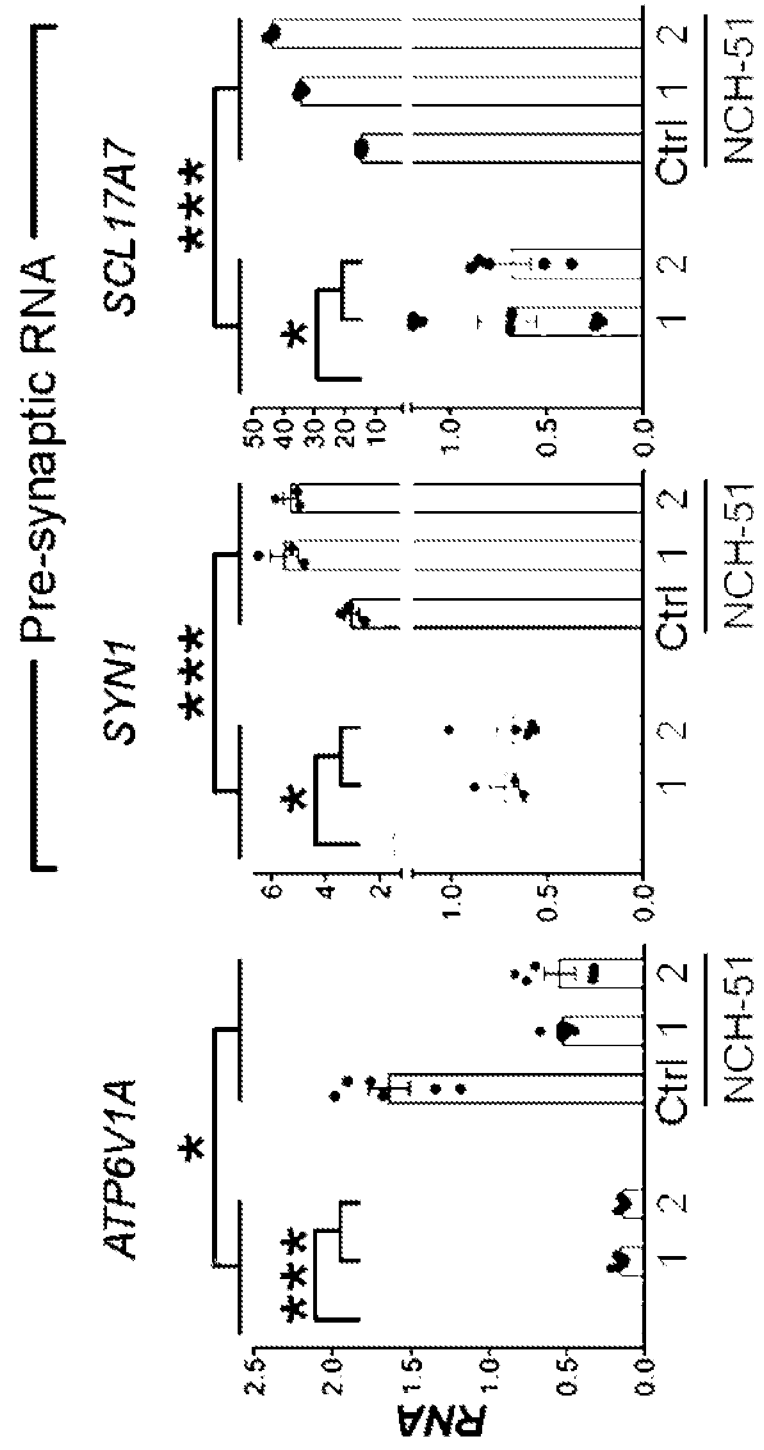
Figure 6F:
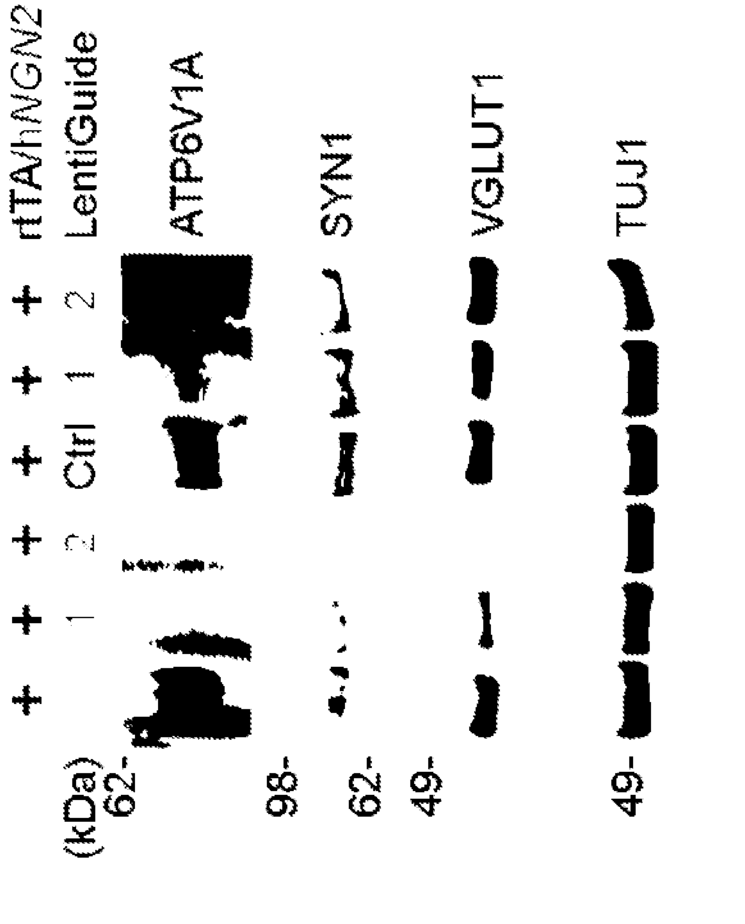
Figure 6G:
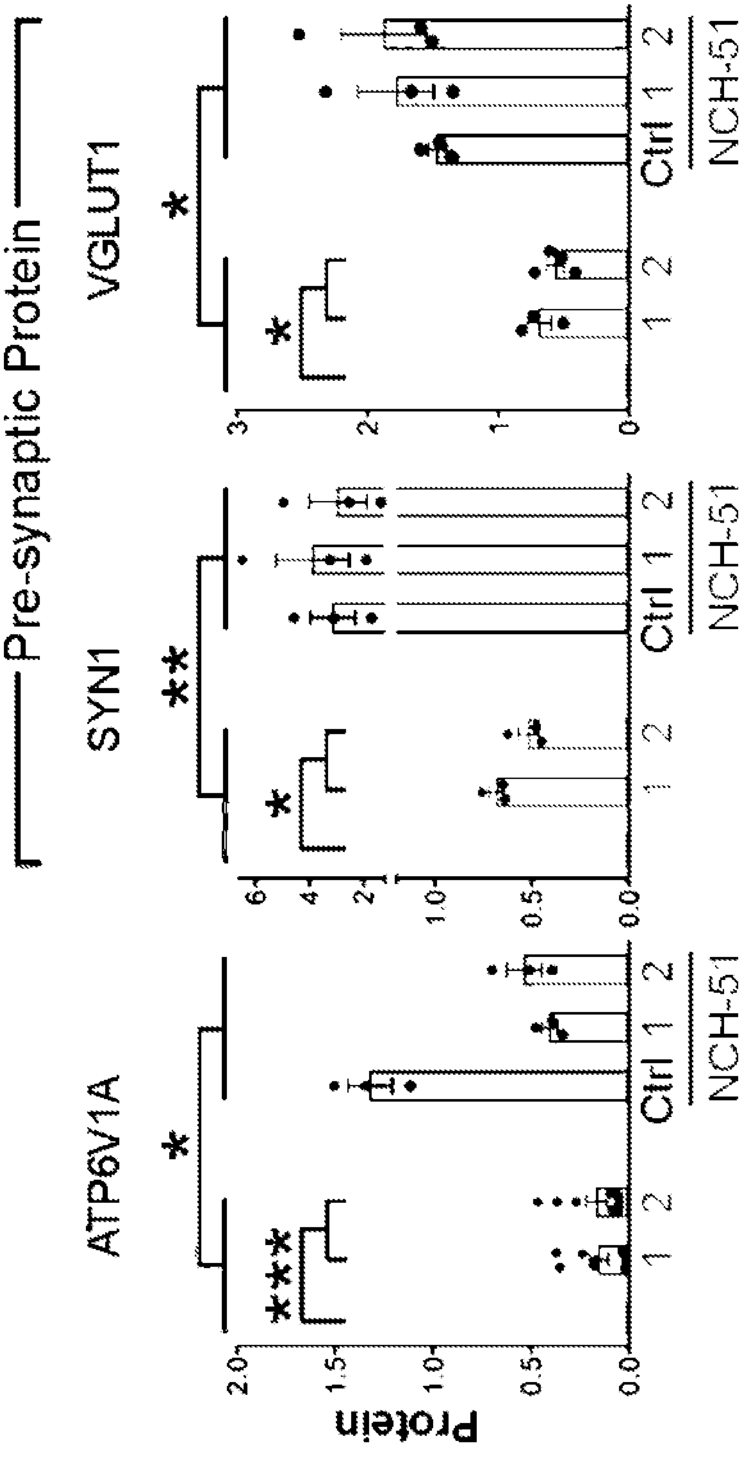
Figure 6H:
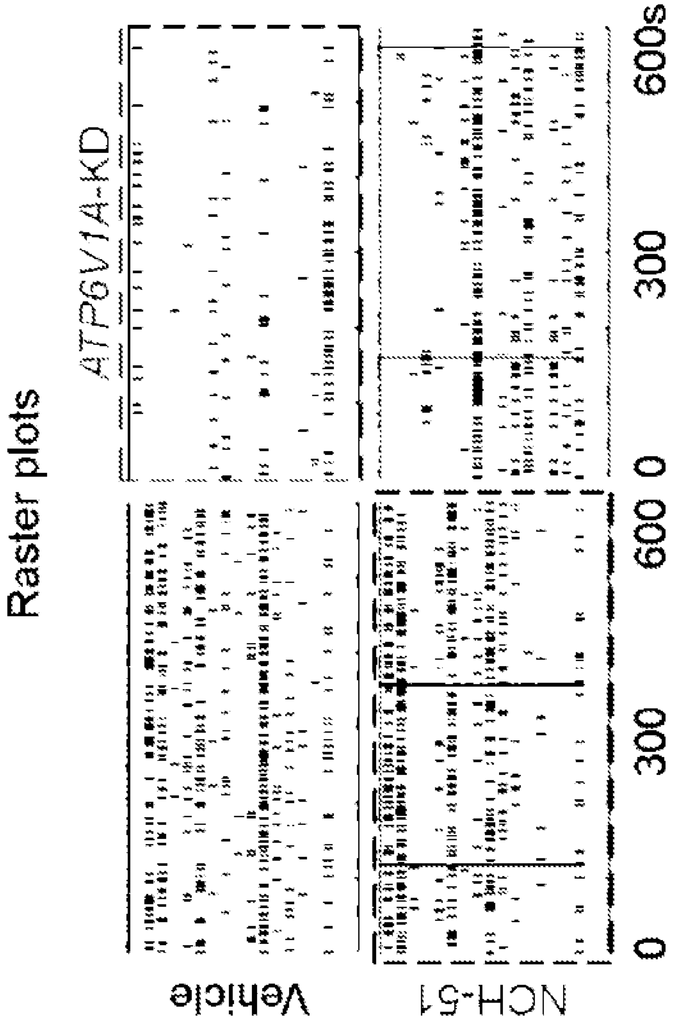
Figure 6J:
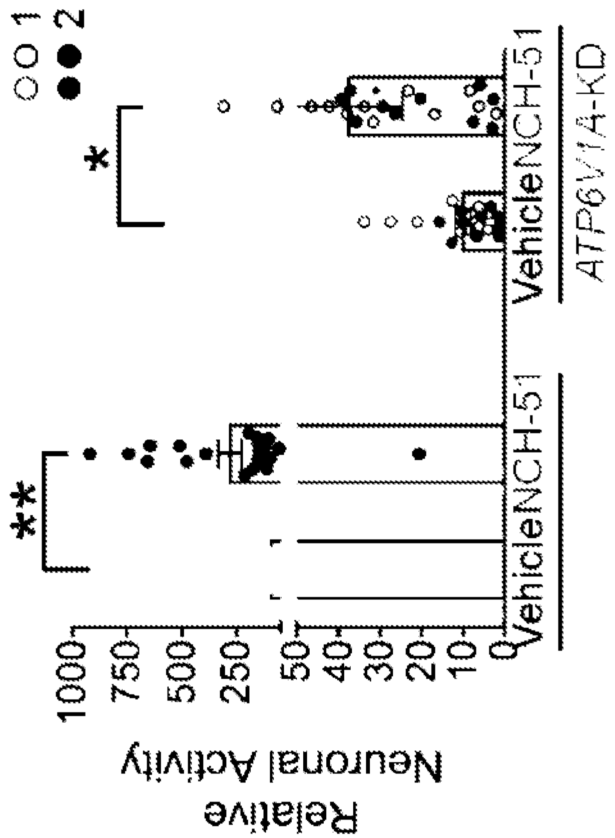
Figure 6I:
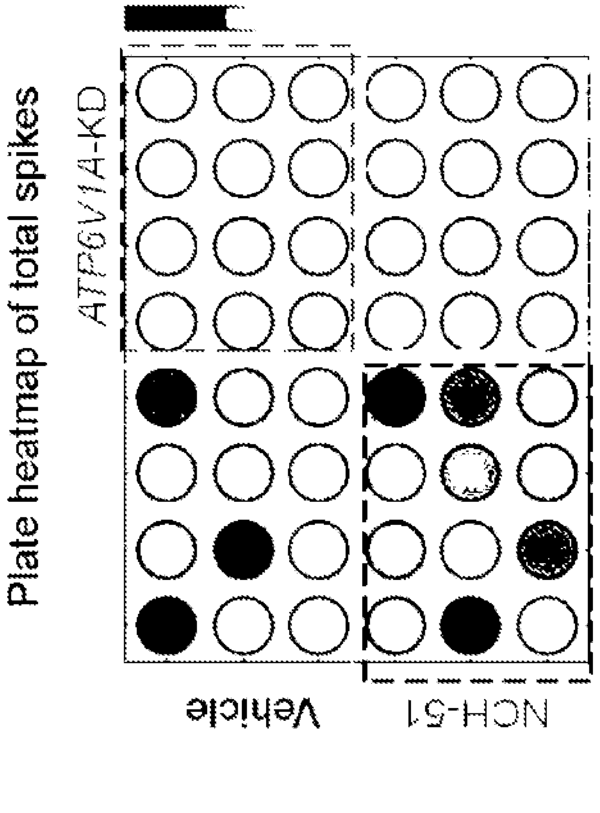

The inventors discovered that NCH-51 (3 μM, 24-hr) dramatically elevates the mRNA levels of ATP6V1A ($P<0.05$), presynaptic SYN1 ($P<0.001$), and SCL17A7 ($P<0.001$), particularly in ATP6V1A KD iNs (FIG. 6E). They also discovered that the protein levels of ATP6V1A ($P<0.05$), SYN1 ($P<0.01$) and VGLUT ($P<0.05$) are similarly increased by NCH-51 (FIG. 6F-G). They determined that NCH-51 had no effect on postsynaptic PSD95, while NCH-51 treatment resulted in increased the HOMER1 levels in either ATP6V1A KD iNs or the isogenic controls (FIG. S24G-I). The inventors also discovered that NCH-51 is a potent activator of neuronal activity using the MEA assay (FIG. 6H-J), partially restoring neuronal activity in ATP6V1A KD iNs (FIG. 6J).

Example 6

Oral Delivery of NCH-51 to Aβ42 Flies

Figure 6K:
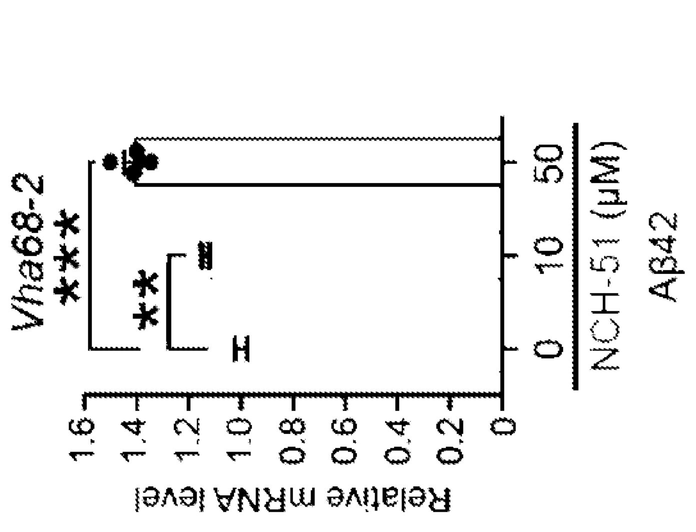

NCH-51 was fed to Aβ42 flies, which significantly increased the mRNA levels of Vha68-2 (FIG. 6K), but not of Vha68-1, in Aβ42 fly brains in a dose-dependent manner. Since Vha68-2 decreased more dramatically compared to Vha68-1 in Aβ42 fly brains (FIG. 4Q), an inference was made that NCH-51 treatment counteracts pathological reductions in Vha68-2 levels. In support, the data revealed that NCH-51 feeding did not increase mRNA levels of either Vha68-1 or Vha68-2 in control flies.

Figure 6L:
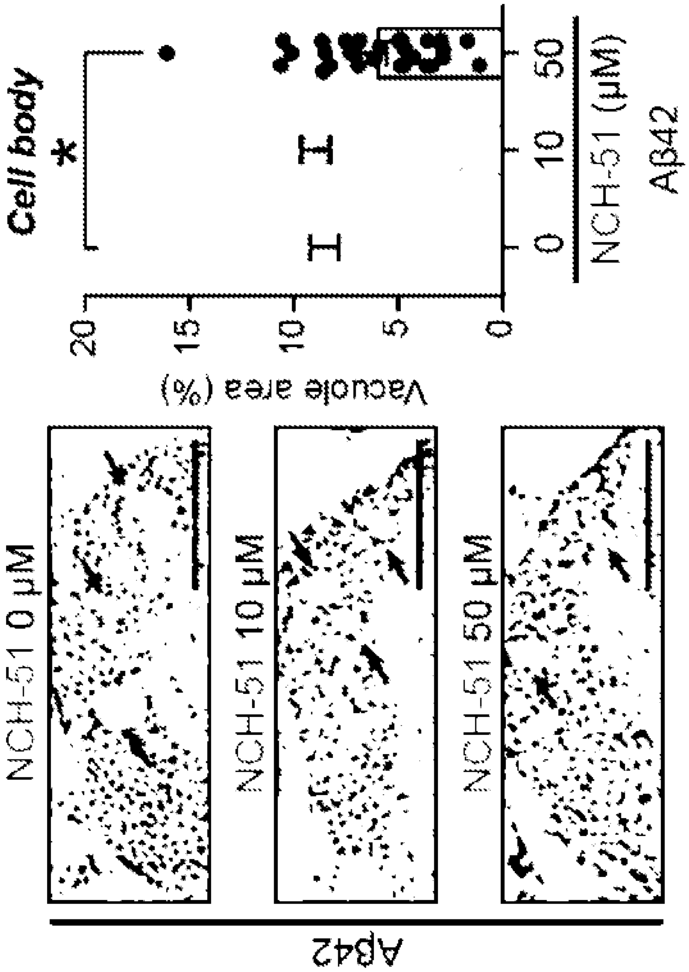
Figure 6M:
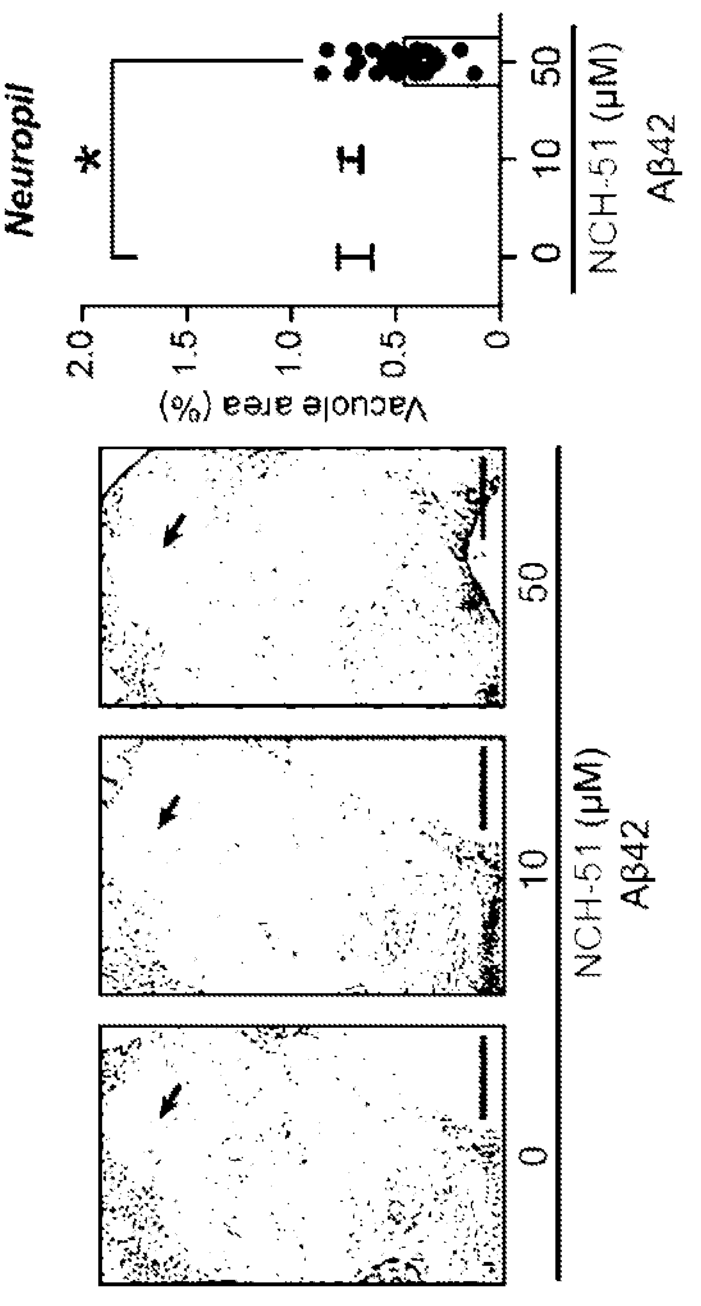
Figure 6N:
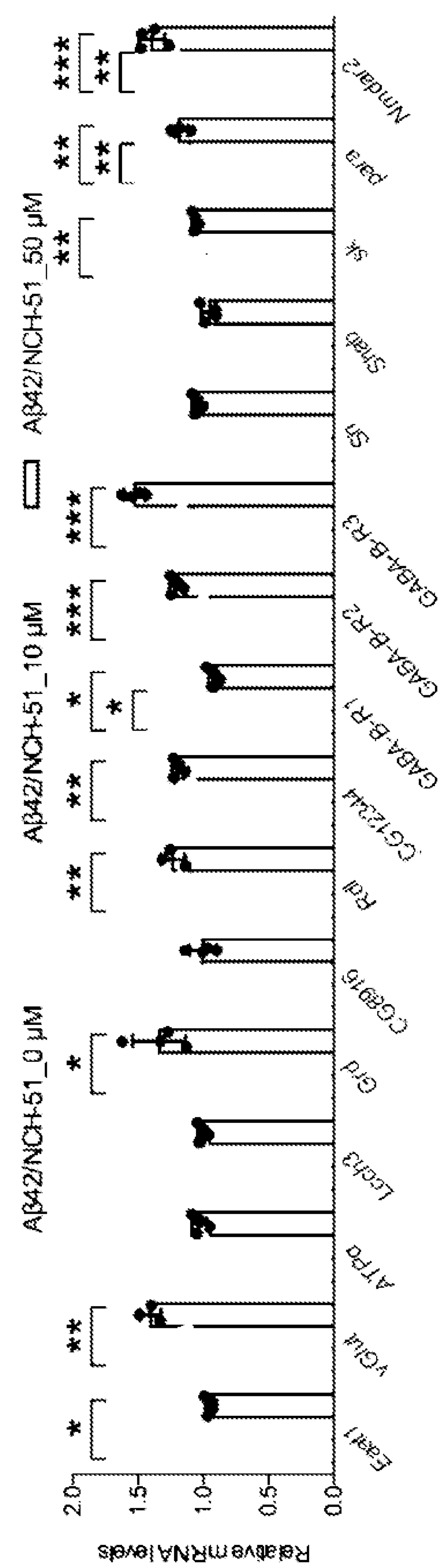

Aβ42 flies were treated with 0, 10, or 50 μM of NCH-51 during aging to examine its effects on neurodegeneration. Treatment with 50 μM of NCH-51 significantly suppressed cell loss (FIG. 6L) and neuropil degeneration (FIG. 6M) when compared to control (0 μM). In addition, NCH-51 did not affect Aβ42 levels in fly brains, showing that the observed effects of NCH-51 are not due to reduced Aβ42 levels. NCH-51 also increased the mRNA levels in 9 out of 16 key regulator genes of neuronal activity, including 4 key driver genes in Aβ42 fly brains: GABRA1/Grd in M62, SCN2A/para in M65, and GABBR2/GABA-B-R2,3 in M6 (FIG. 2D) (FIG. 6N). This data suggests that NCH-51 confers neuroprotective effects by correcting neuronal activity.

Example 7

LQ081-166 Increases the mRNA Level of ATP6V1A and the Neuronal Activities in hiPSC-Derived NPCs.

Given the evidence above that ATP6V1A and its regulated gene network are down regulated in LOAD brains in comparison with normal control brains, the inventors sought to identify compounds that can normalize the mRNA level of ATP6V1A and neuronal activities which were down in LOAD brains. Using gene expression-based testing and multi-electrode array (MEA) analysis in human induced pluripotent stem cell (hiPSC)-derived NPCs and NGN2 neurons, numerous novel compounds were examined for their effect to modulate ATP6V1A mRNA level as well as neuronal activities. The inventors discovered a cluster of compounds with structural similarities that are effective in causing these changes, including, for example, LQ081-166.

Thirty nine new compounds were synthesized by chemical synthesis and evaluated for their capability to elevate the mRNA level of ATP6V1A and the neuronal activities in hiPSC-derived NPCs. The inventors discovered that LQ081-166 most significantly increased ATP6V1A mRNA level (FIG. 1A, **, $p<0.0001$). In view of these results, an additional 18 derivatives of LQ081-166 were synthesized (Figure B). The inventors discovered that most of these derivatives with similar structures showed comparable efficacy (FIG. 1B-C). These disclosures indicate that the chemical structure to the right in LQ081-166 has a structure-activity relationship necessary for ATP6V1A activation. The thioester (—S—CO—) direction is essential because LQ081-32 did not affect ATP6V1A gene expression (FIG. 1B-C). The inventors found that LQ081-166 exhibited a dose-dependent effect (FIG. 1**D), and they chose 3 μM as an activity threshold.

CRISPR inhibition (CRISPRi) was used to repress endogenous ATP6V1A in hiPSC-derived NGN2 neurons. The inventors discovered that ATP6V1A KD neurons exhibited significantly reduced neuronal activity. The inventors also found that β-amyloid (1-42) peptide (AD) administration (5 μM, 24 hours) also considerably decreased spontaneous neuronal activity while had an insignificant decrease in ATP6V1A expression (FIG. 2A-B). Next, the inventors investigated whether LQ081-166 rescued the phenotypes of ATP6V1A deficit and reduced neuronal activity. The inventors found that LQ081-166 (3 μM, 24 hours) significantly increased ATP6V1A mRNA level in NGN2 neurons and was a potent activator of neuronal activity, partially restoring neuronal activity in ATP6V1A KD neurons, regardless of the presence/absence of Aβ exposure (FIG. 2A-B,  $p<0.01$, * $p<0.001$).

Example 8: S-(7-oxo-7-(thiazol-2-ylamino)heptyl) 2-methylpropanethioate (LQ070-27)

Scheme 1. Synthesis of LQ070-27

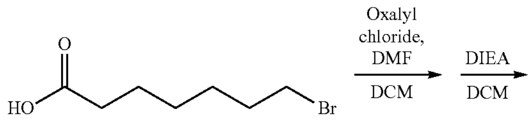

-continued

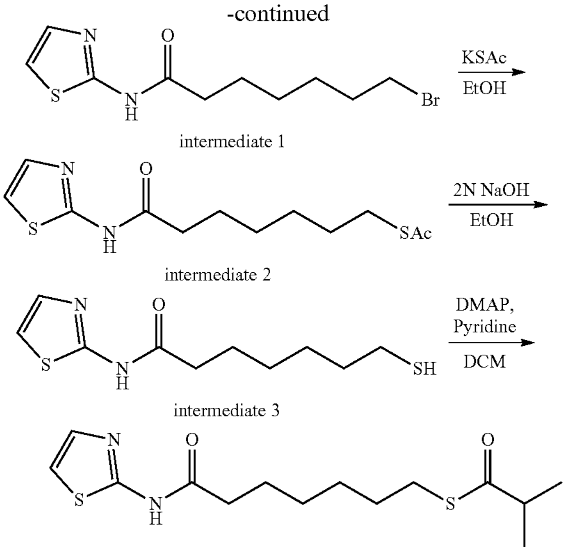

intermediate 1 intermediate 2 intermediate 3

LQ070-27

Intermediate 1: 7-Bromo-N-(thiazol-2-yl)heptanamide

To a solution of 7-bromoheptanoic acid (209 mg, 1 mmol) in DCM were added oxalyl chloride (130 μL, 1.5 mmol) and 1 drop of DMF. The mixture was stirred at room temperature for 2 h, the solvent was removed by evaporation which was used in next step without further purification. To a solution of 2-aminothiazole (100 mg, 1 mmol) and DIEA (200 μL, 1.2 mmol) in DCM was added a solution of the prepared acid chloride in DCM dropwise in an ice bath. The mixture was stirred at RT for 1 h. Then quenched with $NH_4Cl$ solution, the mixture was extracted with ethyl acetate. The combined organic extracts were washed with brine, dried over sodium sulfate, concentrated. The resulting residue was purified by silica gel flash chromatography to give the compound as white solid (280 mg, 96%). MS (ESI): m/z 291.1 $[M+H]^+$, 293.0 $[M+H+2]^+$.

Intermediate 2: S-(7-oxo-7-(thiazol-2-ylamino)heptyl) ethanethioate

A solution of intermediate 1 (280 mg, 0.96 mmol) and potassium thioacetate (439 mg, 3.85 mmol) was stirred at RT overnight. After the reaction was completed, the reaction mixture was diluted with ethyl acetate, and washed with brine, dried and concentrated. The resulting residue was purified by silica gel flash chromatography to give the compound as yellow solid (220 mg, 80%). MS (ESI): m/z 287.1 $[M+H]^+$.

Intermediate 3: 7-Mercapto-N-(thiazol-2-yl)heptanamide

To a solution of intermediate 2 (220 mg, 0.77 mmol) in ethanol was treated with 2N NaOH solution (1 mL, 2 mmol). After stirred at RT for 1h, the mixture was neutralized with 2N HCl solution at ice bath, and then the mixture was extracted with ethyl acetate. The combined organic extracts were washed with brine, dried over sodium sulfate, concentrated. The resulting residue was purified by silica gel flash chromatography to give the compound as yellow solid (163 mg, 86%). MS (ESI): m/z 245.2 $[M+H]^+$.

LQ070-27: S-(7-oxo-7-(thiazol-2-ylamino)heptyl) 2-methylpropanethioate

To a solution of intermediate 3 (40 mg, 0.16 mmol), pyridine (25 μL, 0.32 mmol) and DMAP (5 mg, 0.04 mmol) in DCM, isobutyryl chloride (22 mg, 0.21 mmol) was added at 0° C., and the solution was stirred at RT for 0.5 h. Then the resulting mixture was purified by preparative HPLC (5%-100% acetonitrile/0.1% TFA in $H_2O$) to afford final compound as white solid (32 mg, 63%). $^1H$ NMR (800 MHz, Methanol-$d_4$) δ 7.45 (d, J=3.1 Hz, 1H), 7.13 (d, J=3.7 Hz, 1H), 2.88 (t, J=7.3 Hz, 2H), 2.78-2.73 (m, 1H), 2.51 (t, J=7.5 Hz, 2H), 1.76-1.72 (m, 2H), 1.62-1.58 (m, 2H), 1.47-1.40 (m, 4H), 1.18 (d, J=6.9 Hz, 6H). MS (ESI): m/z 315.1 $[M+H]^+$.

Example 9: S-(7-([1,1'-biphenyl]-4-ylamino)-7-oxoheptyl) 2-methylpropanethioate (LQ070-39)

Compound LQ070-39 was prepared using same procedures as preparing compound LQ070-27 from 4-aminobiphenyl. $^1H$ NMR (800 MHz, Methanol-$d_4$) δ 7.66 (d, J=8.2 Hz, 2H), 7.63-7.58 (m, 4H), 7.43 (t, J=7.6 Hz, 2H), 7.32 (t, J=7.4 Hz, 1H), 2.89 (t, J=7.3 Hz, 2H), 2.78-2.73 (m, 1H), 2.42 (t, J=7.6 Hz, 2H), 1.77-1.72 (m, 2H), 1.64-1.59 (m, 2H), 1.49-1.42 (m, 4H), 1.18 (d, J=7.0 Hz, 6H). MS (ESI): m/z 384.4 $[M+H]^+$.

Example 10: S-(7-(methyl(4-phenylthiazol-2-yl)amino)-7-oxoheptyl) 2-methylpropanethioate (LQ070-40)

Scheme 2: Synthesis of LQ070-40

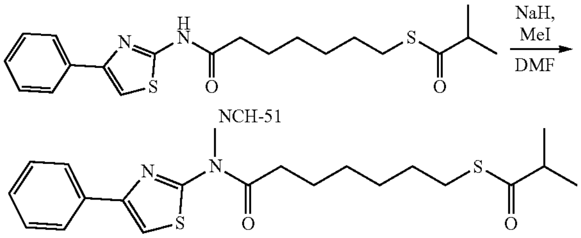

NCH-51

LQ070-40

Sodium hydride (12 mg, 0.3 mmol, 60% in mineral oil) was added to a solution of NCH-51 (Suzuki et al., 2005) (78 mg, 0.2 mmol) in dry dimethylformamide (1 mL) at ice bath. The mixture was stirred for 30 min at the same temperature, then iodomethane (13 μL, 0.21 mmol) was added. The resultant mixture was stirred for 1 h at room temperature. After cooling with ice bath, water was added slowly to quench the excess of sodium hydride. The mixture was extracted with ethyl acetate. Combined organic phases was washed with water and brine, dried over anhydrous sodium sulfate and concentrated. The residue was purified by silica gel flash chromatography to yield the title compound as white solid (50 mg, 62%). $^1H$ NMR (800 MHz, Methanol-$d_4$) δ 7.95 (d, J=7.7 Hz, 2H), 7.43-7.40 (m, 3H), 7.31 (t, J=7.4 Hz, 1H), 3.85 (s, 3H), 2.90 (t, J=7.3 Hz, 2H), 2.80-

2.74 (m, 3H), 1.79-1.75 (m, 2H), 1.65-1.60 (m, 2H), 1.51-1.46 (m, 4H), 1.19 (d, J=7.0 Hz, 6H). MS (ESI): m/z 405.2 $[M+H]^+$.

Example 11: 7-Acetamido-N-(4-phenylthiazol-2-yl) heptanamide (LQ070-41)

Scheme 3: Synthesis of LQ070-41

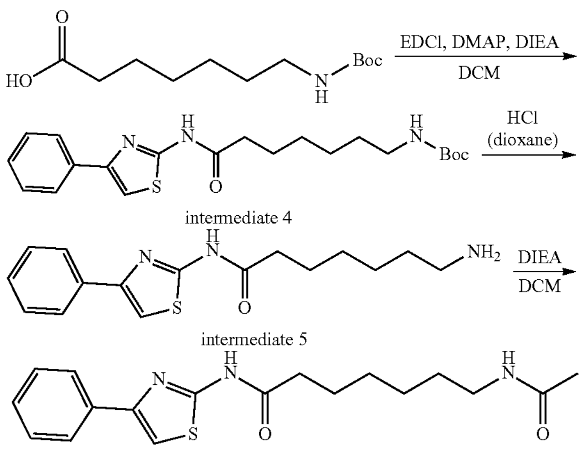

intermediate 4 intermediate 5

LQ070-41

Intermediate 4: tert-butyl (7-oxo-7-((4-phenylthiazol-2-yl)amino)heptyl)carbamate To the solution 7-((tert-Butoxycarbonyl)amino)heptanoic acid (25 mg, 0.1 mmol) in DCM were treated with 2-amino-4-phenylthiazole (18 mg, 0.1 mmol), EDCI (29 mg, 0.15 mmol), DMAP (2 mg, 0.02 mmol) and DIEA (26 μL, 0.15 mmol). After being stirred overnight at room temperature, the mixture was washed with brine, dried over sodium sulfate, concentrated. The resulting residue was purified by silica gel flash chromatography to give the compound as white solid (26 mg, 65%). MS (ESI): m/z 404.3 $[M+H]^+$.

Intermediate 5: 7-Amino-N-(4-phenylthiazol-2-yl)heptanamide

To the solution of intermediate 5 (200 mg, 0.5 mmol) in dioxane were treated with HCl (4M in dioxane, 1 mL). The resulting mixture was stirred at RT for 1 h. After the reaction was completed, the solution was evaporated to dryness, which was used in next step without further purification, $^1$H NMR (600 MHz, Methanol-$d_4$) δ 7.89-7.84 (m, 2H), 7.36 (t, J=7.7 Hz, 2H), 7.31 (s, 1H), 7.29-7.25 (m, 1H), 2.93-2.86 (m, 2H), 2.48 (t, J=7.4 Hz, 2H), 1.72 (p, J=7.3 Hz, 2H), 1.69-1.61 (m, 2H), 1.45-1.38 (m, 4H). MS (ESI): m/z 304.2 $[M+H]^+$.

LQ070-41: 7-Acetamido-N-(4-phenylthiazol-2-yl)heptanamide

To a solution of intermediate 5 (40 mg, 0.13 mmol), DIEA (64 μL, 0.39 mmol) in DCM, acetyl chloride (15 mg, 0.19 mmol) was added at 0° C., and the solution was stirred at RT for 10 min. Then the resulting mixture was purified by preparative HPLC (5%-100% acetonitrile/0.1% TFA in $H_2O$) to afford final compound as white solid (29 mg, 65%). $^1$H NMR (800 MHz, Methanol-$d_4$) δ 7.91 (d, J=7.7 Hz, 2H), 7.40 (t, J=7.6 Hz, 2H), 7.37 (s, 1H), 7.31 (t, J=7.4 Hz, 1H), 3.19 (t, J=7.1 Hz, 2H), 2.52 (t, J=7.5 Hz, 2H), 1.94 (s, 3H), 1.79-1.74 (m, 2H), 1.57-1.52 (m, 2H), 1.47-1.39 (m, 4H). MS (ESI): m/z 346.1 $[M+H]^+$.

Example 12: N-(4-phenylthiazol-2-yl)-7-propionamidoheptanamide (LQ070-42)

Compound LQ070-42 was prepared using same procedures as preparing compound LQ070-41 from propionyl chloride. $^1$H NMR (800 MHz, Methanol-$d_4$) δ 7.91 (d, J=7.7 Hz, 2H), 7.40 (t, J=7.6 Hz, 2H), 7.37 (s, 1H), 7.31 (t, J=7.4 Hz, 1H), 3.19 (t, J=7.2 Hz, 2H), 2.52 (t, J=7.5 Hz, 2H), 2.20 (q, J=7.7 Hz, 2H), 1.79-1.74 (m, 2H), 1.57-1.51 (m, 2H), 1.47-1.38 (m, 4H), 1.14 (t, J=7.7 Hz, 3H). MS (ESI): m/z 360.2 $[M+H]^+$.

Example 13: 7-Isobutyramido-N-(4-phenylthiazol-2-yl)heptanamide (LQ070-43)

Compound LQ070-43 was prepared using same procedures as preparing compound LQ070-41 from isobutyryl chloride. $^1$H NMR (800 MHz, Methanol-$d_4$) δ 7.91 (d, J=7.6 Hz, 2H), 7.40 (t, J=7.6 Hz, 2H), 7.37 (s, 1H), 7.31 (t, J=7.4 Hz, 1H), 3.19 (t, J=7.1 Hz, 2H), 2.52 (t, J=7.5 Hz, 2H), 2.46-2.42 (m, 1H), 1.79-1.73 (m, 2H), 1.57-1.53 (m, 2H), 1.47-1.39 (m, 4H), 1.12 (d, J=6.9 Hz, 6H). MS (ESI): m/z 374.2 $[M+H]^+$.

Example 14: N-(7-oxo-7-((4-phenylthiazol-2-yl)amino)heptyl)cyclopropanecarboxamide (LQ070-44)

Compound LQ070-44 was prepared using same procedures as preparing compound LQ070-41 from cyclopropanecarbonyl chloride. $^1$H NMR (800 MHz, Methanol-$d_4$) δ 7.91 (d, J=7.7 Hz, 2H), 7.40 (t, J=7.6 Hz, 2H), 7.37 (s, 1H), 7.31 (t, J=7.4 Hz, 1H), 3.21 (t, J=7.2 Hz, 2H), 2.52 (t, J=7.5 Hz, 2H), 1.79-1.74 (m, 2H), 1.59-1.53 (m, 3H), 1.47-1.40 (m, 4H), 0.87-0.83 (m, 2H), 0.76-0.73 (m, 2H). MS (ESI): m/z 372.3 $[M+H]^+$.

Example 15: N-(7-oxo-7-((4-phenylthiazol-2-yl)amino)heptyl)cyclohexanecarboxamide (LQ070-45)

Compound LQ070-45 was prepared using same procedures as preparing compound LQ070-41 from cyclohexanecarbonyl chloride. $^1$H NMR (800 MHz, Methanol-$d_4$) δ 7.91 (d, J=7.7 Hz, 1H), 7.40 (t, J=7.6 Hz, 2H), 7.37 (s, 1H), 7.31 (t, J=7.4 Hz, 1H), 3.18 (t, J=7.1 Hz, 2H), 2.52 (t, J=7.5 Hz, 2H), 2.20-2.15 (m, 1H), 1.82-1.73 (m, 6H), 1.72-1.68 (m, 1H), 1.56-1.52 (m, 2H), 1.49-1.38 (m, 6H), 1.36-1.23 (m, 3H). MS (ESI): m/z 414.3 $[M+H]^+$.

Example 16: N-(7-oxo-7-((4-phenylthiazol-2-yl)amino)heptyl)benzamide (LQ070-46)

Compound LQ070-46 was prepared using same procedures as preparing compound LQ070-41 from benzoyl chloride. $^1$H NMR (800 MHz, Methanol-$d_4$) δ 7.91 (d, J=7.7 Hz, 2H), 7.82 (d, J=7.7 Hz, 2H), 7.53 (t, J=7.4 Hz, 1H), 7.47 (t, J=7.6 Hz, 2H), 7.40 (t, J=7.6 Hz, 2H), 7.37 (s, 1H), 7.31 (t, J=7.4 Hz, 1H), 3.41 (t, J=7.2 Hz, 2H), 2.53 (t, J=7.4 Hz, 2H), 1.81-1.76 (m, 2H), 1.71-1.66 (m, 2H), 1.51-1.47 (m, 4H). MS (ESI): m/z 408.3 $[M+H]^+$.

Example 17: 7-oxo-7-((4-phenylthiazol-2-yl)amino) heptyl isobutyrate (LQ070-48)

Scheme 4: Synthesis of LQ070-48

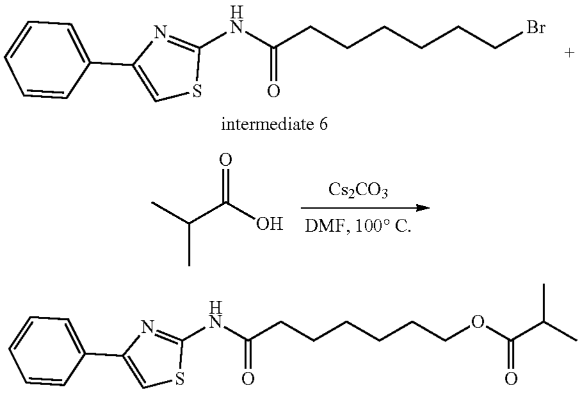

intermediate 6

LQ070-48

A solution of intermediate 6 (Suzuki et al., 2004) (40 mg, 0.1 mmol) and isobutyric acid (14 mg, 0.15 mmol) in 1 mL of DMF was treated with $Cs_2CO_3$ (65 mg, 0.2 mmol). The resulting mixture was stirred overnight at 100° C. After the reaction was completed, then the resulting mixture was purified by preparative HPLC (5%-100% acetonitrile/0.1% TFA in $H_2O$) to afford final compound as white solid (22 mg, 68%). $^1H$ NMR (800 MHz, Methanol-$d_4$) δ 7.91 (d, J=7.7 Hz, 2H), 7.40 (t, J=7.6 Hz, 2H), 7.37 (s, 1H), 7.31 (t, J=7.4 Hz, 1H), 4.10 (t, J=6.6 Hz, 2H), 2.58-2.54 (m, 1H), 2.52 (t, J=7.5 Hz, 2H), 1.80-1.74 (m, 23H), 1.72-1.67 (m, 2H), 1.49-1.43 (m, 4H), 1.16 (d, J=7.1 Hz, 6H). MS (ESI): m/z 375.2 $[M+H]^+$.

Example 18: 7-Isobutyramido-N-(naphthalen-2-yl)heptanamide (LQ076-16)

Scheme 5: Synthesis of LQ076-16

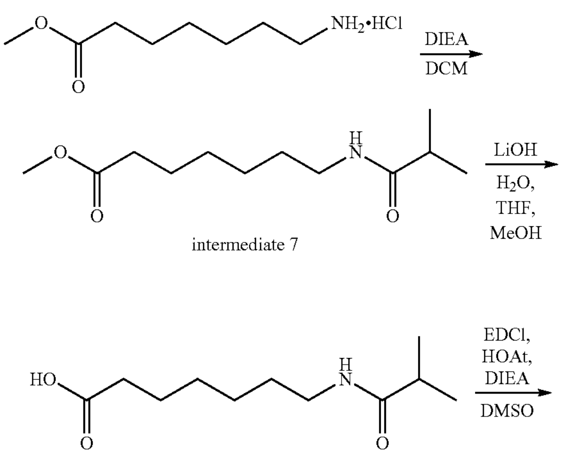

intermediate 7 intermediate 8

-continued

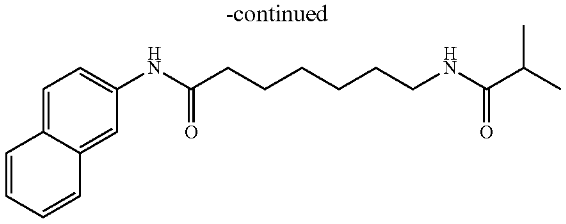

LQ076-16

To a solution of methyl 7-aminoheptanoate hydrochloride (920 mg, 4.7 mmol), DIEA (2 mL, 11.7 mmol) in DCM, isobutyryl chloride (500 mg, 4.7 mmol) was added at 0° C., and the solution was stirred at RT for 1 h. Then the mixture was washed with brine, dried over sodium sulfate, concentrated. The resulting residue was purified by silica gel flash chromatography to give the compound as oil (760 mg, 70%). MS (ESI): m/z 230.3 $[M+H]^+$.

Intermediate 8: 7-Isobutyramidoheptanoic Acid

To a solution of intermediate 7 (760 mg, 3.3 mmol) in 5 mL MeOH, 5 mL $H_2O$, and 5 mL THF, LiOH (120 mg, 5 mmol) was added. The mixture was stirred at RT overnight. Then the mixture was purified by reverse phase C18 column (10%-100% methanol/0.1% TFA in water) to afford intermediate 8 as white solid (486 mg, 68%). $^1H$ NMR (600 MHz, Methanol-$d_4$) δ 3.15 (t, J=7.1 Hz, 2H), 2.48-2.38 (m, 1H), 2.28 (t, J=7.5 Hz, 2H), 1.65-1.56 (m, 2H), 1.50 (p, J=7.2 Hz, 2H), 1.41-1.31 (m, 4H), 1.10 (d, J=7.0 Hz, 6H). MS (ESI): m/z 216.2 $[M+H]^+$.

LQ076-16: 7-Isobutyramido-N-(naphthalen-2-yl)heptanamide

To a solution of intermediate 8 (40 mg, 0.18 mmol) in DMSO (1 mL) were added 2-aminonaphthalene (26 mg, 0.18 mmol), EDCI (42 mg, 0.22 mmol), HOAt (30 mg, 0.22 mmol), and DIEA (36 mg, 0.28 mmol). After being stirred overnight at room temperature, the resulting mixture was purified by preparative HPLC (5%-100% acetonitrile/0.1% TFA in $H_2O$) to afford LQ076-16 as white solid (37 mg, 60%). $^1H$ NMR (600 MHz, Methanol-$d_4$) δ 8.10 (s, 1H), 7.69-7.62 (m, 3H), 7.44 (d, J=8.8 Hz, 1H), 7.32 (t, J=7.5 Hz, 1H), 7.29-7.23 (m, 1H), 3.04 (t, J=7.1 Hz, 2H), 2.33-2.26 (m, 3H), 1.62 (p, J=7.4 Hz, 2H), 1.40 (p, J=7.2 Hz, 2H), 1.34-1.22 (m, 4H), 0.98 (d, J=6.9 Hz, 6H). MS (ESI): m/z 341.2 $[M+H]^+$.

Example 19: 7-Isobutyramido-N-(3-(trifluoromethyl)phenyl)heptanamide (LQ076-17)

Compound LQ076-17 was prepared using same procedures as preparing compound LQ076-16 from 3-(trifluoromethyl)aniline. $^1H$ NMR (600 MHz, DMSO-$d_6$) δ 10.21 (s, 1H), 8.11 (s, 1H), 7.77 (d, J=8.1 Hz, 1H), 7.67 (t, J=5.6 Hz, 1H), 7.52 (t, J=8.0 Hz, 1H), 7.38-7.33 (m, 1H), 3.05-2.99 (m, 2H), 2.37-2.28 (m, 3H), 1.59 (p, J=7.4 Hz, 2H), 1.39 (p, J=7.1 Hz, 2H), 1.33-1.24 (m, 4H), 0.98 (d, J=6.9 Hz, 6H). MS (ESI): m/z 359.2 $[M+H]^+$.

Example 20: N-(benzo[d]thiazol-2-yl)-7-isobutyramidoheptanamide (LQ076-19)

Compound LQ076-19 was prepared using same procedures as preparing compound LQ076-16 from 2-aminobenzothiazole. $^1$H NMR (600 MHz, DMSO-$d_6$) δ 12.26 (s, 1H), 7.91 (d, J=7.9 Hz, 1H), 7.68 (d, J=8.1 Hz, 1H), 7.62 (t, J=5.6 Hz, 1H), 7.38 (t, J=7.7 Hz, 1H), 7.28-7.22 (m, 1H), 3.00-2.94 (m, 2H), 2.44 (t, J=7.5 Hz, 2H), 2.28 (hept, J=6.9 Hz, 1H), 1.57 (p, J=7.4 Hz, 2H), 1.34 (p, J=7.1 Hz, 2H), 1.29-1.20 (m, 4H), 0.94 (d, J=6.9 Hz, 6H). MS (ESI): m/z 348.2 [M+H]$^+$.

Example 21: 7-Isobutyramido-N-(quinolin-3-yl)heptanamide (LQ076-20)

Compound LQ076-20 was prepared using same procedures as preparing compound LQ076-16 from 3-aminoquinoline. $^1$H NMR (600 MHz, DMSO-$d_6$) δ 10.54 (s, 1H), 9.05 (d, J=2.5 Hz, 1H), 8.83 (d, J=2.5 Hz, 1H), 8.00 (dt, J=8.1, 1.6 Hz, 2H), 7.75-7.61 (m, 3H), 3.06-2.99 (m, 2H), 2.41 (t, J=7.4 Hz, 2H), 2.33 (p, J=6.8 Hz, 1H), 1.64 (p, J=7.4 Hz, 2H), 1.40 (p, J=7.2 Hz, 2H), 1.37-1.26 (m, 4H), 0.98 (d, J=6.9 Hz, 6H). MS (ESI): m/z 342.2 [M+H]$^+$.

Example 22: 7-Isobutyramido-N-(3-phenoxyphenyl)heptanamide (LQ076-21)

Compound LQ076-21 was prepared using same procedures as preparing compound LQ076-16 from 3-phenoxyaniline. $^1$H NMR (600 MHz, DMSO-$d_6$) δ 9.86 (s, 1H), 7.59 (t, J=5.6 Hz, 1H), 7.34-7.24 (m, 4H), 7.20 (t, J=8.1 Hz, 1H), 7.10-7.04 (m, 1H), 6.97-6.92 (m, 2H), 6.60 (ddd, J=8.0, 2.5, 1.0 Hz, 1H), 2.97-2.91 (m, 2H), 2.29-2.22 (m, 1H), 2.19 (t, J=7.5 Hz, 2H), 1.48 (p, J=7.1 Hz, 2H), 1.31 (p, J=7.1 Hz, 2H), 1.25-1.15 (m, 4H), 0.91 (d, J=6.9 Hz, 6H). MS (ESI): m/z 383.3 [M+H]$^+$.

Example 23: N-(3-(dimethylamino)phenyl)-7-isobutyramidoheptanamide (LQ076-28)

Compound LQ076-28 was prepared using same procedures as preparing compound LQ076-16 from N,N-dimethylbenzene-1,3-diamine. $^1$H NMR (600 MHz, Methanol-$d_4$) δ 8.17 (t, J=2.1 Hz, 1H), 7.56-7.50 (m, 2H), 7.39-7.35 (m, 1H), 3.17 (t, J=7.1 Hz, 2H), 2.47-2.40 (m, 3H), 1.72 (p, J=7.5 Hz, 2H), 1.53 (p, J=7.2 Hz, 2H), 1.45-1.35 (m, 4H), 1.11 (d, J=6.9 Hz, 6H). MS (ESI): m/z 334.3 [M+H]$^+$.

Example 24: 9-Isobutyramido-N-(4-phenylthiazol-2-yl)nonanamide (LQ076-31)

Scheme 6: Synthesis of LQ076-31

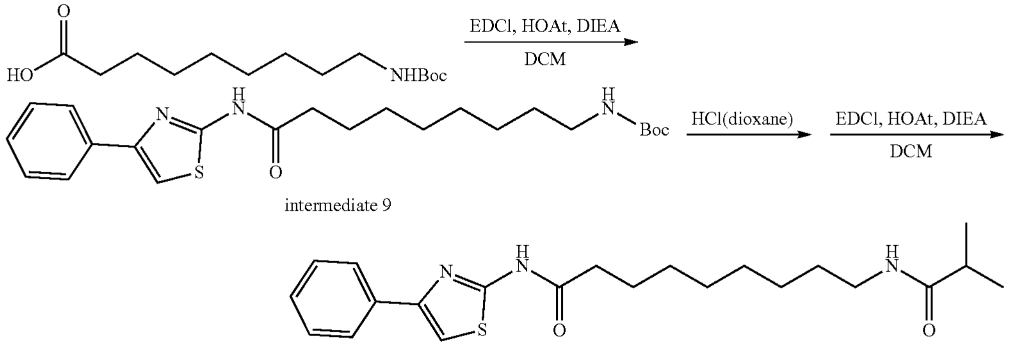

intermediate 9

LQ076-31

Intermediate 9: tert-butyl (9-oxo-9-((4-phenylthiazol-2-yl)amino)nonyl)carbamate To a solution of 9-((tert-Butoxycarbonyl)amino)nonanoic acid (78 mg, 0.28 mmol) in DCM were added 2-amino-4-phenylthiazole (50 mg, 0.28 mmol), EDCI (65 mg, 0.34 mmol), HOAt (46 mg, 0.34 mmol), and DIEA (54 mg, 0.42 mmol). After being stirred overnight at room temperature, the mixture was washed with brine, dried over sodium sulfate, concentrated. The resulting residue was purified by silica gel flash chromatography to give the compound as white solid (80 mg, 66%). MS (ESI): m/z 432.3 [M+H]$^+$.

LQ076-31: 9-Isobutyramido-N-(4-phenylthiazol-2-yl)nonanamide

To the solution of intermediate 9 (50 mg, 0.11 mmol) in dioxane were treated with HCl (4M in dioxane, 1 mL). The resulting mixture was stirred at RT for 1 h. After the reaction was completed, the solution was evaporated to dryness to get a white solid, which was used in next step without further purification. The obtained solid was dissolved in DCM, EDCI (25 mg, 0.14 mmol), HOAt (19 mg, 0.14 mmol), isobutyric acid (10 mg, 0.11 mmol) and DIEA (42 mg, 0.33 mmol) were added. After the reaction was stirred at RT overnight, the resulting mixture was purified by preparative HPLC (5%-100% acetonitrile/0.1% TFA in $H_2O$) to afford final compound as white solid (32 mg, 72%). $^1$H NMR (600 MHz, Methanol-$d_4$) δ 7.92-7.88 (m, 2H), 7.38 (t, J=7.8 Hz, 2H), 7.35 (s, TH), 7.31-7.28 (m, TH), 3.15 (t, J=7.1 Hz, 2H), 2.48 (t, J=7.5 Hz, 2H), 2.45-2.39 (m, 1H), 1.75-1.69 (m, 2H), 1.52-1.46 (m, 2H), 1.41-1.30 (m, 8H), 1.10 (d, J=6.9 Hz, 6H). MS (ESI): m/z 402.2 [M+H]$^+$.

Example 25: 3-Isobutyramido-N-(4-phenylthiazol-2-yl)propanamide (LQ076-32)

Compound LQ076-32 was prepared using same procedures as preparing compound LQ076-31 from Boc-β-Ala- OH. $^1H$ NMR (600 MHz, Methanol-$d_4$) δ 7.90-7.87 (m, 2H), 7.38 (t, J=7.7 Hz, 2H), 7.34 (s, 1H), 7.31-7.28 (m, 1H), 3.55 (t, J=6.6 Hz, 2H), 2.71 (t, J=6.6 Hz, 2H), 2.47-2.41 (m, 1H), 1.11 (d, J=6.9 Hz, 6H). MS (ESI): m/z 318.1 $[M+H]^+$.

Example 26: $N^1$-isopropyl-$N^8$-(4-phenylthiazol-2-yl)octanediamide (LQ076-35)

Scheme 7: Synthesis of LQ076-35

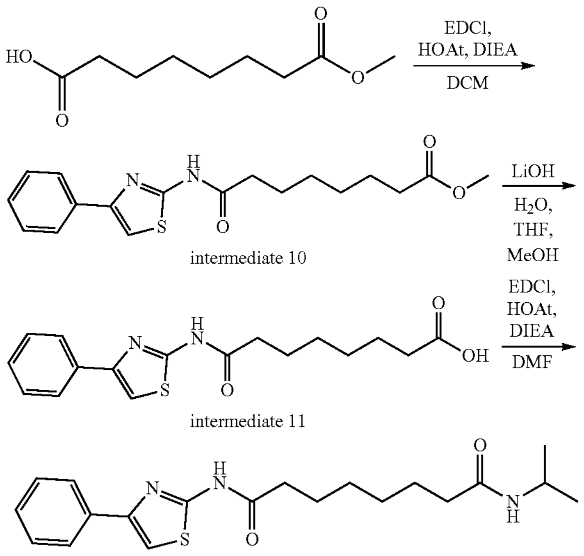

intermediate 10 intermediate 11

LQ076-35

Intermediate 10: Methyl 8-oxo-8-((4-phenylthiazol-2-yl)amino)octanoate

Intermediate 10 was prepared using same procedures as preparing intermediate 9 from suberic acid monomethyl ester. $^1H$ NMR (600 MHz, Methanol-$d_4$) δ 7.91-7.86 (m, 2H), 7.38 (t, J=7.7 Hz, 2H), 7.34 (s, 1H), 7.31-7.26 (m, 1H), 3.64 (s, 3H), 2.48 (t, J=7.5 Hz, 2H), 2.32 (t, J=7.4 Hz, 2H), 1.72 (p, J=7.4 Hz, 2H), 1.63 (p, J=7.5 Hz, 2H), 1.44-1.34 (m, 4H). MS (ESI): m/z 347.2 $[M+H]^+$.

Intermediate 11: 8-oxo-8-((4-phenylthiazol-2-yl)amino)octanoic acid

Intermediate 11 was prepared using same procedures as preparing intermediate 8. $^1H$ NMR (600 MHz, Methanol-$d_4$) δ 7.91-7.86 (m, 2H), 7.37 (t, J=7.7 Hz, 2H), 7.33 (s, 1H), 7.31-7.25 (m, 1H), 2.48 (t, J=7.5 Hz, 2H), 2.29 (t, J=7.4 Hz, 2H), 1.72 (p, J=7.4 Hz, 2H), 1.62 (p, J=7.3 Hz, 2H), 1.45-1.35 (m, 4H). MS (ESI): m/z 333.2 $[M+H]^+$.

LQ076-35: $N^1$-isopropyl-$N^8$-(4-phenylthiazol-2-yl) octanediamide

A solution of intermediate 11 (35 mg, 0.1 mmol) in DMF, EDCI (24 mg, 0.12 mmol), HOAt (16 mg, 0.12 mmol), isopropylamine (6 mg, 0.1 mmol) and DIEA (19 mg, 0.15 mmol) were added. After the reaction was stirred at RT overnight, the resulting mixture was purified by preparative HPLC (5%-100% acetonitrile/0.1% TFA in $H_2O$) to afford final compound as white solid (30 mg, 80%). $^1H$ NMR (600 MHz, Methanol-$d_4$) δ 7.90 (d, J=7.6 Hz, 2H), 7.39 (t, J=7.6 Hz, 2H), 7.35 (s, 1H), 7.30 (t, J=7.4 Hz, 1H), 3.99-3.93 (m, 1H), 2.49 (t, J=7.4 Hz, 2H), 2.16 (t, J=7.5 Hz, 2H), 1.77-1.70 (m, 2H), 1.67-1.58 (m, 2H), 1.45-1.35 (m, 4H), 1.13 (d, J=6.6 Hz, 6H). MS (ESI): m/z 374.3 $[M+H]^+$.

Example 27: $N^1$-isopropyl-$N^1$-methyl-$N^8$-(4-phenylthiazol-2-yl)octanediamide (LQ076-36)

Compound LQ076-36 was prepared using same procedures as preparing compound LQ076-35 from N-isopropylmethylamine. $^1H$ NMR (600 MHz, DMSO-$d_6$) δ 12.14 (s, 1H), 7.85-7.80 (m, 2H), 7.52 (s, 1H), 7.36 (t, J=7.7 Hz, 2H), 7.28-7.22 (m, 1H), 2.67 (s, 3H), 2.38 (t, J=7.4 Hz, 2H), 2.22 (t, J=7.5 Hz, 1H), 2.16 (t, J=7.5 Hz, 1H), 1.54 (p, J=7.4 Hz, 2H), 1.46-1.38 (m, 2H), 1.23 (p, J=3.6 Hz, 4H), 1.03 (d, J=6.6 Hz, 3H), 0.92 (d, J=6.8 Hz, 3H). HRMS m/z $[M+H]^+$ calcd for $C_{21}H_{30}N_3O_2S^+$ 388.2053. found 388.2059.

Example 28: 8-oxo-N-(4-phenylthiazol-2-yl)-8-(piperidin-1-yl)octanamide (LQ076-37)

Compound LQ076-37 was prepared using same procedures as preparing compound LQ076-35 from piperidine. $^1H$ NMR (600 MHz, Methanol-$d_4$) δ 7.91 (d, J=7.7 Hz, 2H), 7.40 (t, J=7.6 Hz, 2H), 7.37 (s, 1H), 7.31 (t, J=7.4 Hz, 1H), 3.54 (t, J=5.6 Hz, 2H), 3.51-3.47 (m, 2H), 2.51 (t, J=7.4 Hz, 2H), 2.40 (t, J=7.6 Hz, 2H), 1.80-1.73 (m, 2H), 1.70-1.57 (m, 6H), 1.55-1.51 (m, 2H), 1.46-1.41 (m, 4H). MS (ESI): m/z 400.3 $[M+H]^+$.

Example 29: 7-(Isopropylamino)-N-(4-phenylthiazol-2-yl)heptanamide (LQ076-38)

Scheme 8: Synthesis of LQ076-38

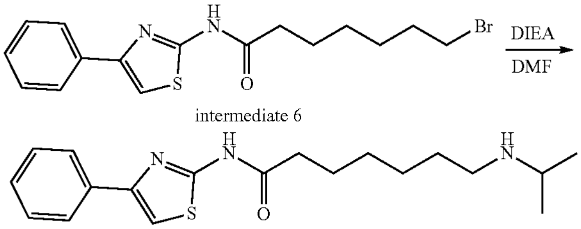

intermediate 6

LQ076-38

A solution of intermediate 6 (Suzuki et al., 2004) (40 mg, 0.1 mmol) and isopropylamine (6 mg, 0.1 mmol) in 1 mL of DMF was treated with DIEA (16 mg, 0.13 mmol). The resulting mixture was stirred overnight at RT. After the reaction was completed, the resulting mixture was purified by preparative HPLC (5%-60% acetonitrile/0.1% TFA in $H_2O$) to afford LQ076-38 as white solid (27 mg, 78%). $^1H$ NMR (600 MHz, Methanol-$d_4$) δ 7.92-7.89 (m, 2H), 7.40 (t, J=7.6 Hz, 2H), 7.36 (s, 1H), 7.32-7.28 (m, 1H), 3.38-3.34 (m, 1H), 3.01-2.96 (m, 2H), 2.53 (t, J=7.3 Hz, 2H), 1.80-1.74 (m, 2H), 1.72-1.66 (m, 2H), 1.50-1.43 (m, 4H), 1.33 (d, J=6.6 Hz, 6H). MS (ESI): m/z 346.2 $[M+H]^+$.

Example 30: 7-(Isopropyl(methyl)amino)-N-(4-phenylthiazol-2-yl)heptanamide (LQ076-39)

Compound LQ076-39 was prepared using same procedures as preparing compound LQ076-38 from N-isopropylmethylamine. $^1H$ NMR (600 MHz, Methanol-$d_4$) δ 7.92-7.89 (m, 2H), 7.40 (t, J=7.7 Hz, 2H), 7.37 (s, 1H), 7.33-7.30 (m, 1H), 3.64-3.59 (m, 1H), 3.19-3.13 (m, 1H), 3.05-3.00 (m, 1H), 2.77 (s, 3H), 2.54 (t, J=7.3 Hz, 2H), 1.82-1.75 (m, 3H), 1.74-1.68 (m, 1H), 1.51-1.44 (m, 4H), 1.35 (d, J=6.7 Hz, 3H), 1.31 (d, J=6.6 Hz, 3H). m/z 360.3 $[M+H]^+$. HRMS m/z $[M+H]^+$ calcd for $C_{20}H_{30}N_3OS^+$ 360.2104. found 360.2108.

Example 31: S-(7-oxo-7-((4-phenylthiazol-2-yl)amino)heptyl) 3-phenylpropanethioate (LQ081-166)

Scheme 9: Synthesis of LQ081-166

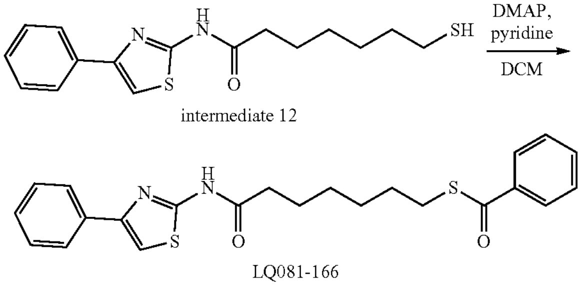

To a solution of intermediate 12 (Suzuki et al., 2005) (32 mg, 0.1 mmol), pyridine (24 μL, 0.3 mmol) and DMAP (5 mg, 0.04 mmol) in DCM, 3-phenylpropionyl chloride (14 mg, 0.1 mmol) was added at 0° C., and the solution was stirred at RT for 0.5 h. Then the resulting mixture was purified by preparative HPLC (5%-100% acetonitrile/0.1% TFA in $H_2O$) to afford final compound as white solid (30 mg, 66%). $^1H$ NMR (600 MHz, Methanol-$d_4$) δ 7.93-7.89 (m, 2H), 7.39 (t, J=7.7 Hz, 2H), 7.36 (s, 1H), 7.30 (t, J=7.4 Hz, 1H), 7.26 (t, J=7.6 Hz, 2H), 7.21-7.15 (m, 3H), 2.94 (t, J=7.5 Hz, 2H), 2.90-2.83 (m, 4H), 2.50 (t, J=7.5 Hz, 2H), 1.76-1.69 (m, 2H), 1.60-1.53 (m, 2H), 1.43-1.37 (m, 4H). HRMS m/z $[M+H]^+$ calcd for $C_{25}H_{29}N_2O_2S_2^+$ 453.1665. found 453.1670.

Example 32: S-(4-oxo-4-((4-phenylthiazol-2-yl)amino)butyl) 2-methylpropanethioate (LQ081-167)

Starting from 2-amino-4-phenylthiazole and 4-bromobutanoic acid, compound LQ081-167 was prepared according to same procedures and synthetic route as compound LQ070-27. $^1H$ NMR (600 MHz, Methanol-$d_4$) δ 7.93-7.88 (m, 2H), 7.40 (t, J=7.6 Hz, 2H), 7.36 (s, 1H), 7.30 (t, J=7.4 Hz, 1H), 2.98 (t, J=7.1 Hz, 2H), 2.80-2.74 (m, 1H), 2.59 (t, J=7.3 Hz, 2H), 1.99 (p, J=7.3 Hz, 2H), 1.19 (d, J=6.9 Hz, 6H). HRMS m/z $[M+H]^+$ calcd for $C_{17}H_{21}N_2O_2S_2^+$ 349.1039. found 349.1033.

Example 33: S-(5-oxo-5-((4-phenylthiazol-2-yl)amino)pentyl) 2-methylpropanethioate (LQ081-168)

Starting from 2-amino-4-phenylthiazole and 5-bromopentanoic acid, compound LQ081-168 was prepared according to same procedures and synthetic route as compound LQ070-27. $^1H$ NMR (600 MHz, Methanol-$d_4$) δ 7.92-7.88 (m, 2H), 7.39 (t, J=7.7 Hz, 2H), 7.36 (s, 1H), 7.30 (t, J=7.4 Hz, 1H), 2.92 (t, J=7.2 Hz, 2H), 2.79-2.72 (m, 1H), 2.52 (t, J=7.5 Hz, 2H), 1.80 (p, J=7.5 Hz, 2H), 1.66 (p, J=7.3 Hz, 2H), 1.17 (d, J=6.9 Hz, 6H). HRMS m/z $[M+H]^+$ calcd for $C_{18}H_{23}N_2O_2S_2^+$ 363.1195. found 363.1192.

Example 34: S-(6-oxo-6-((4-phenylthiazol-2-yl)amino)hexyl) 2-methylpropanethioate (LQ081-169)

Starting from 2-amino-4-phenylthiazole and 6-bromohexanoic Acid, compound LQ081-169 was prepared according to same procedures and synthetic route as compound LQ070-27. $^1H$ NMR (600 MHz, DMSO-$d_6$) δ 12.22 (s, 1H), 7.92-7.87 (m, 2H), 7.59 (s, 1H), 7.43 (t, J=7.8 Hz, 2H), 7.35-7.29 (m, 1H), 2.83 (t, J=7.2 Hz, 2H), 2.77-2.67 (m, 1H), 2.45 (t, J=7.4 Hz, 2H), 1.62 (p, J=7.4 Hz, 2H), 1.53 (p, J=7.4 Hz, 2H), 1.38-1.30 (m, 2H), 1.09 (d, J=6.9 Hz, 6H). HRMS m/z $[M+H]^+$ calcd for $C_{19}H_{25}N_2O_2S_2^+$ 377.1352. found 377.1357.

Example 35: S-(8-oxo-8-((4-phenylthiazol-2-yl)amino)octyl) 2-methylpropanethioate (LQ081-170)

Starting from 2-amino-4-phenylthiazole and 8-bromooctanoic acid, compound LQ081-170 was prepared according to same procedures and synthetic route as compound LQ070-27. $^1H$ NMR (600 MHz, Methanol-$d_4$) δ 7.93-7.88 (m, 2H), 7.39 (t, J=7.7 Hz, 2H), 7.35 (s, 1H), 7.32-7.28 (m, 1H), 2.85 (t, J=7.3 Hz, 2H), 2.73 (p, J=6.8 Hz, 1H), 2.49 (t, J=7.5 Hz, 2H), 1.76-1.70 (m, 2H), 1.56 (p, J=7.2 Hz, 2H), 1.42-1.36 (m, 6H), 1.16 (d, J=6.9 Hz, 6H). HRMS m/z $[M+H]^+$ calcd for $C_{21}H_{29}N_2O_2S_2^+$ 405.1665. found 405.1662.

Example 36: S-(7-oxo-7-((4-phenylthiazol-2-yl)amino)heptyl) benzothioate (LQ081-175)

Compound LQ081-175 was prepared using same procedures as preparing compound LQ081-166 from benzoyl chloride. $^1H$ NMR (600 MHz, Methanol-$d_4$) δ 7.97-7.94 (m, 2H), 7.92-7.89 (m, 2H), 7.62 (t, J=7.5 Hz, 1H), 7.49 (t, J=7.7 Hz, 2H), 7.40 (t, J=7.7 Hz, 2H), 7.36 (s, 1H), 7.31 (t, J=7.4 Hz, 1H), 3.10 (t, J=7.3 Hz, 2H), 2.52 (t, J=7.5 Hz, 2H), 1.81-1.69 (m, 4H), 1.56-1.45 (m, 4H). HRMS m/z $[M+H]^+$ calcd for $C_{23}H_{25}N_2O_2S_2^+$ 425.1352. found 425.1349.

Example 37: S-(7-oxo-7-((4-(pyridin-2-yl)thiazol-2-yl)amino)heptyl) 2-methylpropanethioate (LQ081-176)

Scheme 10: Synthesis of LQ081-176

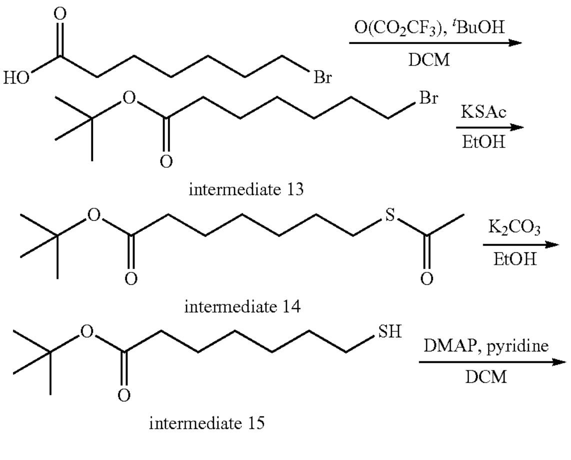

-continued

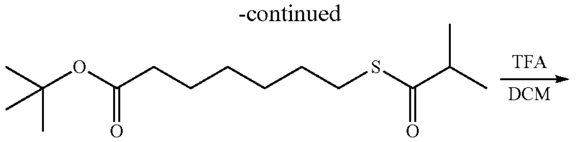

intermediate 16

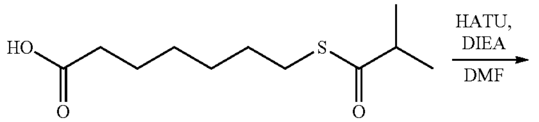

intermediate 17

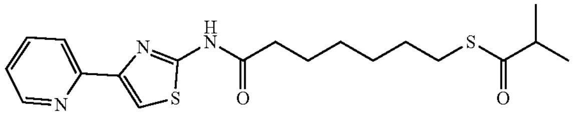

LQ081-176

Intermediate 13: tert-butyl 7-bromoheptanoate

Trifluoroacetic anhydride (420 mg, 2 mmol) was added at 0° C. to a solution of 7-bromoheptanoic acid (210 mg, 1 mmol) in DCM. The solution was stirred at rt for 2 h, then $^{t}$BuOH (222 mg, 3 mmol) was added. The solution was continued to stirred at rt for 1 h. Then saturated $NaHCO_3$ solution was added and the organic layer was separated and concentrated. The resulting residue was purified by silica gel flash chromatography to give the compound as colorless oil (180 mg, 68%). $^1$H NMR (600 MHz, Methanol-$d_4$) δ 3.46 (t, J=6.7 Hz, 2H), 2.25 (t, J=7.4 Hz, 2H), 1.91-1.83 (m, 2H), 1.61 (p, J=7.4 Hz, 2H), 1.52-1.44 (m, 11H), 1.41-1.33 (m, 2H).

Intermediate 14: tert-butyl 7-(acetylthio)heptanoate

Intermediate 14 was prepared using same procedures as preparing intermediate 2. $^1$H NMR (600 MHz, Methanol-$d_4$) δ 2.88 (t, J=7.3 Hz, 2H), 2.32 (s, 3H), 2.23 (t, J=7.4 Hz, 2H), 1.63-1.55 (m, 4H), 1.46 (s, 9H), 1.43-1.32 (m, 4H). MS (ESI): m/z 283.3 $[M+Na]^+$.

Intermediate 15: tert-butyl 7-mercaptoheptanoate

Intermediate 15 was prepared using same procedures as preparing intermediate 3. $^1$H NMR (600 MHz, Methanol-$d_4$) δ 2.54-2.49 (m, 2H), 2.24 (t, J=7.4 Hz, 2H), 1.66-1.55 (m, 4H), 1.48-1.40 (m, 11H), 1.38-1.32 (m, 2H).

Intermediate 16: tert-butyl 7-(isobutyrylthio)heptanoate

Intermediate 16 was prepared using same procedures as preparing compound LQ070-27. MS (ESI): m/z 311.4 $[M+Na]^+$.

Intermediate 17: 7-(Isobutyrylthio)heptanoic acid

Intermediate 16 (300 mg, 1 mmol) was dissolved in 5 mL DCM, to the resulting solution was added 3 mL TFA. After being stirred for 1 h at room temperature, the reaction mixture was concentrated and the residue was purified by reverse phase C18 column (10%-100% methanol/0.1% TFA in water) to afford intermediate 17 as white solid (180 mg, 77%). $^1$H NMR (600 MHz, Methanol-$d_4$) δ 2.87 (t, J=7.3 Hz, 2H), 2.79-2.73 (m, 1H), 2.30 (t, J=7.4 Hz, 2H), 1.66-1.55 (m, 4H), 1.45-1.34 (m, 4H), 1.18 (dd, J=6.9, 2.2 Hz, 6H).

LQ081-176: S-(7-oxo-7-((4-(pyridin-2-yl)thiazol-2-yl)amino)heptyl) 2-methylpropanethioate To the solution of intermediate 17 (24 mg, 0.1 mmol) in DMF were treated with 4-(2-pyridinyl)thiazol-2-amine (18 mg, 0.1 mmol), HATU (42 mg, 0.11 mmol) and DIEA (33 μL, 0.2 mmol). After being stirring overnight at room temperature, then the resulting mixture was purified by preparative HPLC (5%-100% acetonitrile/0.1% TFA in $H_2O$) to afford final compound as white solid (28 mg, 72%). $^1$H NMR (600 MHz, Methanol-$d_4$) δ 8.77 (d, J=5.8 Hz, 1H), 8.57-8.49 (m, 2H), 8.28 (s, 1H), 7.92-7.87 (m, 1H), 2.87 (t, J=7.3 Hz, 2H), 2.77-2.69 (m, 1H), 2.56 (t, J=7.4 Hz, 2H), 1.75 (p, J=7.4 Hz, 2H), 1.63-1.55 (m, 2H), 1.49-1.39 (m, 4H), 1.16 (d, J=6.9 Hz, 6H). HRMS m/z $[M+H]^+$ calcd for $C_{19}H_{26}N_3O_2S_2^+$ 392.1461. found 392.1467.

Example 38: 7-(Methylthio)-N-(4-phenylthiazol-2-yl)heptanamide (LQ081-181)

Scheme 11: Synthesis of LQ081-181

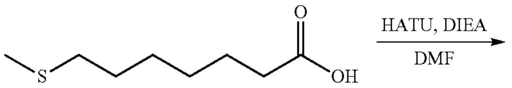

intermediate 18

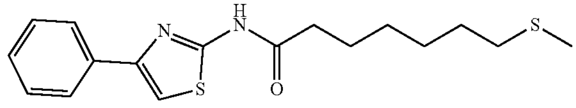

LQ081-181

To the solution of intermediate 18 (Ebner et al., 2010) (18 mg, 0.1 mmol) in DMF were treated with 2-amino-4-phenylthiazole (18 mg, 0.1 mmol), HATU (46 mg, 0.12 mmol) and DIEA (25 μL, 0.15 mmol). After being stirring overnight at room temperature, then the resulting mixture was purified by preparative HPLC (5%-100% acetonitrile/0.1% TFA in $H_2O$) to afford final compound as white solid (23 mg, 69%). $^1$H NMR (600 MHz, Methanol-$d_4$) δ 7.92-7.88 (m, 2H), 7.39 (t, J=7.6 Hz, 2H), 7.36 (s, 1H), 7.30 (t, J=7.4 Hz, 1H), 2.53-2.47 (m, 4H), 2.07 (s, 3H), 1.74 (p, J=7.5 Hz, 2H), 1.62 (p, J=7.3 Hz, 2H), 1.51-1.38 (m, 4H). HRMS m/z $[M+H]^+$ calcd for $C_{17}H_{23}N_2O_1S_2^+$ 335.1246. found 335.1250.

Example 39: S-(7-((1H-indol-6-yl)amino)-7-oxo-heptyl) 2-methylpropanethioate (LQ081-183)

Compound LQ081-183 was prepared using same procedures as preparing compound LQ081-176 from 6-aminoindole. $^1$H NMR (600 MHz, Methanol-$d_4$) δ 7.87 (s, 1H), 7.47 (d, J=8.4 Hz, 1H), 7.19 (d, J=3.1 Hz, 1H), 6.99 (dd, J=8.4, 1.9 Hz, 1H), 6.40 (d, J=3.0 Hz, 1H), 2.86 (t, J=7.3 Hz, 2H), 2.78-2.68 (m, 1H), 2.39 (t, J=7.5 Hz, 2H), 1.72 (p, J=7.6 Hz, 2H), 1.58 (p, J=7.2 Hz, 2H), 1.47-1.37 (m, 5H), 1.16 (d, J=6.9 Hz, 7H). HRMS m/z $[M+H]^+$ calcd for $C_{19}H_{27}N_2O_2S^+$ 347.1788. found 347.1783.

Example 40: S-(7-((3-chlorophenyl)amino)-7-oxoheptyl) 2-methylpropanethioate (LQ081-185)

Compound LQ081-185 was prepared using same procedures as preparing compound LQ081-176 from 3-chloroaniline. $^1H$ NMR (600 MHz, Methanol-$d_4$) δ 7.76 (t, J=2.0 Hz, 1H), 7.44-7.40 (m, 1H), 7.28 (t, J=8.1 Hz, 1H), 7.08 (dd, J=8.3, 2.1 Hz, 1H), 2.87 (t, J=7.3 Hz, 2H), 2.77-2.70 (m, 1H), 2.38 (t, J=7.5 Hz, 2H), 1.70 (p, J=7.4 Hz, 2H), 1.59 (p, J=7.2 Hz, 2H), 1.48-1.36 (m, 4H), 1.17 (d, J=6.9 Hz, 6H). HRMS m/z $[M+H]^+$ calcd for $C_{17}H_{25}ClNO_2S^+$ 342.1289. found 342.1285.

Example 41: S-(7-(benzo[d]oxazol-2-ylamino)-7-oxoheptyl) 2-methylpropanethioate (LQ081-186)

Compound LQ081-186 was prepared using same procedures as preparing compound LQ081-176 from 2-aminobenzoxazole. $^1H$ NMR (600 MHz, Methanol-$d_4$) δ 7.57 (d, J=7.7 Hz, 1H), 7.51 (d, J=7.8 Hz, 1H), 7.36-7.27 (m, 2H), 2.88 (t, J=7.3 Hz, 2H), 2.79-2.69 (m, 1H), 2.58-2.51 (m, 2H), 1.78-1.72 (m, 2H), 1.63-1.57 (m, 2H), 1.48-1.40 (m, 4H), 1.16 (d, J=6.9 Hz, 6H). HRMS m/z $[M+H]^+$ calcd for $C_{18}H_{25}N_2O_3S^+$ 349.1580. found 349.1585.

Example 42: S-(7-oxo-7-((4-phenylthiazol-2-yl)amino)heptyl) 2-phenylethanethioate (LQ108-13)

Compound LQ108-13 was prepared using same procedures as preparing compound LQ081-166 from phenylacetyl chloride. $^1H$ NMR (600 MHz, DMSO-$d_6$) δ 12.14 (s, 1H), 7.85-7.80 (m, 2H), 7.51 (s, 1H), 7.35 (t, J=7.8 Hz, 2H), 7.28-7.22 (m, 3H), 7.21-7.16 (m, 3H), 3.82 (s, 2H), 2.74 (t, J=7.3 Hz, 2H), 2.36 (t, J=7.4 Hz, 2H), 1.51 (p, J=7.4 Hz, 2H), 1.45-1.37 (m, 2H), 1.27-1.17 (m, 4H). HRMS m/z $[M+H]^+$ calcd for $C_{24}H_{27}N_2O_2S_2^+$ 439.1508. found 439.1512.

Example 43: S-(7-oxo-7-((4-phenylthiazol-2-yl)amino)heptyl) 3-phenylbutanethioate (LQ108-15)

Scheme 12: Synthesis of LQ108-15

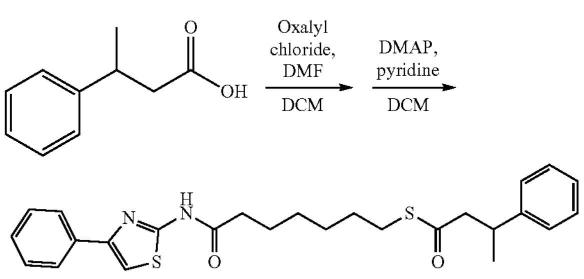

LQ108-15

To a solution of 3-phenylbutyric acid (22 mg, 0.13 mmol) in DCM were added oxalyl chloride (21 μL, 0.25 mmol) and 1 drop of DMF. The mixture was stirred at room temperature for 2 h, the solvent was removed by evaporation which was used in next step without further purification. To a solution of 2-amino-4-phenylthiazole (40 mg, 0.16 mmol), pyridine (25 μL, 0.32 mmol) and DMAP (5 mg, 0.04 mmol) in DCM, the obtained acyl chloride was added at 0° C., and the solution was stirred at RT for 0.5 h. Then the resulting mixture was purified by preparative HPLC (5%-100% acetonitrile/0.1% TFA in $H_2O$) to afford final compound as white solid (31 mg, 55%). $^1H$ NMR (600 MHz, Methanol-$d_4$) δ 7.93-7.89 (m, 2H), 7.40 (t, J=7.7 Hz, 2H), 7.37 (s, 1H), 7.32-7.25 (m, 3H), 7.22-7.20 (m, 2H), 7.19-7.15 (m, 1H), 3.29 (q, J=7.2 Hz, 1H), 2.88-2.77 (m, 4H), 2.49 (t, J=7.4 Hz, 2H), 1.71 (p, J=7.4 Hz, 2H), 1.51 (p, J=7.0 Hz, 2H), 1.41-1.33 (m, 4H), 1.28 (d, J=7.0 Hz, 3H). HRMS m/z $[M+H]^+$ calcd for $C_{26}H_{31}N_2O_3S_2^+$ 467.1821. found 467.1821.

Example 44: S-(7-oxo-7-((4-phenylthiazol-2-yl)amino)heptyl) 4-phenylbutanethioate (LQ108-16)

Compound LQ108-16 was prepared using same procedures as preparing compound LQ081-166 from 4-phenylbutanoyl chloride. $^1H$ NMR (600 MHz, DMSO-$d_6$) δ 12.22 (s, 1H), 7.92-7.87 (m, 2H), 7.59 (s, 1H), 7.43 (t, J=7.7 Hz, 2H), 7.34-7.30 (m, 1H), 7.29-7.25 (m, 2H), 7.20-7.15 (m, 3H), 2.83 (t, J=7.2 Hz, 2H), 2.60-2.53 (m, 4H), 2.45 (t, J=7.4 Hz, 2H), 1.85 (p, J=7.5 Hz, 2H), 1.60 (p, J=7.3 Hz, 2H), 1.50 (p, J=7.2 Hz, 2H), 1.37-1.26 (m, 4H). HRMS m/z $[M+H]^+$ calcd for $C_{26}H_{31}N_2O_3S_2^+$ 467.1821. found 467.1822.

Example 45: S-(7-oxo-7-((4-phenylthiazol-2-yl)amino)heptyl) 3-(4-methoxyphenyl)propanethioate (LQ108-17)

Compound LQ108-17 was prepared using same procedures as preparing compound LQ081-166 from 3-(4-methoxyphenyl)propanoyl chloride. $^1H$ NMR (600 MHz, DMSO-$d_6$) δ 12.22 (s, 1H), 7.92-7.87 (m, 2H), 7.61-7.57 (m, 1H), 7.43 (t, J=7.7 Hz, 2H), 7.35-7.29 (m, 1H), 7.14-7.08 (m, 2H), 6.85-6.79 (m, 2H), 3.70 (s, 3H), 2.87-2.78 (m, 6H), 2.45 (t, J=7.4 Hz, 2H), 1.59 (p, J=7.3 Hz, 2H), 1.48 (p, J=7.2 Hz, 2H), 1.33-1.24 (m, J=5.1, 4.4 Hz, 4H). HRMS m/z $[M+H]^+$ calcd for $C_{26}H_{31}N_2O_3S_2^+$ 483.1771. found 483.1765.

Example 46: S-(7-oxo-7-((4-phenylthiazol-2-yl)amino)heptyl) 3-(3-(trifluoromethyl)phenyl)propanethioate (LQ108-18)

Compound LQ108-18 was prepared using same procedures as preparing compound LQ108-15 from 3-(3-trifluoromethylphenyl)propionic acid. $^1H$ NMR (600 MHz, Methanol-$d_4$) δ 7.92-7.88 (m, 2H), 7.51-7.44 (m, 4H), 7.39 (t, J=7.7 Hz, 2H), 7.35 (s, 1H), 7.32-7.28 (m, 1H), 3.03 (t, J=7.4 Hz, 2H), 2.93-2.84 (m, 4H), 2.49 (t, J=7.5 Hz, 2H), 1.75-1.68 (m, 2H), 1.59-1.51 (m, 2H), 1.43-1.35 (m, 4H). HRMS m/z $[M+H]^+$ calcd for $C_{26}H_{28}F_3N_2O_2S_2^+$ 521.1539. found 521.1545.

Example 47: S-(7-oxo-7-((4-phenylthiazol-2-yl)amino)heptyl) 3-(3-fluorophenyl)propanethioate (LQ108-19)

Compound LQ108-19 was prepared using same procedures as preparing compound LQ108-15 from 3-(3-fluorophenyl)propionic acid. $^1H$ NMR (600 MHz, Methanol-$d_4$) δ 7.93-7.88 (m, 2H), 7.39 (t, J=7.7 Hz, 2H), 7.36 (s, 1H), 7.33-7.24 (m, 2H), 7.03-6.98 (m, 1H), 6.96-6.89 (m, 2H), 2.96 (t, J=7.4 Hz, 2H), 2.90-2.85 (m, 4H), 2.50 (t, J=7.5 Hz, 2H), 1.76-1.70 (m, 2H), 1.59-1.53 (m, 2H), 1.44-1.37 (m, 4H). HRMS m/z $[M+H]^+$ calcd for $C_{25}H_{28}FN_2O_2S_2^+$ 471.1571. found 471.1574.

Example 48: S-(7-oxo-7-((4-phenylthiazol-2-yl)amino)heptyl) 3-(4-fluorophenyl)propanethioate (LQ108-20)

Compound LQ108-20 was prepared using same procedures as preparing compound LQ108-15 from 3-(4-fluorophenyl)propanoic acid. $^1$H NMR (600 MHz, Methanol-$d_4$) δ 7.96-7.83 (m, 2H), 7.47-7.27 (m, 3H), 7.23-7.13 (m, 3H), 7.03-6.91 (m, 2H), 2.92 (t, J=7.4 Hz, 2H), 2.90-2.81 (m, 4H), 2.49 (t, J=7.4 Hz, 2H), 1.83-1.67 (m, 2H), 1.63-1.50 (m, 2H), 1.48-1.32 (m, 4H). HRMS m/z $[M+H]^+$ calcd for $C_{25}H_{28}FN_2O_2S_2^+$ 471.1571. found 471.1577.

Example 49: S-(7-oxo-7-((4-phenylthiazol-2-yl)amino)heptyl) (E)-3-phenylprop-2-enethioate (LQ108-22)

Compound LQ108-22 was prepared using same procedures as preparing compound LQ081-166 from cinnamoyl chloride. $^1$H NMR (600 MHz, Methanol-$d_4$) δ 7.92-7.88 (m, 2H), 7.64-7.59 (m, 3H), 7.43-7.37 (m, 5H), 7.35 (s, 1H), 7.32-7.28 (m, 1H), 6.85 (d, J=15.8 Hz, 1H), 3.03 (t, J=7.3 Hz, 2H), 2.52 (t, J=7.5 Hz, 2H), 1.76 (p, J=7.4 Hz, 2H), 1.68 (p, J=7.3 Hz, 2H), 1.53-1.42 (m, 4H). HRMS m/z $[M+H]^+$ calcd for $C_{25}H_{27}N_2O_2S_2^+$ 451.1508. found 451.1512.

Example 50: S-phenethyl 8-oxo-8-((4-phenylthiazol-2-yl)amino)octanethioate (LQ108-32)

Compound LQ108-32 was prepared using same procedures as preparing compound LQ076-35 from 2-phenylethanethiol. $^1$H NMR (600 MHz, DMSO-$d_6$) δ 12.14 (s, 1H), 7.85-7.80 (m, 2H), 7.52 (s, 1H), 7.36 (t, J=7.7 Hz, 2H), 7.27-7.20 (m, 3H), 7.17-7.12 (m, 3H), 3.04-2.99 (m, 2H), 2.73 (t, J=7.5 Hz, 2H), 2.48 (t, J=7.3 Hz, 2H), 2.37 (t, J=7.4 Hz, 2H), 1.56-1.45 (m, 4H), 1.25-1.18 (m, 4H). HRMS m/z $[M+H]^+$ calcd for $C_{25}H_{29}N_2O_2S_2^+$ 453.1665. found 453.1668.

Example 51: S-(6-(4-phenylthiazole-2-carboxamido)hexyl) 3-phenylpropanethioate (LQ108-41)

Scheme 13: Synthesis of LQ108-41

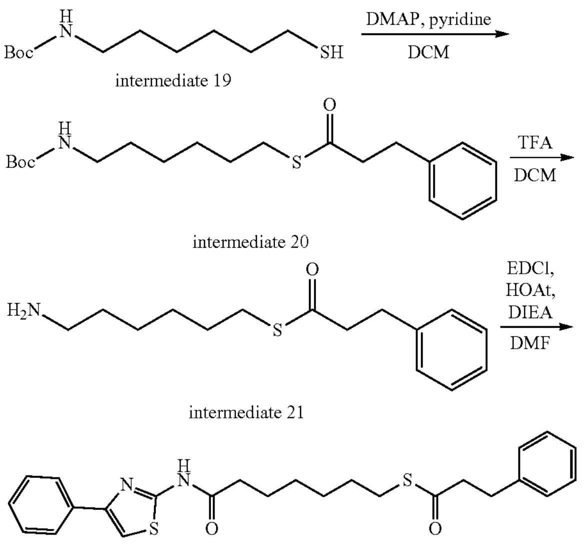

intermediate 19 intermediate 20 intermediate 21

LQ108-41

Intermediate 19: tert-butyl (6-mercaptohexyl)carbamate

Intermediate 19 was prepared using same procedures as preparing intermediate 12 from tert-butyl (6-bromohexyl) carbamate. Intermediate 20: S-(6-((tert-butoxycarbonyl) amino)hexyl) 3-phenylpropanethioate Intermediate 20 was prepared using same procedures as preparing compound LQ081-166. MS (ESI): m/z 388.3 $[M+Na]^+$.

Intermediate 21: S-(6-aminohexyl) 3-phenylpropanethioate

Intermediate 21 was prepared using same procedures as preparing intermediate 17. $^1$H NMR (600 MHz, Methanol-$d_4$) δ 7.28-7.23 (m, 2H), 7.20-7.15 (m, 3H), 2.94 (t, J=7.5 Hz, 2H), 2.92-2.89 (m, 2H), 2.88-2.84 (m, 4H), 1.66-1.61 (m, 2H), 1.56 (p, J=7.2 Hz, 2H), 1.42-1.35 (m, 4H).

LQ108-41: S-(6-(4-phenylthiazole-2-carboxamido)hexyl) 3-phenylpropanethioate

Compound LQ108-41 was prepared using same procedures as preparing compound LQ076-35 from 4-phenylthiazole-2-carboxylic acid. $^1$H NMR (600 MHz, Methanol-$d_4$) δ 8.05 (s, 1H), 8.04-8.00 (m, 2H), 7.46-7.42 (m, 2H), 7.38-7.35 (m, 1H), 7.26-7.22 (m, 2H), 7.18-7.14 (m, 3H), 3.44-3.40 (m, 2H), 2.92 (t, J=7.5 Hz, 2H), 2.88-2.80 (m, 4H), 1.68-1.60 (m, 2H), 1.54 (p, J=7.2 Hz, 2H), 1.44-1.35 (m, 4H). HRMS m/z $[M+H]^+$ calcd for $C_{25}H_{29}N_2O_2S_2^+$ 453.1665. found 454, 1670.

Example 52: N-(benzo[d]thiazol-2-yl)-7-(isopropyl(methyl)amino)heptanamide (LQ108-42)

Scheme 14: Synthesis of LQ108-42

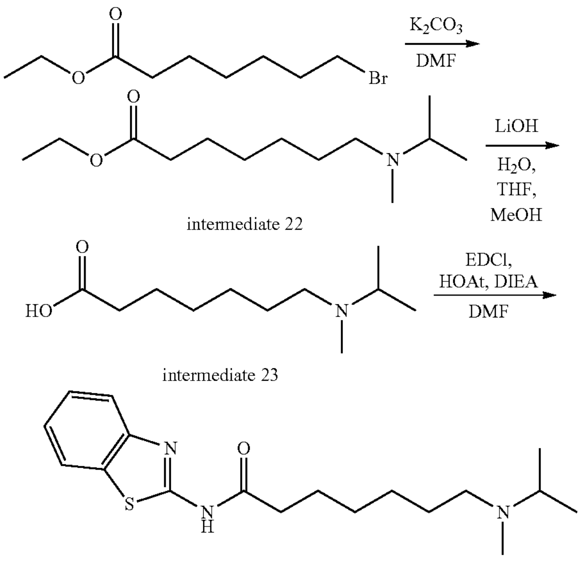

intermediate 22 intermediate 23

LQ108-42

Intermediate 22: Ethyl 7-(isopropyl(methyl)amino)heptanoate

A solution of ethyl 7-bromoheptanoate (1 g, 4.2 mmol) and N-isopropylmethylamine (0.31 g, 4.2 mmol) in 10 mL of DMF was treated with $K_2CO_3$ (869 mg, 6.3 mmol). The resulting mixture was stirred overnight at RT. After the reaction was completed, the reaction mixture was poured into ice water, aqueous phase was extracted with ethyl acetate. The combined organic phase was washed with brine twice, dried and concentrated. The resulting residue was purified by silica gel flash chromatography to give the compound as colorless oil (0.8 g, 83%). MS (ESI): m/z 230.3 $[M+H]^+$.

Intermediate 23: 7-(Isopropyl(methyl)amino)heptanoic acid

Intermediate 23 was prepared using same procedures as preparing intermediate 11. $^1H$ NMR (600 MHz, Methanol-$d_4$) δ 3.65-3.55 (m, 1H), 3.09-3.03 (m, 2H), 2.74 (s, 3H), 2.20 (t, J=7.4 Hz, 2H), 1.76-1.68 (m, 2H), 1.66-1.58 (m, 2H), 1.45-1.38 (m, 4H), 1.32 (d, J=6.6 Hz, 6H). MS (ESI): m/z 202.3 $[M+H]^+$.

LQ108-42: N-(benzo[d]thiazol-2-yl)-7-(isopropyl (methyl)amino)heptanamide

Compound LQ108-42 was prepared using same procedures as preparing compound LQ076-35 from 2-aminobenzothiazole. $^1H$ NMR (600 MHz, Methanol-$d_4$) δ 7.89-7.85 (m, 1H), 7.77-7.73 (m, 1H), 7.46-7.43 (m, 1H), 7.34-7.30 (m, 1H), 3.66-3.59 (m, 1H), 3.22-3.14 (m, 1H), 3.08-3.00 (m, 1H), 2.78 (s, 3H), 2.59 (t, J=7.3 Hz, 2H), 1.85-1.77 (m, 3H), 1.76-1.68 (m, 1H), 1.55-1.43 (m, 4H), 1.36 (d, J=6.7 Hz, 3H), 1.32 (d, J=6.7 Hz, 3H). HRMS m/z $[M+H]^+$ calcd for $C_{18}H_{28}N_{30}S^+$ 334.1948. found 334.1959.

Example 53: 7-(Isopropyl(methyl)amino)-N-(thiazol-2-yl)heptanamide (LQ108-43)

Compound LQ108-43 was prepared using same procedures as preparing compound LQ108-42 from 2-aminobenzothiazole. $^1H$ NMR (600 MHz, Methanol-$d_4$) δ 7.47 (d, J=3.5 Hz, 1H), 7.16 (d, J=3.6 Hz, 1H), 3.66-3.60 (m, 1H), 3.21-3.13 (m, 1H), 3.07-2.99 (m, 1H), 2.78 (s, 3H), 2.55 (t, J=7.3 Hz, 2H), 1.84-1.68 (m, 4H), 1.51-1.44 (m, 4H), 1.36 (d, J=6.7 Hz, 3H), 1.33 (d, J=6.7 Hz, 3H). HRMS m/z $[M+H]^+$ calcd for $C_{14}H_{26}N_3OS^+$ 284.1791. found 284.1794.

Example 54: 7-(Isopropyl(methyl)amino)-N-(thiazolo[5,4-b]pyridin-2-yl)heptanamide (LQ108-44)

Compound LQ108-44 was prepared using same procedures as preparing compound LQ108-42 from thiazolo[5,4-b]pyridin-2-amine. $^1H$ NMR (600 MHz, Methanol-$d_4$) δ 8.45 (dd, J=4.8, 1.5 Hz, 1H), 8.11 (dd, J=8.2, 1.5 Hz, 1H), 7.51 (dd, J=8.2, 4.8 Hz, 1H), 3.67-3.59 (m, 1H), 3.22-3.15 (m, 1H), 3.08-3.01 (m, 1H), 2.79 (s, 3H), 2.60 (t, J=7.2 Hz, 2H), 1.85-1.68 (m, 4H), 1.54-1.45 (m, 4H), 1.37 (d, J=6.7 Hz, 3H), 1.33 (d, J=6.7 Hz, 3H). HRMS m/z $[M+H]^+$ calcd for $C_{17}H_{27}N_4OS^+$ 335.1900. found 335.1910.

Example 55: 7-(Isopropyl(methyl)amino)-N-(4-(pyridin-2-yl)thiazol-2-yl)heptanamide (LQ108-45)

Compound LQ108-45 was prepared using same procedures as preparing compound LQ108-42 from 4-pyridin-2-yl-thiazol-2-ylamine. $^1H$ NMR (600 MHz, Methanol-$d_4$) δ 8.76-8.72 (m, 1H), 8.51-8.47 (m, 2H), 8.24 (s, 1H), 7.88-7.83 (m, 1H), 3.64 (p, J=6.6 Hz, 1H), 3.23-3.15 (m, 1H), 3.08-3.01 (m, 1H), 2.79 (s, 3H), 2.60 (t, J=7.3 Hz, 2H), 1.85-1.69 (m, 4H), 1.54-1.44 (m, 4H), 1.37 (d, J=6.7 Hz, 3H), 1.34 (d, J=6.7 Hz, 3H). HRMS m/z $[M+H]^+$ calcd for $C_{19}H_{29}N_4OS^+$ 361.2057. found 361.2052.

Example 56: S-(7-((4-(4-methoxyphenyl)thiazol-2-yl)amino)-7-oxoheptyl) 3-phenylpropanethioate (LQ108-46)

Scheme 15: Synthesis of LQ108-46

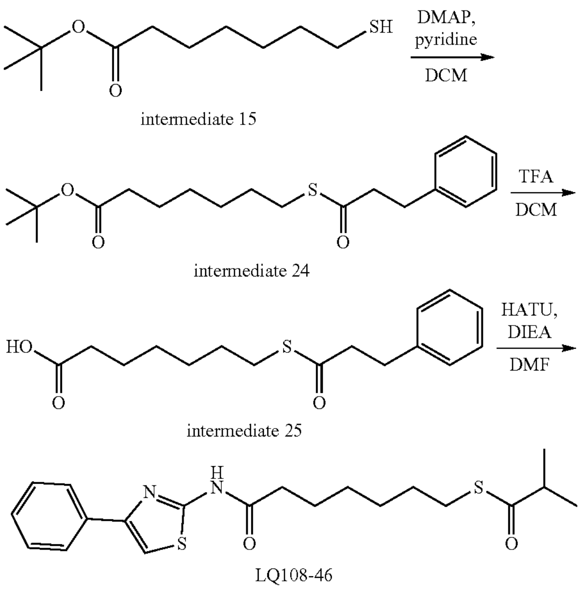

Intermediate 24: tert-butyl 7-((3-phenylpropanoyl)thio)heptanoate

Intermediate 24 was prepared using same procedures as preparing intermediate 16 from 3-phenylpropionyl chloride. MS (ESI): m/z 373.1 $[M+Na]^+$.

Intermediate 25: 7-((3-Phenylpropanoyl)thio)heptanoic acid

Intermediate 25 was prepared using same procedures as preparing intermediate 17. $^1H$ NMR (600 MHz, Methanol-$d_4$) δ 7.27-7.22 (m, 2H), 7.19-7.14 (m, 3H), 2.93 (t, J=7.5 Hz, 2H), 2.87-2.81 (m, 4H), 2.27 (t, J=7.5 Hz, 2H), 1.58 (p, J=6.0, 4.5 Hz, 2H), 1.55-1.48 (m, 2H), 1.38-1.27 (m, J=3.6 Hz, 4H). MS (ESI): m/z 317.1 $[M+Na]^+$.

LQ108-46: S-(7-((4-(4-methoxyphenyl)thiazol-2-yl) amino)-7-oxoheptyl) 3-phenylpropanethioate Compound LQ108-46 was prepared using same procedures as preparing compound LQ081-176 from 4-(4-methoxyphenyl)thiazol-2-amine. $^1H$ NMR (600 MHz, Methanol-$d_4$) δ 7.85-7.81 (m, 2H), 7.29-7.24 (m, 3H), 7.22-7.15 (m, 5H), 6.97-6.94 (m, 2H), 3.83 (s, 3H), 2.95 (t, J=7.5 Hz, 2H), 2.91-2.83 (m, 4H), 2.49 (t, J=7.4 Hz, 2H), 1.75-1.70 (m, 2H), 1.60-1.53 (m, 2H), 1.43-1.36 (m, 4H). HRMS m/z $[M+H]^+$ calcd for $C_{26}H_{31}N_2O_3S_2^+$ 483.1771. found 483.1769.

Example 57: S-(7-((4-(4-fluorophenyl)thiazol-2-yl) amino)-7-oxoheptyl) 3-phenylpropanethioate (LQ108-47)

Compound LQ108-47 was prepared using same procedures as preparing compound LQ108-46 from 2-amino-4-(4-fluorophenyl)-1,3-thiazole. $^1$H NMR (600 MHz, Methanol-$d_4$) δ 7.95-7.91 (m, 2H), 7.33 (s, 1H), 7.28-7.24 (m, 2H), 7.21-7.16 (m, 3H), 7.15-7.10 (m, 2H), 2.95 (t, J=7.5 Hz, 2H), 2.91-2.84 (m, 4H), 2.50 (t, J=7.5 Hz, 2H), 1.76-1.69 (m, 2H), 1.60-1.54 (m, 2H), 1.44-1.36 (m, 4H). HRMS m/z $[M+H]^+$ calcd for $C_{25}H_{28}FN_2O_2S_2^+$ 471.1571. found 471.1566.

Example 58: S-(7-oxo-7-((4-(p-tolyl)thiazol-2-yl) amino)heptyl) 3-phenylpropanethioate (LQ108-48)

Compound LQ108-48 was prepared using same procedures as preparing compound LQ108-46 from 2-amino-4-(p-tolyl)thiazole. $^1$H NMR (600 MHz, Methanol-$d_4$) δ 7.80-7.77 (m, 2H), 7.29 (s, 1H), 7.28-7.24 (m, 2H), 7.23-7.16 (m, 5H), 2.95 (t, J=7.5 Hz, 2H), 2.90-2.84 (m, 4H), 2.50 (t, J=7.5 Hz, 2H), 2.37 (s, 3H), 1.76-1.70 (m, 2H), 1.60-1.54 (m, 2H), 1.44-1.38 (m, 4H). HRMS m/z $[M+H]^+$ calcd for $C_{26}H_{31}N_2O_2S_2^+$ 467.1821. found 467.1831.

Example 59: S-(7-((4-(4-chlorophenyl)thiazol-2-yl) amino)-7-oxoheptyl) 3-phenylpropanethioate (LQ108-49)

Compound LQ108-49 was prepared using same procedures as preparing compound LQ108-46 from 4-(4-chlorophenyl)thiazol-2-amine. $^1$H NMR (600 MHz, Methanol-$d_4$) δ 7.92-7.89 (m, 2H), 7.41-7.38 (m, 3H), 7.26 (t, J=7.6 Hz, 2H), 7.20-7.16 (m, 3H), 2.95 (t, J=7.5 Hz, 2H), 2.90-2.84 (m, 4H), 2.50 (t, J=7.4 Hz, 2H), 1.76-1.69 (m, 2H), 1.60-1.54 (m, 2H), 1.44-1.38 (m, 4H). HRMS m/z $[M+H]^+$ calcd for $C_{25}H_{28}ClN_2O_2S_2^+$ 487.1275. found 487.1261.

Example 60: S-(7-(benzo[d]thiazol-2-ylamino)-7-oxoheptyl) 3-phenylpropanethioate (LQ108-50)

Compound LQ108-50 was prepared using same procedures as preparing compound LQ108-46 from 2-aminobenzothiazole. $^1$H NMR (600 MHz, Methanol-$d_4$) δ 7.86 (d, J=8.0 Hz, 1H), 7.74 (d, J=8.0 Hz, 1H), 7.45-7.41 (m, 1H), 7.31 (td, J=7.6, 7.2, 1.1 Hz, 1H), 7.28-7.24 (m, 2H), 7.20-7.15 (m, 3H), 2.94 (t, J=7.5 Hz, 2H), 2.90-2.82 (m, 4H), 2.54 (t, J=7.5 Hz, 2H), 1.78-1.70 (m, 2H), 1.61-1.53 (m, 2H), 1.45-1.36 (m, 4H). HRMS m/z $[M+H]^+$ calcd for $C_{23}H_{27}N_2O_2S_2^+$ 427.1508. found 427.1502.

Example 61: S-(7-oxo-7-(thiazol-2-ylamino)heptyl) 3-phenylpropanethioate (LQ108-51)

Compound LQ108-51 was prepared using same procedures as preparing compound LQ108-46 from 2-aminothiazole. $^1$H NMR (600 MHz, Methanol-$d_4$) δ 7.57-7.37 (m, 2H), 7.26 (t, J=7.6 Hz, 2H), 7.22-7.15 (m, 3H), 2.95 (t, J=7.5 Hz, 2H), 2.90-2.84 (m, 4H), 2.58-2.44 (m, 2H), 1.76-1.67 (m, 2H), 1.59-1.52 (m, 2H), 1.43-1.37 (m, 4H). HRMS m/z $[M+H]^+$ calcd for $C_{19}H_{25}N_2O_2S_2^+$ 377.1352. found 377.1366.

Example 62: S-(7-oxo-7-(thiazolo[5,4-b]pyridin-2-ylamino)heptyl) 3-phenylpropanethioate (LQ108-52)

Compound LQ108-52 was prepared using same procedures as preparing compound LQ108-46 from thiazolo[5,4-b]pyridin-2-amine. $^1$H NMR (600 MHz, Methanol-$d_4$) δ 8.44 (dd, J=4.7, 1.5 Hz, 1H), 8.09 (dd, J=8.2, 1.5 Hz, 1H), 7.49 (dd, J=8.2, 4.7 Hz, 1H), 7.30-7.24 (m, 2H), 7.22-7.16 (m, 3H), 2.95 (t, J=7.6 Hz, 2H), 2.91-2.83 (m, 4H), 2.56 (t, J=7.4 Hz, 2H), 1.77-1.72 (m, 2H), 1.62-1.54 (m, 2H), 1.46-1.38 (m, 4H). HRMS m/z $[M+H]^+$ calcd for $C_{24}H_{26}N_3O_2S_2^+$ 428.1461. found 428.1473.

Example 63: S-(7-oxo-7-((4-(pyridin-2-yl)thiazol-2-yl)amino)heptyl) 3-phenylpropanethioate (LQ108-53)

Compound LQ108-53 was prepared using same procedures as preparing compound LQ108-46 from 4-(2-pyridinyl)thiazol-2-amine. $^1$H NMR (600 MHz, Methanol-$d_4$) δ 8.73 (dt, J=5.8, 1.2 Hz, 1H), 8.51-8.47 (m, 2H), 8.24 (s, 1H), 7.88-7.84 (m, 1H), 7.28-7.24 (m, 2H), 7.20-7.15 (m, 3H), 2.94 (t, J=7.5 Hz, 2H), 2.90-2.84 (m, 4H), 2.56 (t, J=7.4 Hz, 2H), 1.79-1.72 (m, 2H), 1.61-1.54 (m, 2H), 1.45-1.39 (m, 4H). HRMS m/z $[M+H]^+$ calcd for $C_{24}H_{28}N_3O_2S_2^+$ 454.1617. found 454.1622.

Example 64: S-(7-oxo-7-((4-phenylthiazol-2-yl) amino)heptyl) 2,2-dimethyl-3-phenylpropanethioate (LQ108-184)

Compound LQ108-184 was prepared using same procedures as preparing compound LQ108-15 from 2,2-Dimethyl-3-phenylpropanoic acid. $^1$H NMR (600 MHz, Methanol-$d_4$) δ 7.91-7.87 (m, 2H), 7.38 (t, J=7.7 Hz, 2H), 7.34 (s, 1H), 7.31-7.27 (m, 1H), 7.23-7.19 (m, 2H), 7.18-7.14 (m, 1H), 7.11-7.08 (m, 2H), 2.88-2.82 (m, 4H), 2.50 (t, J=7.5 Hz, 2H), 1.77-1.69 (m, 2H), 1.60-1.54 (m, 2H), 1.45-1.38 (m, 4H), 1.18 (s, 6H). HRMS m/z $[M+H]^+$ calcd for $C_{27}H_{33}N_2O_2S_2^+$ 481.1978. found 481.1981.

TABLE 2

| Examples | Compound code | Structure | Chemical Name |
|---|---|---|---|
| 8 | LQ070-27 | 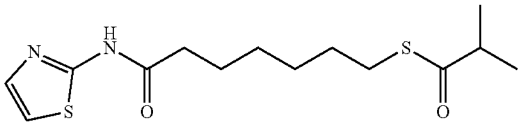 [SMILES: CC(C)C(=O)SCCCCCCC(=O)Nc1nccs1] | S-(7-oxo-7-(thiazol-2-ylamino)heptyl) 2-methyl-propanethioate |

TABLE 2-continued

| Examples | Compound code | Structure | Chemical Name |
| --- | --- | --- | --- |
| 9 | LQ070-39 | 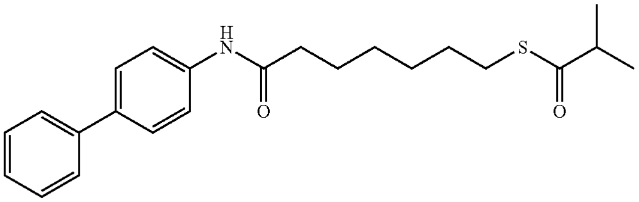 [SMILES: CC(C)C(=O)SCCCCCCC(=O)Nc1ccc(-c2ccccc2)cc1] | S-(7-([1,1'-biphenyl]-4-ylamino)-7-oxoheptyl) 2-methyl-propanethioate |
| 10 | LQ070-40 | 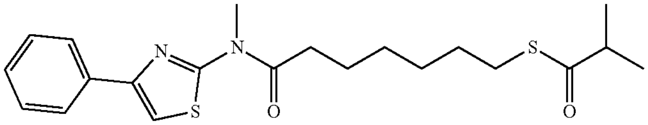 [SMILES: CC(C)C(=O)SCCCCCCC(=O)N(C)c1nc(-c2ccccc2)cs1] | S-(7-(methyl (4-phenylthiazol-2-yl)amino)-7-oxoheptyl) 2-methyl-propanethioate |
| 11 | LQ070-41 | 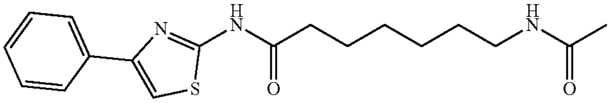 [SMILES: CC(=O)NCCCCCCC(=O)Nc1nc(-c2ccccc2)cs1] | 7-acetamido-N-(4-phenylthiazol-2-yl)heptanamide |
| 12 | LQ070-42 | 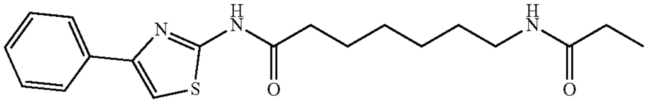 [SMILES: CCC(=O)NCCCCCCC(=O)Nc1nc(-c2ccccc2)cs1] | N-(4-phenyl-thiazol-2-yl)-7-propionamido-heptanamide |
| 13 | LQ070-43 | 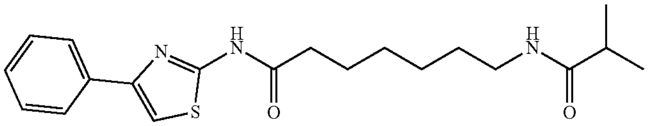 [SMILES: CC(C)C(=O)NCCCCCCC(=O)Nc1nc(-c2ccccc2)cs1] | 7-isobutyramido-N-(4-phenylthiazol-2-yl)heptanamide |
| 14 | LQ070-44 | 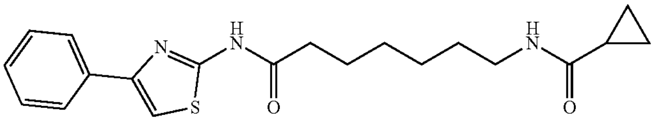 [SMILES: O=C(CCCCCCNC(=O)C1CC1)Nc1nc(-c2ccccc2)cs1] | N-(7-oxo-7-((4-phenylthiazol-2-yl)amino)heptyl) cyclopropane-carboxamide |
| 15 | LQ070-45 | 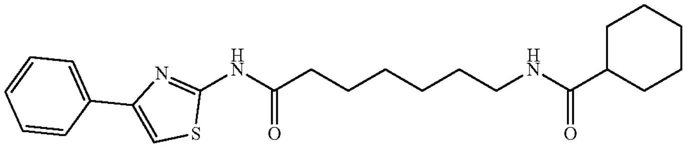 [SMILES: O=C(CCCCCCNC(=O)C1CCCCC1)Nc1nc(-c2ccccc2)cs1] | N-(7-oxo-7-((4-phenylthiazol-2-yl)amino)heptyl) cyclohexane-carboxamide |
| 16 | LQ070-46 | 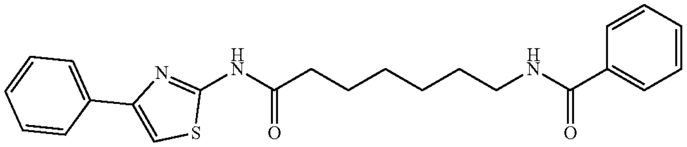 [SMILES: O=C(CCCCCCNC(=O)c1ccccc1)Nc1nc(-c2ccccc2)cs1] | N-(7-oxo-7-((4-phenylthiazol-2-yl)amino)heptyl) benzamide |
| 17 | LQ070-48 | 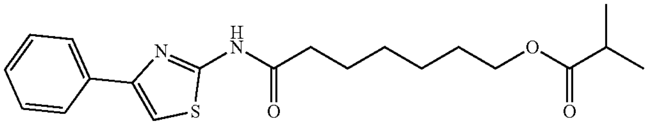 [SMILES: CC(C)C(=O)OCCCCCCC(=O)Nc1nc(-c2ccccc2)cs1] | 7-oxo-7-((4-phenylthiazol-2-yl)amino)heptyl isobutyrate |
| 18 | LQ076-16 | 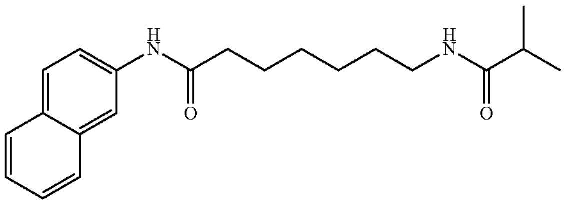 [SMILES: CC(C)C(=O)NCCCCCCC(=O)Nc1ccc2ccccc2c1] | 7-isobutyramido-N-(naphthalen-2-yl)heptanamide |

TABLE 2-continued

| Examples | Compound code | Structure | Chemical Name |
|---|---|---|---|
| 19 | LQ076-17 | 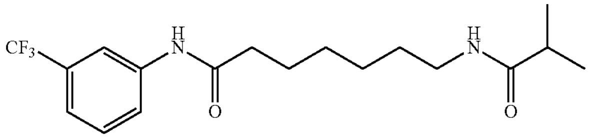 [SMILES: CC(C)C(=O)NCCCCCCC(=O)Nc1cccc(C(F)(F)F)c1] | 7-isobutyramido-N-(3-(trifluoromethyl)phenyl)heptanamide |
| 20 | LQ076-19 | 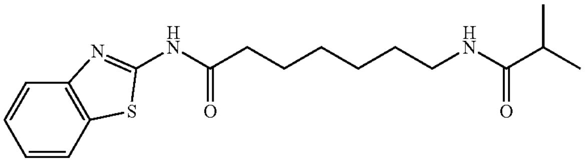 [SMILES: CC(C)C(=O)NCCCCCCC(=O)Nc1nc2ccccc2s1] | N-(benzo[d]thiazol-2-yl)-7-isobutyramido-heptanamide |
| 21 | LQ076-20 | 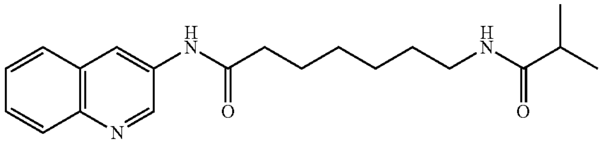 [SMILES: CC(C)C(=O)NCCCCCCC(=O)Nc1cnc2ccccc2c1] | 7-isobutyramido-N-(quinolin-3-yl)heptanamide |
| 22 | LQ076-21 | 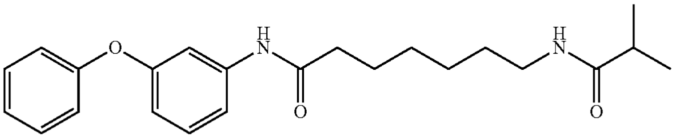 [SMILES: CC(C)C(=O)NCCCCCCC(=O)Nc1cccc(Oc2ccccc2)c1] | 7-isobutyramido-N-(3-phenoxyphenyl)heptanamide |
| 23 | LQ076-28 | 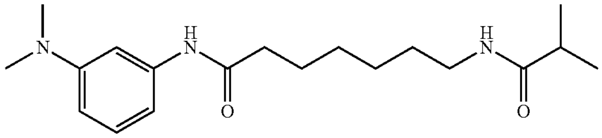 [SMILES: CC(C)C(=O)NCCCCCCC(=O)Nc1cccc(N(C)C)c1] | N-(3-(dimethyl-amino)phenyl)-7-isobutyramido-heptanamide |
| 24 | LQ076-31 | 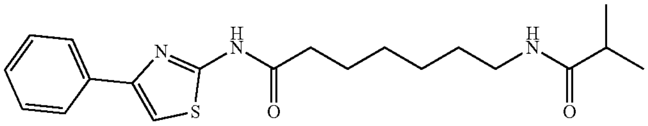 [SMILES: CC(C)C(=O)NCCCCCCC(=O)Nc1nc(-c2ccccc2)cs1] | 9-isobutyramido-N-(4-phenylthiazol-2-yl)nonanamide |
| 25 | LQ076-32 | 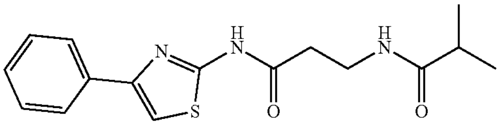 [SMILES: CC(C)C(=O)NCCC(=O)Nc1nc(-c2ccccc2)cs1] | 3-isobutyramido-N-(4-phenylthiazol-2-yl)propanamide |
| 26 | LQ076-35 | 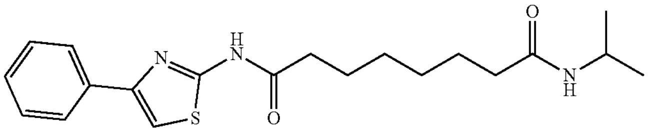 [SMILES: CC(C)NC(=O)CCCCCCC(=O)Nc1nc(-c2ccccc2)cs1] | $N^1$-isopropyl-$N^8$-(4-phenylthiazol-2-yl)octanediamide |
| 27 | LQ076-36 | 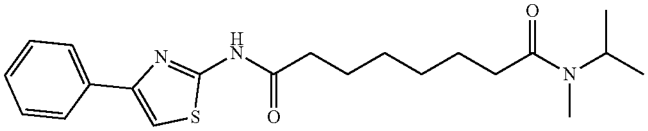 [SMILES: CC(C)N(C)C(=O)CCCCCCC(=O)Nc1nc(-c2ccccc2)cs1] | $N^1$-isopropyl-$N^1$-methyl-$N^8$-(4-phenylthiazol-2-yl)octanediamide |
| 28 | LQ076-37 | 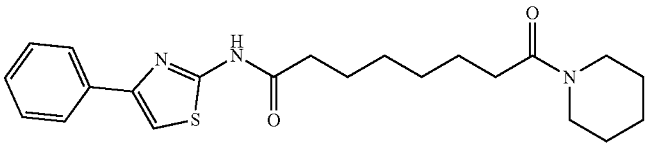 [SMILES: O=C(CCCCCCC(=O)N1CCCCC1)Nc1nc(-c2ccccc2)cs1] | 8-oxo-N-(4-phenylthiazol-2-yl)-8-(piperidin-1-yl)octanamide |

TABLE 2-continued

| Examples | Compound code | Structure | Chemical Name |
|---|---|---|---|
| 29 | LQ076-38 | 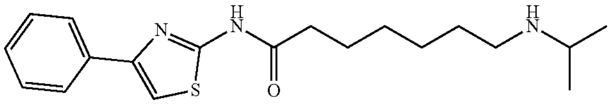 [SMILES: CC(C)NCCCCCCC(=O)Nc1nc(-c2ccccc2)cs1] | 7-(isopropyl-amino)-N-(4-phenylthiazol-2-yl)heptanamide |
| 30 | LQ076-39 | 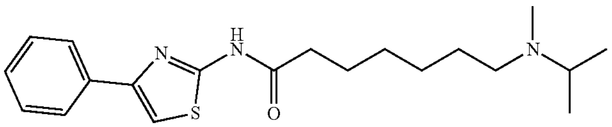 [SMILES: CC(C)N(C)CCCCCCC(=O)Nc1nc(-c2ccccc2)cs1] | 7-(isopropyl (methyl)amino)-N-(4-phenylthiazol-2-yl)heptanamide |
| 31 | LQ081-166 | 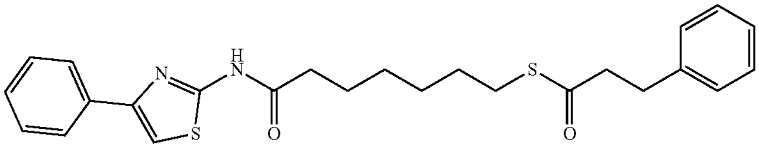 [SMILES: O=C(CCCCCCSC(=O)CCc1ccccc1)Nc1nc(-c2ccccc2)cs1] | S-(7-oxo-7-((4-phenylthiazol-2-yl)amino)heptyl) 3-phenylpropane-thioate |
| 32 | LQ081-167 | 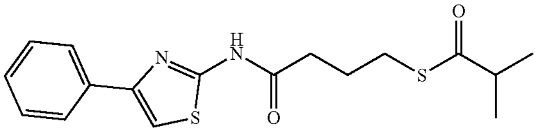 [SMILES: CC(C)C(=O)SCCCC(=O)Nc1nc(-c2ccccc2)cs1] | S-(4-oxo-4-((4-phenylthiazol-2-yl)amino)butyl 2-methylpropane-thioate |
| 33 | LQ081-168 | 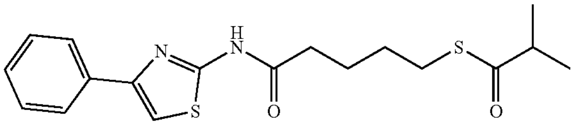 [SMILES: CC(C)C(=O)SCCCCC(=O)Nc1nc(-c2ccccc2)cs1] | S-(5-oxo-5-((4-phenylthiazol-2-yl)amino)pentyl) 2-methylpropane-thioate |
| 34 | LQ081-169 | 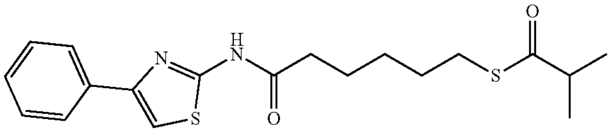 [SMILES: CC(C)C(=O)SCCCCCC(=O)Nc1nc(-c2ccccc2)cs1] | S-(6-oxo-6-((4-phenylthiazol-2-yl)amino)hexyl) 2-methylpropane-thioate |
| 35 | LQ081-170 | 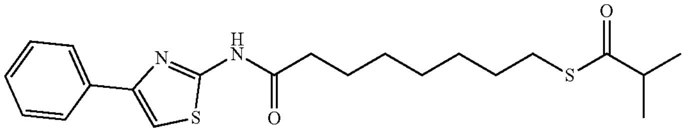 [SMILES: CC(C)C(=O)SCCCCCCCC(=O)Nc1nc(-c2ccccc2)cs1] | S-(8-oxo-8-((4-phenylthiazol-2-yl)amino)octyl) 2-methylpropane-thioate |
| 36 | LQ081-175 | 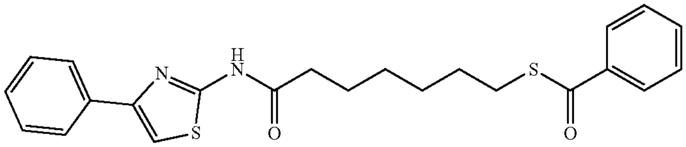 [SMILES: O=C(CCCCCCSC(=O)c1ccccc1)Nc1nc(-c2ccccc2)cs1] | S-(7-oxo-7-((4-phenylthiazol-2-yl)amino)heptyl) benzothioate |
| 37 | LQ081-176 | 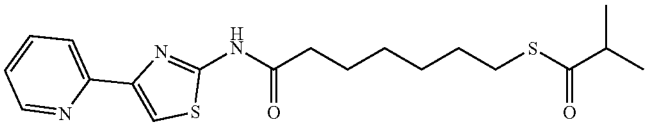 [SMILES: CC(C)C(=O)SCCCCCCC(=O)Nc1nc(-c2ccccn2)cs1] | S-(7-oxo-7-((4-(pyridin-2-yl)thiazol-2-yl) amino)heptyl) 2-methylpropane-thioate |
| 38 | LQ081-181 | 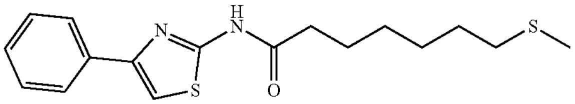 [SMILES: CSCCCCCCC(=O)Nc1nc(-c2ccccc2)cs1] | 7-(methylthio)-N-(4-phenylthiazol-2-yl)heptanamide |
| 39 | LQ081-183 | 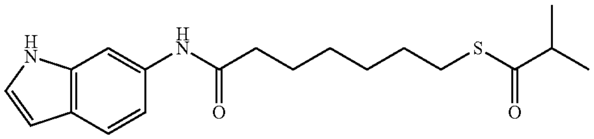 [SMILES: CC(C)C(=O)SCCCCCCC(=O)Nc1ccc2cc[nH]c2c1] | S-(7-((1H-indol-6-yl)amino)-7-oxoheptyl) 2-methylpropane-thioate |

TABLE 2-continued

| Examples | Compound code | Structure | Chemical Name |
|---|---|---|---|
| 40 | LQ081-185 | 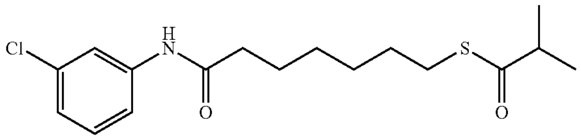 [SMILES: CC(C)C(=O)SCCCCCCC(=O)Nc1cccc(Cl)c1] | S-(7-((3-chlorophenyl) amino)-7-oxoheptyl) 2-methylpropane-thioate |
| 41 | LQ081-186 | 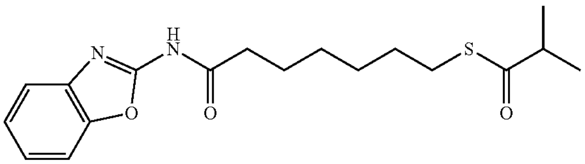 [SMILES: CC(C)C(=O)SCCCCCCC(=O)Nc1nc2ccccc2o1] | S-(7-(benzo[d] oxazol-2-ylamino)-7-oxoheptyl) 2-methylpropane-thioate |
| 42 | LQ108-13 | 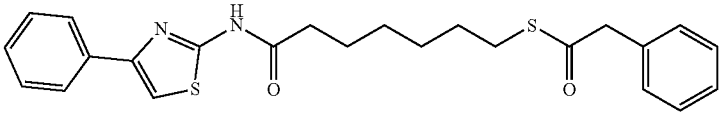 [SMILES: O=C(CCCCCCSC(=O)Cc1ccccc1)Nc1nc(-c2ccccc2)cs1] | S-(7-oxo-7-((4-phenylthiazol-2-yl)amino)heptyl 2-phenylethane-thioate |
| 43 | LQ108-15 | 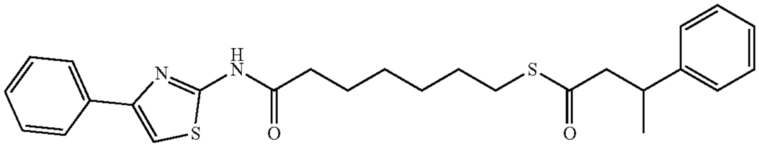 [SMILES: CC(CC(=O)SCCCCCCC(=O)Nc1nc(-c2ccccc2)cs1)c1ccccc1] | S-(7-oxo-7-((4-phenylthiazol-2-yl)amino)heptyl 3-phenylbutane-thioate |
| 44 | LQ108-16 | 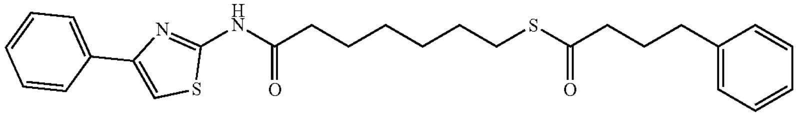 [SMILES: O=C(CCCCCCSC(=O)CCCc1ccccc1)Nc1nc(-c2ccccc2)cs1] | S-(7-oxo-7-((4-phenylthiazol-2-yl)amino)heptyl) 4-phenylbutane-thioate |
| 45 | LQ108-17 | 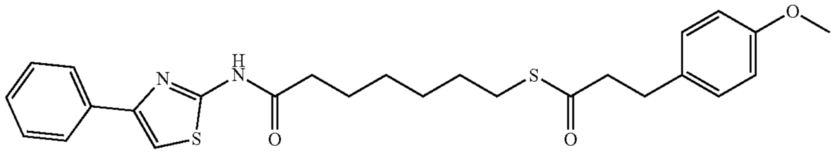 [SMILES: COc1ccc(CCC(=O)SCCCCCCC(=O)Nc2nc(-c3ccccc3)cs2)cc1] | S-(7-oxo-7-((4-phenylthiazol-2-yl)amino)heptyl 3-(4-methoxyphenyl) propanethioate |
| 46 | LQ108-18 | 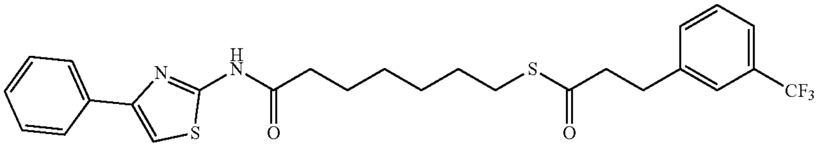 [SMILES: O=C(CCCCCCSC(=O)CCc1cccc(C(F)(F)F)c1)Nc1nc(-c2ccccc2)cs1] | S-(7-oxo-7-((4-phenylthiazol-2-yl)amino)heptyl) 3-(3-(trifluoromethyl) phenyl)propane-thioate |
| 47 | LQ108-19 | 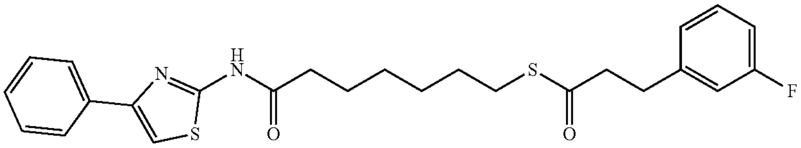 [SMILES: O=C(CCCCCCSC(=O)CCc1cccc(F)c1)Nc1nc(-c2ccccc2)cs1] | S-(7-oxo-7-((4-phenylthiazol-2-yl)amino)heptyl) 3-(3-fluorophenyl) propanethioate |
| 48 | LQ108-20 | 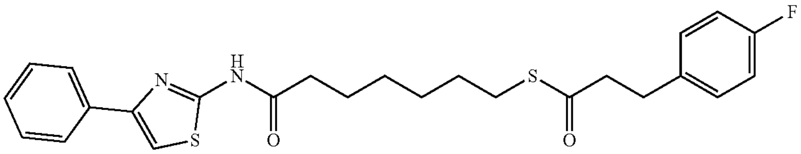 [SMILES: O=C(CCCCCCSC(=O)CCc1ccc(F)cc1)Nc1nc(-c2ccccc2)cs1] | S-(7-oxo-7-((4-phenylthiazol-2-yl)amino)heptyl) 3-(4-fluorophenyl) propanethioate |

TABLE 2-continued

| Examples | Compound code | Structure | Chemical Name |
|---|---|---|---|
| 49 | LQ108-22 | 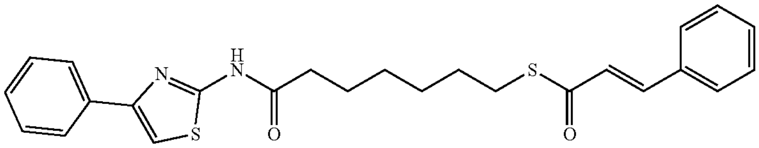 [SMILES: O=C(CCCCCCSC(=O)/C=C/c1ccccc1)Nc1nc(-c2ccccc2)cs1] | S-(7-oxo-7-((4-phenylthiazol-2-yl)amino)heptyl) (E)-3-phenylprop-2-enethioate |
| 50 | LQ108-32 | 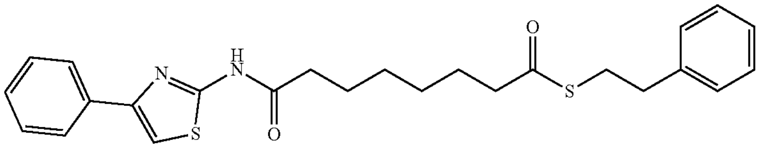 [SMILES: O=C(CCCCCCC(=O)SCCc1ccccc1)Nc1nc(-c2ccccc2)cs1] | S-phenethyl 8-oxo-8-((4-phenylthiazol-2-yl)amino) octanethioate |
| 51 | LQ108-41 | 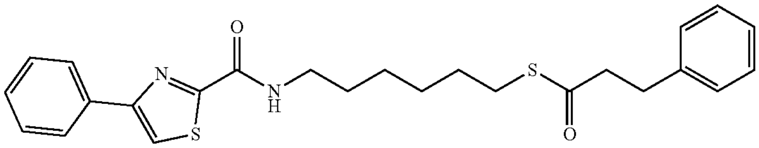 [SMILES: O=C(CCc1ccccc1)SCCCCCCNC(=O)c1nc(-c2ccccc2)cs1] | S-(6-(4-phenylthiazole-2-carboxamido) hexyl) 3-phenyl-propanethioate |
| 52 | LQ108-42 | 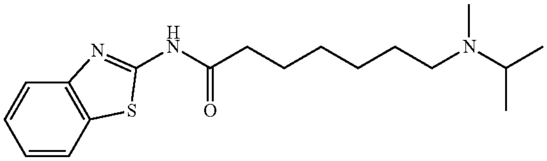 [SMILES: CC(C)N(C)CCCCCCC(=O)Nc1nc2ccccc2s1] | N-(benzo[d] thiazol-2-yl)-7-(isopropyl (methyl)amino) heptanamide |
| 53 | LQ108-43 | 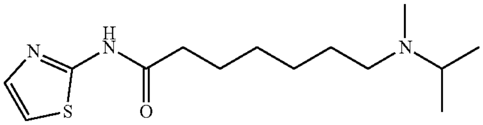 [SMILES: CC(C)N(C)CCCCCCC(=O)Nc1nccs1] | 7-(isopropyl (methyl)amino)-N-(thiazol-2-yl) heptanamide |
| 54 | LQ108-44 | 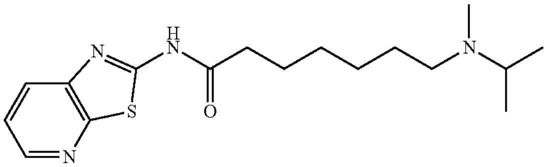 [SMILES: CC(C)N(C)CCCCCCC(=O)Nc1nc2cccnc2s1] | 7-(isopropyl (methyl)amino)-N-(thiazolo[5,4-b] pyridin-2-yl)heptanamide |
| 55 | LQ108-45 | 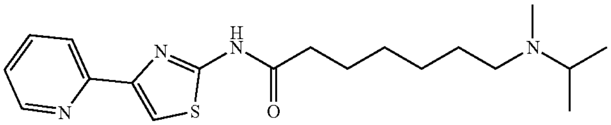 [SMILES: CC(C)N(C)CCCCCCC(=O)Nc1nc(-c2ccccn2)cs1] | 7-(isopropyl (methyl)amino)-N-(4-(pyridin-2-yl) thiazol-2-yl)heptanamide |
| 56 | LQ108-46 | 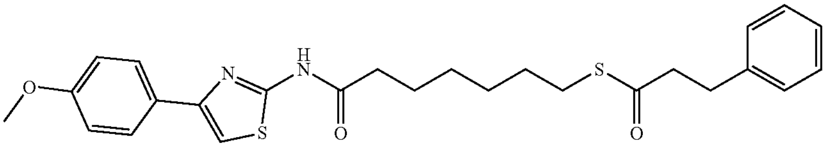 [SMILES: COc1ccc(-c2csc(NC(=O)CCCCCCSC(=O)CCc3ccccc3)n2)cc1] | S-(7-((4-(4-methoxyphenyl) thiazol-2-yl)amino)-7-oxoheptyl) 3-phenylpropane-thioate |
| 57 | LQ108-47 | 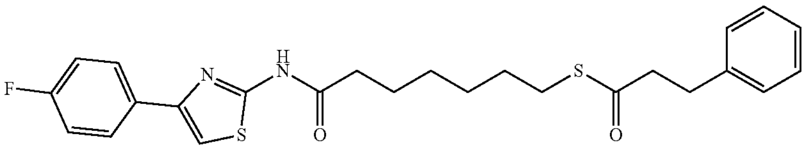 [SMILES: O=C(CCCCCCSC(=O)CCc1ccccc1)Nc1nc(-c2ccc(F)cc2)cs1] | S-(7-((4-(4-fluorophenyl) thiazol-2-yl)amino)-7-oxoheptyl) 3-phenylpropane-thioate |

TABLE 2-continued

| Examples | Compound code | Structure | Chemical Name |
| --- | --- | --- | --- |
| 58 | LQ108-48 | 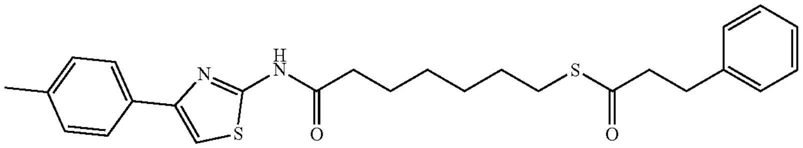 [SMILES: Cc1ccc(-c2csc(NC(=O)CCCCCCSC(=O)CCc3ccccc3)n2)cc1] | S-(7-oxo-7-((4-(p-tolyl)thiazol-2-yl)amino)heptyl) 3-phenylpropanethioate |
| 59 | LQ108-49 | 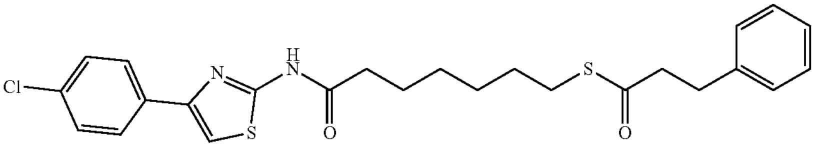 [SMILES: O=C(CCCCCCSC(=O)CCc1ccccc1)Nc1nc(-c2ccc(Cl)cc2)cs1] | S-(7-((4-(4-chlorophenyl) thiazol-2-yl)amino)-7-oxoheptyl) 3-phenylpropanethioate |
| 60 | LQ108-50 | 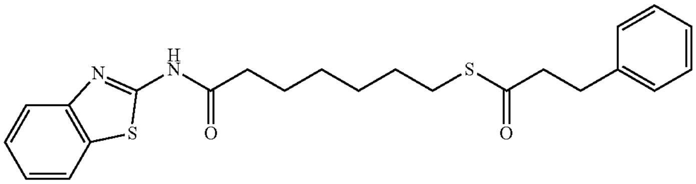 [SMILES: O=C(CCCCCCSC(=O)CCc1ccccc1)Nc1nc2ccccc2s1] | S-(7-(benzo[d] thiazol-2-ylamino)-7-oxoheptyl) 3-phenylpropanethioate |
| 61 | LQ108-51 | 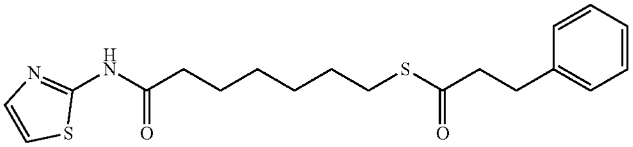 [SMILES: O=C(CCCCCCSC(=O)CCc1ccccc1)Nc1nccs1] | S-(7-oxo-7-(thiazol-2-ylamino)heptyl) 3-phenylpropanethioate |
| 62 | LQ108-52 | 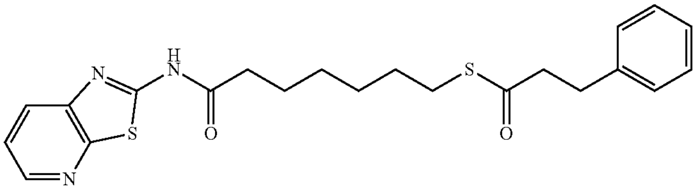 [SMILES: O=C(CCCCCCSC(=O)CCc1ccccc1)Nc1nc2cccnc2s1] | S-(7-oxo-7-(thiazolo[5,4-b]pyridin-2-ylamino)heptyl) 3-phenylpropanethioate |
| 63 | LQ108-53 | 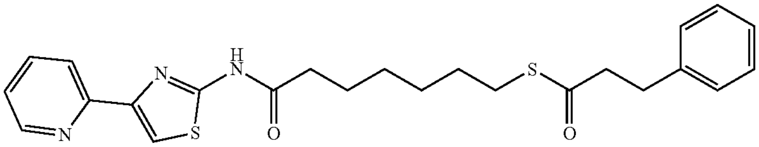 [SMILES: O=C(CCCCCCSC(=O)CCc1ccccc1)Nc1nc(-c2ccccn2)cs1] | S-(7-oxo-7-((4-(pyridin-2-yl)thiazol-2-yl) amino)heptyl) 3-phenylpropanethioate |
| 64 | LQ108-184 | 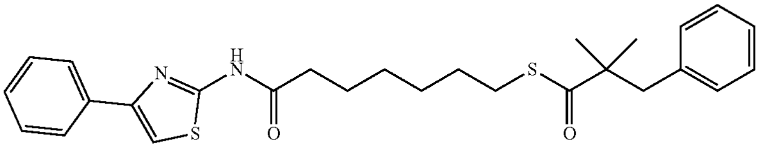 [SMILES: CC(C)(Cc1ccccc1)C(=O)SCCCCCCC(=O)Nc1nc(-c2ccccc2)cs1] | S-(7-oxo-7-((4-phenylthiazol-2-yl)amino)heptyl 2,2-dimethyl-3-phenylpropanethioate |

TABLE 3

| Examples | Structure | Chemical Name |
| --- | --- | --- |
| 65 | 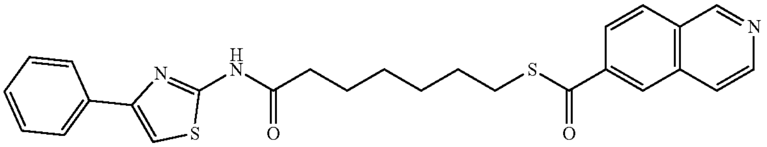 [SMILES: O=C(CCCCCCSC(=O)c1ccc2cnccc2c1)Nc1nc(-c2ccccc2)cs1] | S-(7-oxo-7-((4-phenylthiazol-2-yl)amino)heptyl isoquinoline-6-carbothioate |

TABLE 3-continued

| Examples | Structure | Chemical Name |
| --- | --- | --- |
| 66 | 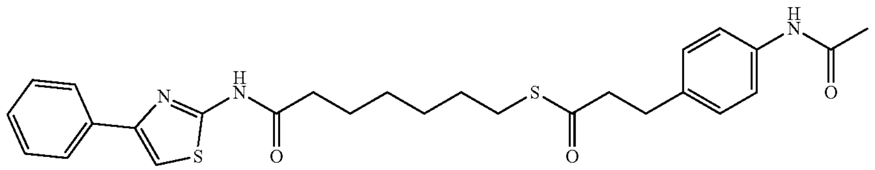 [SMILES: CC(=O)Nc1ccc(CCC(=O)SCCCCCCC(=O)Nc2nc(-c3ccccc3)cs2)cc1] | S-(7-oxo-7-((4-phenylthiazol-2-yl)amino)heptyl) 3-(4-acetamidophenyl) propanethioate |
| 67 | 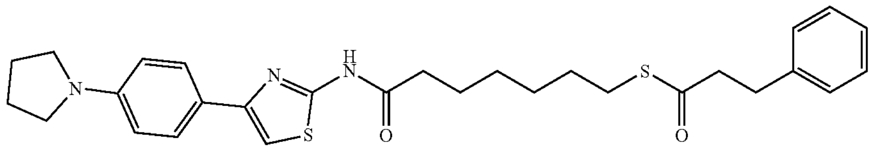 [SMILES: O=C(CCCCCCSC(=O)CCc1ccccc1)Nc1nc(-c2ccc(N3CCCC3)cc2)cs1] | S-(7-oxo-7-((4-(4-(pyrrolidin-1-yl) phenyl)thiazol-2-yl)amino)heptyl) 3-phenylpropane-thioate |
| 68 | 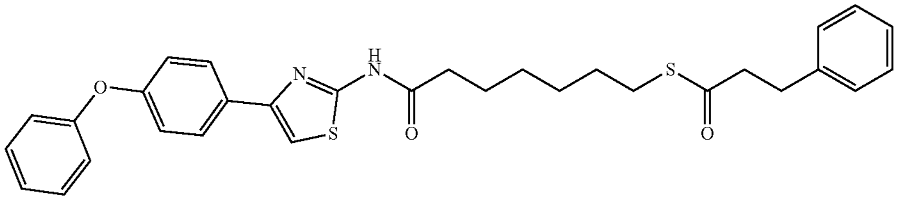 [SMILES: O=C(CCCCCCSC(=O)CCc1ccccc1)Nc1nc(-c2ccc(Oc3ccccc3)cc2)cs1] | S-(7-oxo-7-((4-(4-phenoxyphenyl) thiazol-2-yl)amino)heptyl) 3-phenylpropane-thioate |
| 69 | 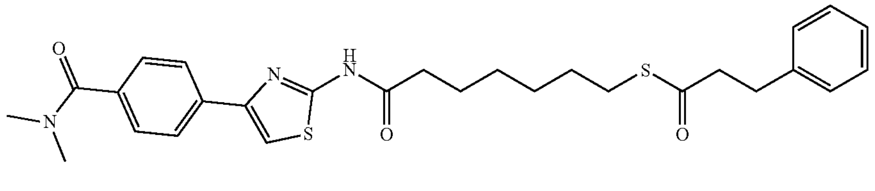 [SMILES: CN(C)C(=O)c1ccc(-c2csc(NC(=O)CCCCCCSC(=O)CCc3ccccc3)n2)cc1] | S-(7-((4-(4-(dimethyl-carbamoyl) phenyl)thiazol-2-yl)amino)-7-oxoheptyl) 3-phenylpropane-thioate |
| 70 | 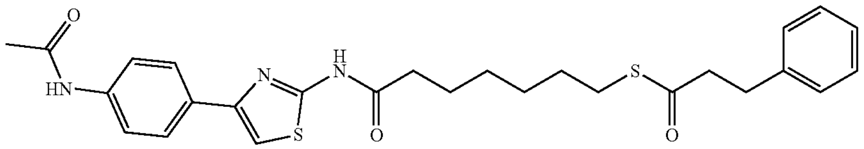 [SMILES: CC(=O)Nc1ccc(-c2csc(NC(=O)CCCCCCSC(=O)CCc3ccccc3)n2)cc1] | S-(7-((4-(4-acetamidophenyl )thiazol-2-yl)amino)-7-oxoheptyl) 3-phenylpropane-thioate |
| 71 | 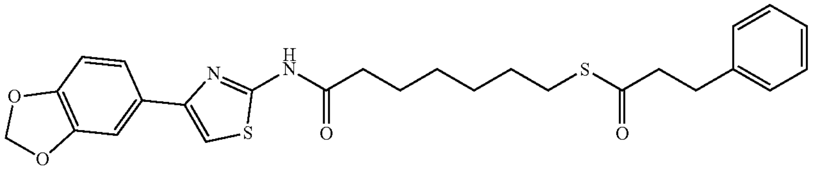 [SMILES: O=C(CCCCCCSC(=O)CCc1ccccc1)Nc1nc(-c2ccc3c(c2)OCO3)cs1] | S-(7-((4-(benzo[d] [1,3]dioxol-5-yl)thiazol-2-yl) amino)-7-oxoheptyl) 3-phenylpropane-thioate |
| 72 | 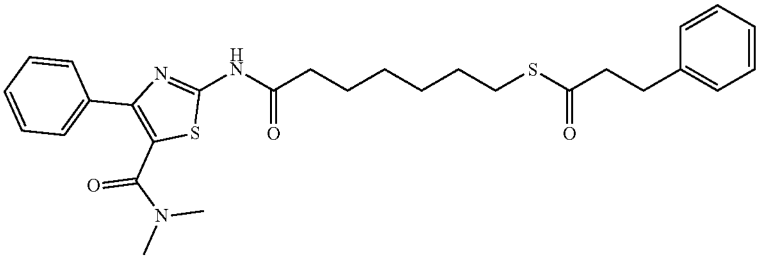 [SMILES: CN(C)C(=O)c1sc(NC(=O)CCCCCCSC(=O)CCc2ccccc2)nc1-c1ccccc1] | S-(7-((5-(dimethyl-carbamoyl)-4-phenylthiazol-2-yl)amino)-7-oxoheptyl) 3-phenylpropane-thioate |
| 73 | 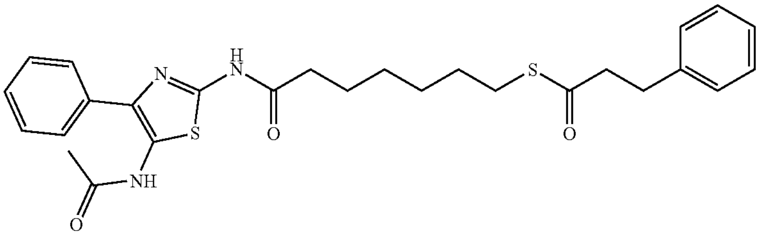 [SMILES: CC(=O)Nc1sc(NC(=O)CCCCCCSC(=O)CCc2ccccc2)nc1-c1ccccc1] | S-(7-((5-acetamido)-4-phenylthiazol-2-yl)amino)-7-oxoheptyl) 3-phenylpropane-thioate |

TABLE 3-continued

| Examples | Structure | Chemical Name |
|---|---|---|
| 74 | 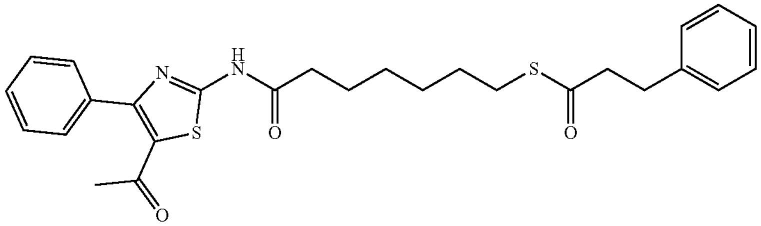 [SMILES: CC(=O)c1sc(NC(=O)CCCCCCSC(=O)CCc2ccccc2)nc1-c1ccccc1] | S-(7-((5-acetyl-4-phenylthiazol-2-yl)amino)-7-oxoheptyl) 3-phenylpropanethioate |
| 75 | 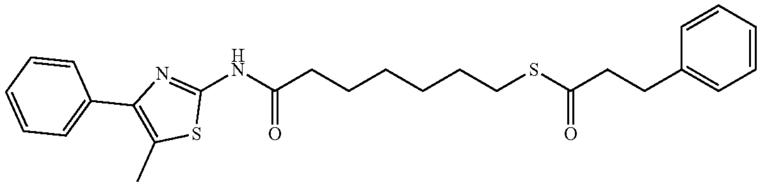 [SMILES: Cc1sc(NC(=O)CCCCCCSC(=O)CCc2ccccc2)nc1-c1ccccc1] | S-(7-((5-methyl-4-phenylthiazol-2-yl)amino)-7-oxoheptyl) 3-phenylpropanethioate |

Examples 65-75 can be synthesized using the methods disclosed herein.

Example 76

Efficacy Evaluation of Novel Compounds for Treating Alzheimer's Disease

The inventors identified ATP6V1A as a key regulator of a top-ranked neuronal subnetwork underlying late-onset Alzheimer's disease. In particular, the present disclosure shows that ATP6V1A and its regulated gene network were down-regulated in LOAD brains in comparison with the normal control brains. To identify drugs for targeting this key regulator, the inventors used gene expression-based testing and multi-electrode array (MEA) analysis in human induced pluripotent stem cell (hiPSC)-derived NPCs and NGN2 neurons to examine the capability of the novel compounds disclosed herein to modulate ATP6V1A mRNA level and neuronal activity, with a particular focus on the top compound LQ081-166. The inventors discovered that LQ081-166 can not only effectively increase the expression of ATP6V1A but also enhance neuronal activity.

LQ081-166, a New Compound, Increases ATP6V1A Gene Expression.

Figure 7A:
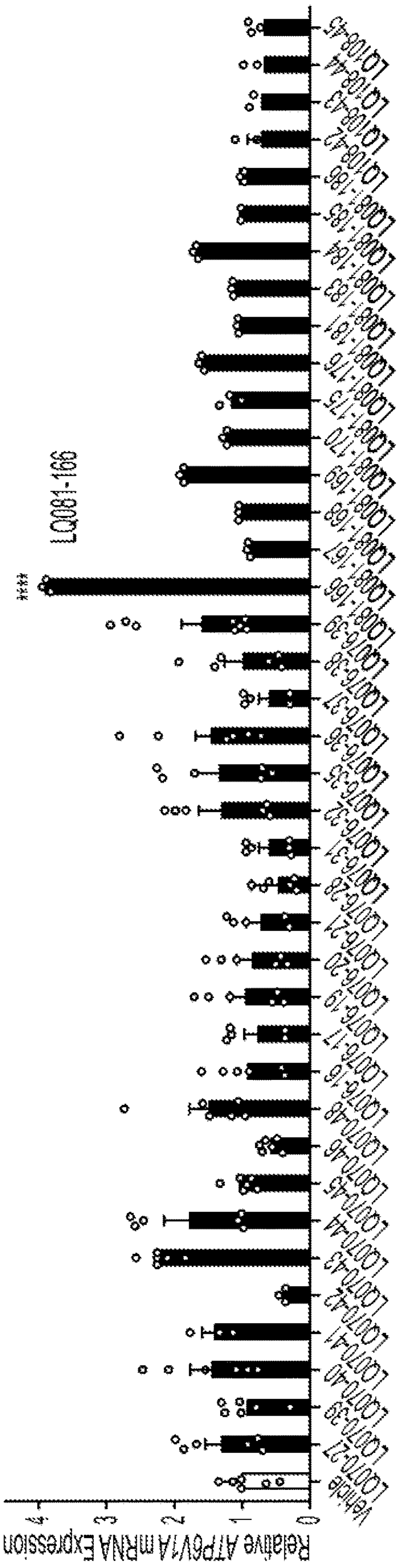
FIG. 7 shows ATP6V1A gene expression-based compounds testing.

Work by the inventors suggested that increasing the mRNA level of ATP6V1A led to a promising therapeutic effect for treating LOAD. To identify useful drugs for targeting this novel therapeutic target, the inventors synthesized 39 new compounds by chemical synthesis and evaluated their capability of elevating the mRNA level of ATP6V1A and neuronal activity in hiPSC-derived NPCs. The gene expression-based screening assay indicated that LQ081-166 most significantly increased ATP6V1A mRNA level (FIG. 7A, ****, $p<0.0001$).

Figure 7B:
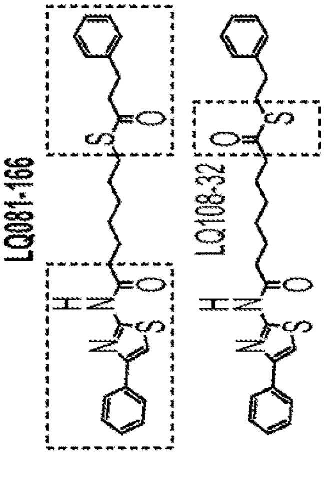
Figure 7C:
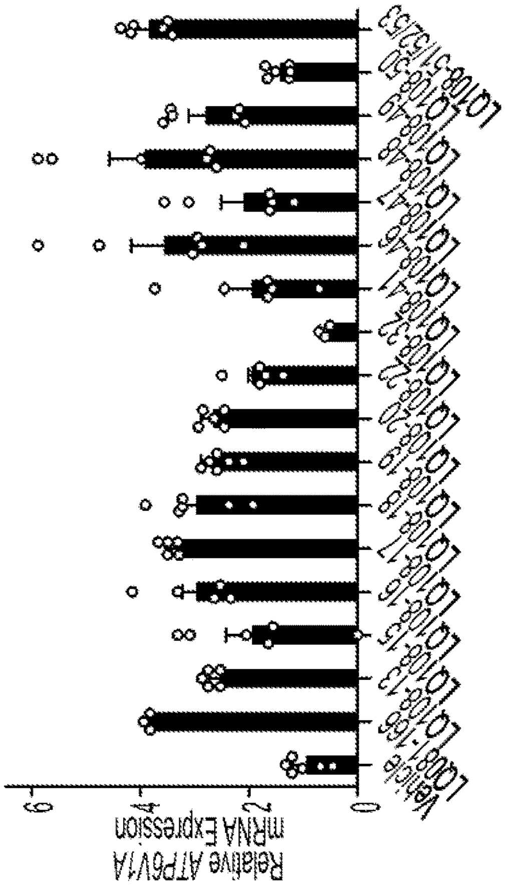
Figure 7D:
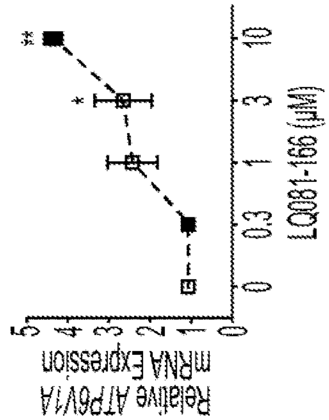

To improve the potency and efficacy of the drugs, an additional 18 derivatives based on LQ081-166 were synthesized (FIG. 7B). The inventors discovered that most derivatives with similar structures showed comparable efficacy (FIG. 7B-C). The inventors determined that the thioester and benzyl group in LQ081-166 has a structure-activity relationship necessary for ATP6V1A activation. The inventors concluded that the thioester (—S—CO—) direction is essential, as indicated by LQ081-32's inability to affect ATP6V1A gene expression (FIG. 7B-C). The inventors discovered that LQ081-166 exhibited a dose-dependent effect (FIG. 7D), and chose 3 μM as an activity threshold.

LQ081-166 Rescues the Neuronal Activity of Aβ-Treated and ATP6V1A KD hiPSC-Derived NGN2 Neurons.

CRISPR inhibition (CRISPRi) was utilized to repress endogenous ATP6V1A in hiPSC-derived NGN2 neurons. The resulting ATP6V1A KD neurons exhibited significantly reduced neuronal activity. In addition, β-amyloid (1-42) peptide (AD) administration (5 μM, 24 hours) considerably decreased spontaneous neuronal activity, while having an insignificant effect on ATP6V1A expression.

Figure 8A:
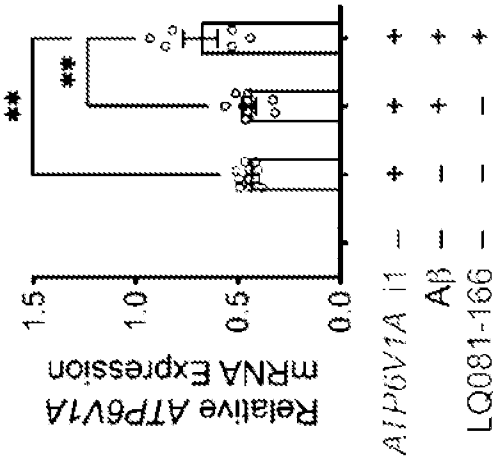
FIG. 8 shows that LQ081-166 recues ATP6V1A expression and neuronal activity.
Figure 8B:
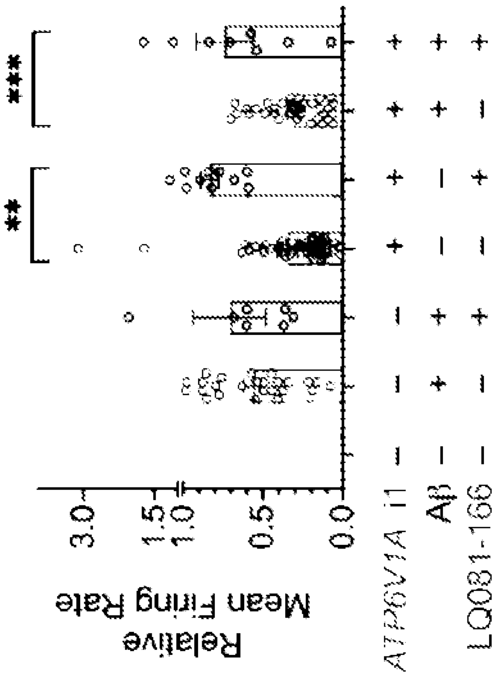

Next, the inventors investigated whether LQ081-166 could rescue the decreased ATP6V1A gene expression and reduced neuronal activity. The inventors discovered that LQ081-166 (3 μM, 24 hours) significantly increased ATP6V1A mRNA level in NGN2 neurons and was a potent activator of neuronal activity, partially restoring neuronal activity in ATP6V1A KD neurons, regardless of the presence/absence of Aβ exposure (FIG. 8A-B,  $p<0.01$, * $p<0.001$).

FIGURES

FIG. 1: A transformative network modeling platform for mechanism discovery, target identification, and therapeutics development for Alzheimer's disease. (A-C) Functional genomic data from disease modified brains and AD-related clinical and pathological phenotypes are collected. (D) The input data are integrated to identify disease gene signatures and co-expressed gene modules using MEGENA. (E) The top modules are projected onto causal networks to identify key driver genes of the disease. (F-H) Candidate drugs that can reverse the disease gene signatures and driver genes are predicted by an advanced pattern matching algorithm. (I-L) The disease relevance of key drivers (e.g., ATP6V1A) is tested in model systems like hiPSC-derived brain cells and *Drosophila* through (i) gene perturbations and (ii) drug rescue experiments.

FIG. 2: Gene coexpression network analysis prioritizes neuronal modules associated with LOAD. (A) The MEGENA network in BM36-PHG. Node greyscaling denotes module membership. Font size of gene name is proportional to degree of connectivity. (B) The 25 top-ranked modules. The heatmap shows the module ranking (number) and functional annotation (color) in track 1, the correlations (r) with the traits including bbscore, CDR, CERAD, and PlaqueMean in tracks 2-5, and adjusted P values of enrichment for down- (tracks 6-14) and up-regulated (tracks 15-24) DEGs. (C) Sunburst plots showing the module hierarchy and correlation with CDR, enrichment for CDR demented-vs-nondemented DEGs, and enrichment for cell type markers. Numbers 1-13 denote 13 top-ranked modules as listed to the right. ast stands for astrocytes, end for endothelial, mic for microglia, neu for neurons and oli for oligodendrocytes. (D) Networks of the top ranked neuronal modules M62, M65, M6, and M64. Node color denotes expression change in demented brains. Node size is proportional to node connectivity. (E) Top-ranked neuronal modules enriched for GO biological process (BP) hierarchy in relation to synaptic function, neuronal development, and transportation. Each node denotes a GO/BP term, with a pie-chart displaying the significance of enrichment for the 4 neuronal modules in D.

FIG. 3. Bayesian probabilistic causal network (BN) analysis identifies novel key drivers of LOAD. A, BN in the BM36-PHG. B, Validation of the BN structure. The left panel shows the percentage of the global BN key drivers whose network neighborhoods are enriched for the perturbation signature. The right panel shows the same analysis for the non-driver nodes. C, Projection of the modules M62 and M64 onto the BM36-PHG BN. Node labels are shown for the module key drivers. D-G, A novel network key driver ATP6V1A is down-regulated in LOAD. D, ATP6V1A expression in the RNA-seq data of the BM36-PHG region as stratified by CDR. E-G, Validation of ATP6V1A expression change in MSBB BM36-PHG samples using western blot (WB) (E-F) and qRT-PCR (G) analyses. E, Representative WB of ATP6V1A level. (t-test or ANOVA with Dunnett's test. Error bars represent SE. *p<0.05. p<0.01. *p<0.001. **p<0.0001. NS, no significance.). NL, normal control. See also FIG. S12-14** & Table S14-15.

FIG. 4. Repression of ATP6V1A leads to neuronal malfunction in human NGN2-neurons and Aβ42 transgenic flies. A, ATP6V1A gene editing by the CRISPR/dCas9-KRAB system. Six different gRNAs are designed for targeting the ATP6V1A promoter. TSS: transcription start site. ATG translation initiation codon is in exon 2. B, qRT-PCR analysis (n=4) confirms the decreased ATP6V1A RNA by gRNA candidates 1 & 2 (i1 and i2) in 2 independent cell lines of iNs (i.e., C1 and C2). C-D, Representative WB and quantitative analysis (n=4) of ATP6V1A protein level in iNs. β-Actin is a loading control. E-F, Representative raster plots of spike events over 10 min and analysis (n=6~45 wells) of D21 iNs. G, Current-voltage (I-V) plot for inward sodium ($I_{Na}$) and outward potassium ($I_K$) currents. Current density (pA/pF) is shown. Holding potential was −80 mV. H, Representative examples of putative inward voltage-gated sodium current at 0 mV. I, Bar plot shows mean inward sodium current densities at 0 mV for ATP6V1A KD (n=17) and control neurons (n=18), (p=0.015). J, Box plots show the fraction of neurons that displayed a full action potential (AP), spikelets, or no events with a current injection step (0.1 nA) positive to the threshold for control and KD neurons. Inset shows representative examples of AP & spikelet. K, Representative confocal images of synaptic proteins (SYN1, red; HOMER1, green) and pan-neuronal marker MAP2 (blue). Bar, 20 μm. L, Analysis of SYN1 and HOMER1-immunoreactive puncta numbers (n=3). M-N, Representative WB and quantitative analysis (n=4) of SYN1 and HOMER1 levels. O-P, Multi-electrode array after exposure to 5 μM Aβ at 24 hours. O, Plate map of total spike events; P, Analysis of spike events (n=12 wells). Q, mRNA levels of Vha68-1 and Vha68-2 were decreased in the Aβ42 fly heads (n=4). R, Vha68-1 KD in neurons exacerbated locomotor deficits caused by Aβ42 as revealed by climbing assay. n=5 except for 7-day (n=2). S, Neuronal KD of Vha68-1 significantly worsened neurodegeneration in Aβ42 fly brains. Representative images show the central neuropil of 33-day-old fly brains. Scale bars: 50 μm. Percentages of vacuole areas (indicated by arrows) were analyzed. n=12-24 hemispheres. T, mRNA levels of genes related to synapse biology were significantly reduced in Aβ42-expressing flies with neuronal KD of ATP6V1A/Vha68-1 (n=4). See also FIG. S16-21. (See FIG. 3 for statistical test and P value annotations).

FIG. 5. RNA-seq analysis of ATP6V1A KD neurons validates ATP6V1A regulated neuronal networks in LOAD brains. A, Top MSigDB gene sets and human AD signatures enriched in the perturbations of iNs. Plus (+) and minus (−) symbols denote the sign of the GSEA enrichment score (ES). Brown color in the x-axis of the left panel highlights the neuronal related terms. Cyan color in the x-axis of the two right panels highlights the down-regulated signatures. B-C, Analysis of synergistic effect between ATP6V1A KD and Aβ treatment in iNs. B, Summary of the functional categories that are likely to be impacted by the synergistic effect. C, Pie-chart shows percentages of genes that exhibit synergistic difference following combinatorial treatment compared to the expected additive model. Bar-chart shows pathways enriched for genes with "more up" regulation. D, Genes within a path length of 3 from ATP6V1A on the BM36-PHG BN were enriched for down-regulated signals of AD-KD vs. V-WT (GSEA normalized ES=2.3, adjusted P-value=8.3E-6).

FIG. 6. A novel compound NCH-51 increases ATP6V1A expression and partially restores neuronal function. A, The procedure for predicting compounds that could increase ATP6V1A expression and reverse transcriptomic signature of LOAD. B, Chemical structure of NCH-51. C, Effects of NCH-51 at 1, 3, 10, 30 μM on ATP6V1A mRNA level post 24-h exposure. D, Effects of NCH-51 at 0.003, 0.03, 0.3, 3 μM on ATP6V1A protein level post 48-h exposure. β-Actin is a loading control. A blue dotted line is curve fitted for the set of data points. E, mRNA expression of ATP6V1A and the presynaptic SYN1 and SCL17A7 in iNs in the absence and presence of 3 μM NCH-51. n=3-12. F-G, Representative WB and quantitative analysis (n=3-8) of ATP6V1A, SYN1, and VGLUT1 proteins. TUJ1 is a loading control. H-J, Multi-electrodes array after exposure to 3 μM NCH-51. H, Representative raster plots of the spike events over 10 minutes. I, plate map of total spike events; J, analysis of spike events (n=24 wells). K, NCH-51 increased mRNA levels of Vha68-2 in Aβ42 flies. n=4. L-M, NCH-51 suppressed neurodegeneration in both the cell body (L) and central neuropil regions (M) in 21-day-old Aβ42 fly brains. Scale bars: 200 μm. Percentages of vacuole areas (indicated by arrows) were analyzed. n=22-28 hemispheres. N, NCH-51 increased mRNA levels of synaptic biology related genes in Aβ42 fly brains in a dose-dependent manner (n=4). (See FIG. 3 for statistical test and P value annotations)

FIG. 7. ATP6V1A gene expression-based compounds screening. (A) qRT-PCR analysis (N=3-12) to determine the relative changes in ATP6V1A gene expression after exposure to 40 chemical compounds. ****, p<0.0001 (one-way ANOVA). DMSO serves as vehicle control. (B) Molecular modification of LQ081-166 and chemical structure of LQ108-32. (C) qRT-PCR analysis of relative ATP6V1A gene expression after exposure to LQ081-166 derivatives. Grey scale bars in the graph are associated with the categories of molecular modification. Note that LQ108-51/52/53 is a small pool of three LQ081-166 derivatives. (D) Effects of LQ081-166 at 0.3, 1, 3, and 10 μM on ATP6V1A mRNA level after 24-h exposure. *, $p<0.05$; **, $p<0.01$ (one-way ANOVA).

FIG. 8. LQ081-166 recues ATP6V1A expression and neuronal activity. (A) LQ081-166 restores ATP6V1A mRNA level in ATP6V1A KD hiPSC-derived NGN2 neurons. ATP6V1A_i1 is a validated gRNA to repress ATP6V1A gene expression. DMSO serves as vehicle control. (B) Multi-electrode array (MEA) recordings of neuronal activity in NGN2 neurons treated with ATP6V1A_i1, Aβ (5 μM) and/or LQ081-166.  $p<0.01$, * $p<0.001$.

Electronic Data Availability

The human postmortem sequencing data are available via the AD Knowledge Portal (https://adknowledgeportal.synapse.org). The AD Knowledge Portal is a platform for accessing data, analyses, and tools generated by the Accelerating Medicines Partnership (AMP-AD) Target Discovery Program and other National Institute on Aging (NIA)-supported programs to enable open-science practices and accelerate translational learning. The data, analyses and tools are shared early in the research cycle without a publication embargo on secondary use. Data is available for general research use according to the following requirements for data access and data attribution (https://adknowledgeportal.synapse.org/DataAccess/Instructions).

Human Postmortem Brain Tissue Samples

The MSBB-AD cohort included 364 human brains accessed from the Mount Sinai/JJ Peters VA Medical Center Brain Bank (MSBB). The postmortem interval (PMI) is ranged from 75 to 1800 minutes (min), with a mean of 436.5 min, a median of 312 min, and a standard deviation of 323 min. Each donor and corresponding brain sample was assessed for multiple cognitive, medical, and neurological features, including mean plaque density, Braak staging for neurofibrillary tangles (NFT), clinical dementia rating (CDR), and neuropathology scale as determined by the Consortium to Establish a Registry for Alzheimer's Disease (CERAD) protocol. Mean plaque density was calculated as the average of neuritic plaque density measures in five regions, including middle frontal gyrus, orbital frontal cortex, superior temporal gyrus, inferior parietal lobule and occipital cortex. Because many of the donors were nursing home residents and some experienced dementia that was more severe than that captured by the 0-3 scale of CDR, the validated version of the "extended" CDR which adds "profound" (CDR=4) and "terminal" (CDR=5) to the original 5 point scale was used. These four cognitive/neuropathological traits were scored as semi-quantitative features ranging from normal to severe disease stages, reflecting the continuum and divergence of pathologic and clinical diagnoses of AD beyond a simple case-control classification. Donor brains with no discernable neuropathology (by CERAD assessment) or only neuropathologic feature characteristic of LOAD were selected from over 2,000 brains in the MSBB.

Human Induced Pluripotent Stem Cell Lines iPSC-derived NPCs (2607-1-4, 553-S1-1; both male) were generated by Dr. Kristen Brennand Lab at the Icahn School of Medicine at Mount Sinai. The iPSCs (NSB553, NSB2607) were originally from the National Institute of Mental Health (NIMH) childhood-onset schizophrenia (COS) cohort. Human Astrocytes (Cat #1800) were purchased from ScienCell Research Laboratories, Inc. All hiPSC research was conducted under the oversight of the Institutional Review Board (IRB) and Embryonic Stem Cell Research Overview (ESCRO) committees at the Icahn School of Medicine at Mount Sinai (ISSMS). Informed consent was obtained from all skin cell donors as part of a study directed by Judith Rapoport MD at the National Institute of Mental Health (NIMH).

*Drosophila* Models

Flies were maintained in standard cornmeal media at 25° C. Transgenic fly lines carrying UAS-Aβ42 and UAS-Tau were previously described (Iijima et al., 2004; Sekiya et al., 2017). The elav-GAL4 (#458), GMR-GAL4 (#1104), UAS-mcherry RNAi (#35785), UAS-Vha68-1 RNAi (#50726 and #42888), Vha68-11 (#82466), and UAS-Vha68-2 RNAi (#34582) were obtained from the Bloomington *Drosophila* Stock Center. UAS-Vha68-1 RNAi (#46397) and UAS-Vha68-2 RNAi (#110600) were obtained from the Vienna *Drosophila* Resource Center. The UAS-Luciferase RNAi Transgenic flies were generated by PhiC31 integrase-mediated transgenesis systems (Best Gene Inc.). Genotypes and ages of all flies used in this study are provided in figure legends. Experiments were performed using age-matched male flies and genetic background of the flies was controlled. For example, for RNAi experiments, we crossed virgin females from elav-GAL4; UAS-Aβ42 (double transgenic flies expressing Aβ42 pan-neuronally) and males from UAS-Vha68-1 RNAi lines (experimental group) or a UAS-mcherry RNAi line with the same genetic background as the RNAi lines (control group). The resultant offspring from each cross has the same hybrid genetic background and these flies were used for the experiments.

MSBB-AD Cohort QC and Pre-Processing

As described previously (Wang et al., 2018), whole genome sequencing (WGS) as well as RNA-sequencing (RNA-seq) data was generated in four brain regions from majority of the cases, including Brodmann area 10 (frontal pole, BM10-FP), Brodmann area 22 (superior temporal gyrus, BM22-STG), Brodmann area 36 (parahippocampal gyrus, BM36-PHG) and Brodmann area 44 (inferior frontal gyrus, BM44-IFG). Mislabeled or duplicated molecular profiles were identified through an iterative QC and adjustment procedure, which examined the genetic similarity between every pair of molecular profiles across different data types and multiple brain regions. All mislabeled samples were set aside for downstream analyses. For RNA-seq, the RNA-seq libraries with RNA integrity number (RIN) less than 4 or rRNA rate larger than 5% were removed. Instead, one with the best sequencing coverage for the duplicated sequencing libraries was selected.

In the QCed dataset, the RIN is ranged from 4 to 10, with a mean of 6.8, a median of 6.6, and a standard deviation of 1.5. To avoid any artificial regional difference, the data from all four brain regions were merged and processed together. Genes with at least 1 count per million (CPM) reads in at least 10% of the libraries were considered expressed and hence retained for further analysis; others were removed. After filtering, 23,201 genes were retained. The gene read counts data were normalized using the trimmed mean of M-values normalization (TMM)(Robinson et al., 2010) method in the R/Bioconductor edgeR package to adjust for sequencing library size differences. It is critical to identify and correct for confounding factors in the RNA-seq data. For this purpose, R/Bioconductor variancePartition (Hoffman and Schadt, 2016) package was used to evaluate the impact of multiple sources of biological and technical variation in gene expression experiments, including sex, race, age, RIN, postmortem interval (PMI), sequencing batch, rate of exonic reads, and rate of rRNA reads, together with the four cognitive/neuropathological features identified.

Sequencing batch, exonic rate and brain donor were found to contribute to the most variance. The contributions from the cognitive/neuropathological variables were similar and ranked in the middle among all the variables. While rRNA rate generally did not explain a large proportion of variation, it contributed more overall variance than did sex and race. Therefore, in addition to the usual confounding factors that are commonly corrected in postmortem brain gene expression data, including batch, sex, race, age, RIN, and PMI, exonic rate and rRNA rate were also included as covariates. As there were more than 30 batches, the batch was firstly regressed out with a random effect model using variancePartition (Hoffman and Schadt, 2016), and the other covariates were corrected by linear regression in R Differential Expression Analysis For each neuropathological/cognitive trait in each brain region, the samples were grouped into multiple disease severity stages and gene expression between every two groups was compared using limma's moderated t-test analysis. Specifically, for CDR, samples were classified into cognitive normal (nondemented) (CDR=0), mild cognitive impairment (MCI) (CDR=0.5), and demented (CDR≥1). For Braak score, samples were classified into normal (NL) when Braak score ≤2, and AD when Braak score >2. For plaque mean density (PlaqueMean), samples were classified into 4 categories, namely normal (PlaqueMean=0), mild (0<PlaqueMean≤6), medium (6<PlaqueMean≤12), and severe (PlaqueMean >12) groups. With CERAD score, two types of samples classification schemes were used. First, samples were classified into normal (NL) (CERAD=1), definite AD (CERAD=2), probable AD (CERAD=3) and possible AD (CERAD=4). Second, samples were classified into two groups, normal (NL) when CERAD=1 and AD when CERAD >1. To adjust for multiple tests, false discovery rate (FDR) was estimated using the Benjamini-Hochberg (BH) method (Benjamini and Hochberg, 1995). Genes showing at least 1.2-fold change (FC) and FDR adjusted P values less than 0.05 were considered significant. The gene showing the largest fold increase in all comparisons is LTF (lactotransferrin) (3.8-fold, adjusted P value 3.9E-5) as identified in BM36-PHG with respect to the PlaqueMean trait. Lactotransferrin is a major component of mammals' innate immune system, protecting from direct antimicrobial activities to anti-inflammatory and anticancer activities (Legrand et al., 2008). NEUROD6 (neuronal differentiation factor 6) showed the largest fold decrease across all contrasts (0.34-fold, adjusted P value=6.3E-9). NEUROD6 encodes a transcription activator that may be involved in neuronal development and differentiation. Down-regulation of NEUROD6 in LOAD has been consistently observed in several previous studies (Fowler et al., 2015; Satoh et al., 2014).

To systematically validate the present DEG signatures of LOAD related traits, public ALOD signatures were assembled from 10 studies, including Zhang et al 2013 (Zhang et al., 2013a), Webster et al 2009 (Webster et al., 2009), Satoh et al 2014 (Satoh et al., 2014), Miller et al 2013 (Miller et al., 2013), Avramopoulos et al 2011 (Avramopoulos et al., 2011), Liang et al 2008 (Liang et al., 2008), Colangelo et al 2002 (Colangelo et al., 2002), Blalock et al 2004 (Blalock et al., 2004), Mostafavi et al 2018 (Mostafavi et al., 2018), and Allen et al 2018 (Allen et al., 2018). Then the overlap between the present DEGs and these previously published LOAD signatures were evaluated using the Fisher's exact test (FET). A highly significant overlap (adjusted P value up to 1.0E-100) was observed for almost every differential contrast in public LOAD signatures. When up- and down-regulated DEGs were separated, the inventors found significant enrichments in consistent directions with respect to expression changes in this analysis. The relatively mild enrichment for the signatures in BM10-FP and BM44-IFG was due to the small number of genes identified in the two regions. To further investigate if the present expression signatures from bulk tissue RNA-seq tend to reflect cell-type changes, a set of cell type-specific DEGs identified from a recent single-nuclei RNA-seq (snRNA-seq) analysis of LOAD postmortem brains (Mathys et al., 2019) was collected. Here, the inventors used cell type-specific DEGs computed from the cell-level model. These results demonstrate a robust set of LOAD related gene signatures across all brain regions profiled.

To understand what biological processes are represented in the DEGs, the inventors tested these signatures for enrichment of gene ontology (GO) and canonical functional pathway gene sets from the Molecular Signatures Database (MSigDB) gene annotation database v6.1(Liberzon et al., 2011; Subramanian et al., 2005). For convenience, the MSigDB gene set collections have been assembled into an R package called "msigdb" which is publicly available from https://github.com/mw201608/msigdb. The inventors overlapped the DEGs with the MSigDB gene sets and computed the fold enrichment (FE) and P value significance using the algorithms described in the next section "Overlap and functional enrichment analysis".

Overlap and Functional Enrichment Analysis

Functional enrichment analysis (or overlap test) P value was calculated using the hypergeometric test (equivalent to the Fisher's exact test, FET) assuming the sets of genes, such as DEGs, were identically independently sampled from all the genome-wide genes detected by RNA-seq except otherwise specifically stated. Fold enrichment (FE) was calculated as the ratio between observed overlap size and expected overlap size. To control for multiple testing, the Benjamini-Hochberg (BH) approach (Benjamini and Hochberg, 1995) was employed to constrain the FDR. For GO and pathway enrichment analysis, the functional gene set collections from the Molecular Signatures Database (MSigDB) v6 were utilized.

For brain cell type marker gene enrichment, the analysis focused on the 5 major brain cell types, i.e. neurons, microglia, astrocytes, oligodendrocytes and endothelial and used for each type the top 500 ranked consensus cell type-specific genes derived from a meta-analysis of 5 cell type-specific or single cell RNA-seq datasets (McKenzie et al., 2018).

Cell-Type Deconvolution Analysis

Cell-type deconvolution analysis was performed to estimate the major brain cell-type proportions using a Digital Sorting Algorithm (DSA). From the normalized gene expression matrix and cell-type marker genes, DSA estimates the cell type frequencies by solving a restricted linear model. Here the inventors focused on 5 major brain cell types (i.e., neurons, astrocytes, oligodendrocytes, microglia, and endothelial), and used for each type 5 markers that were top ranked for cell type specificity according to their recent brain cell type specific transcriptomic analysis (McKenzie et al., 2018). The diseased brains showed progressive neuronal loss as the severity advanced, which was accompanied by the increase of glia cells. The neuronal cell frequencies were negatively correlated with disease traits in all brain regions. For example, the Spearman correlation between neuronal frequencies and CDR ranged from −0.18 to -0.41 (P value=3.1E-3~2.6E-10). The proportion of microglia cells was not estimable, likely due to the low sensitivity in estimating cells with low abundance.

Megena Gene Coexpression Network Analysis

For MEGENA (Song and Zhang, 2015), Pearson correlation coefficients (PCCs) were computed for all gene pairs in every brain region. Significant PCCs at a permutation-based FDR cutoff of 0.05 were ranked and iteratively tested for planarity to grow a Planar Filtered Network (PFN) by using the PMFG algorithm. Multiscale Clustering Analysis (MCA) was conducted with the resulting PFN to identify coexpression modules at different network scale topology. The inventors identified 475, 527, 441 and 423 coherent gene expression modules in BM10-FP, BM22-STG, BM36-PHG and BM44-IFG, respectively. To annotate the potential biological functions associated with the modules, the inventors performed MSigDB gene set enrichment analysis using FET as described above. Most of these modules (53.9% to 67.3%) were enriched for MSigDB GO/pathway gene sets (adjusted P value <0.05), showing that MEGENA can capture data-driven, biologically meaningful, context-dependent co-regulation signals beyond what is represented in canonical pathways from ontology databases. For simplicity, modules were annotated by the top enriched functional category.

To prioritize the gene modules with respect to their association to LOAD pathology, the inventors applied an ensemble ranking metric (Wang et al., 2016) across multiple feature types (FIG. 2B-C), including 1) correlations between module eigengenes (i.e. the first principal component of module gene expression profile) and cognitive/pathological traits associated with LOAD, and 2) enrichment for the DEG signatures identified above. The ranking of the top 25 MEGENA modules are illustrated in FIG. 2B, with each top module coming from the BM36-PHG region The inventors annotated the potential cell type specificity of the modules by evaluating enrichment of brain cell type-specific marker as described above. The inventors found many top-ranked modules were enriched for neuronal or microglia-specific cell types (FIG. 2B-C) based on enrichment analysis of cell type-specific markers of five major brain cell types, including neurons, microglia, endothelial, astrocytes and oligodendrocytes (McKenzie et al., 2018). A large-scale single-nucleus RNA-seq data of inhibitory and excitatory neurons isolated from six different regions of the human cerebral cortex (Lake et al., 2016) was utilized to test whether the top-ranked neuronal system modules reflected distinct neuronal subtypes, we utilized. The preprocessed gene expression data (transcripts per million, TPM) was downloaded from this published study and genes with at least 1 TPM in at least 10% of the cells in one subtype were further selected. The inventors then computed genes that showed differential expression between cell types using limma's moderated t-test analysis. The brain region providing the source of the cells was incorporated as a covariate. The inventors focused on the genes differentiate between the two major neuron cell types (i.e. inhibitory and excitatory). Genes were labeled as inhibitory neuron-enriched if they presented at least 4-fold higher expression in inhibitory neuron cells than in excitatory neuron cells with FDR <0.05 and as excitatory neuron-enriched if they presented at least 4-fold higher expression in excitatory neuron cells than in inhibitory neuron cells with FDR <0.05. As a result, the inventors identified 1008 excitatory neuron-enriched genes and 413 inhibitory neuron-enriched genes. Lastly, the inventors overlapped the cell type-enriched genes with the top-ranked neuronal modules and discovered that module M64 was overrepresented with inhibitory neuron-enriched genes while M6, M87, M65, M236, M62, and M252 were overrepresented with excitatory neuron-enriched genes.

The inventors further discovered that numerous LOAD GWAS risk genes were present in their top-ranked modules, including MEF2C (M62), CELF1, MADD, PLD3, PTK2B, and ZCWPW1 (M6), and APP and SORL1 (M64), CLU and CRI (M17), and APOE, CASS4, CD33, HLA-DRB1/HLA-DRB5, INPP5D, MS4A4A/MS4A6A and TREM2 (M153 and M14).

Network Connectivity Preservation Analysis

The inventors investigated the preservation of global MEGENA co-expression network between their MSBB RNA-seq data and the ROSMAP RNA-seq data (Mostafavi et al., 2018), using the network-based statistics calculated by the modulePreservation function from WGCNA. Since modulePreservation does not allow a single gene to be present in multiple modules as in MEGENA, the inventors considered each gene-module combination as a unique gene and renamed the genes, then created a new expression matrix accordingly. The inventors reported module preservation with the main network-based statistics Zsummary-.pres and followed the original software guideline to denote a module as strongly preserved (Zsummary.pres >10), weakly to moderately preserved (2<Zsummary.pres <10), or not preserved (Zsummary.pres <2).

Discovery of Region-Wide Expression Quantitative Trait Loci (eQTLs)

Given the well-established relationships between gene expression and interactions with genetic and environment factors, the inventors mapped expression quantitative trait loci (eQTLs) by integrating the RNA-seq and WGS-based Single-nucleotide polymorphism (SNP) genotype data. SNPs significantly associated with gene expression traits were identified using the MatrixEQTL package. Significant SNPs (eSNPs) were classified into cis- and trans-acting elements according to whether they are located within 1-MB from the gene or not. At a conservative Bonferroni corrected P value threshold of 0.05 (equivalent to a nominal P value cutoff of 3.0E-10), 1214, 922, 762, and 1054 genes were identified to be regulated by at least one proximal SNP within 1 million base (Mb) from the gene, termed cis-eSNP, in BM10-FP, BM22-STG, BM36-PHG, and BM44-IFG, respectively. For simplicity, genes with significant eSNPs are referred to as eGenes and a significant association between a SNP and a gene as an eSNP-eGene pair. Using such a definition, 126,799, 101,705, 92,336, and 112,139 cis-eSNP-eGene pairs were identified in BM10-FP, BM22-STG, BM36-PHG and BM44-IFG, respectively. Notably, there are redundant eSNPs for the same eGene due to linkage disequilibrium (LD) of the SNPs. The inventors discovered that 66.1% to 90.7% of the cis-eSNP-eGene pairs identified in one brain region were also detected in at least one other brain region. In addition, the inventors found that 71,298 cis-eSNP-eGene pairs from 548 unique genes were shared by all 4 brain regions.

The inventors detected 20,657, 14,011, 14,766, and 17,125 trans-eSNP-eGene pairs from BM10-FP, BM22-STG, BM36-PHG and BM44-IFG, respectively. For each brain region, the inventors found that 28.5 to 70.1% of the identified trans-eSNP-eGene pairs were also detected in at least one other brain region. Bonferroni corrected significant SNPs within a 5-Mb interval were grouped into a single peak because of insufficient resolution to break LD over such narrow windows. Each peak was represented by the most significant eSNP in the window, referred to as the lead eSNP, for a given trans-eGene. The inventors identified 2,411, 1,965, 1,392 and 2,460 trans-eQTL peaks from BM10-FP, BM22-STG, BM36-PHG and BM44-IFG, respectively.

Early eQTL studies noted the existence of master trans-genetic regulators, which the inventors labeled to as eQTL hotspots, which regulate many genes throughout the human genome. The trans-eQTL hotpots were defined as those peaks associated with 10 or more trans-eGenes. At this definition, the inventors identified 24, 12, 2 and 27 trans-eQTL hotpots from BM10-FP, BM22-STG, BM36-PHG and BM44-IFG, respectively, with nine trans-eQTL hotspots shared between 2 or 3 brain regions. Each of these hotspots were associated with 10 to 36 trans-eQTL genes. The inventors discovered that the hotspot associated with the greatest number of trans-eQTL genes (36 genes) was located at a region near 84.4-Mb on chromosome 17 (lead eSNP rs10264300) in BM44-IFG. SNP rs10264300 is 181 kilo-bases upstream of AC003984.1 (a long intergenic noncoding RNA, lincRNA) and 82.5 kilobases downstream of AC093716.1 (a pseudogene gene). The inventors found that about half (16) of the gene targets of this hotspot encode enzyme binding proteins (6.4-FE, adjusted FET=7.1E-5). Interestingly, the inventors further discovered synaptic pathway genes were enriched for the targets of a hotpot near lead SNP rs34072069 on chromosome 10 in BM10-FP (17.1-FE, adjusted FET P=4.9E-6). SNP rs34072069 is 44.5 kilo-bases (KB) upstream of RNU6-535P (a small nuclear RNA gene) and 1.9 KB downstream of RP11-385N23.1 (an antisense gene).

The inventors evaluated whether any modules were enriched for the identified cis-eGenes. They discovered that twelve MEGENA modules were significantly enriched for cis-eQTL genes, among which four were associated with GTPase mediated signal transduction (one from each brain region (>17.9-FE, adjusted FET P<3.5E-11) and three were associated with transferase activity (one from each of 3 brain regions except BM44-IFG; >10.9-FE, adjusted FET P<2.3E-4). The inventors found that the genes in the GTPase mediated signal transduction modules were concentrated in chromosome region 17q21, while the transferase activity modules in chromosome region 8p23, suggesting the genetic regulation of these modules by common eQTLs shared by multiple brain regions.

The inventors have replicated a significant percentage of the eQTLs using an independent LOAD postmortem brain RNA-seq dataset generated from the ROSMAP cohort, the largest sampled RNA-seq based eQTL analysis of LOAD in a single brain region (494 individuals). Cis-eQTLs were identified for 3,388 genes from the ROSMAP cohort. Since no trans-eQTLs were reported for the ROSMAP cohort, however, the inventors focused on the replication of cis-eQTLs for the present invention, particularly the cis-eSNP-eGene pairs that were available in both datasets. To avoid including dependent signals induced by LD among adjacent SNPs, only the associations comprising the top SNP for each eGene were included in the replication rate calculations. To circumvent the statistical power difference caused by different sample sizes (494 individuals in ROSMAP and 215-261 individuals across the present four brain regions), the inventors first assessed the replication rate of LOAD brain cis-eSNP-eGene discovered in the ROSMAP cohort in the present data set using the $\pi_1$ statistic, which estimated the proportion of reported ROSMAP cis-eSNP-eGene pairs that are also significant in the current data set based on their P-value distribution. The inventors found that the $\pi_1$ values of the ROSMAP cis-eSNP-eGene pairs were 0.698, 0.674, 0.637, and 0.670 in the brain regions BM10-FP, BM22-STG, BM36-PHG, and BM44-IFG, respectively. These values were significantly larger than their empirical null mean of 0.025-0.038 from 10,000 random samples of P values of associations that did not overlap with the eQTLs (one-tailed P value <0.0001). Analogously, the inventors applied the same $\pi_1$ statistic to estimate the replication rate of the present region-wide eQTLs in the ROSMAP data but found that the P value distributions of the MSBB cis-eSNP-eGene pairs were truncated (maximum P value=0.92) with majority of the values approaching 0 (93% to 96% were less than 0.05) in the ROSMAP data. In fact, 81.6%, 84.3%, 89.0% and 82.5% of the cis-eSNP-eGene pairs identified in BM10-FP, BM22-STG, BM36-PHG, and BM44-IFG, respectively, were also called genome-wide significant in the ROSMAP data, indicating most of the present cis-eQTLs were replicated, while the rest 11~18% are likely novel cis-eQTLs or false positives. Nonetheless, these results indicate marked common genetic regulation occurring across different brain regions.

Integrating eQTL, Gene Expression Traits, and LOAS GWAS Loci to Identify Causal LOAD Genes The inventors did not find significant enrichment for cis-eGenes in the LOAD-related DEGs or brain cell type-specific markers in each brain region (with less than 8% of the cis-eGenes detected as DEGs and less than 6% of the DEGs detected as cis-eGenes, FET P value >0.1), suggesting a lack of detectable cis-genetic regulation among the genes dysregulated in LOAD brains. For the most strongly associated SNPs across all cis-eGenes, however, the inventors discovered a significant enrichment (P<0.05) for LOAD genetic association signals based on the SNP-level summary statistics from a recent meta-analysis of AD GWAS (Kunkle et al., 2019), compared to random samples of SNPs of the same size. In this analysis, strongly associated SNPs across all cis-eGenes were selected and their SNP-level LOAD GWAS chi-square statistics were extracted from the AD GWAS study. The mean chi-square statistics among those cis-eSNPs was compared to a null distribution which was obtained by randomly sampling the same number of SNPs for 10,000 times. Enrichment P value was computed as the proportion of randomly sampled SNP sets with mean chi-squared values larger than the observed one.

Moreover, cis-eQTLs overlapped the genome-wide significant LOAD GWAS SNPs at GWAS risk loci HLA-DRB1/HLA-DRB5 and ZCWPW1. To aid in the identification of candidate causal genes in these GWAS loci, the inventors applied the summary-data-based mendelian randomization (SMR) (Zhu et al., 2016b) method to test if the effects of the top GWAS SNPs in the HLA-DRB1/HLA-DRB5 and ZCWPW1 loci were mediated by gene expression associated with eQTL coincident with the GWAS loci. By integrating eQTLs and GWAS signals, the inventors prioritized the most likely functionally relevant genes underlying the effects of causal variants on the disease phenotype at two LOAD GWAS risk loci. The eQTL results and AD GWAS SNP-level summary statistics data files were reformatted in accordance to the manual of the SMR software. The inventors then ran region wide SMR analysis using the default parameter. For each locus, the region wide rather than the experiment-wise significance threshold was used because the inventors were interested in gene discovery for each specific locus in each brain region rather than the joint analysis of all regions as a whole. For the genes with significant association by the SMR test, the heterogeneity in dependent instruments (HEIDI) test (Zhu et al., 2016b) was further employed to distinguish whether the association was caused by pleiotropy of the same causal variant underlying the disease risk, or due to linkage of distinct variant to the one causal to the disease.

The GWAS and eQTL P value profiles at the HLA-DRB1/HLA-DRB5 locus as well as the SMR test results were examined in four brain regions. In a 2-Mb region centered on HLA-DRB1, the inventors discovered 11-12 genes with cis-eQTLs across the four brain regions. For example, they identified 12 genes as having cis-eQTLs in BM10-FP; the SMR test was significant for HLA-DRB5 at a Bonferroni corrected P value threshold of 4.5E-3, while the gene HLA-DRB1 was not significant. To distinguish whether the significant association in the SMR test was caused by pleiotropy that gene expression and the trait affected by the same underlying causal variant, or due to linkage that the top associated cis-eQTL being in LD with two distinct causal variants, one affecting the disease trait and the other affecting the gene expression, the inventors further performed the heterogeneity in dependent instruments (HEIDI) test as in Zhu et al (Zhu et al., 2016b). The inventors found that HLA-DRB5 showed no significant heterogeneity by the HEIDI test (P value >0.05), supporting the null hypothesis that there is a single causal variant affecting both gene expression and disease trait phenotype. In summary, the inventors discovered that HLA-DRB5 passed both SMR and HEIDI tests in all four brain regions, HLA-DQA1 passed both SMR and HEIDI tests in BM36-PHG and BM22-STG, HLA-DRB1 passed both SMR and HEIDI tests in BM36-PHG, and HLA-DQB2 passed both SMR and HEIDI tests in BM44-IFG. This supports the conclusion that HLA-DQA1, HLA-DQB2, HLA-DRB1, and especially HLA-DRB5 are the most functionally relevant targets underlying the GWAS hits at this locus At a 2-Mb region surrounding gene ZCWPW1, the inventors found 3 to 6 genes with cis-eQTLs across the different brain regions. The inventors found that the PVRIG passed the SMR test in BM36-PHG. PVRIG, also known as CD112R, encodes a protein that recruits tyrosine phosphatases for signal transduction and could act as a coinhibitory receptor that suppresses T cell receptor (TCR) signaling (Zhu et al., 2016a). The inventors found that none of the genes passed the HEIDI test, rejecting the null hypothesis that there is a single causal variant affecting both gene expression and disease trait phenotype.

The present analysis shows that eQTL prioritized genes may not be necessarily the genes nearest to the peak SNP as reported in the association studies. Further independent replications and experimental validations are required to verify the potential causal relationships inferred from the current integrative analysis.

Bayesian Probabilistic Causal Network Inference and Key Driver Analysis

To construct Bayesian probabilistic causal Network (BN), the inventors made use of genetic perturbations in biological systems (e.g. WGS SNP variants) and known transcription factor (TF)-target relationships from the ENCODE project as prior for inferring regulatory relationships between genes. In the causal network construction, the TFs are allowed to be parent node of their target genes; but targets are inhibited to be parent nodes of their TFs. To infer gene regulatory relationship from genetic data, cis- and trans-eQTLs were computed for each expression trait using WGS-based SNP variants and then a causal inference was employed to infer the causal probability between gene pairs associated with the same eQTL. Since a gene pair associated with the same eSNP may be causally regulated from one to another or independently regulated by a genetic factor in LD with the eSNP, we derived genetic priors under two scenarios. In the first scenario, genes with cis-acting eSNP could be parent nodes of genes with trans-acting eSNP, but the opposite direction was not permitted following previous practices (Zhu et al., 2007b; Zhu et al., 2008). In the second scenario where the genes are both cis-regulated or both trans-regulated, either gene can be the parent node of the other and hence there are two possible directions. For the latter scenario, the inventors applied a formal causality inference test (CIT) (Millstein et al., 2009; Schadt et al., 2005b) to distinguish the causal/reactive and independent relationships between the gene expression traits by modeling the gene pair and associated eSNP with a "chain" of mathematical conditions. For each trio (a gene pair and one eSNP), CIT will compute the probability of the causal "chain" in which one gene is mediating the causal impact of the eSNP to the other gene when the regulatory direction is allowed. In cases that the gene pair is associated with multiple common eSNPs, the individual causality test P values of each trio were aggregated using Fisher's method to make a collective call for the gene pair.

As the conservative Bonferroni corrected P value threshold of 0.05 in the eQTL analysis gave a very limited number of gene pairs associated with common SNPs, the inventors relaxed the cutoff to a BH FDR adjusted P value threshold of 0.05 to increase the pool of potential causal-reactive gene pairs. The causal relationships thus inferred by CIT were combined with TF-target relationships, and together they were used as structure priors for building a brain region-wide BN from all 23,201 expressed genes through a Monte Carlo Markov Chain (MCMC) simulation-based procedure. Following previous practices (Zhu et al., 2007b; Zhu et al., 2008), the inventors employed a network averaging strategy in which 1,000 networks were generated by this MCMC process starting with different random structure, and links that appeared in more than 30% of the networks were used to define a final consensus network. If loops were present in the consensus network, the weakly supported link involved in a loop was removed to ensure the final network structure was a directed acyclic graph.

From the region wide BNs, the inventors used the Key Driver Analysis (KDA) to identify network key drivers that are predicted to modulate numerous downstream nodes, and as a result, to modulate the state of the network. All the BN nodes were loaded as input in the KDA and, hence the resulting key drivers were called global network key drivers, which were different from the pathway (such as the neuronal modules) context dependent key drivers described later. There were 1,545, 1,418, 1,454, and 1,371 global key drivers in the BNs from BM10-FP, BM22-STG, BM36-PHG and BM44-IFG, respectively. Surprisingly, the inventors discovered that key drivers were significantly conserved across the region-wide BNs, with any two BNs sharing a significant number of key drivers (7.2<FE<8.2, FET P values <1.0E-320), while 325 key drivers were shared across four BNs (929.4-FE, Super Exact Test P value <1.0E-320). This finding shows that there is a high degree of conservation of the regulatory architecture in the brain regions that the inventors profiled.

To perform a comprehensive validation of the BN topological structures and the global key drivers that modulate them, the inventors downloaded a library of 2,460 single gene perturbation signatures curated at the Enrichr server. After filtering for central nervous system (CNS) or immune system-related studies and requiring the perturbed genes to be present in the current dataset, the inventors obtained 649 signatures from 320 studies for 287 unique perturbed genes.

These gene perturbation signatures were collected from the gene expression omnibus (GEO) database, and the original experiments were conducted in a diversity of conditions (different cell lines or tissues from different species). 66 of these perturbed genes were global key drivers in at least one of our four brain region-wide BNs. For each of these perturbed global key drivers, the inventors examined whether the experimental perturbation signature was enriched for genes in the network neighborhood of the key driver in in the identified BNs (examining genes that were within a path length of 6 of the key driver gene) to determine whether the experimentally perturbations signature was predicted by the identified networks. Despite the vast heterogeneity of the gene perturbation studies compared to the present human postmortem brain tissues used to generate the present data for the region-wide BNs, the inventors discovered that 50 to 60% of the key driver perturbation signatures were enriched in the network neighborhoods of the corresponding key drivers across the four region-wide BNs (FIG. 3B). The significance levels of the enrichments are observed to increase as path lengths defining the network neighborhoods are increased, given the BNs were sparse, with a limited number of neighboring nodes closer to the key driver gene, which serves to reduce the power to make such detections, especially in the context of multiple testing. In contrast, the inventors found that the proportion of significantly enriched perturbation signatures decreased to 20~30% in the network neighborhood of non-driver genes.

The inventors performed KDA on the top ranked MEGENA neuronal modules to identify their master regulators. In this analysis, the inventors projected the module genes onto the region-wide BN and searched for key driver genes whose network neighborhood were enriched for the module genes. Different from the global key drivers described above, the inventors found that here the key drivers were context dependent, in this case, related to neuronal system subnetworks. This yielded 42 unique key driver genes across 9 modules that are predicted to be the network key drivers. 10 key drivers were root nodes in the BM36-PHG BN without parental nodes. To further verify the root node status beyond a single region-based network, the inventors sought to integrate information from all 4 region-wide BNs to build a union BN that contained a union of directed links from all 4 individual BNs by following previous practices. Like region wide BNs, loops in the union BN were broken by removing the weakly supported links. Two key drivers, ATP6V1A (module M64), and GABRB2, (module M62), remained as root nodes in this union BN.

Gamma-aminobutyric acid (GABA) is the major inhibitory neurotransmitter in the mammalian brain and GABA type A (GABA-A) receptors mediate the inhibition effect. GABA-A receptors form pentameric complexes by combinations of more than 10 subunits and marked functional remodeling GABA-A receptors, including change of subunit composition and reduced expression of principal subunits, had been observed in LOAD brains. In the present disclosure, the inventors observed a significant down-regulation of the subunits α1-6, β2-3 and γ2-3 in diseased brains compared to control. It has been reported that GABA-A β2 (GABRB2) subunit, paralleled with some other subunits like α1, α2, α5, β3, and γ2, showed altered brain region- and cell layer-specific expression (Kwakowsky et al., 2018). Its protein level was significantly decreased in the dentate gyrus stratum moleculare, but increased in the stratum oriens and stratum radiatum of the hippocampal CA2 region, and stratum radiatum of the hippocampal CA3 region (Kwakowsky et al., 2018), indicating a region-dependent up- or down-dysregulation of this gene in LOAD.

Drug Identification

To identify existing drugs that can restore the molecular expression change in the LOAD brains, the inventors performed a drug repositioning analysis using EMUDRA, which provides a novel computational algorithm to match disease signatures and drug-induced signatures. The inventors downloaded drug-treated gene expression profiles (level 3 data of quantile-normalized and log 2 transformed expression levels from human iPSC-derived neural progenitor cells (NPCs) from the Library of Integrated Network-Based Cellular Signatures (LINCS) program. After removing probes sets mapping to multiple genes or without known gene annotation, the remaining data were adjusted for batch effects using linear regression. The mean expression level of multiple probe sets that match to the same gene was used as the expression level for that gene. For each drug, the applied drug signature was the transcriptome-wide expression difference between drug-treated and DMSO-treated gene expression profiles. The inventors matched each of the drug signatures to the LOAD signature using EMUDRA to find drugs that could reverse the LOAD signature. For LOAD signature, the inventors used the DEGs between CERAD definite AD and normal control brains in the BM36-PHG region (3,000 up- and 2,076 down-regulated genes). In total, 3,629 drug signatures were analyzed and ranked. The inventors further prioritized the top-ranked drugs that can increase ATP6V1A mRNA expression in the NPCs.

Lentivirus Generation

Third-generation VSV.G pseudotyped HIV-1 lentiviruses (below) were produced by polyethylenimine (PEI, Polysciences #23966-2)-transfection of HEK293T cells and packaged with VSVG-coats using established methods (Tiscornia et al., 2006). Lentiviral FUW-M2rtTA (Addgene #20342), pLV-TetO-hNGN2-eGFP-neo (TBD), lentiGuide-Hygro-mTagBFP2, and 6 lentiGuide vectors with insertion were generated. Physical titration of lentivirus was performed by qPCR (qPCR Lentivirus Titration Kit, ABM good #LV900). Lentiviruses were then used to transduce cells according to their physical titer as described below, calculated through the company's website (https://www.abmgood.com/High-Titer-Lentivirus-Calculation.html).

gRNA Design and Cloning gRNA design and cloning were performed as previously described. Specifically, 6 gRNA candidates for ATP6V1A were designed by using CRISPR-ERA web tool (crispr-era.stanford.edu): 6 gRNA sequences targeting promoter region (between +658 bps and transcription start site) of ATP6V1A. For lentiviral cloning, the gRNA sequences were inserted into LentiGuide-Hygro-mTagBFP2 (Addgene #99374). Oligonucleotides encoding gRNA sequences were annealed, diluted and then ligated into BsmBI-digested LentiGuide vectors as previously described. Sanger sequencing using U6 promoter confirmed all constructions.

| Oligo ID | Location | gRNA (E, S score) | gRNA Sequence (5'-3') |
| --- | --- | --- | --- |
| ATP6V1i_#1-1 | +260 | #1 (20, 0) | (SEQ ID NO: 1) 5'-CACCGGCGGGAACGACCACACTTGG |

-continued

| Oligo ID | Location | gRNA (E, S score) | gRNA Sequence (5'-3') |
|---|---|---|---|
| ATP6V1i_#1-2 | | | (SEQ ID NO: 2) 5'-AAACCCAAGTGTGGTCGTTCCCGCC |
| ATP6V1i_#2-1 | +101 | #2 (20, 0) | (SEQ ID NO: 3) 5'-CACCGGGCGACCGGTAACTGGCGAG |
| ATP6V1i_#2-2 | | | (SEQ ID NO: 4) 5'-AAACCTCGCCAGTTACCGGTCGCCC |
| ATP6V1i_#3-1 | +94 | #3 (20, 0) | (SEQ ID NO: 5)5'-CACCGGGTGAGCGGCGACCGGTAAC |
| ATP6V1i_#3-2 | | | (SEQ ID NO: 6)5'-AAACGTTACCGGTCGCCGCTCACCC |
| ATP6V1i_#4-1 | +14 | #4 (20, -2) | (SEQ ID NO: 7)5'-CACCGGGGGAAGTCCTCAGCTGCAC |
| ATP6V1i_#4-2 | | | (SEQ ID NO: 8)5'-AAACGTGCAGCTGAGGACTTCCCCC |
| ATP6V1i_#5-1 | +266 | #5 (20, -2) | (SEQ ID NO: 9)5'-CACCGGTGGTCGTTCCCGCTACTT |
| ATP6V1i_#5-2 | | | (SEQ ID NO: 10)5'-AAACAAGTAGCGGGAACGACCACC |
| ATP6V1i_#6-1 | +658 | #6 (15, 0) | (SEQ ID NO: 11)5'-CACCGGATGTTCACGTGCTTCGGAT |
| ATP6V1i_#6-2 | | | (SEQ ID NO: 12)5'-AAACATCCGAAGCACGTGAACATCC |

hiPSC-NPC Culture and NGN2 Neuronal Differentiation

Two stable hiPSC-derived neuronal progenitor cells (hiPSC-NPCs) (553KRAB and 2607KRAB) expressing dCas9$^{-KRAB}$ were generated as previously described and cultured in hNPC media (DMEM/F12 (Life Technologies #10565), 1×N2 (Life Technologies #17502-048), 1×B27-RA (Life Technologies #12587-010), 20 ng/ml FGF2 (Life Technologies), and 0.3 pg/mL puromycin) on Matrigel (Corning, #354230). NPCs at full confluence (1-1.5×$10^7$ cells/well of a 6-well plate) were dissociated with Accutase (Innovative Cell Technologies) for 5 mins, spun down (5 mins×1000 g), resuspended and seeded onto Matrigel-coated plates at 3-5×$10^6$ cells/well. Media was replaced every two days for four to seven days until next split At day −2, NPCs were seeded as 4-6×$10^5$ cells/well in a 24-well plate coated with Matrigel (coverslips are put in a plate and coated with Matrigel for immunostaining). At day −1, cells were transduced with rtTA, pLV-TetO-hNGN2-eGFP-Neo and ATP6V1Ai gRNA or empty lentiguide-Hygro-mTagBFP2 (Addgene 99374) lentiviruses via spinfection. Medium was switched to non-viral medium 3 hours post-spinfection. At Day 0, 1 μg/ml dox was added to induce NGN2-expression. At Day 1, transduced hiPSC-NPCs were treated with corresponding antibiotics to the lentiviruses (300 ng/ml puromycin for dCas9-effectors-Puro, 1 mg/ml G-418 for hNGN2-eGFP-neo and 1 mg/ml HygroB for lentiguide-Hygro-mTagBFP2) in order to increase the purity of transduced NPCs. At day 3, NPC medium was switched to neuronal medium (Brainphys (Stemcell Technologies, #05790), 1×N2 (Life Technologies #17502-048), 1×B27-RA (Life Technologies #12587-010), 1 μg/ml Natural Mouse Laminin (Life Technologies), 20 ng/ml BDNF (Peprotech #450-02), 20 ng/ml GDNF (Peptrotech #450-10), 500 μg/ml Dibutyryl cyclic-AMP (Sigma #D0627), 200 nM L-ascorbic acid (Sigma #A0278)) including 1 μg/ml Dox, along with antibiotic withdrawal. 50% of the medium was replaced with fresh neuronal medium (lacking dox once every second day. At day 11, full medium change withdrew residual dox completely. At day 13, NGN2-neurons were treated with 200 nM Ara-C to reduce the proliferation of non-neuronal cells in the culture, followed by half medium change by day 17. At Day 17, Ara-C was completely withdrawn by full medium change, followed by half medium changes until the neurons were fixed or harvested around day 21-24.

Primary Human Astrocyte (pHA) Co-Culture

Commercially available pHAs (Sciencell, #1800; isolated from fetal female brain) were thawed onto a matrigel-coated 100 mm culture dish with commercial astrocyte medium (Sciencell, #1801). While their growing, the astrocytes were fed with fresh astrocyte medium for five days according to the company's manual. Upon their confluence at 90%, astrocytes were detached by TrypLE™ (Thermo Fisher Scientific, #12605010), spun down (200 g×5 mins), resuspended with freezing medium (astrocyte medium supplemented with 10% DMSO) and banked in liquid nitrogen.

At day −2, pHAs were thawed and seeded onto the matrigel-coated 100 mm culture dish and cultured for five days. At day 3, cells were detached, spun down and resuspended with Brainphys basal medium supplemented with Antibiotic-Antimycotic (Anti/Anti; Thermo Fisher Scientific, #15240062) and 2% fetal bovine serum (FBS; Sigma, F4135). Then, cells were split as 1×$10^5$ cells/well on a matrigel-coated coverslip. At day 5, pHAs were fed by full medium change with the Brainphys medium (2% FBS+Anti/Anti). At day 7, neurons were split on the pHAs with neuronal medium supplemented with 2% FBS.

Until day 7, NGN2-neurons, when co-cultured with pHAs, were prepared as described above. At day 7, NGN2-neurons were gently detached with Accutase, spun down (1000 g×5 mins) and resuspended in neuronal medium supplemented with 2% FBS. After counting cells with a hemacytometer, NGN2-neurons were seeded on astrocyte culture at different cell densities according to assays (4.5-6×$10^5$ cells/coverslip for presynaptic ICC and 7.5-10×$10^4$ cells/well for MEA). Since day 9, the culture was fed by half medium change along with treatment with 2 μM Ara-C until the day of analysis.

The present disclosure focuses on the phenotypic analyses in 21-day-old NGN2-induced neurons because it is the earliest time point that various studies consistently observe spontaneous synaptic activity across donors. ATP6V1A is robustly expressed across developmental stage in the human brain. Overexpression of NGN2 induces glutamatergic neurons with robust expression of glutamatergic genes and excitatory post-synaptic currents (EPSCs) by 21 days across dozens of donors in the inventors' neuronal cultures (FIG. 4). In hiPSC-derived NGN2-neurons, ATP6V1A expression is elevated within 14-days of neuronal induction and remains relatively stable thereafter (21, 28, and 35 days) tested.

RNA Sequencing Data Processing of ATP6V1A KD and Aβ-Treated Neurons

RNA Sequencing libraries were prepared using the Kapa Total RNA library prep kit. Paired-end sequencing reads (100 bp) were generated on a NovaSeq platform. Raw reads were aligned to hg19 using STAR aligner (v2.5.2a) and gene-level expression were quantified by featureCounts (v1.6.3) based on Ensembl GRCh37.70 annotation model. Genes with over 1 count per million (CPM) in at least 1 sample were retained. After filtering, the raw read counts were normalized by the voom function in limma and differential expression was computed by the moderated t-test implemented in limma.

The inventors examined the GO/pathways impacted by ATP6V1A deficit and/or Aβ treatment by employing the Gene Set Enrichment Analysis (GSEA), a weighted enrichment test using all genes devoid of setting a hard threshold to select significant ones since there was a relatively small number of DEGs in KD-V vs WT-V passing the stringent multiple-test correction and no individual gene met the threshold for statistical significance between the Aβ-treated cells and the vehicle-treated cells. In these analyses, the t-test statistics from the differential expression contrast were used to rank genes in the GSEA. Permutations (up to 100,000 times) were used to assess the GSEA enrichment P value.

ATP6V1A KD and Aβ-Treatment Synergistic Effect Analysis from the RNA-seq Data

The synergistic effect between ATP6V1A KD and Aβ-treatment was performed by limma's linear model analysis with formula: Gene expression~Sample treatment. The coefficients, standard deviations and correlation matrix were calculated, using contrasts.fit, in terms of the comparisons of interest. Empirical Bayes moderation was applied using the eBayes function to obtain more precise estimates of gene-wise variability. P-values were adjusted for multiple hypotheses testing using false discovery rate (FDR) estimation, and differentially expressed genes were determined as those with an estimated FDR <5%, unless stated otherwise.

The expected additive effect was modeled through addition of the individual comparisons: (KD-V vs WT-V)+(WT-Aβ vs WT-V). The synergistic effect was modeled by subtraction of the additive effect from the combinatorial perturbation comparison: (KD-Aβ vs WT-V)−(KD-V vs WT-V)−(WT-Aβ vs WT-V). Fitting of this model for differential expression gives genes that show a difference in the differential expression computed for the additive model and that computed for the combinatorial perturbation. However, interpretation of the resulting DEGs depends on several factors, such as the direction of fold change (FC) in all three models. To identify genes of interest, namely those whose magnitude of change is larger in the combinatorial perturbation vs. the additive model, all genes were categorized by the direction of their change in both models and their $\log_2$(FC) in the synergistic model. First, $\log_2$(FC) standard errors (SE) were calculated for all samples. Genes were then grouped into 'positive synergy' if their FC was larger than SE and 'negative synergy' if smaller than −SE. If the corresponding additive model $\log_2$(FC) showed the same or no direction, the gene was classified as "more" differentially expressed in the combinatorial perturbation than predicted. 2925 genes were computed to be in this category (1152 more down, 1773 more up).

GSEA was performed on a curated subset of the MAGMA collection using the limma package camera function, which tests if genes are ranked highly in comparison to other genes in terms of differential expression, while accounting for inter-gene correlation. Due to the small sample size in this study and moderate fold changes in Aβ treatment, changes in gene expression may be small and distributed across many genes. However, similar to previous studies, more powerful enrichment analyses in the limma package were used. These evaluate enrichment based on genes that are not necessarily genome-wide significant and identify sets of genes for which the distribution of t-statistics differs from expectation. Over-representation analysis (ORA) was performed when subsets of DEGs were of interest, such as the synergistic 'more up' and 'more down' genes. The genes of interests were ranked by −log 10 (p-value) and enrichment was performed against a background of all expressed genes using the WebGestaltR package.

Quantitative RT-PCR (qRT-PCR) of ATP6V1A

Quantitative reverse transcription PCR (qRT-PCR) was performed as previously described. Specifically, cell cultures were harvested with Trizol and total RNA extraction was carried out following the manufacturer's instructions. Quantitative transcript analysis was performed using a QuantStudio 7 Flex Real-Time PCR System with the Power SYBR Green RNA-to-Ct Real-Time qPCR Kit (all Thermo Fisher Scientific). Total RNA template (25 ng per reaction) was added to the PCR mix, including primers listed below. qPCR conditions were as follows; 48° C. for 30 min, 95° C. for 10 min followed by 40 cycles (95° C. for 15 s, 60° C. for 60 s). All qPCR data is collected from at least 3 independent biological replicates of one experiment. Data analyses were performed using GraphPad PRISM 6 software.

| Gene_id | Primer_FWD | Primer_REV | Length |
|---|---|---|---|
| ATP6V1A | (SEQ ID NO: 13) GAGATCCTGTACTTCGCACTG | (SEQ ID NO: 15) GGGATGTAGATGCTTTGGGTC | 130 |
| β-Actin | (SEQ ID NO: 14) TGTCCCCCAACTTGAGATGT | (SEQ ID NO: 16) TGTGCACTTTTATTCAACTGGTC | 109 |

Preparation of Cell Lysates and Western Blotting

Cells were rinsed with ice-cold phosphate-buffered saline (PBS), pelleted, and lyzed in RIPA Lysis and Extraction Buffer (Thermo Fisher Scientific, #89900) containing Halt™ Protease and Phosphatase Inhibitor Cocktail (Thermo Fisher Scientific, #78440). Alternatively, MSBB BM36 brain samples were homogenized with similar methods. Samples were sonicated for 1 minute then centrifuged at 13,000× rpm for 10 min. The supernatant was collected, and total protein concentration was determined using Quick Start™ Bradford Protein Assay (Bio-Rad, 5000201) following the manufacturer's instructions.

Western blotting was performed as previously described using antibodies listed in the table below. Images were captured and quantified using the Odyssey® Imaging Systems (LI-COR. Inc.).

| Item Name | Catalog | Species | WB | IF |
|---|---|---|---|---|
| ATP6V1A | ab199326 | Rabbit | 1:1000 | — |
| Homer 1 | 160 003 | Rabbit | 1:1000 | 1:200-500 |
| PSD-95 | clone K28/43 | Mouse IgG2 | 1:500 | 1:1000 |
| Synapsin 1 | 106 011 | Mouse | 1:1000 | 1:500 |
| Synaptophysin 1 | 101 002 | Rabbit | 1:2000 | 1:500 |
| VGLUT 1 | 135 303 | Rabbit | 1:2000 | 1:1000 |
| SOX1 | AF3369 | Goat | — | 1:100 |
| TUJ1 | 801202 | Mouse IgG2a | 1:1000 | 1:1000 |

Immunofluorescence and Microscopy

NGN2-neurons (on coverslips) were washed with PBS and fixed with 4% paraformaldehyde (PFA) at pH 7.4 for 10 mins, room temperature. Then, fixative solution was replaced with PBS. After 3 times wash, NGN2-neurons were incubated with blocking solution (0.1% Tween-20, 0.5% bovine serum albumin in PBS) for 1 hour, room temperature. The blocking solution was aspirated and replaced with the same solution with primary antibodies listed above and incubated overnight at 4° C. Neurons were then incubated with secondary antibodies in blocking solution, for 1 hour at room temperature, followed by PBS-washing 3 times.

20 μL of AquaPolymount mounting solution (Polysciences Inc., #18606-20) per coverslip was placed onto each microscopic slide and the coverslips were gently mounted onto the slides with the neuron side facing down. Mounted coverslips were air-dried for two days at ambient temperature. For synaptic ICC imaging, images were acquired using a confocal microscope (LSM 780, Zeiss) with a 63× objective lens. These puncta analyses were assessed using NIH ImageJ. Total synapsin1 and homer1 puncta number per image were divided by that image's respective MAP2-positive area to calculate synapsin1 and homer1 puncta counts normalized to MAP2 levels. Data from 3 independent experiments were analyzed using GraphPad PRISM 6 software.

β-Amyloid Preparation and Treatment

Human D-amyloid (1-42) peptide was purchased from GenScript (#RP10017, 1 mg; MW: 4514.1). 1 mg of lyophilized Aβ was completely dissolved in 221.5 μL of 1,1,1,3,3,3-Hexafluoro-2-propanol (Hexafluoroisopropanol, HFIP, Sigma, 52517-10ML). 10 μL of 1 mM Aβ-HFIP (0.045 mg) in 0.5 mL EP tube was dried overnight in the hood. Dried Aβ were centrifuged for 1 hour at 1,000×g, 4° C., and stored at −80° C. Before use, allow Aβ to come to room temperature. 5 mM Aβ-DMSO stock was prepared using 2 μL fresh dry Dimethyl sulfoxide (DMSO, Sigma, D5879) to 0.045 mg Aβ. Aβ-DMSO solution was sonicated for 10 min in a bath sonicator. 21-day isogenic pairs of ATP6V1A-manipulated NGN2-neurons were exposed to 5 μM Aβ for 24 hours and then used in qPCR, MEA assays, and RNA sequencing.

Multi-Electrode Array (MEA)

To evaluate electrical activity of NGN2-neurons by MEA, density-matched isogenic NGN2-neuronal populations, co-cultured with pHAs, were prepared as described above. Specifically, at day 3, pHAs were split as 17,000 cells/well in a Matrigel-coated 48W MEA plate (Axion Biosystems, M768-tMEA-48W) and maintained as above. At day 7, NGN2-neurons were detached, spun down and seeded on the pHA culture. Outer space of each well in the plate was filled up with autoclaved/deionized water to minimize the evaporation of marginal wells ("edge effect") during long-term culture. Half volume of neuronal medium (supplemented with 2% FBS) was replaced with fresh medium including 200 nM Ara-C from day 9 until the end of MEA recording. Electrical activity of neurons was recorded daily during day 14-24. On the recording day, the plate was loaded into the Axion Maestro MEA reader (Axion Biosystems). Recording was performed via AxiS 2.4 for 10 mins. Quantitative analysis of the recording was exported as a Microsoft excel sheet. Data were analyzed using GraphPad PRISM 6 software.

Electrophysiology

For whole-cell patch-clamp recordings, 1.0-1.5×104 human astrocytes were first seeded onto Matrigel-coated 12-mm glass coverslips in 24-well plates, and then seeded with 1.0×105 neurons after ~5 days. Neurons were recorded at 4-5 weeks following dox-induction, with media exchange every 3-4 days. Cells were visualized on a Nikon inverted microscope equipped with fluorescence and Hoffman optics. Neurons were recorded with an Axopatch 200B amplifier (Molecular Devices), digitized using a Digidata 1320a (Molecular Devices) and filtered between 1-10 kHz, using Clampex 10 software (Molecular Devices). Series resistance compensation was applied (70-100%). Patch pipettes were pulled from borosilicate glass electrodes (Warner Instruments) to a final tip resistance of 3-5M Q using a vertical gravity puller (Narishige). Neurons were bathed in artificial cerebral spinal fluid (ACSF) containing (in mM): NaCl, 119, CaCl22); KCl, 2.5; MgCl2, 1.3; d-glucose, 11; $NaHCO_3$, 26.2; NaPO4, 1, at a pH of 7.4. The internal patch solution contained (in mM): K-d-gluconate, 140; NaCl, 4; MgCl2, 2; EGTA, 1.1; HEPES, 5; Na2ATP, 2; sodium creatine phosphate, 5; Na3GTP, 0.6, at a pH of 7.4. Osmolarity was 290-295 mOsm. All chemicals were purchased from Sigma-Aldrich Co. (St. Louis, MO). Neurons were chosen at random using DIC or with BFP+ expression. Current-clamp recordings were used for measuring evoked (current injected to hyperpolarize to approx. −80 mV) activity. Spikelets were defined as small, outward spikes with a peak amplitude of less than 25 mV and occurred at voltages positive to threshold (~−30 mV). In voltage-clamp recordings, voltage steps were applied from −80 mV to +50 mV (10 mV increments) to elicit voltage-gated ionic currents. All recordings were made at room temperature (−22 C). Difference between sodium current densities at 0 mV were tested for statistical significance (P<0.05) using a student's t-test between control (n=18) and ATP6V1A KD neurons (n=17), pooling over two experimental replicates. Voltages are corrected for a junction potential of ~−15 mV. Values are reported as mean±SEM.

ATP6V1A Orthologs in Fly

According to the DIOPT (DRSC Integrative Ortholog Prediction Tool), *Drosophila* Vacuolar $H^+$ ATPase 68 kD subunit 1 (Vha68-1, CG12403) and Vha68-2 (CG3762) are the best orthologs of human ATP6V1A proteins (DIOPT score 13 for both genes). Vha68-1 and ATP6V1A exhibit 83% identity and 91% similarity in primary amino acid sequence and have similar size (614 and 617 amino acids, respectively), while Vha68-2 and ATP6V1A exhibit 83% identity and 92% similarity in primary amino acid sequence with similar size (614 and 617 amino acids, respectively).

RNA Extraction and Quantitative RT-PCR Analysis

More than 25 flies for each genotype were collected and frozen. Heads were mechanically isolated, and total RNA was extracted using TRIzol Reagent (Thermo Fisher Scientific) according to the manufacturer's protocol with an additional centrifugation step (16,000×g for 10 min) to remove cuticle membranes prior to the addition of chloroform. Total RNA was reverse-transcribed using PrimeScript RT-PCR kit (TaKaRa Bio), and qRT-PCR was performed using Thunderbird SYBR qPCR Mix (Toyobo) on a CFX96 real time PCR detection system (Bio-Rad Laboratories). The average threshold cycle value was calculated from at least three replicates per sample. Expression of genes of interest was standardized relative to GAPDH1. Primer sequences are provided below.

| Fly | Human | Forward primer sequence (5' to 3') | Reverse primer sequence (5' to 3') |
|---|---|---|---|
| Gapdh | GAPDH1 | GACGAAATCAAGGCTAAGGTCG (SEQ ID NO: 17) | AATGGGTGTCGCTGAAGAAGTC (SEQ ID NO: 37) |
| Vha68-1* | ATP6V1A | ACTACGCACCAAGGTCAAGG (SEQ ID NO: 18) | CTTTGCCACTTCCAGGGTCA (SEQ ID NO: 38) |
| Vha68-1** | ATP6V1A | ACCTCTTTCCGTGGAACTTGG (SEQ ID NO: 19) | GCAGTTGTGTTGACACCTTTGG (SEQ ID NO: 39) |
| Vha68-2 | ATP6V1A | CAAATATGGACGTGTCTTCGC (SEQ ID NO: 20) | CCGGATCTCCGACAGTTACG (SEQ ID NO: 40) |
| Eaat1 | SLC1A2 | TGCTCTGTTCATCGCCCAAT (SEQ ID NO: 21) | CGACGGCTATGATGAGGGAC (SEQ ID NO: 41) |
| VGlut | SLC17A6-8 | TTCATCGCCTCCAAGTTCCC (SEQ ID NO: 22) | GCTGGATAGGTAACGCCCTC (SEQ ID NO: 42) |
| Atpα | ATP1A1-3 | ACATGGTGCCAGCCATTTCA (SEQ ID NO: 23) | AAGCCGTTCTCAGCCATGAT (SEQ ID NO: 43) |
| Lcch3 | GABRB1-3 | CCGAGACGTGTTCAACGACA (SEQ ID NO: 24) | GGCTATGTCCGGTGCCATAA (SEQ ID NO: 44) |
| Grd | GABRA1-6 | TTTGGCTACACAACGTCGGA (SEQ ID NO: 25) | GGTCGTGGTGGATCCTTGTT (SEQ ID NO: 45) |
| CG8916 | GABRA6 | TTGAGTCCAAGAGCGGTGTC (SEQ ID NO: 26) | CGTTTGGGTGGTTCTCTCCA (SEQ ID NO: 46) |
| Rdl | GABRP | TGGCTCAATCGCAATGCAAC (SEQ ID NO: 27) | GACCGTGGCGTATTCCAGTA (SEQ ID NO: 47) |
| CG12344 | GLRA2 | CGAGAGCTTCTCGTCGAACA (SEQ ID NO: 28) | GAAGTATACGGTGAGGCGGG (SEQ ID NO: 48) |
| GABA-B-R1 | GABBR1 | CTCAGGGCGATCGTATTGCT (SEQ ID NO: 29) | GGTGCGTAGAACATGGGTGA (SEQ ID NO: 49:) |
| GABA-B-R2 | GABBR2 | TGGCGGGTGCATTCGATATT (SEQ ID NO: 30) | TCTCGTGATGCAAGGGTTCC (SEQ ID NO: 50) |
| GABA-B-R3 | GABBR2 | AATTCGCACAGCAATCTGCC (SEQ ID NO: 31) | ACAGCTCAAAGAGTCCGAGC (SEQ ID NO: 51) |
| Sh | KCNA1-7,10 | TGTCAGGTTCCTCGCATGTC (SEQ ID NO: 32) | CTGACTGGCGCTTTTGGAAG (SEQ ID NO: 52) |
| Shab | KCNB1,2 | CGTGCTCGCGTTTAGTGATG (SEQ ID NO: 33) | TTCTGGTACTCGGCGCATTT (SEQ ID NO: 53) |
| SK | KCNN1-3 | GGTTATCGAAAACGAACTGAGCA (SEQ ID NO: 34) | CTTCCAAAGCATGGTAAGCTAC (SEQ ID NO: 54) |
| para | KCNB1,2 | ACGAGGATGAAGGTCCACAAC (SEQ ID NO: 35) | ACGACGTATCGGATTGAATGG (SEQ ID NO: 55) |
| Nmdar2 | GRIN2A-D | GGCATCCCGGTTATCTCGTG (SEQ ID NO: 36) | AGAACTGGTGCCACTTGTAGC (SEQ ID NO: 56) |

Climbing Assay

Approximately 25 male flies were placed in an empty plastic vial. The vial was then gently tapped to knock all of the flies to the bottom. The numbers of flies in the top, middle, or bottom thirds of the vial were pictured and scored after 10 seconds. Statistical analyses were performed to determine the percentage of flies that remained at the bottom of the vial during the experiment.

Histological Analysis

Heads of male flies were fixed in 4% paraformaldehyde for 24 hours at 4° C. and embedded in paraffin. Serial sections (6 μm thickness) through the entire heads were prepared, stained with hematoxylin and eosin (Sigma-Aldrich), and examined by bright-field microscopy. Images of the sections were captured with AxioCam 105 color (Carl Zeiss). To score brain vacuolization, the inventors performed microscopy of serial brain sections within the central neuropil regions and selected the images with the most severe vacuolization from each fly to score area of vacuolization. The inventors selected the section with the most severe neurodegeneration in the same brain area from each individual fly and the area of vacuoles was measured using Image J (NIH). The analyses were performed more than two times and two to three persons were independently involved in these tasks to avoid any bias.

Drug Feeding

Flies were fed with the food containing 10 μM or 50 μM NCH51 or vehicle (final concentration 0.02% dimethyl sulfoxide) from the day after eclosion. These food vials were changed every 3-4 days.

Western Blotting Analysis

Western blotting was performed as described previously. To detect human Aβ42, ten fly heads for each genotype were homogenized in Tris-Glycine SDS sample buffer, and the same amount of the lysate was loaded to 18% Tris-Glycine gels and transferred to nitrocellulose membrane. The membranes were boiled in PBS for 3 min, blocked with 5% nonfat dry milk, blotted with the anti-AD 6E10 antibody (Signet, Covance), incubated with appropriate secondary antibody and developed using ECL Western Blotting Detection Reagents (GE Healthcare Life Sciences). The membranes were also probed with anti-tubulin (Sigma-Aldrich) as the loading control in each experiment. To detect human tau, ten fly heads for each genotype were homogenized in Tris-Glycine SDS sample buffer, and the same amount of the lysate was loaded to each lane of 10% Tris-Glycine gels and transferred to nitrocellulose membrane. The membranes were blocked with 5% nonfat dry milk, blotted with the antibodies described below, incubated with the appropriate secondary antibody and developed using ECL Prime Western Blotting Detection Reagent (GE Healthcare Life Sciences). The membranes were also probed with anti-Nervana and used as the loading control in each experiment. Anti-tau (Merck Millipore), anti-pSer202/pThr205 tau (Thermo Fisher Scientific), anti-Nervana (Developmental Studies Hybridoma Bank) antibodies were purchased. Imaging was performed with ImageQuant LAS 4000 (GE Healthcare Life Sciences), and the signal intensity was quantified using Image J (NIH).

Compound (LQ081-166) Storage and Working Solution

A stock solution of LQ081-166 (molecular weight: 452.63) at 3 mM is prepared in dimethyl sulfoxide (DMSO). Once prepared, aliquot the stock solution into 100 μL amounts and store at −80° C. Avoid repeated freeze-thaw cycles. The stock is diluted 1000× into neuronal medium to obtain 3 μM for assays. After 24-hour treatment, RNA was extracted from cells for quantitative PCR. In the MEA assay, LQ081-166 was added on neuronal differentiation day 14. Replace with medium containing drug or vehicle every 2-3 days until the final recording day.

General Chemistry Methods

For the synthesis of intermediates and examples, HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 ml/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker DRX-600 spectrometer with 600 MHz for proton ($^1H$ NMR) and 150 MHz for carbon ($^{13}C$ NMR); chemical shifts are reported in (δ). Preparative HPLC was performed on Agilent Prep 1200 series with UV detector set to 254 nm. Samples were injected onto a Phenomenex Luna 250×30 mm, 5 μm, Cis column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All final compounds had >95% purity using the HPLC methods described above.

Quantification and Statistical Analysis

The analytical approaches and software used for quantification were specified for each assay. All available brain tissues from MSBB were sent for sequencing analysis, without randomization process. For sample processing, clustering, differential expression and network analyses, all investigators were blinded to outcomes. The statistical test used and sample size n are indicated in the figure legends and the corresponding methods section. Statistical significance is defined as $p<0.05$ (*=p<0.05; =p<0.01, *=p<0.001, ****=p<0.0001).

What is claimed is:

1. A compound, or therapeutically acceptable salt thereof, selected from the group consisting of:

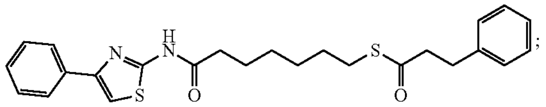

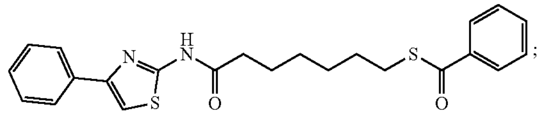

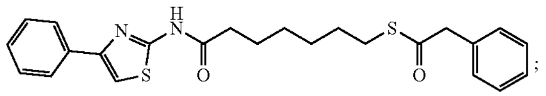

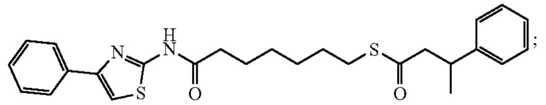

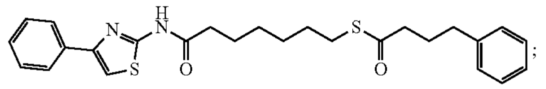

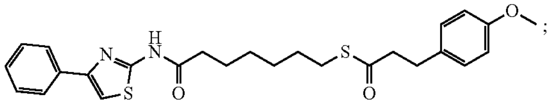

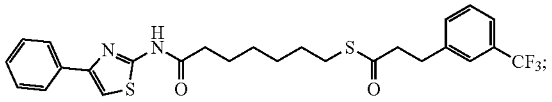

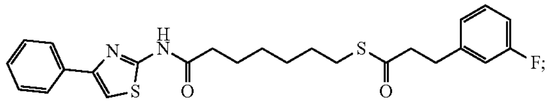

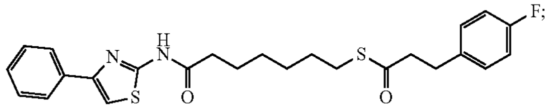

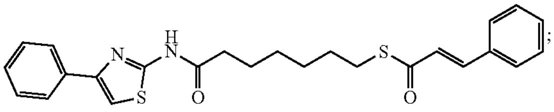

-continued

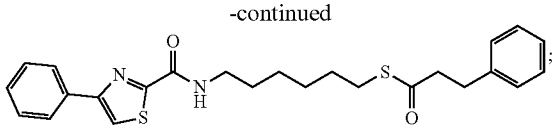

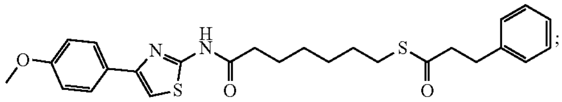

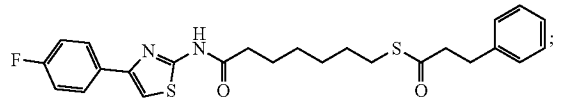

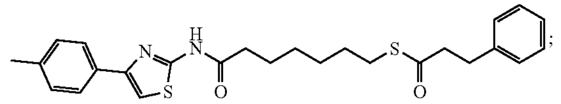

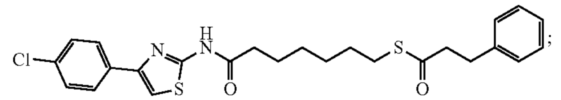

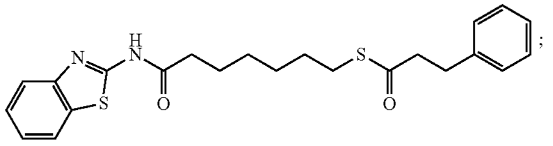

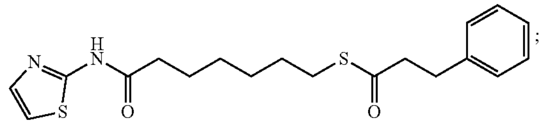

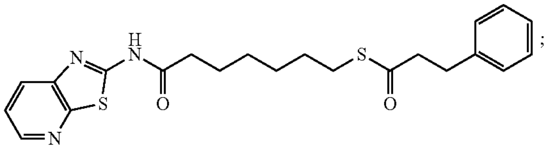

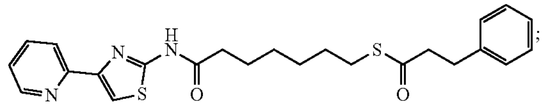

and

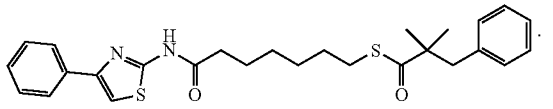

-continued
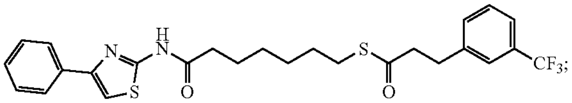
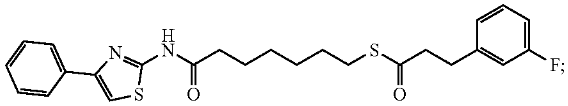
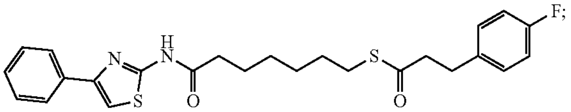
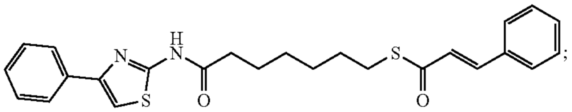
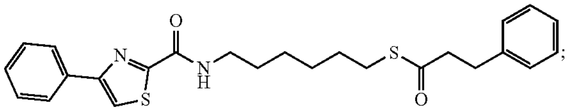
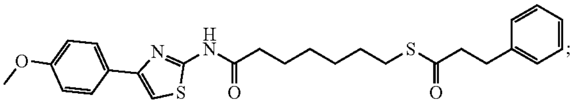
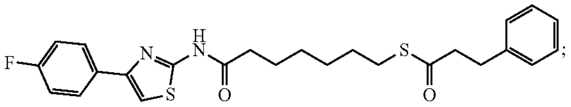
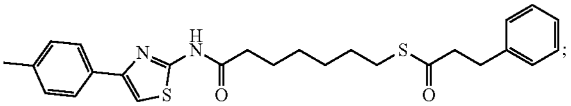
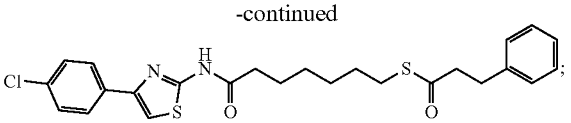
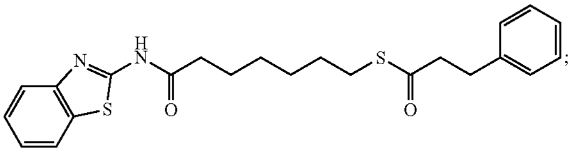
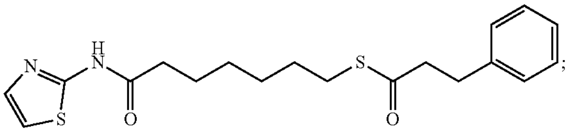
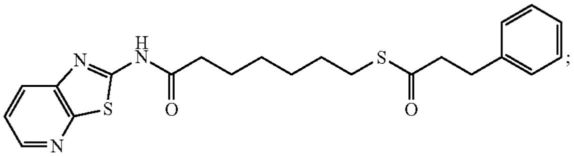
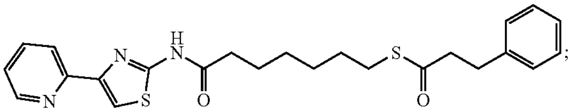
and
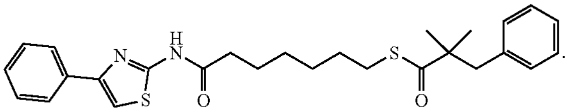
2. The compound of claim 1, or therapeutically acceptable salt thereof, consisting of:
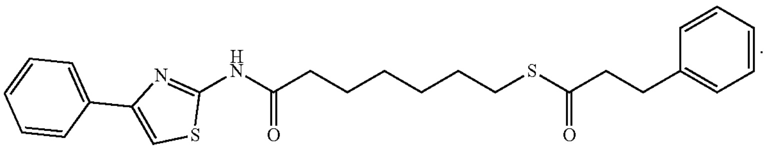 [SMILES: O=C(CCCCCCSC(=O)CCc1ccccc1)Nc1nc(-c2ccccc2)cs1]
3. A compound, or therapeutically acceptable salt thereof, selected from the group consisting of:
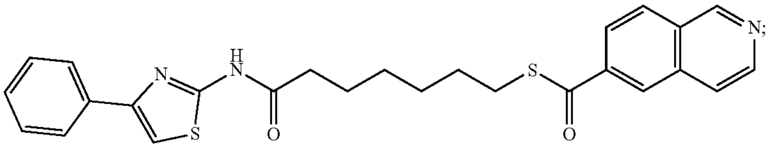
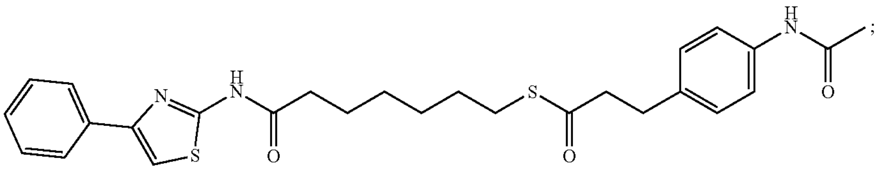
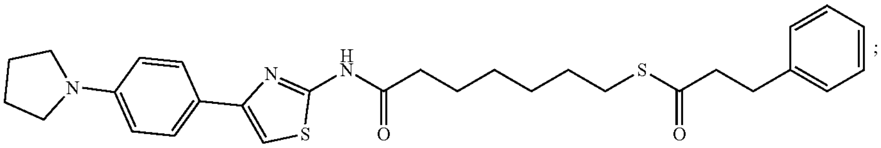

-continued
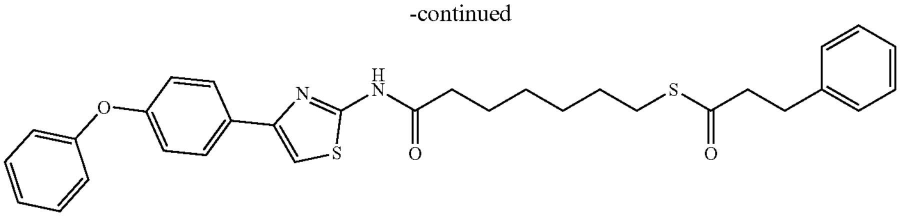
;
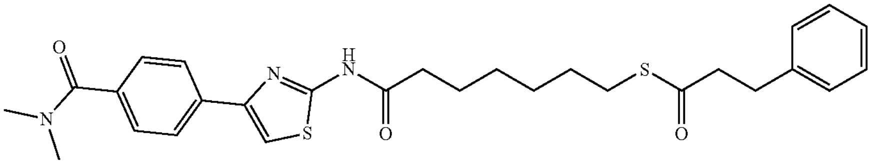
;
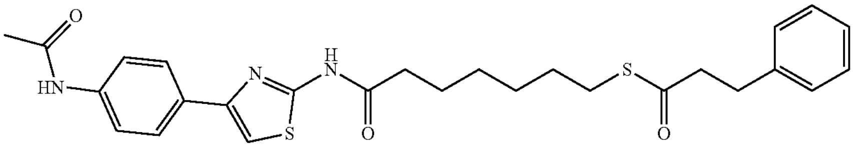
;
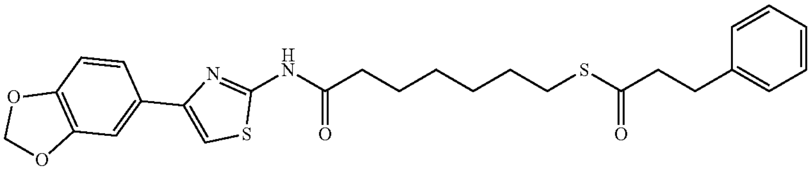
;
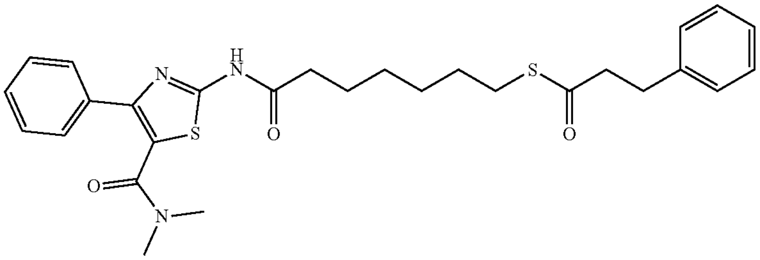
;
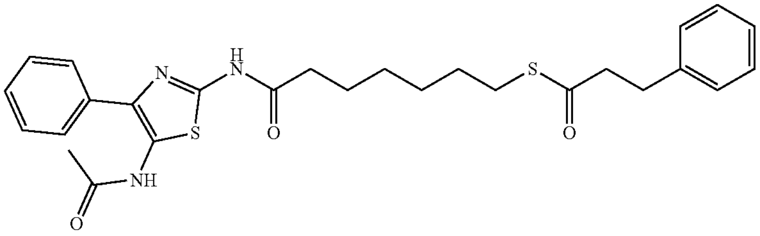
;
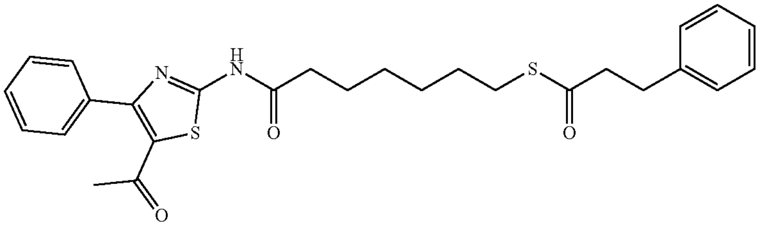
; and
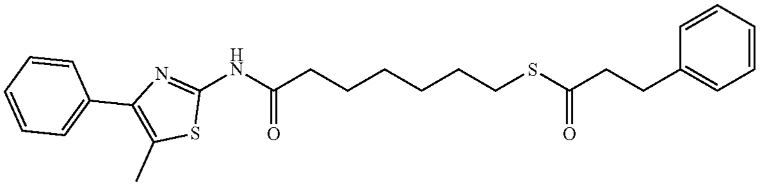
.
* * * * *